United States Patent
Boyd et al.

(10) Patent No.: US 6,780,587 B2
(45) Date of Patent: Aug. 24, 2004

(54) METHODS FOR DIAGNOSING PSEUDOXANTHOMA ELASTICUM

(75) Inventors: Charles D. Boyd, Honolulu, HI (US); Katalin Csiszar, Honolulu, HI (US); Olivier LeSaux, Honolulu, HI (US); Zsolt Urban, Honolulu, HI (US); Sharon Terry, Sharon, MA (US)

(73) Assignees: PXE International, Inc., Washington, DC (US); The University of Hawaii, Honolulu, HI (US)

( * ) Notice: Subject to any disclaimer, the term of this patent is extended or adjusted under 35 U.S.C. 154(b) by 117 days.

(21) Appl. No.: 09/792,616

(22) Filed: Feb. 23, 2001

(65) Prior Publication Data

US 2003/0165828 A1 Sep. 4, 2003

Related U.S. Application Data

(60) Provisional application No. 60/184,269, filed on Feb. 23, 2000.

(51) Int. Cl.$^7$ .......................... C12Q 1/68; C12P 19/34; C07H 21/04
(52) U.S. Cl. ................. 435/6; 435/91.1; 435/91.2; 536/23.1; 536/24.1; 536/24.2; 536/24.3; 536/24.33
(58) Field of Search .................. 435/6, 91.1, 91.2; 536/23.1, 24.1, 24.2, 24.3, 24.33

(56) References Cited

FOREIGN PATENT DOCUMENTS

WO     WO 98/37764     9/1998

OTHER PUBLICATIONS

Le Saux et al. (Genomics (1999) vol. 62, pp. 1–10.*

Cotton, (1993), "Current methods of mutation detection." *Mutation Research*, 285:125–144.

Le Saux et al., (1999), "*Pseudoxanthoma Elasticum* Maps to an 820–kb Region of the p13.1 Region of Chromosome 16," *Genomics*, 62:1–10.

Le Saux et al., (2000), "Mutations in a gene encoding an ABC transporter cause *pseudoxanthoma elasticum*," *Nature Genetics*, 25:2:223–227, abstract only.

Ringpfeil et al., (2000), "*Pseudoxanthoma elasticum*: Mutations in the *MRP6* gene encoding a transmembrane ATP–binding cassette (ABC) transporter," *Proc. Natl. Acad. Sci.*, 97:11:6001–6006.

International Search Report for International Patent Application Ser. No. PCT/US01/05741, dated Jul. 18, 2002, 3 pages.

* cited by examiner

*Primary Examiner*—Carla J. Myers
*Assistant Examiner*—Alexander H. Spiegler
(74) *Attorney, Agent, or Firm*—Testa, Hurwitz & Thibeault, LLP

(57) ABSTRACT

Methods and compositions are provided for diagnosing and treating *Pseudoxanthoma elasticum* (PXE) patients and PXE carriers. Methods and compositions are based on the discovery that PXE mutations are located in the MRP6 (ABCC6) gene.

10 Claims, 6 Drawing Sheets

MAAPAEPCAGQGVWNQTEPEPAATSLLSLCFLRTAGVWVPPMYLWVLGPIYLLFIHHHGR
GYLWMSPLFKAKMVLGFALIVLCTSSVAVALWKIQQGTPEAPEFLIHPTVWLTTMSFAVF
LIHTERKKGVQSSGVLFGYWLLCFVLPATNAAQQASGAGFQSDPVRHLSTYLCLSLVVAQ
FVLSCLADQPPFFPEDPQQSNPCPETGAAFPSKATFWWVSGLVWRGYRRPLRPKDLWSLG
RENSSEELVSRLEKEWMRNRSAARRHNKAIAFKRKGGSGMKAPETEPFLRQEGSQWRPLL
KAIWQVFHSTFLLGTLSLIISDVFRFTVPKLLSLFLEFIGDPKPPAWKGYLLAVLMFLSA
CLQTLFEQQNMYRLKVLQMRLRSAITGLVYRKVLALSSGSRKASAVGDVVNLVSVDVQRL
TESVLYLNGLWLPLVWIVVCFVYLWQLLGPSALTAIAVFLSLLPLNFFISKKRNHHQEEQ
MRQKDSRARLTSSILRNSKTIKFHGWEGAFLDRVLGIRGQELGALRTSGLLFSVLVSFQ
VSTFLVALVVFAVHTLVAENAMNAEKAFVTLTVLNILNKAQAFLPFSIHSLVQARVSFDR
LVTFLCLEEVDPGVVDSSSSGSAAGKDCITIHSATFAWSQESPPCLHRINLTVPQGCLLA
VVGPVGAGKSSLLSALLGELSKVEGFVSIEGAVAYVPQEAWVQNTSVVENVCFGQELDPP
WLERVLEACALQPDVDSFPEGIHTSIGEQGMNLSGGQKQRLSLARAVYRKAAVYLLDDPL
AALDAHVGQHVFNQVIGPGGLLQGTFRILVTHALHILPQADWIIVLANGAIAEMGSYQEL
LQRKGALVCLLDQARQPGDRGEGETEPGTSTKDPRGTSAGRRPELRRERSIKSVPEKDRT
TSEAQTEVPLDDDPDRAGWPAGKDSIQYGRVKATVHLAYLRAVGTPLCLYALFLFLCQQVA
SFCRGYWLSLNADDPAVGGQQTQAALRGGIFGLLGCLQAIGLFASMAAVLLGGARASRLL
FQRLLWDVVRSPISFFERTPIGHLLNRFSKETDTVDVDIPDKLRSLLMYAFGLLEVSLVV
AVATPLATVAILPLFLLYAGFQSLYVVSSCQLRRLESASYSSVCSHMAETFQGSTVVRAF
RTQAPFVAQNNARVDESQRISFPRLVADRWLAANVELLGNGLVFAAATCAVLSKAHLSAG
LVGFSVSAALQVTQTLQWVVRNWTDLENSIVSVERMQDYAWTPKEAPWRLPTCAAQPPWP
QGGQIEFRDFGLRYRPELPLAVQGVSFKIHAGEKVGIVGRTGAGKSSLASGLLRLQEAAE
GGIWIDGVPIAHVGLHTLRSRISIIPQDPILEPGSLRMNLDLLQEHSDEAIWAALETVQL
KALVASLPGQLQYKCADRGEDLSVGQKQLLCLARALLRKTQILILDEATAAVDPGTELQM
QAMLGSWFAQCTVLLIAHRLRSVMDCARVLVMDKGQVAESGSPAQLLAQKGLFYRLAQES
GLV

FIG. 3

SEQUENCE LISTING

<160> NUMBER OF SEQ ID NOS: 27

<210> SEQ ID NO 1
<211> LENGTH: 107820
<212> TYPE: DNA
<213> ORGANISM: Homo sapiens
<220> FEATURE:
<221> NAME/KEY: misc_feature
<223> OTHER INFORMATION: "n" can be an A or a T or a G or a C

<400> SEQUENCE: 1

| | | | | | | |
|---|---|---|---|---|---|---|
| aagcttgcag | aaggtggttg | gcttttgttc | tgaatctaac | aagacttatc | gggaggctct | 60 |
| tggtgcctgg | cactggctga | atgcccaggt | tgggggaggc | agagcagatg | aagcatctgc | 120 |
| ccgcgagggt | gggtggagct | gcttgtgaaa | cgtatcatcg | tagcccggga | gctgggacac | 180 |
| tgaagcccgg | agaaggtgct | catggaggat | gggaagggct | tcccgaggaa | gtgacatctg | 240 |
| tgctcccatc | tgctgggtga | tgaggaatgg | cctggacggg | atgggcatgg | tgggtggagg | 300 |
| caggcggcct | gtgtgcaggg | aaggaagggg | agagttacag | gatgagatga | gttgagggaa | 360 |
| gaagcatggt | tggcaactct | aacagcgctg | ggaggccatc | ggaggggggt | gacgagattg | 420 |
| accctatcct | catgggcatc | tcagctgggc | tgagtgtgct | ggaaccggcc | attgcatgga | 480 |
| cacagtcact | cctgagggga | tgtgatcaac | aggcggaatt | ctgtcactta | atgataacaa | 540 |
| tagtcaccag | ctaactgaat | gcttactgtt | aggtcaaact | atatgaaact | gctaatactt | 600 |
| atttcttatc | tacagaaaca | gctatttcct | gtggttcaac | ctagtattac | caggcactgt | 660 |
| gcttagtgac | atcatgcata | tctatatgat | ttatgaaata | atgtgtccac | gcaaatacac | 720 |
| atcacatgta | agactgtaac | tcttacatgt | caccctcaca | atgaccccgt | gaagcaagct | 780 |
| ttgttttgtt | tcgtttgttt | tcttaataat | attttatttt | tgtagagatg | gcattttgcc | 840 |
| atgtgcctgg | gctggtctca | gactcctggc | ctcaagtgat | ctcccgcctc | tgcctcctga | 900 |
| agtgcgggta | ttacaagcat | gagccacccc | acctggccga | gcaagccttg | ttgttcccat | 960 |
| tttacagata | aggaaactga | ggcttagaga | agtaaagtgt | tagtcgtgtt | tatattgcca | 1020 |
| gtcagtagtt | gagtcaggat | ttgaactgag | gtctcgttga | cctcaaagcc | tatgctgaaa | 1080 |
| accacactgc | tggttccaga | aaaccctaga | ggtgaaaggc | ttcagagagg | cagtacaggg | 1140 |
| tagaggttag | cactttgcag | cccagatggc | ctgggtttga | atcccagttc | tgcccccttgc | 1200 |
| tagccatgtg | accttgggga | ggagattaac | tagcttcttt | gtgccttagt | ctacccatca | 1260 |
| catataggaa | tgagcacctc | aggtttttttg | tgaggattga | atgaactgat | gtttgtaaaa | 1320 |
| ctgcttagaa | cgatgcctgg | ggctgtgggc | tttgtataag | cgtgagctat | tattgtcact | 1380 |

```
gtccttgtca ttggtggtgc tattcctgtg gttcaccagg tgagtgggca cccctgtgag    1440
ggcagcccgg ctctaacatt ttgcctcctg gaggtatcgg ttacgtctag atgttctcca    1500
gcacagccct gccctgggag gatggcagga gggaaccttc atcaactccc cgcgtctgtt    1560
ctctacccca gaggttctac gtggcttcct cccggcagct gaagcgcctc gagtcggtca    1620
gccgctcccc ggtctattcc catttcaacg agaccttgct gggggtcagc gtcattcgag    1680
ccttcgagga gcaggagcgc ttcatccacc agagtgacct gaaggtggac gagaaccaga    1740
aggcctatta ccccagcatc gtggccaaca gtgggcatg gtgggcctgc aggagcgggt     1800
ggaggaggcc gccttagcac cttgtctctt tgcctcgatc ttttcctcgc accttgagct    1860
gggtataaag ccaaaccccg gccttgcaga aggatggag aggcttgatg agcgcggagg     1920
acagatgaat cattaagagc agacagcggc actgtagaca tgcagtgccc gcggcattta    1980
agtgcaggga cacagctctt ctggagtcag aaagccctgc aagtgcttcc cgttaactgt    2040
catcctagtg atgcaagact gccagcgacc gactctgcta ttgagtatct tcataccgct    2100
gttcccgtct gggggtgatc atgcaccct gggtgatgtg tgtcagaagc aatttactaa     2160
tactaagcta aaccatatga gattgtcatc ttgtgggcca gatgtcatgg ctcacgcctg    2220
taatcccagt actttgggag gctgaggcag gaggatccat tagattccag gccagcctgg    2280
gcaacatagc aagacccca tctctcttaa aaaaaaaaa aaaaaaaaa agtagcccat       2340 catggtggtg tgtgcctgta gtcctagctt ctcgagaggc tgaggctgga ggatcgtttc    2400
agcccaggag ttcaaagttg cattgagcta tgattacacc actgcactcc agcctgggtg    2460
acagagtgag accctgtctc tggaaaaaca aaaaaggag atgggggtgg gagattgaca     2520
tcttgtggat cacagataat agcatcaatc caaagaggc agaagtttgc taattatttg     2580
ctgaatttag agaagtgtcc ctctcaccca tttgcatcct tatagacttt tctgaaaaag    2640
tgacagcacc ccagaggtgt cccataacca ttagcccgtc ttacacactc taatcccata    2700
gcgtaagtct gggtgggcta accctgaatg attacagacc ttgacttccc ttcagaattt    2760
ttagggagtt tgtcacaatc tggctgtgtc tgtcggagta gtgaggatca gtcacttggt    2820
tcataagggc tgcaatggag aaaagatcaa cacccatct tcctagaatg ctttatattt     2880
tagaacatta aaataatagt tctagtgcta tatgatatca tacgaagcct agctttaaac    2940
aaataagatg gccaggcgcg gtggctcaca tctgtaatcc cagcactttg ggatgccaaa    3000
gtgggtggat cacctgaggt caggagttca agaccagcct ggtcaacatg gcaaaatccc    3060
atctatatta aaaatacaaa aaattagcc gggcatgatg tgggtgcct gtacttggga     3120 ggctgaggca ggagaatcac ttgaacccaa gaggcagagg ttgcagtgag ccaagaccgc    3180
accattgcac tccagcctgg gcaacgagag cgaaactcta tctgaagaaa taatagaaga    3240
gaagagaaga ataaaataaa aagtaaaata aatagttct gatggtacat gataccatac     3300
taaacctagc tttaaacaaa taagatgacc aggcacattg gttgacacct gtaatctcag    3360
cactttgggt ggccaaggca ggcgggtcac ttgagcccag cagttcgaga ccagcctggg    3420 cactctaggag agaccctgtc tctaaaaaca aaacaaaaaa ccaaaaattt gccaggtgtg    3480
gtggcatggg cctgtagtcg cagctactca ggctgaggca ggaggatcac tggaacttgg    3540
aaggttgagg cggcagtgag ctgtgatcat gtcatccaca ctccagcctg gatggcagag    3600
taagacccca tctcaaaaaa acaaaatgac agaaacatg atttctgttt ctattttaaa     3660
gggtaaaata gtatatttta acactttgaa atgaagagtc tgggcttggg aacgttacaa    3720
tgatgtttac tcgtactagt tacgcactcc cctcccagat ctgtctcgta acaagagact    3780
```

-continued

```
gttattttct acttgttttt agccaaaagg ccgagaaacg atggttattt taaatcccta    3840
gtgtctctta cagttgatgt cttcttagta tttaggaatt tccaggacat ctttttgttg    3900
ttgttaatgc actgtgtgtg tgtgtgtgta tgtgtgtgtg tgattatagg             3960
agtgacccac tacgcccggc tgtgtgtgtg tgtgtgtgtg tgtgtgtggg tgtgtgtgta    4020
tgtgtgtgtg tgtgattata ggagtgaccc actacgcccg gcctatgtgt atgtatttta    4080
aaggcttcaa tgagaaaaaa gttggttctt aaaaaggcaa gcttcagatt ccagggaaga    4140
ttgcctctgg agagctctgt tttaatccat gggtttgcca gattaatgag gatttactgg    4200
cctcgtgcct tcggccctcc ctaccctgcg cccattgtgc atgttttgaa aaagcagtgc    4260
caggaaggac tctctctgga attactgcgg agttacttga gttagcaaag aatcccttc     4320
ctcccccaag agctgtaagc caagtctctg tagagctgac tccatgcctg tttgtctgcc    4380
tgtgtgtctt ggcgcaggtg gctggccgtg cggctggagt gtgtgggcaa ctgcatcgtt    4440
ctgtttgctg ccctgtttgc ggtgatctcc aggcacagcc tcagtgctgg cttggtgggc    4500
ctctcagtgt cttactcatt gcaggtaaga ggggatgctc ttggctggat tattaaagtc    4560
tgttaatggg ggagccagtt gtccttggct ttggattcca gctccaacag gaatggggga    4620
gaggaacttg agaggtacgg agtttgagga gcaggtacag tgccacagtg cctggtgacc    4680
aactagagca ggagacggat ttgacatgtg gccaggattt tccccatcag tcacacagat    4740
tccttagtgg cccaagagga tacttccagg tacgagggga atgcttttaa agctatgaat    4800
ttccctctaa gaactgcttt agctgcatct cacaaatgat gatacattgt gttttcatat    4860
tgtcacctgg ctaaaaatat tttccagttt cttattatgt ggcccatgag ttattttgga    4920
aatgtgtgtg cttaggagat ggcaatgtgg caggcctggg tgatggctat acctggggtt    4980
gctaatttcg gtacctttct tacctgaatg tttcataact cataaccttt tatttttatt    5040
tatttatttt ttttggagac ggaatctcac tctgtcaccc aggctggaat gcagtggtgg    5100
gatctcggct cactgcaacc tctgcctcct gggttcaagt gattcttctg cctcagcctc    5160
ccaaatagct gggtttacag gtgtgcgtca ccatgcctgg ctaattttta tattttagt     5220
agtgactgat ggggtttcgc cacatcggcc aggctggtct caaacccctg acctcaggtg    5280
atctgaccgc ctcagcctcc cataattcat acttgttgaa aataaatttgt ttcctattat    5340
ctcagtggaa aaaaaaaaaa aaagaaaaag gaaagtcaag tacgcccgct tactctagaa    5400
atgccacgtg actcttccac tcacaggtca ccacgtactt gaactggctg gttcggatgt    5460
catctgaaat ggaaaccaac atcgtggccg tggagaggct caaggagtat tcagagactg    5520
agaaggaggt aggcaagggc ccctggctgg acctcttggt cttttggtgta gctttacccc    5580
aaggagatct ctggacccta tcctgtgcac ctctgcctct gagctggata cctcaccagg    5640
tagaagtgca tcttaacgct tgtccagtct ttttgcagca cttatttaga gcccggtttt    5700
agggtgaaaa tagtttaccg gctttaccca agatctgggg tatccatata cgagactgtg    5760
ggatgctgtc agggcattca gaaggtattc acattgtgaa gaagtttccc cctctatttc    5820
tctttcataa cttctgatgg tatcacagag aaagtcttag tctgggcta gcaggtcttt     5880
aacaccttag caattgagat gatctcccctt caacagacag ataaacagca gcccctcacac    5940
ttggagtctt caacaggacg gcttctgtct atcagaaata accttctgtt atttgttatg    6000
aatttggttt tttgtgtgt gtgatggagt ctcactgtca cccaggctgg agtgcagtgg    6060
cacaatctcg gctcactgca acctcctcct cccaggttca gtaattctc ctgcctcagc    6120
```

```
ctcccaaata gttgggatta caggtgcctg tcatcatgcc tggctaattt ttgtattttt    6180
agtagagatg ggggtttcac taagttggcc agtctggtct caaactcttg acctcaggtg    6240
atccgcctgc ctcagcctcc caaagtgctg ggattacagg cgtgagccac tgcgcctggc    6300
ctgttatgta tttgtatagg ggactcctgt tacggaaaat aatactactt ttccttttgt    6360
gattgtaata aattttcctc ttaagtaagt tgagaaatta agtctaagtg acttgattaa    6420
gcatattaaa acaacaagag aatgagtaca tgcatactac acgaatgatg tagctgggaa    6480
ctgaccaaag tttgggaaac cctgcagtta ttgaacccca gtccccttt tatagatgga    6540
gaaaaggga acctggggag ggacaacagc tgatccaagg tcccacgtgg cttggtagaa    6600
cagctgggac taggacctgt gcctccagtc tttgatgttg cgttgcccct aataactgcc    6660
ttcttaggcc ctgaacagca gcacaagtag gaacagcagt gataatagat aatcacaata    6720
atgcctggcg acacccccac cctacattaa tgataacagg gacacacata gtgccttgta    6780
gaatgtcagg cccagactta aacgtttaat atagagtaat gcactcagtc tttaccccgc    6840
tctatgactg attttgaga cacggtctca ctcttgcccg ggttggagtg tagtgcgatc    6900
tcattcgctg cctcccaggc tcaagtgatt ctcctacctc tgcctcctga gtgtctggga    6960
ccacgggcat atgccatcac accggactga ttttgtatt tttagtagag acgggatttt    7020
gcccagactc atcttgatct cctgagctct agtgatctgc ctgccttggc ctcccaaagt    7080
gctgggatta caagcgggag ccaccatgcc cagcccagcc ctataattta gatgctacta    7140
ttaccccat tttacaggtg aggaaactga gacaaaagc tgaagttact tgcccaagat    7200
cacatggctg gtaaatggca gacctaggcg ttgagcctgt gcctcctcag agaccctatc    7260
cagtgccatg ggagtcatgc tacccggcct cctgaggaga gatgcccctt gggagtgaga    7320
ccaaggcctc tgtaaggtct gtcctcctga ggaattcaca gaggtgacct cggcccactc    7380
cttaacatt ctgactgggt gaaccaggtc ccatgtcacg ggtgagcatt gtaagaatgg    7440
cgtgagtgcc cccgtgagga accaagggtg tattacaccg gcggcttcca acttgacact    7500
gaatttaatt cacttacaag gtatttcatt aggttttttt ttttttttt ttttagatg    7560
gaatttggct ttttttttgc ccaggctgga atgcagtggc acgatctcag ctcactgcaa    7620
cctccacctc ctgggttcaa gtgattctcc tgcctcagcc tcccaattag ctgggattac    7680
aagtacccac caccccgccc agctaactta tttcattagt ttttataata gcctcattga    7740
catgtgaatt tcacatgcca tggaattcac ccagttaaag cgttcagtta gattgaattc    7800
agtttttttt tgtttgtttg agacttaagt ctcgctccag cctggagtgc agtggcatga    7860
tctcagctca ctgcaacctc cttctcctgg gttcaagcga ttcccagcct cctgagtagc    7920
tgggattaca ggcgattttt gtattttag tagagaaggg atttcaccat gttggccgg    7980
ctggtctcga actcctgacc tcgtgatcca cccgcctcag cctcccaaag tgctgggatc    8040
acaggtgtga gccaccacac ccggcctgag ttcagttttt aaaagcattt tactttgac   8100
tgacttttat attttagaa ggatcgtgtt tgacaaaccc aagagaaagt aattgtcctc    8160
attagtccta ccactattct gtatttgcat gtatttttat atatagatag aaagttccac    8220
atacttctct ccattccgct cactgtgttg ttatagcatc tcccttcaa ttatgtacat    8280
aaattataaa atagagatac acttgttgtt ttaaaaaga aaaatcaat acagggctgg    8340
acacagtggc ccacgcctgc aatcccagca ctttgagagg ccaaggtggg tggatcactt    8400
gaagccagga gttcgagacc agcctggcca acggtgaatc ccgtctctac taaaaataca    8460
aaaattagtt ggcatggtgg caggtgccta taattccagc tacttgggag gctgaggtgg    8520
```

-continued

```
gaggatcgct ggaacccggg aggtggaggt tgcagtgagc tgaagaaaca tcactgcact    8580
ccagcctggg tgacagagtg agactctgtc tcgaaaaaca aaaaacaaa gaagtttatg     8640 gtggagaaag acagtttgtt cctgttcgcc ccgttcctct cctctccaga gagaggcccc    8700
attagcattc gggtgaattt cccccaaaac tttcccgtgt ggattcccac ataccccaac    8760
acttttgttt gcttgtttct ttttctttta acgtaagtgg aatctacctg ttatcctgtg    8820
aaaccttttc tttaaccatg aggcaccttt gcatctgtgt atagtaacag tcactgcctc    8880
taagggctgc tgtgaggctc agatgagatc atgggtctca agtgctgagc agagcaactt    8940
gccttagttg cattgtaagc gctcaataat aacatttatt ttttggccag gcgcggtggc    9000
tcacgcctgt aatcccagca ctttgggagg ccaaggcaga tggatcactt gagcccagga    9060
gtttgagacg atcctgggca acatggtgag acatcgtctc tacaaaacaa aaataatac     9120 ttttttgttgt tggcggtggt ggtgggttt ttttttgttt ttttttttttt gagacagagg   9180 agtcttgctg tgtcacccag actggagtgt agtggtttta tcttggctca ctgcaacctc    9240
tgcctcccag attctagtga tcgtcgtgtc tcaacctccc aagtagctga gattacaggc    9300
tcccaccatc aggcccagct aattttttgta ttttttagtag agccagggtt tcaccatgtt   9360
ggtcaggctg gtctcaaact cctgacctca agtgttctgc ccacctcggc ctccctaagt    9420
gctgggatta caggtgtgag ccactgcgcc ggcaacgctg tgattttata gcacgtccac    9480
aaaagggctg catgtcttgc ctaaaagttg cccggcgttt tcttgttatg tgccgtctgc    9540
agtgcccctg agcttggcca tgtgctctgc agcctggttc agcacctgtg tgtgccctgg    9600
acggggaggt gcattcccg aggctaaaac cagtgaacct ggcccaggcc atatccagct     9660
gtgggcctca ggaaatgctg aactgaacta cttttcaaaa ggagggttgt gtgtccctgg    9720
gcaagttacc gcccctctct gtgtctcagt ctccttgtgt gtaaactggg gataatgaaa    9780
ggaccctccc acatggggtt gctgtgagga ttggatgaga cactgcgata cagatgctgc    9840
ttttatcctt gccttcctgc cggggtgggc agccagggta actcactttt attgtcgtgt    9900
ctgtccagag aagaccactc atttcattga ctccatttat aaatatttat ttaaatttttt   9960 ttttatcaaa aagtaagttt tattggcatc taaaaacaaa attcacccaa cactgaaaca   10020
tacttcaata tttatgttat tgttttcttg tttctttttt actcactgca gtgtgaggaa    10080
caaatcacat ttactttgga gaaacagaga ccatagtgta gattttacaa aatcacttt    10140 taaactctct gtattgcgct cctcaaatac ctagagccag tctgtgcata acatggcaca   10200
ctgttgtcta aaccgtaaaa ttttgcatca gcctaaagat atggataaga tatacctcca   10260
cttgctcttt tgaaatacat ctattacctt atccagccta atgatagtta cctaaaaaat    10320
tctttgttcc gtaggaagtc tctgacaagc tgttattcat ttccttgacg ttaaaagaat    10380 ctggggggcaa catttatatt ttatcagaaa aactttttaa aagtttacct atcatgttca  10440
tattgagaac aatgtctgtg gcgggcatgg tggctcacgc ctgtaatccc agcactttgg   10500
gaggtagagg tgggcggatc atgaggtcag gagttagaga ccagcctggc caacatggtg   10560
aaaccacatc tctactaaaa atacaaaaat tagctgggtg tggtggcggg tgtctgtaat    10620
cccagctact caggaggctg aggcaggaga gtcgcttgaa cctgggaggc aggggttgca    10680
gtgagctgag atcatgccat tgcactccag cctgggcgac agagtgagac tccgtctcaa    10740
aaaaaaaaga acaatgtcta tacaaatcag ttgtacaatt attttaaaag aatggtgagc   10800
atgaacgtca cgttaattct ggcagacaaa aatgaacaac tatggtccat tgagccatta    10860
```

-continued

```
tctgttacac agagatgaca gctttacaga aggtatctct gacctactga gggatgatca  10920
tgtcctctca gtttctgtgc cttctaccac tagttcactt tctatatcag cagctgtgtc  10980
actcttcttg tttatgttca taaatgtgtg ttgaacacct actatgtgct ctgagccctg  11040
ggatacagca gtgaacaatt agagcctgtc ctcattgagt ggatggtgca gtgggtgtgg  11100
gagacagaat acactcaagc atgcgagccc aagagggct ggggacaggc agtgccctga   11160
aggagaaggc agtgcgggag gggacagagg gacacagggc tgagagggtg ctctgtatcg  11220
accagagatc cacaggatgc aagggggtca tttgggaat  aacattccag gaagggcaac   11280
cccccagtgc tgaggcctgg gaggccacct tgggcagcag agtgagtgag aggggaggtc  11340
aggggagtca cagctttacc agatggactg gaaattcctt actctctccc ttcactgcga  11400
tcgaaggcgc cctggcaaat ccaggagaca gctccgccca gcagctggcc ccaggtgggc  11460
cgagtggaat tccggaacta ctgcctgcgc taccgagagg acctggactt cgttctcagg  11520
cacatcaatg tcacgatcaa tggggagaa  aaggtgggta cacatcgccc cattccctca   11580
cccattccca gtcgggcaca gggtgccatc gggcaggtga acctagctgc agcgtctccc  11640
cagtcactca cggctccaca cctttgcttg aatggctttt tgggggctg  ggagtggact   11700
gtggcagtaa aagctgttca gagcgcatac aacttgcaga agtgaaggct tttaggtgaa  11760
ctgacagcct gaagaccaaa tgagccccac agatttgttt tggaagattt tttgttgttg  11820
ttgttgagag agggtcttgc tctgttaccc aggctagagt gcagtggtgt gatctcagcc  11880
cactgcagcg gcagcctccc aagtggggg  actacacatg gttgggagtg caggtgtgtg   11940
ccactgcacc tggccatttt ttgtatttt  tgtagagatg ggggtcctac tatgttgtcc    12000
aggctgatct ggaactcttg agctcaaccg gtctgcccgc tcagcttcc  caaagtgctg    12060
ggattacagg aatcagccac cattcctggc ccctggaaga agttctttt  ttgttttttg    12120
gttggttgtt tttttttttt ttttttttt  tttttgaga  tggagtctta ctctgttgcc     12180
aaggccagag tgcaggggcc cgatctcagc tcactgcaac ttctgcctcc tgggttcaag  12240
tgattctcct gccttagcct cccgagtagc tgggactaca gcatgcgcc  accatgccta    12300
gctaattttt gtgttattag tagagatggg gttttgccat gttggccagg gtggtcttga  12360
actcctgacc tcaactgatc cacccgcctc agcctcccca agtgctggga ttacaggtgt  12420
gagccactgc acctggcctg gaagaaattt gaataagttg caaatactga aaaatctgga  12480
agacttaata taaaaattta ttttctgctt ttttttggaag atcagaacat ctggcaacat  12540
caggtcaatc ctcccccgcc tggctctttc tagtcaacct gtgagcctcc tggttcaccc  12600
cagtccctcc ctgtcccatt cattgcctag ttggcccctc caaaacatta gaatttgtga  12660
tctctagaat aaggtgtcac catcccttct aggggatgg  ctcaagggaa gtgagaaatt   12720
gtcagaattt tggaaccttc tcttggttcc gagctgttct tggaagaggt tccttgacct  12780
gagtgatacc cttagacttt cctctggaat tggtctgaca gtcttcctgg ccatttgctg  12840
ggggacaagg ctgctttcac ctctgaacat atggacttat tgaactgttc ctacgtacct  12900
cccacaaagc tcagaacatt ctgttcccag cagataattt ctctctgagt tacagagaag  12960
agcagagtgg gtgatgttct tgctgtcttt ttttgttttt gttttgttt  ttgtttttgt     13020
ttttgttttg ttttgttttg tttttgagaca gcctctcact ctgtcaccca ggctggagtc  13080
cagtggtgct atttcggctc actgcaacct ccgtcccctg ggttcaagtg attctcctgc  13140
ctccgtctcc cgagtatctg ggactacagg tgcatgccac cacgcccagc taattttgt   13200
agttttagta gagatggggt tttaccatgt tggccaggct ggtctcgaac tcctgacctt  13260
```

-continued

```
ctctgatcca ccttcctcgg cctcccaaag tgctggaact acaggcatga gccaccgtgc    13320
cccagccctt gttgagtctt tatggcttat ctcacgtcat gagaatttt gcacgcatgc    13380 tgctctgtga caccctgta ggagggaaga aggagcccac ttctcaagag ccaggcagga    13440
aggggagaac tggaggtcag gaacatcatc ctttggccat tagctagaga acctagttcc    13500
ttcaagagag gatgcatgga gaccaggtca tagcaaaggg ccggaagatc tgcctgaatc    13560
tttcagatat ttcaacaact catgatggga aactcaccat caaaggtgtg aaaaacagtg    13620
gggaaatgag gaaatgcctg attattactt aatagtttct tgagtctaaa caaatagggc    13680
tttgttggaa attccttctg cctcttctgt atctcttttg aggtctctag taacttataa    13740
aaagccgagt cattcctttt gggagcctgg caaagggaag agagtccttc ttgaccttcg    13800
gccgaaacac ccttaaagga gtgtctctgg gcagcgcgca agggagaggg ctgtcgagtt    13860
gggttgacca gatgactgat gcctgaggtg gggccgagat gagggcactt tggggcaggg    13920
acaagtccgg atgccagcat tcccaccaca cctgggccct tctgtcctgc aggtcggcat    13980
cgtggggcgg acgggagctg ggaagtcgtc cctgaccctg gcttatttc ggatcaacga    14040 gtctgccgaa ggagagatca tcatcgatgg catcaacatc gccaagatcg gcctgcacga    14100
cctccgcttc aagatcacca tcatccccca gtgggggtct gggtgtggcc caggggtga    14160 gccagagctg gcaagcccta tgattgcact gacagtggtg tatgtatatt tttggggcaa    14220
acatacattt ggccctactt catcgttctt tttttttttt tttttttttt tcctgaaaca    14280
gggtctcgct ctgttgccca gagtggagtg cgctggcgca atctcagctc actgcaacct    14340
ccgtctccca ggctcaagcg attctcccac cccagcctcc tgagtagctg ggactacagg    14400
cacatgccac cacacccagc taaatttgtt ttgtactttt ttgtggagat ggggttccac    14460
tgtgttgccc aggctgccct tgaactcctg ggctcaagca atccaccac cttggcctcc    14520 aaaagtgctg ggattacagg catgaggcac cgtggctggc cttcattgtt tttattgaag    14580
ttaggctgtg ctgctgcttc cctgaatttc ctcttagtat atgattaaca acgtgggaat    14640
taactgacta tcagtcccga cttcctgtcc ccggggagggg tagtttcaga gcatctagaa    14700
aaatccaaaa agacaccgtc ttctctctct gctgccagag tcagactgag catctctaac    14760
ccttccaaga gctagacaag aaataagact ttttaatttt cgattcacgg ggtgcacctg    14820
caggcttgtt acgtgggtat attgtgtgat gctgatgctt cggcttctat ggatctcatc    14880
acccaactat tgaacagagt acccgagaga gagtagtttc tcaaccatta ccctcctcca    14940
tctgtcccca cttatggagg ctccagtgtt tatcatttcc atctttacaa ccatgagtac    15000
gcagagttta gctccctctt acaagtgaga acacacagta tttggtgaga ataaggatt    15060 ttcttttct ttctctttc ttttttttct tttttaact gagacggagt ctcactctgt    15120
cacccagtgc agtggcacga tctcagctta ctgcaacctg cacctcctgg gttcaagcga    15180
ttcttctgcc tcagcttccc aagtagctgg gattataggc acgcaccacc atgcgtggct    15240
agtttttgta ttttttagtag aaacgggggtt tcaccatgtt acccaggctg gtctcaaact    15300
cctgacctcg agtgatctgc ctgcctcggc ctcccatagt gctgggatta cagggtgag    15360 ccaacatgct tggctgaaat aaggatttc tagaccaatc cccgcaggtg gattccttaa    15420
tatgttgcct tttagtgtaa tcttccctaa agtgtcttag aagattctct tctgtggttg    15480
gatgacggga gaatccacgg gactttactg ttaggaatca cctgtgctgc gtctcatttc    15540
tggaggttct caacccactt gcatattgaa ggctccagga agttgtatgg aaaggaaatc    15600
```

```
tgttgtattc tgccaaactc agactttcca gactttttttt tttttttccat tattaaggca   15660
atttttttttt tggagataga gtcttgctct ggagtgcagt ggcacaatct tggctcactg   15720
caacttccgt ctcccgggtt caagtgattc tcctgcctca gtctcctgag tagctgggac   15780
tacaggtatg caccaccatg cccagctaat ttttgtattt ttactagaga cagggtgttg   15840
ccatgttggc caggctggtc tcgaactcct gaccttaagt gatccactcg cctcggcctg   15900
ccaaagtgct gggattacag gcgtgaacca ccgtacctgg cctttttctc cattattaac   15960
atctccagaa atagtgattc caaggagctc tgatacccca ccttcaacag tcctggccag   16020
aagtccttag gtcgcctcca tccatgtcag catgacacag tgtcacatg ccgtccactc    16080
tcttctctct gaacaggacc ctgttttgtt ttcgggttcc ctccgaatga acctggaccc   16140
attcagccag tactcggatg aagaagtctg gacgtccctg gagctggccc acctgaagga   16200
cttcgtgtca gcccttcctg acaagctaga ccatgaatgt gcagaaggcg gggagaacct   16260
caggtaggcg ggggtgaaca aggagacacc gggtaaggtg tcctaggcgc catctcggta   16320
ggggtgtttg aagattctgt ccagatctgt gtcacctgga tttgagtccc agatgaccat   16380
ttgtcccttc acctcttgga gcctcagttt ctgtatctgt aaaacgggtc tcaatccagg   16440
ctctttgtac catgaggtag aataaccagg atgaccagta catttccttt tatacacacc   16500
agctccattc agttgatagt ggctgtcagt tgttaagcta tggaaagtct tctgtaccag   16560
ttggtcacta gcactgctct gagcccccag gtccccatgc actaccccag ctgtcttggt   16620
ctctaccagg atcctggagc tctgtccatg acccagcaac taaagcatta atgcctggca   16680
caccagcgga acctctgggg tcctgctttg gtggtgttg ttagtgcctg gttctggttc    16740
tgttatccgt ctccatgaca accaaccata aagcctcagg catgttcaac cataaagcaa   16800
cgatcattgc tgccatacga gggcagtcag ccaggtggct ctgctgatct cggctgggct   16860
cacatgcatg tctgggagtc agctggctgt tggctgatct cggggtcagc tggcttttgg   16920
cctcaggtgg ggcaagaagg gtatgttccg tgcatccctc attctccagc agaccagctt   16980
gggcatgttg tcatggcgat ggcaggggca caagagcgtg caagccccta ttgcatctaa   17040
cagtattctt ttggctgtcc ttacttttgc tggtgtccca ttggccaaag caaggaacat   17100
gtctgattcc agagccacct ctcatggccc cacagttgga taaggatgc atgggtatga    17160
ggcctttttt ttttttttttt tttttttttt tgagacggag ggtctcactc tatcacccag   17220
gctggagtgc agtggcgcaa tctcatctgc aacctccgcc cccaggctca agcaattgtt   17280
ctgcctctgc ctcctaagta gctgggatga caggtgcctg tcaccatgcc cagttaaatt   17340
ttgcatttttt agtagagatg gggtatcacc acattgtcca ggctagtctc aaactcctgg   17400
cctcaagcga tccacccgcc ttagcctcac aaggtgctgg gatactaggt gtgagccact   17460
gtgcccggct cttatttttt ttttattttta ttttttttaa gagacagtgt ctcactctgt   17520
tgcctaggct ggagtacagt ggattgatct cggactctta actcctggac tcaagcaatc   17580
ctgcctcagc ctcccagtaa ctgggactac aagagcatgc accacaccc agctaatttg    17640
tttatttttg ttttttggaga gatgggggtc ttgctttttt gcccaggctg gtctcaaatt   17700
cctggcttca agctatcctc ccacctcagc ctcccaaagt gctcagattg taggtgtgag   17760
ctgctgtttt gagaatgatt ctgaacctgc atccttgctga ataggagatg tgctctgatt   17820
gattagtgat gtctgctgca gacacagatg ttgggagtgg acatgctttc ctggtcaagc   17880
aacatagagt gtccctttc gcttctccca gcctgggcct aggttcaggg tcaggggtgg   17940
tttgacccaa cactatctcc tggtttttttt cttccggtca agtgtcgggc agcgccagct   18000
```

```
tgtgtgccta gcccgggccc tgctgaggaa gacgaagatc cttgtgttgg atgaggccac    18060
ggcagccgtg gacctggaaa cggacgacct catccagtcc accatccgga cacagttcga    18120
ggactgcacc gtcctcacca tcgcccaccg gctcaacacc atcatggact acacaaggtg    18180
atgccactgg cacagtggcc tctaggcttt gggagtttgc cttactcact ggctcactca    18240
ttaattcatt aattcattca acactgtcct tatccctagt gacagcccca gtgggtggat    18300
cctctcttca tcctggatgg taccagctat ttcttttttt tttttttttt ttgagacaga    18360
gtctcgcttc atctctggag tgcagtggtg tgatctcggc tcactgcaac ctctgcctct    18420
ggggttcaag catttctcct gcctcagact cccgaatagc tggaactaca ggaatgtgcc    18480
accacgccca tctaactttt atatttttag tagtgacagg ttttgccat gttggccagg     18540 ctggtctcga actcctgacc tcaggcgatc tgcccgcctc cgcctcccaa attgctggga    18600
ttacaggcat gaaccgctgt gcccagtggt accaggtatt tctaatatca tctagtcatt    18660
cattcacgtc agcgcacctg cggtgttccc agacactggg gactctgtag gctgctgtca    18720
gacaaagtcc ctgcctccag gaccaagtag cttattagat ggaggagaca aaaatatac    18780 agagcaataa accaacagga ttccagaggg cagcaggtgc tgggaaggac gcttgccaag    18840
gagacgggat agcgagtgct gggcagggcc actgtttcca ttgaacactg caggcccagt    18900
gcgtggggcc cacaaaaagg ttttattttt tttaaaaaat cagaagcagg ccaggtgcgg    18960
tggctcacgg ctgtaatccc agcactttgg gaggccgagg caggcagatc acctgaggtc    19020
gatagtttga ccagcttg gccaacacgg tgagaccctg tcaccattaa aaatacaaaa     19080
agtagccaag tgtggtggtg cgtgcccata atcccaggta cttgggaggc tgaggaagga    19140
gaattgcttg aacctgggag gtggaggttg cagtgagctg agattgtgcc actgcagtcc    19200
agcctgggca acagagtgag actccatctc aaaaaaaaaa aaaaaaaaa aaaaaaaga     19260 atataatcca acctggattt tatttatact aacacagtca taaatagaa tttctagcat     19320 tttgtgtgga gaaagccacc tccgtaggca tcagtgccgg ggaccacaaa agtcagaatg    19380
ctgccatagt gccagggtcc tgggggggttt tgagttttgt gtgggtcatc tctgaagagg    19440
tgacatttta gctgagacct gaacaatgaa aaggagtcag ccttgagaag atctgggaca    19500
gcgatctgca accttgttct taagggccgg ggtagtttca gctttgtggg ccacatggcc    19560
tctcagccac ttgactccag tgttgccgtg tgaaagcagt catagatagt gcacgaatga    19620
atgagcatgg ctatgttcca ataaaacttt attcataaaa acaggcaagg ggtcagattt    19680
ggcctgcagg ccacagtttg ccaaccttgg atctaaagga agaacattct aggcagccgg    19740
tacagccgaa tgtaaaaatg aatgcgctta atgaatttga aggctagcat gaggaggcca    19800
tgtacctaga ggttggaatt gagtggacag gggcaggaga ttaggccaga aaggtaggca    19860
ggggctggat cttagagcac catgtaacca cggtgagaag cttggaactt actctaagag    19920
ccctataaag ccattggaag gttttaagca gggaagtgac atgagtttct attttatttt    19980 atatatttt gagacagggt ctcaccctgt cgcccaggct ggagtgcagt ggtgggatca     20040
cagctcactg cggcctcaag tgatcctcct gcctcagcct ccaaagtgc tgggattata     20100 ggcgtgagtc tctgcaccca gctgacatga tgtttctagt tcactgagta ccacctacta    20160
agtggcagat gctgagttgg tgcttttgaa atataggaca tagaaatgag gacagaagtg    20220
ggcagtgtca aatcttacag gacctaaaat attaggggtc agccaactat ggcccacagg    20280
ccacagatct ggcccctgc gtgttttat gaataaagtt ttattggcac gcagccacat      20340
```

```
ctgttcattt tcctgttgtc tctggcagct ttcacactat aaatacagca gagatgcgta   20400
gttgtaacag aaagcatatg gcctgcagag cctcaagtat ttactatctg gccttttca    20460 gaaaaatgtt gccaatcgtt attgtagact gtggtaagat cttttttattt tactctgaat  20520 gtaatggaac agtgaatgtg aacagtcaac actgttaata ccattcacac catgattgat   20580
gtggggtaga tattaaggag ctggcctcat gggaatctga cattgactag aaatagggat   20640
tgagggtgag caaccagctg gaaggtactg caccagtcct agcaaaaagt gttaggggcc   20700
tgacccgaag cagtgacttg cccaggtcag ttgtcccagg ggcacgaggt gctcacccct   20760
cccctttccc tcatgtctgt atcccctctc cctcaggtg atcgtcttgg acaaaggaga    20820
aatccaggag tacggcgccc catcggacct cctgcagcag agaggtcttt tctacagcat   20880
ggccaaagac gccggcttgg tgtgagcccc agagctggca tatctggtca gaactgcagg   20940
gcctatatgc cagcgcccag ggaggagtca gtaccctgg taaaccaagc ctcccacact    21000
gaaaccaaaa cataaaaacc aaacccagac aaccaaaaca tattcaaagc agcagccacc   21060
gccatccggt ccctgcctg gaactggctg tgaagaccca ggagagacag agatgcgaac    21120
cacccaaaac acgcacaccc tgcccctggt gccctgagac agacacacag cctcacgccc   21180
ccaggaatgc aagtggtttc ctggtgcttc ccacggagga gttttggcag ccagacttct   21240
ggaggaattg gttgtataga agatcctagt gaccaaattc agcctactgc ctcggatctc   21300
tccagccgaa gtctgtggac tgcaagtctt tgagatgctt ctggctccca tcacctctaa   21360
catccttgtc tgggtctacc aggaacgctt catttccttg gggctgcagt tttgtggttg   21420
aggggcctgg agaaaatcat tttctcccct tggcagtgtc ccagggccct ggatggtcct   21480
cttaccaaca tctggtcttc caggcactca aaagctggga accagcatct cagcgccagc   21540
tctaccagtt ctcgttttgg gccagaggca gcctctgcac tcccacgcct gtcctcctgg   21600
aagggacctg gttggactaa cggctaacct ggacctggaa ctgtagggcc aggggattgt   21660
ctcagggccg acgttccacc tggggcttcc ctccccaccc accccgactc caggctttcc   21720
cttttttctt ttgttcaaca ttgtaagaac aatcaatgct gttattactg atcccaccat   21780
gattgatgtg gggtaaatat taaggagatg gcctcatggg aatttgacct tgactagaaa   21840
tagagactga gagtgagcaa ccagctggaa ggtactatgc cagtcctagc agaaaaatgt   21900 gttagggggcc tggcccaaag cagtgttggt tgcttacagt gttgattgat tttgttcttt   21960
tttcttacca cctcttttct ttccctctca tggtacctgc tcatggttat gaagctttca   22020
aagtaaagaa cacgaaatac ctcccaagta ttaccagtgg gtaccaaaaa aatgtcccct   22080
tgagtctttt ccttgttttt agatgttaat tctctccctt ggcatccggt tagccccca    22140 gggggggcag cattgtggag aacttgatat ttagttactg atgctcttcc aggacacgaa   22200
aagaacccat ctttgaatat caatgatttt tttttttta agtactgttc cggggagaaa    22260
aacagtctca aaacttgaac ttcttgggaa gagaagtgtt gggctgagaa gtaacattcc   22320
caggaaatag tgagaagctc gccctgtgtt tgaaccgtg ttggtctctg tgttcctgga    22380
agaaaacagg gaagcagcat cttttaaagc ctgttcttta aggtgtctcg ttagagccca   22440
aagtggaatc cggaaggcag ccagagctga ggctgcccca agactcagac ttgctaagaa   22500
ttacgccgcc gacttcaaac ccagagagca tctttctttt aggcgaaaac gcatatattt   22560 atttttgta agttataccca ttctttcaca ttagataaac taagttttgg gggatccttt    22620
tgtaatgact tacactggaa atgcgaacat ttgcagtaaa aaatatata tatatctata    22680 tatttattt cttttctaaag aatggttccc tttcctttgg ggcctcggcg agggttccag   22740
```

-continued

```
ccatgtcctc tgcagggtca ggatgtggca tcttcctgtt tctgttcttt ccttttgaca    22800
acaagtcgcc tctagtggga gctgttgcca gaaagggcaa gttgtagaga tcactagtca    22860
gatggggttt agtgggaagg cgggacagcc gcaaggtgga cggagcccag gttttggggt    22920
tggacagacc ctggcttgag tcctgctctt gtcatttgct gttcttgtga ccctggggaa    22980
gtcactcagc ctctgtgcct cacttgcttt gtctgtaaaa tgaggctgat cgtacttacc    23040
ctgtgagcag tgatgtgtgc ggtactcgta gcctcggtca ggttctaaga cacaggcgag    23100
gcagaaatca catgtggcca gaacgatcct tgaaaatcct gccctcgccc tgccttttt    23160
tttttttttt tttttttttt ttttttttgc tagaggcacg tctcactct gttgcccagg    23220
ctggtgtgca gtggcacgat catagctcac tgcagcctca aactcctggg cttacgcaat    23280
cttcctgcct cagcctcctg ggtagctggg actacaggca tgtgcccagc taatttttaa    23340
aaattttat agagtcaggg tcttgctatg ttacccaggt tgttcttaaa ctcctgggct    23400
ctggggatcc tcctgcctga gcctcccaaa gtgctgggt tcaggcacct ggcctgaaaa    23460
tcccttatg ttagtccaga gaggcgaggc tgcgctgcag taacaaattc gccgtaaaat    23520
cttcggaaat gatcacaagg ctttatttct tgctcacgca gttcttggtg agggtcagct    23580
gcctctccag ggtaggtgac ttccctgtga caagtgatcc aggctgtcct ggttttgtga    23640
catggcctcc caagggttgg cctccaggtc cccacagtgg gagaagggag agtggacgac    23700
tctcacccac tcttctgtgt ctgaaaccgg aactgacgca gttaatccca ctcacagccc    23760
attggccaaa atgagtcaca tggccccaac ccaaccactg cgggagctgg gaaatggagc    23820
ggtgcctgtg gaagagaagg atttctccct ttcctaactg atgtggttct ggagttttgg    23880
atagcggagt agtcagacta gtgtgttcgg tttctaactt cgaactgggt gagtctgggc    23940
agtaaggaat gtctgtattt ggggagcaca ccatttctgc cacacctaaa accatgcacc    24000
aagtacatgt gcagatagaa cgttctagca ctgccattgt tccctcaagc tttcctgtcc    24060
cctgattgaa attgttggct tgcactaggg actgtggtgt acaaggtgc tcaggaaga    24120
gccggcgagg tggtgaccat tagaatgagt agtagtgtct gggtgcagtg actcatgccc    24180
cattgaaact gttggcttgc attagggact gcagagtgtg aaggtgccta gtgaaaagcc    24240
agtaaggtca taaccattag aataggtagt atcagccagc cgggcatggt ggctcatgcc    24300
tgaatgatgt cattggcttg cattaggaac cacagagtat gaaggtgccc agtgaaaaac    24360
tggtgacgtt gtgactatta gaattagcag tattggctag acgaggtggc tcatgcctgt    24420
aatcccagca ctttgagagg ctgagacagg aggactgctt gagctgaaga gttcaaaacc    24480
agcctaggca acatagtgga actctttcta tataaaaact ttttttttgt taaattagaa    24540
gtagttgagg ctgggtgcag tggctgacgc ctgtaatccc aggactttgg gaggctgagg    24600
cgggtggatt gcctgaggtc aggagttcaa gaccagcctg atcaacatgg tgaaccccg    24660
tctctactaa aaacacaaaa attagttggg catggtggca catgcctgta gtcccagcta    24720
ctggggaggc tgacaagaga attgcttgaa tgtgggagat aaaggttgca gtgggctgaa    24780
atcaagtcat tgcactccag cctgggcaac agagcaagcc gagactccat ttcaaaagag    24840
tagtagttgg atctaccagc gggaatctta atagggatgt gagatgtgtt tagatctcaa    24900
agcctgaccc tgagtcttaa aatcccaggt cagatcctaa gcagtcccag agagctccac    24960
ctggtgtgca tctgtgccag tgtcttgggg tggggcagct gcatgctcag gtggaatccg    25020
gggctgagtt caagtttaat ccactttatg aagaggaggc agagtgaggc ataactcctc    25080
```

| | |
|---|---|
| atccagggga gtggaagtac tgtggaagga agctctgttt tgtacctact acgtgctggc | 25140 |
| cctggcctca ctgtgcagaa ctctccacat tggaaaggat ccccccagac cagagaggcg | 25200 |
| taaggagggg gctggtgctt tccagtgttg aactgttcat ctgtcctcac acccaccatc | 25260 |
| gggtcctaca gcaaatttgt tgattttct gcaaaacacc cagaatctat ccactccccg | 25320 |
| tcctcccatt gccaccacgc tggtcccagc caccccactt tctccctgca tccctacaac | 25380 |
| agctgccaca gtggtctcga ggcttttgcc cccagccccc cacacacaca tcagtgtcct | 25440 |
| caacctggtg gctgtagtga ccttatgaaa acacgcactg gccgggcacg gtggctcacg | 25500 |
| cctgtcatcc cagcactttg ggaggccgag gcaggcagat cacctgaggt caggagttcg | 25560 |
| agaccagcct ggccaacatg gtgaaatcct gtctctacta aaaatacaaa aattagccag | 25620 |
| gtgtggtggc gagtgcctgt aattccagct acttgggaga ctgaggcata agaattgctt | 25680 |
| gaactgggag gtggaggttg cagtgagcca agatcacgcc actgcacttc agcctgggtg | 25740 |
| acagagtgag tgactgatgg tgaggacacg ggctctgaag ccacactgct tgggcagaga | 25800 |
| tgccactcat tctgtttgtt ttctcatctg tcaaagggc ctgatggtag taccttcctc | 25860 |
| atcaaaacgt tccagtaagg ggcccagtga ggtggcttcc tcctctggtc cactgaatgc | 25920 |
| gtgcgtggcg ggcatttaaa gcagtgtcag gtatacgtag ttacgtgttt gcagtggcga | 25980 |
| ggtggactgt tgagttttaa agagtctact gggcgcaggc actgaccaga gaggaagtct | 26040 |
| gcagccttga tggatgaaat tcgtgttcca cccaccagcc agaccctact ggcagcagcc | 26100 |
| catggcgggg gtattaatgg cctgggcatc ccctctggcg cgtctccaga ctgccgtggt | 26160 |
| gtgggcccaa cagcagtctc gttagcaggc tggcaggtgc cggttcccac gtgctggccg | 26220 |
| cctgtggccc accctctgct ccctggcaca cagcctagga aagagagtct ggtggccctg | 26280 |
| ggtcatcccc agctgagttt gccaaatgcc cacatggcag cccctgccta gggtcactct | 26340 |
| gcaaggcagg tggctcagct ccagccagag aagacaggct gcatctgccg cccttccttt | 26400 |
| ctctaaagga caaatgtgcc ctgtgcaatg actttggtat tacacccaga aacagatccc | 26460 |
| cactctgtcc ttactgactg ggtcaacttg gcaagtcatg tcaacccctt gagcctcagt | 26520 |
| ttcctcacct gtgaaatgga gctaggaata ggtagttgtg ggtccacagc tttgcaggca | 26580 |
| tgactagggg caggtcaaga atgcggactt cctgccccac tttgaaggtg gtagaagctg | 26640 |
| cagttagaag tttactccag gccaaagggg gcatcacaaa acctgtgagg atgggccatc | 26700 |
| agaaagtccc atgacctgat gggcggagca ggccctgtgt ccttaagaaa aggtggagtt | 26760 |
| cttgccctgc caccctgac accagcaaag ccactgctca agtatctgtg gatgatggat | 26820 |
| ggcagcgggg caggttagac cggggattct caaccaagtg ggtcttttg ttttgtgttt | 26880 |
| tttcagacag tcttgctctg tcacccagcc tggagtgcag tggtgtgatc ttggctcact | 26940 |
| gcaaccttct ctgcctgggt tcaggcgatt ctcctgcctc agccttcaga gtagctggga | 27000 |
| ttataggcac ctgctaccac acccggctaa tttttgtatg tctggtagag ccaggggttc | 27060 |
| accttgttgt ccaggctggt ctcgaactcc tgacctcaag tgattcacct gcctccgcct | 27120 |
| cccaaagcac tgggattaca ggcatgagcc actgcacccg gcccaactag gtggctttga | 27180 |
| cccccctgggg gattaatggc agtgtcacaa gtctggtggc ggtagaagga ggatgttatt | 27240 |
| ggcatctagt gaagaagagg ccaggggcgc tgctgaacgt cctacgatgt gcaggacatg | 27300 |
| tccccacagc acagaactat ctggccccac gtgtcaataa ggttcagaaa gcctggggga | 27360 |
| ttgccttctg tgcttccacg aacacatatc catgtattat gtcattcttg cggcaatgcc | 27420 |
| acgaggtcag tgagactccc tgactagcat acataatgtt aggatctagg gagttgtcta | 27480 |

```
atgtctcacg ctgcccttcc cagcgatcta tgtgtggcct taggcttggc tactttagac    27540
ttagtccctc ttttccggtg cctgcagctg gtttggtgag tccagtatta atatactgac    27600
cgctgtcaga agaggagtg aggaggctgg gcatgatggt tcacgcctgt aatcccagca     27660
cttttggagg ccgaggtggg cagatcacct gaggtcagga gttcaagacc aacctggcca    27720
acatggtgaa accccgtctc tagtaaaaat acaaaaataa ttagccaggt gtggtggtgg    27780
gtgcctataa tcccagctac ccggcaggct gtagcaggag aatcgcttga acctgggagg    27840
cagaggttgc agtgagccga gatcttgcca ctgcacttta gcctaggtga cagagtaaga    27900
ctctgtctca aaaacaaaa aaagaaatgt gtgaggaatg caacaagctg tgcattgacc     27960
acccttggtt acagcaagtt ctccacgctc agccgggtcc agcctttggc tgtcagcagc    28020
atctggagcg gaactgtgaa cagaaacact ccaggtgttc cgacgggtgc tggggcgccc    28080
ccagggagct ggaatttggt ttttagcaac cacatatagg aaatgaaccc gccagccaca    28140
gtatctcacg cctgtaatcc cagcactttg ggaagctaag gccagcggat cacctgaggt    28200
caggagtttg agaccagcct ggccaacatg gtgaaacccc gtctctacta aaaatacaaa    28260
aatcagctgg gcgtggtggt gggcgcctgt aatcccagct gctccagagg ctgaggtggg    28320
agaatcgctt gagcccggga ggtggaggtt gcagtgagtc aagattgcac ccctgcactc    28380
cggcttgggt gacagagtga gactttgtct cggacaaaaa aaaaaaaaaa aaaaaagaa    28440 ccaagtcctc gggcaaattc tcccattgag ggctgtgaag tcttggctcc tctgttgttt    28500 gttttgaaa ccaaacttgc atatttgact ttctcatgcg tggagaggac ccatgcttgg     28560
catggggggg cacctggttt ttgtgtcctt ggagctcatc tctggtgggg gaggaggagc    28620
agcaggagat gcgagggctg tagttctcag tcctggccgc acattggaat cctatggggg    28680
agctttaaaa ttatacacca aactcggcca ggtgcggtag ctcacgcctg ttatcccaac    28740
actttgggag gccgaggagg gtggatcaca tgaggccagg agttcaagac cagcctggcc    28800
aatatgctga aacctcgtat ctaataaaaa ttacacaagt tagccaggca tggtggcgca    28860
cgcctgtaat ctcagctgca cgggaggctg aggcaggaga attgcttgaa cccaggatgt    28920
ggaggttgca gtgagctgag attgagccac tgcacttcag cctgagcaac agagtgagac    28980
tctgtctcaa aaaaaaaaaa aaaaaaaat acacacacac acacacacac acacacac      29040 acaactggag aacagagcat ggtcactggg ggcaggagcg agagtgatgg gtgtggtcgg    29100
aaaatggtgg tggctattcc gtatcctcac cctggtgtgg attcatgagc ctacatgtgt    29160
gataaaactg catgggacaa aataaacaca cacacacaca ggagtacagg taaaacggga    29220
aatcgagcaa gattgttgtg tcaatgtcaa caccctggct gtgatgcttt atcctagagt    29280
tttgcaagat gttaccattg ggtgaaatgg ggtaccaagt acacgaatct ctctatatta    29340
ttgtttcttt aactgcatgt gagtctggga ttatcccaaa ataaaagtgt taatttgtaa    29400
aaagtacaca cagcatggca gttcccagcc tcagagattc tgatttaagg gtctagccgg    29460
gagcctgggc atgtgcttga ggcccccagg tgagtccaga gtacagcggg gctgagagtc    29520
gctgttgaca ttggctgcag ggtggacagg gcgagatggg ccctgcccgg gcagacctgt    29580
gtattgctag gtccttccgg ctctgatgct ctgtgataat tggccacttt ctctgccatt    29640
ttcctcccag agagcaaaca caggtctaga ctcaatatcg tgtggagcta tcgatgacca    29700
cgggtcactt ccatctccag cactgcaggc tgtgcgggct ggtccaactg ggtacggtt     29760 gagggtcctg gctcagacca ggcctgactc ctgggccagt ctgtaaaaca ggcccttctg    29820
```

-continued

| | | | | |
|---|---|---|---|---|
| ggccagcagc | tgggccgggc | tgccgctctc | tgccacctgc | cccttgtcca tgaccagaac | 29880 |
| cctgtggggg | agagggagac | agagaggctc | tctggacacc | agcccaggct ctcggcagct | 29940 |
| gtgagagccc | agtgtgtctg | cgctgaggtt | ttctccatag | aagtcctgct ttccatgcgg | 30000 |
| ctccctggcc | ctcacagctg | ggttggaagc | gtgtgctggg | cgcatgtcct tgggcagctt | 30060 |
| tcccacttgg | catgtgttcc | cgggcattcc | tcccgctctg | gccccattca ggacccctcc | 30120 |
| agctctaacc | cgaagcccag | tggcccagga | ctgcctccgc | ctccttcccc caccactgca | 30180 |
| gggctgctgt | gaggtcaggc | cggggcggga | gccttaccgg | gcacagtcca tcacggagcg | 30240 |
| caggcggtgg | gcaatgagca | gcacagtgca | ctgtgcaaac | cagctcccga gcatggcctg | 30300 |
| catctgcagc | tccgtgccag | ggtccacggc | agcagtagcc | tcgtccagga tgaggatctg | 30360 |
| ggtcttccgg | agaagggcac | gtgccagaca | caggagctgt | ttctggccca cgctgggaac | 30420 |
| gattgggaca | attagctggg | acgtgcgttt | gtcggcacat | ggtgatgtgt gggtgtgccc | 30480 |
| agaaacaggt | ccctgaagca | gtgcaggagt | gaggtgcctg | tgttcaggca tccccacaca | 30540 |
| tggggtctgg | ggtctgtggt | ctgcagaact | gataggaagc | ctgttcctgc catctttgag | 30600 |
| caggctgact | gtaggcaggt | cattcaaacc | ctttgtgcct | cagtttcccc acctgtgaaa | 30660 |
| tggctatttt | cttttttctg | tttatggctc | ttttttttctt | cttcgttttt ctttttttt | 30720 |
| ttgagacgga | gtcttgctct | gccacccagg | ctggcgtgca | atggcacaat ctcagctcgc | 30780 |
| tgcaacttct | gcctcccggt | tcaagcagtt | ttcctgcctc | agcctcccaa gtagctggaa | 30840 |
| ttacagtcat | gcgccaccat | gcctggcttt | tgtattttta | aagtagagat ggggtttcac | 30900 |
| catgttggtc | cgacttgttt | gaaactctca | ggtgatccac | ctacctcagc ctcccaaagt | 30960 |
| gctgggatta | caggcgtgag | ccactgcgcc | ccggtagttc | tatttctagt ttgtttttg | 31020 |
| agaaatcatc | atactatttt | ccatagtgac | tgtactaatt | tatatttccc ccaacagcga | 31080 |
| aagcacagct | ttcacttcag | tcatgccgtt | gcaaacaaac | ctacaatgac tcactgctgc | 31140 |
| ttcaagaatc | aaatctacag | tcttcctaag | acattcaagg | ctggtgtcac gtgggcctta | 31200 |
| aatacagatg | tgtacaacac | ctgggtggga | ttccaggcgt | gatccaccgt gcctggcctg | 31260 |
| tttatggcta | tgtccagttc | tatttctagt | ttccaccttg | tgccaaacac attctaagtg | 31320 |
| cttgtatata | ttcactcaat | cctcataatg | tccaccaagg | tagatattat tgttctcttc | 31380 |
| ttttgagaga | agaggacaca | gatacagaga | agctcagtgg | cttgaccaag gtctcaaggc | 31440 |
| tagtggtggg | tccataattt | gaacccaagt | cctctgaccc | cagagtctgt gctcctaatg | 31500 |
| gatccgtcct | cgctgaatcg | tgacgacatg | gcacataaaa | gtgtgtgggt ggcggggcac | 31560 |
| ggcggctcac | acctgtaatc | ccagcacttt | gggaggctga | ggtgggcgga tcacgagatc | 31620 |
| aggagatcga | gaccatcctg | gctaacacgg | tgaaaccctg | tatgtactaa aaatacaaaa | 31680 |
| aattagccgg | gcgtggtggc | gggcgcttgt | agtcccaggt | actcaggagg ctgaggcaga | 31740 |
| agaatggtgt | gaacccggga | ggcagagctt | gcaagtgagc | caagatcgcg ccactgcact | 31800 |
| ccagcctggg | cgacagagca | agactctgtc | tcaaaaaaaa | aaaaaaaaa aaaaaaagt | 31860 |
| gtgtaggctt | gtcacagaat | aagcccttgg | catggagtag | cacccttcgt ggagggtgga | 31920 |
| ggagttgaga | ttccaggttg | tgagcccagt | gagcccctga | cccaggtggg aactgacccc | 31980 |
| tggggcccca | gcatggctgt | cttgcacagt | aagcccttcc | atgaaacagc atccttttac | 32040 |
| atgatcagaa | cctactatgg | tcatgcaggc | gttagagtgc | ctgggtcttg tcccaacctc | 32100 |
| actactttta | agctgtgtga | cgtcaggcaa | gccccaggcc | tccaattcca actctgtgaa | 32160 |
| atgatgttat | caggagtgtg | actcaggact | aaaatgagta | tttactcttt gctctatgcc | 32220 |

-continued

```
tgccactgtt tcaacaactt tgtgcatata attcaatcct tgcaaggtag gtaggtgcta   32280
ttattcccac cttacagatg aggaaactga ggcacacaag ataagttgcc taagatccta   32340
cagctagtaa gtggcagggc ggggcggggg tgggggtgtg gggtgggggg cctggatttg   32400
agcccaggca gtctgtcacc tgtgtatact cttacccacc aagcaacgct gcctctctag   32460
tgctggaaat tattgcctac cacaagccct cggacaccc tcagggtcag aggggtttat    32520
aaatccagaa caccttaggt tttttttgt tttttttgag acggagtctt actctgtcac    32580
ccaggctgga gtgcagtggc acaatcttgg ctcactgaaa cctctgcctc ccgggttcaa   32640
gcgattctcc tgtctcagtg tcttagcctc ccacgtaact gggattacag gcgcctgccg   32700
ccacacccag ctaattttg tattttagt agagacgggg cttcaccata ttggtcaggc     32760
tggtcttgaa ctcctgacct caggtgatcc acccgcctcg gcctcccata gtgctaggat   32820
tacaggcatg agccaccgcg cccagccact ttggttttc taaaggcata tacctataca    32880
cctatgttca tagtggcatt attcaaaacg gccaagaggt ggaaacagcc tgggtatcta   32940
ctggcagata aacggataag caaaatgtgg tctatccatg tagtggaaaa ttattcggcc   33000
ttaaaaaggt agagaatctg acacatgcta cgatgtggat gacccttgaa gacatcatgc   33060
tgtgtgaaat aagccagtca caaaggaca gatcctatga ttctgcgtct atgcagtgtc    33120
tagagtagtc acactcagag agacaggaga atgctggtgg ctgggcgctg ggggagggga   33180
caaggagagt tagggtttca tgggtacaga gttgtagttc tgttgtgtaa cagtgtgaat   33240
gtacctaaca ctacagaaac tatacactga aaaatgggtg agatgggccc ggcgtggctg   33300
ctcacacctg taatcccagc actttgggag gcctacgcaa gttcgactgt agcctgggca   33360
acatggtgaa accctgtctc tacaaaaaat aaaaagatta cctggccctg gtggctcaca   33420
cctgtaaccc cagctactcg ggaggctgag gtgggaggaa tgcttgagcc tgggaggtgg   33480
aggttgcagc gagccttgac ctcaccactg cactctagcc tgaatgacag agccagaccc   33540
tgtctccaaa gaaaagaaa aaaaaaaaa aaggttgaga tagtaaattt tatgtgtatc     33600
tttccacaca gcttttgtt gttgagacga agcccaggat ggagtgcagt ggtgcaatat    33660
cggctcactg caaccttcgc ctccctggct caagcgttct tcccacctca gcctcccaag   33720
taactaggac tacaggtgca tgccaccata cctggctaat actgttgtcc acagagatag   33780
ggtcttgcta tgttgcccag actagtctcg aactcctggg ctcaagcaat cctcctctct   33840
cagcctcctg aagtgctggg attacaggca tgagccactg tgcccagtcc acacttgaca   33900
tttaccaaaa aaaaaaatcc tatattatag tcccagtgag tggtgaggtt accacccgat   33960
atcaaacaat attttcatag caaataaat actgagcaag agcaataaag gctatcagta    34020
gccctgtgtc agttgaggtt gggttttgcc accaagtaaa tatagaagac taactgctaa   34080
tttagggggg aaaaccttgg tattcagaga ctgtgtcaga gcttggaatt gcagataaga   34140
gacatgtggt tattaatgta acagagtgat aatcctatcg ggggaggcat ttcctgaagg   34200
cccttgggga gggcatggcc atcccctcct ctcccacctg caggtcccag ccatggtggg   34260
acgaccatac ctcaggtcct cgcctcggtc agcacacttg tactgcagct ggccgggcag   34320
gctggccacc aaggctttga gctgcaccgt ctccagggct gcccagatag cctcgtccga   34380
gtgctcctgc agcaggtcga ggttcatccg cagagagcca gggaacagga tggggtcctg   34440
gcggggaggg gcggtgggtc agagccgggt cccaccatgc ctcccatctt tgcccacccc   34500
ctccaccagc ctcacctggg ggatgatgct gatcctggag cgcagtgtgt gcagcccac    34560
```

```
gtgggcaatg gggacccegt cgatccagat cccaccctca gctgcctcct ggagccgcag   34620
cagcccactg gccagggagg acttccctgc cccggtcctg ccaacgatgc ccacctgccc   34680
ggggttggga ggaaaggcct gctctgacca gagggtttgt gggcatttat tggggagatc   34740
tttctgctgt acccgagatc tgtctatcca tccctcattg tgtaaaggtc taccttccat   34800
ctctctttcc atctgtctac ctttctatat atccacccat caatccatcc agtcttccat   34860
ctgtgttctt ctctatcttt cccttatcct gatatctctc tcccatcttt ctccccaccc   34920
ttcctttagt tcctccatct ttcctcatcc ttctatttac acctctccat catctctcat   34980
ccttttttct accccatccc atccatctgt ctgtccgtcc atccatccct tatccttttt   35040
tccaccccat cctgccatcc atccatccat catccatcct caatcccatc cctccatctc   35100
tcttccaccc cattccattc atccatccat tcatctgtct atccgtctct cgtttcttct   35160
tccctattca tccatcaatt cactaatcct ttcattcatt tattttctcc catccatcca   35220
tccagtccat ccttccctca tccatccttc cattcatcct ccatcttatc catgtgtcca   35280
ttctgttatc catctcccat gctgttatcc accctccatc cttatctctc ttgctactat   35340
tgcatcctca gtgtctgaca catggtgtgg gttcaacatt atttgtttaa ttaatgatgg   35400
aaacatgtgg gtcaccccac tgtatgccaa gtacctgttt aggcaccgga agtatagaaa   35460
ttaaagagtc cttgctccag tgtgcccatc atccggtcta ggaaacagtg caattgagta   35520
aatgtaatac agtgtgatga acaatgcttt atttatttat ttatttattt attttttgaga   35580 taaagtcttg ctctattgcc caggctggag tgcagtggtg cgatctcagc tcactgcaac   35640
ctccacctcc caggttcaag caattctcct gcctcagcct ccctagtagc tgggactgca   35700
ggtgcctgtc accatgctcg gctaatttttt gtatttttag tagacacggg atttcaccat   35760
gttggccagg ctggtctcaa acttctggcc tcaagtgatc tgcccacctt ggcctcctaa   35820
agtgctggga ttacaggtat aagccacagc acccagccaa caatgctgtt tattatcaag   35880
gtctggacct ctggcaatta agggaagcaa ggcagtgctg ctcatgctgc ctgggatttg   35940
acagaggtaa taagagaaga cctcatggag gaagggatac ttgcatggaa gcttgaagga   36000
tcaataggag ttcaaggaag gggaacactc caggtaaacc acaccaagtg ggtttccaaa   36060
actagaagct catggagctc acagcaccat gtgccccccct ggccgagagg cagctgctcc   36120
acaatgttgg ctaagccctg gcagagcaat gaatgagagg gggaggttgg cagggcctgg   36180
gttgggtaga gccttgaatg ccaagctcag gaattcacac tttacceccaa gggaagctgg   36240 aactagtaga aggttttgag caggggaatg acatgcagtg tcattcatgc tgataaaggt   36300
cacaggatgg ctgggcatgg tgggtcatgc ctgtagtccc agcactttgg gaggccgagg   36360
ggggtgattg aggtcagaag tttgatagca gcctggccaa catggtgaaa ccctgtctct   36420
actaaaaata caaaaattag ccgggtgtgg tggcaggtgc ctgtaatccc agctactcag   36480
gaggctgagg caggagaatc acttgaatct gggaggcgga ggttgcagtg atctaaggtc   36540
acaccactgc actccagcct gggcaacaga gtgagactct gtctcaaaaa aaaaaaaaa   36600 aaaaaaatca caggagagca gattggagct ggtgagacag gatccactgc tttttagggg   36660
acaaggagag gacagggagg aagcctctgt aggttcagag ggagggagga aagggattca   36720
gtgaaggggc ctgatgaggc atctgtaaaa tgggatagta ctagcacctc acttaggggt   36780
tgttgtgaga gtgaaaacgc aaataataaa agcattagta aacatttctg gagcactttc   36840
tatgagctaa gcatgttcta tgtattaact caaacttcac aacaactcag agatcagtat   36900
taccagtccc aatttacaga tgggaaaact gagactgagc tatgaagtgc ttttcccaat   36960
```

-continued

```
gtctcccagc tgaaagcaaa tatcccattt gtgcaaactg aaaatgtac ctggagcatt    37020 taacacactg cccagcacat attaggtgct gggttaatgt taaaggaaga aggaagtcac    37080
ggagttgctt cctcatctgg ggacaccaag gtggatgagg aagtcaccag atggaagcag    37140
gtttggggaa ggtgaggagt tcattttagg gggtaatggg tctgaaagct aggggacctg    37200
aggtggggac actgtggagg tagctggtgc ccagggttta gggccttgtc cctggagtcc    37260
tttggcctaa actccatgaa aagacattg tgagagaacc actcaccttc tctcctgcgt    37320
ggatcttgaa ggacacgccc tgcacagcca gcgggagctc aggtcggtat cttagcccaa    37380
agtcccggaa ctcgatctgc ccgccctgag gccagggggg ctgagctgca catgtgggca    37440
gcctccaggg agcctggagc aggaggggaa actgagtcag aggagccttc ctctaagact    37500
tcacacaaga tggcccacct ctatcagctt cagttttctc ttccgcaaaa tggacgtatt    37560
tattgctgtt ttacagggtt gttatgggaa ttcaacaaga gagggcatgg actatgtcaa    37620
tgctaaaaac agatggtggt ggctactttt agtctatttt attgttatta ttagccactg    37680
tttattataa aataatctct tttttctatag tgggagcaga catttctctt tgtctttgtg    37740
aaaggacatg actgtgcagt gggaagacca atactgcctt tgctgtgccc gtgaccttga    37800
acagatcatt ctaccccctt gagtcttggt tttccaatct gggaaatagg gctaataaga    37860
gcagcagaca tgtattgagt gtttgcaatg gaccaggcac tctattaaat catttctttg    37920
caggatctca tttgatcctc ccagtaaact caacgctgtt atgttactgt tacattagtg    37980
ctatgctgct gttcttatcc tttcttccac ccaatcccat ccatccattc atccatccat    38040
ctcttatcct ttatccaccc catcccaccc atccatccat ccatgcatcc atccatccat    38100
ctccaatccc atccctccat ctctcattct tccatcccat tccatccatt catctgtcca    38160
tctctcacca tttcttctac cctattcatc aactaattaa ttcttccttg ttctgttact    38220
gtaatgttac tgttatattg ctaacacatt atatcatgtt gctgttttgt taccgttgcg    38280
ttgctatgtt gctgttctgt ccttataatg ctactgttat gttgctggaa ttttgccatc    38340
atgttactat aatgttgctg ttttcttact gttacattgc catgttgcta ttccgttact    38400
ataatttcag ttattttgct ggaatgttgc catcatgtta ctataatgtt gctgttttgt    38460
tactgttaca ttgttatgtt gctactctgt tactctgtta cagtcgtgtt gctgggatgt    38520
tgctgtcatg ttatgatgtt gctgttgtgt tactattgca ttgctatgtt gctgttttgt    38580
ttctatcatg ttactaaaat gttgctatta cgttactatt acattgctat gttgtggttg    38640
tattgctgga atgttgccat catgttacta taatgtctct attatgttac tattacactg    38700
ctatgttgct attctggtac tgcaatattg tggttatgtt gctgttacat tactgttaca    38760
ttgctgttgc attactctca tgttctggaa tattgccatt gtgttgctgt tgccattatg    38820
ttactatcat gttgcagcta tgttgctgtt gcaatgctgt tccttgtggt tccctgcact    38880 cccatggtg acctgctttc ctcaagctca gaagcaaagg aaccaagatt tggcctggct    38940
ccaaacctta tgctcctaac cactgctgcc accctgtctg tgactctgac ctatagtggt    39000
gggggttgag tgaggggaga agagggtata aactccaaag cctgtagcag atgtcaacag    39060
ggacccattg ccccccccac aatatgtcct tgctgggacc ccctccccac ctcccgccca    39120
tcacctcctt gggcgtccag gcatagtcct gcatccgctc cactgacacg atgctgttct    39180
ctaggtctgt ccagttgcga acaacccact gcagtgtctg ggtcacctgg tgcaagaaag    39240
cctctctggc tgggtttggc aaggccactt gagggcttgc aacagccccc ctggtttccc    39300
```

```
aacctttttct gggaggccag acccagggga gtaaagaggg gaggcaggaa tgggacagtc    39360
tgaggacctg ggcccagggg attgggattt ggatacaacc aacaggtccc tctcttcctt    39420
cagtagaacc agagcatgca gagcaaaaag aagccctcag acatcagctt gtacaaactg    39480
gcttgatgca ggtgagtaga caggatcaga gagggtgtgt ggccctccca aggacacaca    39540
gcaggaccca ggcccactga ttccattctg acggctttct cgcagcgact gggtggccac    39600
caatttccca tgacacttag aaccactcca agctcctccc tatgagccat tagcagctct    39660
agccctgcca tcccatcccc aaccttgtct cccagcaccc ctgccttcac ccaccctctc    39720
cagccacacc cgtcttcttg ctgttcctct aacacaccag ggatgaacct tcaactccca    39780
ggccttttct tcctgctgtt aacctcactt cctcctaagt cacctcctca gagaggcctt    39840
tctggatgca gtaggaaagt tccctcactg ccacccaaca tgctccagcc tcttacttca    39900
tccttaagct tagcagcctt gactgtaaaa tgaggataat aacagtgctt ctctgatggg    39960
gttgtgggca gtattaagtg agttaatatt tataaaattc ttgtgcacag tggctcatgc    40020
ctataatccc agcttttttgg aagtctaagc aggaagattg tttgaaccca ggaattgaag    40080
gctgcagtga gctgtgatca caccactgca ctccagtctg ggcaaaagag tgagaccttg    40140
tctcaaaaca aaacagctgg gcatggtggc tcacacctat aatctcagca ttttgggagg    40200
ctggggcagg cagaccactt gaacctagag tttgagacca ggttgggcaa catggtgaaa    40260
ctgtttctac caaaaaaaaa aaaaaaaaa aaaaaaaaa attagccagg catggtggtg    40320
catgcttgta gtcccagcta attgggaaag tgaggtggga gaatcccttg agcctggaga    40380
tggaggctga agtgagccaa gatcatgcca ctgcactcaa gcctaggcaa caaaatgaga    40440
tcctgtctca aacagcaaca acaacaaacc aaaacgaaca aaaacatata aagctcttag    40500
aataatgcct cctccataac aaatgcttat gagtgtatat atatattttt ttcgtagatg    40560
tcatgaactg acattacata ctgttaatag ttaacaaaaa ttagccaggc atagtggctc    40620
acgcctgtaa ttccagcaac ttgggaggct gaggcataag aatcgcttga acccaggagg    40680
cagagttctc agtgagccga gattgcacca ctgcactcca gcctgagtaa agagagaga    40740 ctctgtcttc aaaacaaaac aaaagttaac aatgcactag aaatgtcctc cacaggatat    40800
gctttgtctc aactagtctt tataacatca gaagtagtgg gatttctggc ctgtctttcc    40860
aaggagcaca ctgacactcc acaaggaaag actcttgccc aaggttgcaa gttcaccttac   40920 gctgagtctg gctcttgtag agctgcgtgt ccctccttgg tggagggact ccacacacca    40980
tggtggtttg gacacagggt cttcaaaggt cccactagca ggggtccgac agtctctgcc    41040
tctgtctgtc cctcaagccc agtttgggga tgtggggagt acctggaggg cagcagagac    41100
agagaagccc acgaggccag cactgaggtg ggctttgctc agcacagcac acgtggcagc    41160
tgcaaacacc aggccattcc ccaggagctc cacattggcc gcaagccacc tgcaaaggga    41220
agcgacagca gggtgagtgg ttactctcat ctgcagggag atgcttctct gggcacaagg    41280
actggtcatc acaccagctt tgtacacaca ggggtcccag caatggcctc cacatgcaac    41340
ccaggctcag ggagtagagg aagatgacac cgtcctgtct caactaagcc cacttttaggg   41400 tctggggtac actcggtgtt ctgaagagca tccctgtgtg gctgcttttc tgtccctgga    41460
atttgccaag ccatgtccac ctgccattcc cctggcctga accatggcct ccatggtttg    41520
gctctgtgtc cccacccaaa tctcatctca aattgtaatc cccacatgtg gagggaggga    41580
tctggtggga ggtgactgga tcatgggggc agttttcccc atattgttct cgagatagtg    41640
agttctcaca agatcatatg gcgtaaaagg atgcggcagt tcccacctca tgctctccct    41700
```

```
ctcctgctgc catgtaagac gtgccttgct tccctttcca ccatgattgt aagtttcctg   41760
aggcctcccc agccacgtgg aactgagtca attaaacctt cctttctttca taaattactc   41820 agtctcaggt agttctttttt agcagtgtga agatggacta atacacagcc ccagctggct   41880
ggggacctga gatgaaagga aaaaggactt cacatgtatt gagcacctag tgtgtacttg   41940
accctctcca cactctggta ccagactgct tggattcaaa tcctggctct gccagtatta   42000
gctgtgagac cctggacaag tttccaaacc tcactgtgcc taggatttat catctataga   42060
acagtttctt cctggtgaag ctgttagcag aattaaataa attaatctac atagattgct   42120
cagaacagtg ccaggcatgc agtaagcatg ttacaggtct tacctatgag tgtctgtatt   42180
taatcctcat atccactcca tgagcacgat cccagtttga caaatgaggc tcagagaggt   42240
tatgtaactt gcctgaaatc aaccagctgg taagtggcag agctgggatt tgaacctgtg   42300
tctatttgtg cttaaagctt gtgttcttgt tcttgcttag tacctaaaga tggctgagga   42360
tgcttatatg gctgctttat caccaaggca aaagaggttg atccagttgc ctggcaacag   42420
aagcttcttc ctgtacccccc cgcccaccctg ctgttgagaa tctctcggtc atgttccatc   42480
tgcccacggt gagaactgat agactgcctg tgggatctag cctcaactat gtccctgact   42540
ctctgggtga cctcgctacc atacaatatg acctcaggtc tcaccctcta aggatatgga   42600
tgaattgcaa ggtcttctct gccctggctc ttcctacctg tcagccacca gtcgcgggaa   42660
actgatcctc tggctttcat ctacgcgagc attgttctga ccacaaagg gggcctgggt   42720 tcggaatgcc cggaccactg tgctgccctg gaacgtctca gccatgtggg agcagacaga   42780
cgagtagctg gctgactcca agcgtctcag ctggcatgag ctaaccacat acaggctctg   42840
agaaggatgg atgggagagg gaagaggaga agccacagac atagagaggt agtttccaga   42900
agcacagaga gccccaagta caggattcca gaccaggatc tgttaacagc ttactgtgtg   42960
accttgggct agttgcttgc cctctctggg ttctcatttc cttgcagaat cagagttcta   43020 tggtttttttt gaaaatcacc tggggagctt caaaaacctc taatgcccca ccccagaatg   43080
actgaatcgg aatctctgga aatgtcacct tgactttggt gctgtttaaa tagccttcca   43140
gatgattcta agggacagcc agggttgaga aaccaccaat ttagtttaag tgtctcactt   43200
cccagcactg aggccgacta cttcatttac ggctggtcag tgggagaaca aaactgtaag   43260
gggcaatgaa ggcagttggc caagtcagtt tcactcatgt aacccaaggg ttacatgcca   43320
ggtgatgtgc agaaaatatt cgttatttgg tttgcagctg caggttgggt gcagctggca   43380
gacaggcagg cagggaggaa ctgaatttgc tgaacaccca actgtatgtg ccaggctttt   43440
cacacagtgt ctcattcatt gcagagtgag cattcgcgtc attcatcagt tagtggtgag   43500
aacatccaag gctcggggga ttcagcagct gtcctgagtg ccacagtaag tgatagagcc   43560
tggatttaaa cccatctttg cttgactcta aagcttgaga cagaaacagc ccatcctcgg   43620
agtcaagtga acttagagaa gacctaggac aattgtcggg gacagtggta gccatgggtt   43680
ttgttgtttg ttttttgaga tggagtctct ctctgtcacc caggctggag tgcagtggtg   43740
caatctcagc tcgctgcaac ctctgcctcc cgggctcaag caatcctccc gcctcatcct   43800
cccaagaagc tgggattaca agcatgcgcc accacactgg ctaaatttttt gtatttttag   43860 tagacggagt ttcaccatgt tgaccaggct ggtctcgaac tcctgacctc aagtgatctg   43920
cccacctcag cctcccaaag tgctgtgatt agatgtgtga gccaccatgc ctagccctag   43980
ccatggtttt tatctgacta ccatgttttc tacttctggt ttcctgtggg aaagggctgg   44040
```

-continued

```
gttggggtgc tgtcaatcat gggacctgat cagagaggtg gtcacatgat gcagcctagt    44100
gtatcagaat ctactatcca ttcagttact gtgacgagtt cagagatgga cacatgatcc    44160
acaaagggcc aatcagaacc ttccctggga ttaatatatg actactgagc tgaagaaacg    44220
ttttttgcat gttgagttgc taaggtgaga tgatatgata gctagtggcc ataagacctg    44280
ccctggaaag agagcgtgta caaaattaga ccagaggtaa gccagtggtt cctaaacatt    44340
tgtgtacatc agaattactt ggagggttaa ttaaaaccta gattcatggg ccgacccaca    44400
tagtatctga ggcagtagtc ctgggctggg gcctaagaat gtactttgct aactagtccc    44460
caggtgatac tactgctggt cctggggtca cactttgaga agcactgagt gaagatatgg    44520
agagagtcac tgtgtcctga tgacaactgg gcccatgccc ccaaggaaat ataagccatt    44580
aaattctatt cttttggtta agctaatttt agttggtcgc tggtcccagc aattgaaaga    44640
atctagcttc atataatagc ctttgagacc ttgcaatgcc ttttttggctt ccagataatt    44700 ggagaggaag aaattacggc aggataaaaa cattacgcgt gaaaggctct ggcccttaat    44760
atttaactgt gccgtggggc acaggggctc atgccctgta atcccagaac tttgggaggc    44820
caaggtggga ggatcacttg gggccaggaa ttcgagacca gcctgggcaa cacaggaaga    44880
cacttgtcct acaaaaataa atttaaaaat tagccagtca tggtggcacg tgcctgtagt    44940
cccagctact tgagaggctg aggtaggagg atcacctgaa cccaggagtt caaggctgca    45000
gggagctatg atcacctatt gcacttcagc cttggcagga gagcaagatt ctgtctctct    45060
aaaaaaaaga actttgatgt gaacatttag agacagacac tagtggagat accagaaaga    45120
ctgtagtgtc cctgtccctg ggaattctag gaacagcccc tagatgtcca gctgggtgaa    45180
acctcatata tggagtcttc cccagagaca ggggactggc tgagttgacc tcagccggtc    45240
ccggaagcct ccctgacctc tccgtacctg aaacccagcg tagaggagaa acagtggcag    45300
gatggccaca gtggccagtg gggtagccac tgccaccacc aggctgacct ccaggagtcc    45360
aaaggcgtac atcagcaggg accggagttt gtctggaatg tccacgtcaa ccgtgtctgt    45420
ctccttggag aagcggttta gcaggtgacc aatgggtgtc cgctcaaaga agctgatggg    45480
agatcgcacc acatcccaca ggagcctctg gaagagcaac ctggatgccc gggccccacc    45540
taggagcacc gcagccatgg aggcaaacag cccaatggct ggggagggag aggaggtaag    45600
agcatgaggg ctggagaccc tcaggagcgg cccacggggc cctgcgcagg tctctcccgc    45660
taccccatgg tggacatctt atggcttggc caccctgatt attatatttt tttgagacag    45720
ggtctcactc tgtcacccat gttgaagtgc agtagcatga tgatggctca gtgcagcctt    45780
gacctcctgc actcaagcga tcctcctgcc tcaccctccg agtagctggg accacaggtg    45840
tacgccacca tgccggctaa tttgggtat ttttgtagag atgggatctt gctatgctgt    45900
ccaggctggt ctcgaactcc tgggatcaag tgatctgcct gccttggcct cccaaagtgc    45960
tgagatgaca ggcatgagcc actgcgcctg taccctgctt gtttcttgat gtaatgggtt    46020
gaagagtgtc ccccaaaatt catttgggat gggtcctaaa ttcagtgact gccatttata    46080
taagaatact agaggatact cagagacaca gcaggagata tgaagatggt gacacagatg    46140
ggagggtgta tctacaagcc aaggaatgcc agcgactgcc ggcgaccacc agaaaccagg    46200
agagaagcct ggggtgtatt ctccatcaga gcctccacga ggggccgggc acagtggctc    46260
atgcctgtaa tcacagcact ttgggaggcc aaggcgggtg gatcacctga ggtcaggagt    46320
tcgagaccag cctgagcaac acggtgaaac cctactaaac cctactctct actaaaaata    46380
caaaaattag ctgggcgtgg tggcaggcac ctgtagtcct agctactcag gaggcttagt    46440
```

```
caggagaaac actggaaccc aggaggcaga ggttgcagtg agccataagc cgagatcgtg    46500
ctactgcact ccagcctggt tgacagagca agactccgtc tcagaaaaaa caaacaaaca    46560
aacaaacaaa aaaaccaaaa aaacctccac aaagagttaa cactgctgac accttgattt    46620
tagacttcag gcctcagaac tgcgacagaa caaatttcaa ttgtgctggg ctcccaagtt    46680
tgtggcaact tgtttggcag tagccctgtg agagaaatgc acatccttcc tcccagtgct    46740
aatctgtatg cctggggtgg ggctaacttc tcctctgggg tggggcaaat ttcatccatg    46800
gccaatccaa accactgcag ttggttcagg atgaacaca taacccaagt caggccaatg    46860
acagggagac ctgggacttc actagaactt ttggaaaagt ggtacttggt tgttggaggt    46920
agccaagctg gagctgtgga atatcatctt actgccaggg gcagcagcta agctggacag    46980
gaagctgtca cagaggaggg aaataaagcg atttcttgtt tggaccccta catccagcca    47040
tacctgaagc cagaaatcta gggatactgg tcccaagagc caatcaattc tcttgttgct    47100
taaacacttt gaattggagc tgaatttgtt tattttcaga cggagtcctg ctctgtcacc    47160
caggctggag tgcagtggtg caatctctgc tcactgcaaa ctccacctcc caggttcaag    47220
cgattctcct tcctcagcct cccaagtagc tgggattaca aacactgaca ccatgcctgg    47280 ctaattttg tatttttagt agagacgggg tttcaccatg ttcgccaggc tgatcttgaa    47340
ctcctgacct caagtgatcc acccgcctcg gcctcccaaa gtgctgggat tacaggcatg    47400
agccactgta tctggcctgg agctgaattt tttattcttt gtattcgaga gtcataacca    47460
atttctctct ctcagctccc atctctccat ctttagggga gagtaagact tgcccttagc    47520
tatcaaatga gggatggaag tggaaggatt ttgaaagggc tatttgccac ccaaatgagg    47580
atttgggtta attccaggc tcggctgact ctgagaatcc ctaatttcct cttggttaag    47640
taaccattcg ccttgagtat tccactgtac atgcagttgt ggtgagtagg tgtacaggtt    47700
cttaggacta gaagagtcct caagttcagg cctggcgccc cctatttac aggggaggtc    47760 acaggctcac agcattttgg tgatgtggcc aatgtcaccc agtgaatgag gacgaatcaa    47820
catgaaaacg aggcaactgt cctttaaaga tgaagccagg ccgggcgtgg tggctcatgc    47880
ctgtgatccc aacactttgg gagtttgagg cggaggattg cctgagccca ggagtttgag    47940
accaggccgg gcctggtggc tcatgcctgt gatcccaaca cttttgggagg ttgaggcgga    48000 ggattgcctg agcccaggag tttgagacca gcctgggcaa cacggcgaaa ctgtctctat    48060
caaaaacaaa aattagccag catggtggca tgtgcatgta gtcccagcta ctcgggaggc    48120
tgaggtggga ggattgcttg agcccaggag gcagaggttg cagtgagccg agttcgtgcc    48180
actgcattcc agcctgggtg acaaagccag acccagtcta tatatatgtg tgtgtgtgta    48240
taaataagaa gccaaactca catgtgcact cctgttactc ccttcagcca ggccacgtat    48300
taaaaggaga agaaccaggg gttgggggaca gggtgggcga ggcaggagaa gggtgggtgt    48360
ggttgcaaaa gggcaacacg agagcgcctc gtggtgacgg tgttgttcag tatctcaact    48420
gtcaaccatc gtgatggatg cgagagactg aacaggggat acgactgcac agaggcaaac    48480
atgcgcacac ccacgtgcaa gcaaaactgg ggaaatcaca atgagatcca tagggccggg    48540
tgcgggggct cacacctgta atcccaacac tctgggaggc cgaggcgggc agatcatttg    48600
aggtcaggag tttgagacca gcttggccaa catggtgaaa ccccatctct actaaaaata    48660
caaaaattaa ccaggctgca cacttgtaat cccagcttcc agctactcag gaagctgagg    48720
taggagaact gcttgaacct cggagatggg ggttgcagtg agccgagacg gcagcactgc    48780
```

```
cctccagccc gggcaacaga gcaagactct gtctcaaaat aaaataaaca aataaataaa    48840
taaataaata attgagatcc atggattgat gggtgtcagg atcctttgtg tgatacttta    48900
ctatcagttt gcaaaatatc accaatggga gaaactgggc agactgttca aggtagctgg    48960
ctgccttatt tcctagaact gcatgtgaat ctacaattat ttcaagaaga agtctttcca    49020
tttttgacga ggagaagaag gagtgatagc ggtgatgcat ttgttaggga gggtctggct    49080
ctgtctggag gtttgggggc aggcactgaa agccaccagc aggcaggcct tgcagacgcc    49140
ttccgctagt ggggagggac tgggagaggt tctgaagctt ccagaaaagg agggatgtgc    49200
cctgtccttc ccgttccctc cagcctcatc ttaaggacac agatctttgc ctggacccca    49260
gacgttttgc acactgttcc agggggacag ggtgacccag ggaggggtgg ggtaaaggag    49320
tcctgagcac cccttggtgc agctgggagg agagggatga ggagggcagg tgaggcgtac    49380
cttggagaca gccgaggagc ccgaagatcc cgccacgcag ggctgcctgc gtctgctgcc    49440
cacctactgc agggtcgtcc gcccacaggc tcagccagta gccccggcag aaggaggcca    49500
cttgctggca gaggaagagg aagagtgcgt agaggcagag gggggtgccc acggcacgca    49560
ggtaggccag gtgcactgtg gccttcacct gtagcacaca tgaggagag ggaggcagag    49620
agagccccca gtgggagggg tgggttgagg caaggccagg cgaggctccc agaaaacatg    49680
cccatggcag atgggaccac cacgcagacc tcaccggttc tcccgctgtg cctcccacca    49740
ggagcaccat ttccccgaca ggccccagcc agccttagaa cccccatctc ctatacaatc    49800
cccagggagc tagtattaat atttttctt ttctttttt tttttgagg acagggtctt    49860
gctttgtcgc ccatgtcacc caggctggag tacactggca tgatcatggc tcactgcagc    49920
cttgaactcc taggctcaag taatccccc gcctcagcct cccgagtagt caggactaga    49980
ggtttgtacc accatgtttt gttaattttc atagttttaa agagatggag tctcgctgtg    50040
ttgcccaggc tagtctcaga ctcctggcct caagcgatcc tccctcctcg gccttccaaa    50100
gtgcttggat tacaggtgtg agccaccaca cccagctaga agggttttct tgaacaccca    50160
ccataggtca ggcatgtgtc tctccttata acaacctcca tttcacagat aaggaaactg    50220
aggcacagag aggttcagcc actggcttaa ggtcctgctc ctacaaatct gaagttctct    50280
gcacagctgc agccaggcgg gactgttgaa aacattaatc taattatatc ttgtcgttgg    50340
cctgtccatg gctatctctt gctcttagaa gaaatcccag ccaggagggg tggctcatac    50400
ctgtaagcac tttgggaggc caaggcgggt gtgtcacctg agctcaggag tttgagacca    50460
gcctggacca acgtagtgaa acccgtctc tactaaaaat acaaaaatta gccacgtgtg    50520
gtggcaggca cctgtagtcc cagctactcg agaggctaag gcaagagaat cgtttgaagc    50580
caggaggtgg aggttgcagt gagctgagat tgcgccatta cactcttctc tgggcgacaa    50640
gagcgaaact ctgtctcaaa aaaaaaaaa aaaaaaaaa aaaagaaag aagaaagaa    50700
agaaagaaat tccaagcttc ttatctcgcc cccactcact gcctgccagc ctcatgggac    50760
cccttttctct ggcaccctaa gctacttccc acctcggagc cattgcacct gctgctctct    50820
ctgcctggag cgctctttct cctgcccttt gtatgattga ttccttcaca cattctttgg    50880
ggaagctcaa atgtcacttc tcagagcatc ctgtccatac caaccatggt atggtttctc    50940
agtggtctct atttcatcat tctttctttt aagaggcagg gtctcactct gtcacccagg    51000
ctggattgca gtgacatgat catagctcac tgcagcctcg aactcctggc ctcaagcaat    51060
cctcctgcct cagcctctga aagtgttggg attacaggca tgagccactg cgcctgatca    51120
ttcttatttt ctttatagca cttattgtta ttggacatag cttacttatt agcataatta    51180
```

```
tttactctcc gtctatcctc actagtgtct aatctctacc agacttagcc tggcacatag   51240
tgggtattgt gtacatgttt gctggatgga tgaggagggt aggtgggtga ataaatgagc   51300
gggtgggtag gtaggtaggt gtgtaatga gtggatgaat ggatggaaag atcaatgaat   51360
ggatgaacag ctgaacagac agatgcatag gtgagggaat ggttggatgt attgttaggt   51420
gggatagatg gatgggtaag agaatgggat ggataaatga gtaggtgggt gagtggatgg   51480
gttggacaga taaatgagtg ggtgggatag atggataaat gagtggatgg gatggacaga   51540
taaatgagtg cctgggatgg atggataaat gagtgggtgg ggatggataa atgagttggt   51600
gggagggatg gataaatgac taggtgggat ggatggataa atgaatgggt gggtgggtgg   51660
catggataaa tgagtgggtg ggatggataa atgagtggtt gggtggtgg  datggataaa   51720 taagtggatg ggatggataa atgggagggt gggatggata aatgagtagg tgggatgcat   51780
aaatgagtgg gatggataaa tgagtgggtg ggatggctaa atgagtggnn nnnnnnnnnn   51840 nnnnnnnnn  nnnnnnnnnn nnnnnnnnnn nnngtaggtg aatggatggg atggataaat   51900
gagtgggtgg gatggatagg tgggtgggtg gatgagcatc taggtggatg atggaatggg   51960
taagtaggtg ggtggagata catagcagta tagaagatga gaaacagtgt aagcttcaga   52020
ctcagattgg cctagatttg agtcccaggt tgtgtcccag gctagatatg aaaacacaaa   52080
caagtctctt aactctttaa gacttcagtt tcttggctgg gcacagtggc tcacacctgt   52140
aaccccagca ctttgggagg cagaggccag aggatcactt gagcccagga gttccagacc   52200
aacctgggca acatggcaaa acccatctct actgaaaata caaacattag ctgggcatgg   52260
tggcacacgc ctgtagtccc agctacttga gagactgagg taggaggatt gcttgagccc   52320
aggaggtcga ggctgccgtg agctatgatt acatcactgc ggtccagcct gggtgagtga   52380
gcgagccact ttctcaaaat caaaataaaa taaattttaa aagaattcag tttctttatg   52440
tctgaaatag acctatcata tctatttttt agggtggttg tgaggattaa gaaaatgaac   52500
atctagaatg ctactggcac atagtaggtg ctcaagaaag gtgagtatca ctgccaagtg   52560
ctacatttgg tgggaggact tgggcccctg gaggtggcac agtgggtggg gaggggtggg   52620
tgaagctggt ggttaccctg ccgtattgga tgctgtcctt tcctgctggc catcctgccc   52680
tgtcagggtc atccagagga acctctgtct gggcttctga agtggtacgg tccttctcag   52740
ggactgactt gatggacctg tcatttagag gaaatgaaga caaagtcagt atctctccca   52800 atggtgggt  gtatgtgcct aaccctcagg cccactgaca gccactgagc tctgggtaca   52860
ctctgtactc tttcattcat tcatttatct aacagaatac tgaccagata tcacacttcc   52920
cttcttccca tatggtaccc agctaaatgc catctattac cccagggtca agcaagccca   52980
ttcttctgat gccaattcac aggatgaact taacttgccc accattggaa ctctgttctc   53040
agaattttct ttcttttttt ttttttttttg agatggggtc ttgctgcatt gcccaggttg   53100
gtctcaaact cctgagctca agcaatccac ctgcctcagc ctcccaaagt gctgggatta   53160
caggcatgag ccaccatgcc cagcctgttc tcagaatttt tattttggct taagctttcg   53220
tgcaattgtt ttgttcctac tgtataccat cagatttgtc agtccaactg gcagaatata   53280
aattatgcac aattcagatg ctaaagactc tttgaatgtt ttatctgtgg atgagtaggc   53340
tgacttaacc tctgtgcctc agtttcctca gctgtaaaaa taggaatatt atctatctat   53400
ccatccatcc atttatccat tcatctcat  acctgtatat ctacatatac atgtctacct   53460
accttctatt aaattgaggt tagcccaaag ctgcctcctt acatatttta agtttggcct   53520
```

```
aaaggttttc cccgtacata gtgaactgta acctaattgg actcaaacag actgcaacct    53580
actcctgtgt caatcactga gtttcagcca atcaaaggca accaaccgtt caaaccatgt    53640
tccaataaag caaacgctga gctgtaacca atccggctgt ttctgtacct cacttctgtt    53700
ttctgtcctt caccttcctt tttctgtcta ttaatctttg accccgtggc tgtaccagag    53760
cctctctgga cgtattctgg ttcagggact gcccgatgtg cggatcattc tttgcttagt    53820
taacctctgt tagccaggtg cagtggctca cgtgtgtaat cccagcactt tgggaggctg    53880
aggcaggtgg aacacctgaa gtcaggagtt tgagaccatc ctggacaaca tggcaaaacc    53940
ctgtctctac taaaaataca aaattagcc gggcctggtc acatgtgcct gtagtcccag    54000
ctactcaaga gactgaggca tgagaatcgc ttgaacctgg gagacgggga ttgcagtgag    54060
ccgagattgt gccattgcac tccagcctgg gcgacagagc aagattctgt ctcaaacccc    54120
gccccccccg caaaaaacaa aaacctcag acacattaaa tttgctagag gttaatttgg    54180
cacaatctcg gctcactgca acctccgcct ccgaggttca agtgattctc gtgcctcagc    54240
ctcccgagta gctgggacta caggcacatg ccaccacgcc ggcttttttt tttaaattta    54300
cttatttttt attttagta gagacgggtt caccatgttg gccaggctgg tctcgaactc    54360
ctgacctcta gctagtgatc cacccgcttc agtttcccaa agtgctggga ttacaggtgt    54420
gagccaccgt gcccagcctt aatgtgtcta ctggttttct tttaacatga ctacctatcc    54480
atctgatctt acttcagatt cttgtgcgct gtgaaggtgg tgggatttct cagtgtgtgt    54540
gtgattgaga agtgccctca gggtggctag ctgggatggg ggtcagcccc aatggtccct    54600
ggggactgag gcccctcaag atcgctgccg cccaccaccc ctgtatagca ggcacttaag    54660
ctcaggccat ctggtatcag tggcctgttg ttctgcttcc caagacccct tcattaaga    54720
ggggagagta tcaggcagca ggtccttctg ctgcagacag ctccacagtg aacccagctg    54780
tgtcctggct ggagggagct gagaaaagag gggaccggag gcctcctcct ggccccttgc    54840
ccacgtgttc tggccagcgt caagtgatgc tgtgcataca gacccaagcc ctgtgcatag    54900
ccagcctgtc aaagcataag tggccgggcc tggcatggtg gtttacagct atggggagga    54960
accagtcctg ccctactgca gcattcagac aactccagca agctggcctc ggcccacttg    55020
aagacatcca tcaattggaa ggcatattgt tcattccatg aactggcctt atggggggcct    55080
aatcatcttg gctaactgga ccaattttgg taaattatcc ctcagcaggg caccatgggg    55140
ggacttcagc aggttctcta tccataatgg ttttggttgc ccgcctaact gcccgagatg    55200
cgggtggtcc cttcagctac ttcagcttca gcctgtgccc ttctgagtgt ggcaccatgg    55260
tggactcacc tctcgcgtct aagctcgggc ctcctgcctg cagaggtgcc tctggggtcc    55320
ttggtgctgg tcccaggttc tgtttctgca aggtcaagag agtcctgtca cgcaacacgg    55380
cccagatacc cactttgaca cccactgact atgtggcctt aaccgctctg accatccatt    55440
tcccctgatc tggctcctgc cacgtctcca gcaacctctc tcaacacccc actctgagtt    55500
cttccaggaa catccttcag gcattcactc actcattcat ttcttcaatc agtgataact    55560
gagcacctac tatgaacttg aggttggaaa acagcattt aacactgtac aaagtcaagt    55620
tacctctgtt tcccccaaca gccttgctca agcagttcct tgtgtctgga atgctctttt    55680
ctggctaact ctcacctacc ctcaggtacc atctcccccta ggaaggacac ctccccacca    55740
ctatccccca ggtgtggcca gtaactgaaa gcaaatctgt agtagtttaa ccacagacct    55800
gtaagcaaca agtaactgct actgtaagct gctaggattt gggggctat ttgttacaca    55860
gcatcatcac agcaaaagct gaccaacaca aacaggcaag ttctatcttc aagcttcagg    55920
```

```
actgtgacat tgtgaatcaa cacttaaggt tttaaccagg ttgggccagt gctaagcaga    55980
tgttctcaga agaagcaaag cctgagattg agggagacct ggatgtgaat ccttgctttg    56040
tcatgaaggg atagtgtaga gggtagcaat taaaaaacac attctctgga atcaagttgc    56100
ttgggttcaa atcccagtgc tgccacttac aagccatgta acctgggact agttccttaa    56160
cttctgggcc tcagtttcct catctgtgaa atggaaatga ttctagtacc agcctcacag    56220
gggcattatg ttgattaaat gagctaacct ctgtgatgtg ctgttagttg ctacttttca    56280
gtcattgtga gtgagcttgg cttggcaact ttacttccag aaccttgcca tgtatccagc    56340
acactgtttt tttggattat tagaaaccct agctagcatg gtgtagcttg ctaggcatca    56400
aagtccttct tgggctgtct ccatagcaac tgcaagcata gactctggag ctggacatac    56460
tcaagttcta atcttgtgac cttgggcaag tgatttaact ctctttgcct cagtttgctc    56520
atctgtaaaa tgacagcaat aacttcacat gcctctgggg catgtgtgag aatcaaatga    56580
aatagtgtat ttttttacaga agcacttagc acaacccctg gctcatggat gatgttatcg    56640
gctattcttg gagaaaggtg acctattaag agagctgtct gcttccaggc ctaggcctgc    56700
agacagggtg tggccagagc actccattca tgccagtagg acccttcgag cctttccccc    56760
caagggtggc aggagccagg cctggagaat cagcaaagcc cacctagtac ctccttctcc    56820
tctatctcct ggctgtctgg cttgatccag aagacacacg agggccccct tcctctgcag    56880
aagctcctgg taggaaccca tctctgcgat ggccccattt gccagcacta tgatccaatc    56940
agcctggggc aggatgtgga gtgcgtgcgt cacgagaatc cgtgtctggg cagggaaggg    57000
gtagaagtta cacacatgtg gccgggtgca gtggctcatg cctgtaatcc caacactttg    57060
ggaagccaaa gcatgtggat cacttgaggc cagaagttcg agaccagcct ggctgacacg    57120
gctaagccct atctctacta aaaatacaaa aattagctag gtgaggtggc gcacacctgt    57180
agtctcagct actttggagg ctaaggcaag agaatcactt aaacctggga ggtggagctt    57240
gcagtgaggc gagattggac cacagcactc catcctgggt gacagagcaa gactctgtca    57300
agaaaggaaa gaaagaaaga gaagaaaaga aagaagaaaa gaaagaaaac aaaggaagga    57360
aggaaagaga gagagagaga aagaaagaaa aaaaaatgt acggccgagc gcagtggctc    57420
atgcctgtaa tcccagcact ttgggaggcc gaggcagatg gatcacctga ggtcaggagt    57480
tcgagaccag cctggccaac atggtgaaac cctttctcta ctaaaaatac aaaaaattag    57540
ctgggcgtgg tggcgggcac ctgtagtccc agctactcgg gaggctgagg caggagaatg    57600
gcgtgaaccc gggagccgga gcttccagtg agcggagatc gcaccactgc cctccagact    57660
gaaagacaga gcgagactcc atctcaaaaa aaaagaaaa agaaaaaagt tacacacatg    57720
tgcttggcca gcctcctgag ctgggggttg gggtgggggt attgtccctg gactcagagt    57780
ggggacagct ccccttcttg tgctcctgcc gcctttcttg taaacagcat atccaaatag    57840
agaaacagag gggactccct tagcctgtgt ctcaaaacaa gaagacaagg agtacatctg    57900
accctggcca atcatccaag gcaaagctgt agtagttaaa tcacagatcc ataaggaaga    57960
aacacctgct gttgtaagct gctgggatct gggggttgtt tgttacatag cattgtcaca    58020
gcaaaagctg accaatacaa agaggaaatt ggactcaagt ggaaggggga ggtgagataa    58080
acttgggtta ggactggatg ctaagtgctt cctctgcctt tgccctgtac tgtctgacac    58140
atgttcccaa acttactgtt ccctggagta gccaccagg cccaatgacc tggttgaaga    58200
catgctggcc aacgtgggca tccagggccg ccaggggggt catccagcagg tacacagctg    58260
```

```
cctttctgta tacagcccgg gccaggctca gccgctgctt ctggcctccg gagagattca   58320
tgccctgtgg ccacaaaagg aacagtggcc tgagtcagca tctacagggt gaaactgggg   58380
tgcccaggct gtggcaggtc agggcacacc tgcccatcag ggtgaggtac agctcaacat   58440
gcctattccc tggggacagg cccagcttcc aaggcactcg ctctcaagcc aacaatgcct   58500
ccatccttac ccgacctcac ttctccactt cccaagcacg cttcctggag gagttaccta   58560
cacttcccaa tccactctgt ctcctcctgc tcactctctc tatctctttg agtccaactc   58620
ttgtttccct ttctccactg agaccaccat ccatttccct attccctcat ccagtggcag   58680
cttttcagtc ctacttttgt attttaaatt ttaattgttt tcttttagtt ttcattgata   58740
tgtaatagtt gtaactattc gaggggcaca agtggtattt ggatacctgt agggcagtgg   58800
tccccagcct ttttggcacc agggaccagt tttgtagaag acgattttc catgacctg    58860
ggggcagggg gatggtccgg gggatggttt caggacgatt caagcacatt acgttgattg   58920
tgcacttcta ttattattat tactgctgtt gtcgttgtta ttattgagat ggagttttgc   58980
tcttgtcacc caggctggga gtgcaatggc atgatcttga ctcactgcaa cctctgcctc   59040
ctgggttcaa gcaattctcc tgcctcagcc tcctgagtag ctggaattac aggcacccac   59100
taccacgcct ggctagtttc tgtatttta gtagagatgg ggtttcacca tggtggccag   59160
gctggtctcg aactcctgcc ctcaggtgat ccgcccacct tggcctccca aagtgctggg   59220
attacaggcg tgagccactg cgcccggcct acttgtatta ttattgcatt gtaatatata   59280
atgactcacc atcatgcagt atcagtggga gccctgagct tgttttcctg aaactagata   59340
gtcccttctg gggatgatgg gaggcagtga cagatcatca ggcattagat tctcataaga   59400
tccctcacat gtgcagttta cagtagggtt tgtgctccta tgagaatcta atgctgccac   59460
tgatctgaca ggaggtggag ctcaggcggt gatgggaaca ataaggaatg gctgtaaata   59520
cagatgaaac ctcactcgcc tgccctctgc ccacctcctg ctgtgctgcc tgcccagttc   59580
ctaacaggcc acagactggt gctgatccat ggcccggggg ttggggaccc ctgctgtaga   59640
caatatgtaa tgatcaaatc agggtaactg agatagtcat cacctcaaat atttatcttt   59700
tgtattgcga acacaaccat ccttctcttc tagctatctt gaaatataca agtaaatgat   59760
cattaactat aatttccctt gtgcactatt gattacttta acttattcct tctatctagg   59820
ccttcttgtc tttcattcat tcttttaaaa cttattttta tttattttg agatggagtt   59880
ccactctgac acccaggctg gagtgcaatg gcttgatctc ggctcactgc aacctctgcc   59940
tactgggttc aagcgattct cctgcctcag cctcccaagt agctgggatt acaggtacgc   60000
caccatgcct ggctaattt tgtattttta gtagagatgg ggcttcacca tgttggccag   60060
gctggtctca aactcctgac ctcaagcaac cctcccgcct tggcttccca aagtgctggg   60120
attacaggca tgagccaccg tacccagcca ttcattcatt cttacattca gtcattccac   60180
taataaccac tgcctcgtta tcataaacca ggcatggttc taggctctgg agaaacagca   60240
atgagcaaaa caaagttgct gctctcttaa tggatccatc attctcatga aggggacaga   60300
gacaggcaat ccataaacaa gtaaggcaga cagcacatca ggtggaaagt gctatgaaga   60360
ataaatagta aagcagggg agccaggttc aggggctcac gcctgtaatc ccagcacttt   60420
gggaggcgga gctgggtgga tcacttgagg tcagaagttc aagaccagcc tggccaacat   60480
ggtgaaaccc catctctact aaaagtacaa aaaaaatta gccagttgtg gtggtacatg   60540
gctgtaattc tagctactca tgaggctgag gtggaggat tgcttgaact actcatgagg   60600
ctgaggtggg aggaatgctt gaactcagga ggtggaggtt acagtgagcc aagattgtgc   60660
```

```
cactgcactc cagcctgggc aacagagcga gactccgtct cagaaaaaaa aaaaaaaaaa  60720
gagaaaaagc aggtgcaggt gtagggtgca ctaacaatag tagggtggct gtggtggtag  60780
ataaggtggt caggaaaggc ctctctgtga aggtgataga agtgagggat gagccctggg  60840
gactcctggg gagagctttc cagcagaggg aacagcagtg caaaggccct ggggccagag  60900
tgtgctgtgg gggatcaggg aatatcacag agactaaggt ggctgcagta aagctgagag  60960
gtgatgatgg gagatggggc taatggatac cagagccagg tcacagggac cttgccaggg  61020
attgtcatga cttgggcttt gtctctgagg taaatgggga gatcacctga ggtccggagt  61080
ttgagaccag cctggccaac atggtgaaac cctgtctcta ctaaaaatat aaaaattagc  61140
caggtatggt ggcatgtgcc tgtaattcca gctactcagg aggctgaggt gtgagaattg  61200
cttgaacgtg ggaggcggag gttgcagtga gccgagattg catcactgca tgccagcctg  61260
tgcaacagag caagactctg tctccaaaac aaaacaaaaa acaaaaccac aagtggtggg  61320
ctggatttgg cttggggtca cagtttgcca acccctgccc aatccatagc tccagatgca  61380
tatatcctgt ttcttggaca tctctgtcca gacccttggg tgaggcccag agaggggaag  61440
caattacacc aacattactc agcaaggcag ggcagagtaa gacaggagtc taggtcttct  61500
cactctcagt tgtcagagag ctcctcactg ccaatccctg ccacaactcc ctgcctctct  61560
ctttgtgtct atttctgctt atcaattagt gattacgtat tgagcaccta gcacgtgctt  61620
gacgctgagc tgagcccttt ttctccgcta cttccctaac cattcctctc atttctccat  61680
catactgccc atgatgagtc ggggacccaa atgactccca actgcaatgt ctccctgtcc  61740
caaaagacc cccaaactct cacctgctcc ccaattgaag tgtggattcc ctcagggaag  61800
ctgtccacat ctggctgcag ggcacaggct tctagtactc tctccagcca gggtgggtcc  61860
agctcctgcc cgaagcacac attctctacc acagaggtgt tctgcaccca ggcctcctgg  61920
ggcacgtagg ccacagcacc ctaaaacaca acttactttg gtcacaggag gatgatgggg  61980
acagaggtgg gataggtttt gaggagcagt gggagctggg ctctcagtgg tgggtgagag  62040
gtggagagaa tgagtgaaag tgaacttggc tgggatgggg agggtgggaa ggcagcgagg  62100
aagtgggact ttcaggatgg ggacatccta gcagacaggc tgggggtggc ctcacctcga  62160
tgctcacgaa ccccctccacc tttgacagct ccccaaggag ggcggacagc agggaggact  62220
tccctgcccc cactggaccg acaacagcca gcagacagcc ctggggcacc gtgaggttta  62280
ttctggacac gcaagagggg agacatgacc ttggttaggg ttcagcccgc ctctgtgagg  62340
aaggatgagc cccagacgga gctgagcttt cctgctctgg gagtctccaa gaggacctgt  62400
ggggctgttc ttttttcccag tccttgtcta gctatttgag gaactatcct gtgcacatct  62460
gtgcatgtac acatgcacac aaagcgtgca cacatgcatg cacatttgca cactcataca  62520
agcatgctag catgcacagc aacacaatgt gggcacgcat ccacacacac acaagtgcat  62580
gcacatacccc aatcaatcca tgctcacacg catacatgtg tgcacacatg cacaccacgc  62640
acacacacac agggttgact atagcctgag ggtttcacca gcctggcctc ctgccttggc  62700
tcttgcgata aataggctct ttcctccctc cctcccgcta ctcttggtcc cgccccactc  62760
ctgtccacgt cccacagccc atcctccacc cagtgaccag agggatctgt taaaacccaa  62820
gtcagatcgt gacacttccc agctaaaccc gccagcactc ccatttcact cagggtcaaa  62880
gctaaagtcc tgacgatcag gaatgacatc tcccgcctcc ttccgctctg tgcctcagct  62940
gctcggcccct ggccttgctg acctccttgc tgtttcttga acacaaaagg ccagtggttc  63000
```

-continued

```
tcaccagggg gtgactgcat cccccaggag tcatttggca agatctagag atattttggg   63060
atgtcacaac cagtaggggg tgctgctggc atcagtggg tagagactgg ggtcagctaa    63120
acatcccaca atgcacacga cagcccccaa caaaggagtt tcagcccaaa atatcaacca   63180
tgctgaggtt gagaaaccca ggtccaggca ctctcctgcc ccaggacctt tgctgatgcc   63240
attcccaccg cctagaaggt tcttctccca ggccgggcac ggtggctcat gcctgtaatc   63300
ctagtccttt gggaactgag gcaggtggat cacttgaggt caggagttgg agaccagcct   63360
gacgaacatg gtaaaaccca tctctactaa aaatacaaaa attagctggg tgtggtagca   63420
tgcgcctgta atcccagcta ctcgggaggc tgaggcagga gaattgcttg aatccggaag   63480
gtggaggttg cagtgagccg agatcatgcc attgcactcc agcccgcgtg atagagcaag   63540
actccgtttc aaaaaaaaaa aaaaaaaaa aaaaaaaga acagctcttc tcccagacac    63600
tccttcctta tgatctcggc ttgaatgcaa agccttccct cgctagacat gccatcgtac   63660
tctgttccct tgctctggtt ttctgtttgg gcctcacctc tatcagcatg tcaccccacg   63720
agagcagggc ccttgtctgt ttccttcgcc ctatccccaa tacctagaac agagcgtggc   63780
ccatacctag tgctctatcg atgaagtgag tgaatgacaa ccaatacaaa tactacctgg   63840
ggcatattcc ttctcttctt agggagtttc agggctgtct gagattttttg gccacaaaga   63900 ccaagcgata gagttggaga ctatagatga tcatgacctc ggactgatac aggaggcaca   63960
gaagtgagca cagctgatag ggctgaacct tggggctcct ctcagccagc cctcccttgg   64020
catcgtcttg gccagcctgg gagcacaggg gtgtctcccc ctaatggggg aggctcagat   64080
gccctggtcc ccgtctgcag gagatactgg tctatgctgt gcaggtcccc accttcagga   64140
ggtagagatg tatcctgaga acctccccgg cagagcccca gcccagccaa acccacccctc   64200 cagtcccagg ctggaaacct acaccacctc tcaggtggga ggcagcagga gccccatgca   64260
tcttctccct aaaacatga ggctggttac tacgggtgtc gttctgtacc tgtggaggca   64320
gggagggctt tcctgggacc aggcgaaggt ggcactgtgt atggtgatgc aatccttccc   64380
ggcagctgca gggcacaaga ggccatttac aggagacccc tgacctggcc ggcctctgca   64440
tcggagaggc ccccaggcac catcccccgc ccccccagg ggcagaggct gcaggaagaa   64500
atctctccca ctgaacaaat tgccctgcta ctcactggct tgtgggtgac cccgcagggt   64560
tcttgttctg tccgtgtccc atggctacat aatccagggg gaggcaaact gtggcccaga   64620
gaccaaatcc tgcctgctgc ctttttcttat aaataaagtt ttattggaac acggccacat   64680
ccattcattt ctctatttca tgctttgagc agttgtgaca gagactgtgt ggcccacagg   64740
cctaaaatat gcacaatctg gtcatttatg gaaaaagtta gtgaatttct gaaataaatt   64800
atcatcaaat cccagccttc ccagagtgaa ggggggtgtta ttaatttcac tgtggccggc   64860
acagtgtctc atgcctgtaa tcccagcact ttaggaagca gaggtggtag gatcacttga   64920
ggtcaggagt ttgagaccag cctggccaac atggcaaaac cctgcctcta ccaaaaaata   64980
caaaaattag ccaggcgtgg tggtgggcgc ctgtaatcac agctacttga gaggctaagg   65040
caggagaatt gcttgaaccc aggaggcgga ggttgcagag aaccaagatt gcaccactgc   65100
actccagcct ggatgacgga gtaagactgt gtctcaaaaa tactactgct actactacta   65160
attattatta ttatttcact gtgataacaa gtgtaattag attagtggtt cttgatcctt   65220
aagacgtagt tagaattgcc tgaaagattt tctaaaaatc aaagctctca tggcttagcc   65280
cagatcaatt aaattcatcg tcacaattag ctgctataac gattaacatg cccatttggg   65340
agatgggaac acggaagctc agagagatga tctacttgtc aggatcaccc agctagtcag   65400
```

-continued

```
tgctggggct gggatttgga cctgggcagt tgaatgccac aggctcggct tcttaccact   65460
atgtgggtgt tttccaggta cacagtttgc ccaggttctt cagtgcaaca agggggaggg   65520
tgtcttggcc cgtggcataa agaaggatg gggtggaggg ggaagcccag gtaacttgag    65580
cttggtaagt ctcatcgtgc aatggtgctt gaaatgctgc tattttccag cttgatcaaa   65640
atgctgtcat gcttattacc tgggactttc tgcatgagga caaggacctg gtctgttaga   65700
gcaggagtcc tcaaccccca ggccacagac tggtaccagt ctgcagcctc ttaggaactg   65760
ggccatacag caggaggtga cgcagggca ggtgagcaga gtgtcatctg tgtttatagc    65820
cactccccat cactcccatc accgcctgag ctccacctcc tgccaaatca gcagcagcaa   65880
tagattctca aaggagcacg aacacttgtg aactgtgcat gtgaggaatc tgggttgcgt   65940
gttccttata agaatctaat gcctgatgat ctctgtctcc catcacccgc tttggggcca   66000
tctagttgac ggaaagcaag ctcagggctc ccactggttc tacgttatgg tgagttgtat   66060
aattatttca ttatatagta caatgtaata ataataaagg gcacaataaa tggaatgtgt   66120
ttgaatcatc ccaaaccac gcgcctctcc ccggtccgtg ggaaaactgt cttccacaaa    66180
accagtccct ggtgccaaaa agcttgggga ccactgtgtt agagtgttcc ctgttgtaca   66240
cccaggatgg tacaaagtgg gcgctcagtc agtggtcgct gaatggctag cagaaagaag   66300
agcagcacgg tgccagtttc caagtgacac gcagatggcg tgatctgcac gtgtcatcca   66360
ttgcccgcag cccccatctc cccccagtac tgatgctggc ttgccattat gggccggggt   66420
ggcccccaca tcccccatcc ctcccacacc cctcctgcca gactcagcac tcaccgcttc   66480
cagaggaact tgagtctacg acaccagggt caacttcttc caggcagagg aaggtgacca   66540
gacggtcaaa ggacacccgg gcctaggaaa accgaagccg caggtcaccc agcaagaaga   66600
gcaaagaact caggttttgg gtgtcggtgt ctcaagatgt gtggcaacag cttcctgtct   66660
accaagctct gtgcatagga ggcgtgagga caaagctttc tagttcatgg gaaacgatgc   66720
aacccgagtg gtgaccttga tggtggtgat ctcccacctc tgcgatccta caaatcagtg   66780
acaccgaagc aagccagctg ccattctgca gacaagatct gggaagagga tggtggcttt   66840
tccaataagg ttatcaagcc attgtgtgga acaatttcaa atgttgtcca cctggggggcg   66900
ctctctccca gtcacaaacc catctttggg gaagaaagag accagtcgtt aaaatagaga   66960
ttaggccagg tgcagcggct catgccggta atcccagcac tttgggaagc caagtgcagg   67020
aggatcactt gaggccagga gttggagacc tggggaacat agcaagactc tttgtttcta   67080
caaaaaatta aaaaaattag ccggatgtgg tggcccatgc ctgtagtccc agctactcag   67140
gaggctggga ggtagaagca tcacttgagt ccaggagttt gagcatgcag tgagctgaga   67200
tcgtgccact gcactccagc ctgggtgaca gagtgagaca ctgtctcaat aaataaatta   67260
aataaataaa taaataaata aataaataaa taaataaggc ggccaggcgc ggtggctcat   67320
gcctgtaatc ctagcacttt gggaggctga ggcgggctta ttacatgagg tcggggttc    67380
aagaccagcc tggcctggcc aacatggtga accctgtct ctactaaaaa cacaataaat    67440
aaataaataa gactgggtgc agtggctcat gtctgtaatc agcactttgg gaggccaagg   67500
tgggcagatc acctgaggtc agcggttcaa gacctgcctg ccaacatgg tgaaatctca    67560
tctctactaa aaatacaaaa aaaaaaaaaa aaattagctg gcatggttg tgcatgcctg    67620
tggtcccagc tacttggcag gctgggcag gagaatcact tgaatctgcg aggtagatct    67680
tgcagtgagc cgagattgca ccactgcact ccagcctggg tgacagagtg agactccatc   67740
```

```
tcaaataaat aaataaataa aaataaaaaa taaaaaacat ggagatggct caggtatgcc   67800
gccgtttctt gttttcacca tgctgaaagg actagagata gcaaaggaag agaaacaaaa   67860
tcgctttgta taaaaaggg aactgacatg attgcttgta tgtggaattg ctgggcagat    67920
ggacaagtat gcatgttctg aggtgtgtgt ggaaaggtct gcacattgcc ctccaaaggc   67980
tgacccttc cagatgtatt tgctgtactc tctgcccgcc tctgttcttg ccctacccg     68040
cctcttttcc agctccacac catccctctc cctcccactc tgtcttccct ctcctctgca   68100
aatggcaggg gtagggaagc tggagccagg tgtagcccac gcactctccc aggatggctc   68160
cagcccttgc acccacctca cctggacgag ggagtggatg gagaagggca ggaaagcctg   68220
ggccttgttg aggatgttga gaactgtgag agtcacaaag gctttctctg cattcatagc   68280
attctcggcc accagagtgt ggacagcaaa caccaccagt gcgacctggg gggtgggggg   68340
gacacgtggg gcaacagtga gacacgcaag catggatagg gcagcctggg caagctgtgg   68400
tgcctgcacg gtccatgtgg cccacccgcc atgtccgcat gtgcttccct ccgtagatcc   68460
cactcccagt cctgctaaca catgtcctct ccgcagtcat aagctacata aggctctctc   68520
taaagacaca gcgcattgct aatggtgatg agtgcgcagc cccacggctc taggcatcac   68580
tagaacctag gggagaacct aatgcctcta ggttccaggc atcgggggac agcagagttt   68640
ttgatcttgg tagccctgtt gttctagacg tggtggaact tgtgattcta gagtcccttg   68700
gaagatgact ctaaagttgc aggcaggagc agcacttgag ggctctaggt gttggtgcca   68760
tttgtggtgc tttttttttt tttttgaga tgaagtcttg ctctgtcgcc caggctggag   68820
tacagtggca tgatctcggc tcactgcaac ctctgcctcc tgggttcaag tgattctcct   68880
gcctcagact cccaagtagc tgggattaca ggcgcccgcc actgcaacca gctaattttt   68940
gtatttttag tagagacagg gtttcgccat gttggccagg ctggtcttga actcctgacc   69000
tcaggtgatc cacccacctc ggcctcccaa agtattggga cgacaggcat gagccaccac   69060
acccagccta cgtatcaaat tttttaaaac tgtggtttag gaaggttgtt ctgacagcaa   69120
tatgaaataa attacagaat ggcaggacaa ggatcacgtc cagtgacagg gtggctatgg   69180
acatctgctg gccaggatca gggaagtcac tctgacccag gattctacct ctgccacccc   69240
cctgcatctg taccctcctc cccacatcgg tagaagcctg gaactctctc tgagagttca   69300
gcagactta tcagccactg ccaccttgc tagaataata tgattaatta gttcttgtag    69360
aagacagcag ggacccagag agaacaggat ccagaatgag tgggttttga tggacggggt   69420
ggtaggatct ggggggctcc acctacctca ccctgccccc accccgcac tccttcccca   69480
gtgctgctca gcatagagac tagagtgacg tcaccagaaa tgtagacact tggaaggaca   69540
ccagcgacac agagaagagg aggccggagg tccgcaaggc gcccagctcc tggcctcgga   69600
tgcccaggac tctgtccaga aaggctccct cccagccatg gaacttgatg gtcttcgagt   69660
tcctgaggat agagctggtg agccgtgccc gtgagtcctt ctgcctcatt tgctcctcct   69720
gggatcggag ggaaaagag agatgaagac agggacagtt gagaattctt ccctgcaccc    69780
tgacagccac ccttcagcaa atcccattca tctcaccaaa ctgcgtccca aacctgtctg   69840
cctctcagca cctctgaccc tcactcctgg tccaaccacc atcatcctgt acctggactt   69900
ctgcaggagt gcccctggga taatgtgccc cacggaggaa gcctctgatg cccggagaac   69960
agaggcagcc tgagcccacc tgggtatgac accatcagga aggctacctg gaggtggttg   70020
atgcctgagc tacgtctttt ttttttttta ccttttacat ttttttgtgga gttggggtct   70080
cactatgttg cccaggttgg cctcgagctc ctgggctcaa gtgatcctct gccctcagcc   70140
```

-continued

```
tcctaaaatg ctgggattac agcctgagct aaatcttaaa tgaccaggaa gtgcgtgctg    70200
agcaggcaga ggatgggggg atggagctgg agaagaaggg aggggagggg cttgagatgg    70260 gggtggggggg tggggctgg ggggtagggg ggtggcgggg gcagctaaaa cccaggcaca    70320
gggaatagca tgactcagag gacactcagt gtgaccagag gaccgtgtgg gcagggtcac    70380
ttggcacttt aaagtcaggc agaagaattc agggtctctt gtgcttcacc atggggcggg    70440
ggcatcatca gagggcagc tgcctggaga aggttttact ttttgagacc gagtcttcct     70500
ctgtcgccca ggctggagtg cagtggtgtg gtctcggctc actgtaacct ccgcctcctg    70560
ggttcaagcg attctcctgc ctgagcctcc cgagtagctg ggattacagg cgcccgccac    70620
cacgcccggc taaattttat atttttttgtg gaggcagggt tatgccatgt tggccaggct   70680
ggttttgaac tcctgacctc aggtgatctg cctgcctcgg cctcccaaag tgctgggatt    70740
acaggtgtgg cctcccaaag tgctgggatt acaggtgtca gccactgtgc ccagcctaga   70800
atgttttaga ggagtccacg caggaggctg aagaaacagc ccaggtgaca gacggacact    70860
gggacagctg ggccaagaga ggaaataagt tccttccctc catccccat ctctccctct     70920 ctctttcccg ccttttcttt ccttccttcc ctatctcctt tcttcctctt tcctttgctt    70980 tcttcccctct ttcatttcct tccctcccctc ccccctttct tccttctctc cctcattcct  71040
tctcttcctc cctcaattct ttccttccct ccttccctct gtccttcctc ccctttccta   71100
tctttccttc cctccctcct ttttctcct tccctcccct tcttcctctc ctccttttcct   71160 tcttccctcc ctcctttctt ccatagttca caaacactta ctgagaacct tctgcctgcc   71220
aagcactaac tagatgccga gttggccaca atcagtggcc tgtgctgttg caaagcttcc   71280
agttaaggaa aacaaggcaa tcaaccctgc cgggtgcttc ctgtaggacc ctgtatgttg    71340
tgggaagtgc tgtggggggga aaaaagcaaa aacaatccca gggcaggcaa aggagaggct  71400
gctgctggga ggggagggat ggacgtgcca tttccttgct ggagggtggt gagggaagcc    71460
gccctgactg cagggaggtg acagaggatc ttcgggagtg agggtgatcc aggtggaggg    71520
aacagctaaa gcgaaggcct gcaggatgt gtgagatcgg gcaggtttga ggatgggaga    71580
tgtgtgggga aaggcaggga aggagggggag atgggtagaa ggtgaggttg gaagcaataa   71640
ggccagctca gggcgggcct ggtggccac tgtggggtct ttggctcagt ctgaggaaaa    71700
tggggccgct gtgggtctga gtagaggagg ggtacaacgt atttggtttg cataggtctc    71760
ctctggctgg gagtggagag aggctgaggg cagaggcggg gagtgagcca ggggcttgct    71820
gctgtgacct gggttagaga tcatggggtt tggagagcct atgctgggaa gtgtgacatt    71880
ttggatgcat tttgaaggtg atgccaagca aatctgctga cagatgggat gtgagagaaa   71940
aaggcattga actgacccag ggcctgtggc ctgaacattg gagggacgga gccactgtcc   72000
attgagagga taggggagg gggtgcaggt ctgagtgatg ggcagctcac agacgacaag    72060
aacaaagcca gacccgtggg ctcgcactca gctctcccct ccccatctcc cacaccagga   72120
cctgtggctt cctccctact tcctgcctgg tccgtccctt tcccaaaagc caaacctgat    72180
ggtggttcct tttcttggag atgaagaaat tcagagggag gaggctcagg aagacagcga    72240
tggcagtgag ggcggagggc cccaggagct gggggatagaa ggggcaggat gtcaggagat   72300
cccgaggagc ccagctctca gaggcacgtg aaccagagca actccatctt gaatagggac    72360
tgggtaaaat gaggctgaga cctactgggc tgcattccca gacggttagg gtattgtaag   72420
tcacaggatg agataggagg tcggcacaag atacaggtca caaagacctt cctgataaaa   72480
```

-continued

```
caggttgcag taaagaaggc ggccaaatcc caccaaaacc aagatggcta cgagagtgac    72540
ctcccgtcat cctcactgct acactccacc agcgccatga cagtttacaa atgccatggc    72600
aacatcagga agttaccata tatggtctaa gaaggaaagg catgaataat ccaccccttg    72660
tttagcatat catcaagaaa taaccataaa atgggcaac cagcagccct ctgggttgct     72720
ctctctatgg agtagccatt cttttagatc tttactttac taaaaaactt gcttttggcc    72780
gggcacggtg gatcatgcct gtaataccag cactttggga ggccgaggc gggcagatca     72840 cctgaggtca ggagtttgag accagcctgg ccaacatagt gaaacacagt ctctactaaa    72900
aatataaaaa ctatccaggt gtggtggtgg gcacctgtga tcccagctac tcgagaggct    72960
gaggcaggag aatagcttga acccaggagg cggagcttac agtgagccac gatcgcacca    73020
ctgcactcca gcctgggtgg cagagtgaga ctccgtctca aaaaacaaac aaacaaacac    73080
ttgctttcac tttatggact cgccctgaat tctttcttgc acgagatcca agaaccctct    73140
tttgggatct ggatcaggac ccctttctg taacacagct gcagacccg aaggtggtca      73200 gacttgggtc ctaagatggg gatgtcaggg aatctgataa gggcagccac caggtcccag    73260
ggatctgtgc tcatgggtc tgctgtgtca ggagatgcct gctgaaggtg gggtccttca     73320
atgtcaggga gggaaacagc cctcttacac gatagggaga gagttatatt caagacagat    73380
tgtgcacaca cacgagtggg actgggggt gttcccagcc acaacagtaa agttgagacc     73440
tatggaatca ggggacctgg ttcaaatcct gaccctgaga gttttgagtg tggccttggg    73500
gcaagtcatc tcccttaggt gcaattctct tgtctgcaaa atgggaatag agttgttctc    73560
atttggcatt ttctcttatt gcgtttaatt attttcctaa tcttcatttc atccctcgca    73620
agggttgtca gatttagtaa atcatcatac agaatgccca gttacatttg aagataaaga    73680
gtgaataagg ttttagtcta agtctcgtga aatatttggg acatacactg agaaattctt    73740
ccgtttgtct gaaactcaca cttcactgaa tgtcctgtgt tttctctggc aaccctgctc    73800
ccccaccaac gtggtgattt tgggatggtt atcttccccc tctcagcttt ggtttctata    73860
tctggaaaat gtggaagtgg ggggtagaat aaatgatttt taagttgctg tgactttctg    73920
agatttctgc acaggttatt tggacccatt ctcttgacaa gccccacccc aactccagtc    73980
tgtgtgcctc agtttcccgt ctcagtcctt aggaacacta tgtttattta tttatttatt    74040
tgtttgttta ttttgagatg gattcttgtt ctgtgaccca ggctggagtg cagtctcatg    74100
atcttggctc actgcaacct ctgcttccca agcgattctc ctgtctcagc ctcctgagta    74160
gctgggatta caggcatgtg tcactcggct aattttgta tttttagtag agatgggtt      74220 tcaccacgtt gcccaggctg gtctcgaact cctggcctca agtgatccac ccacctcagc    74280
ctcccaaagt gctgatatta caggtttgag ccaccccacc tggcctggga acactatttt    74340
ctaacattgg gccagtttgt ttcatttatg cggcaatggc gctacctagt ggctcaatgg    74400
agaagggcgc agagggtaaa caccagccca cagcagggct tggaaaaaca ctcaaggaat    74460
gtgagcagaa gatgaacatc tctgtctggg ggaaaaatgg tatcattaaa ctgtagcaac    74520
ctcagtgtcc actcctcctt caccaagacc tcacggtgat gttaggaact gtctaccaag    74580
aggcaggtaa agtacacaag caaagtaaca tggtgcatta tctatggata tcttgttggt    74640
ctcatctaat ttttttttt tttttttttt tttttttaga aggagtctca ctctgtcgtc      74700
caggctgcag tgcagtgatg tgatctcagc tcactgcaac ctccacctcc cgggttcaag    74760
tgattctcct gcctcagcct ctctagtagc tgggattaca ggcacatgcc accatgcccg    74820 gctaatttt atattttcag tagagacagg gttttgccat gttggccagg ctggtcttga    74880
```

```
actcctgacc tcaagtgttc tgccggcctt cacctcccaa agtgctggga ttacaggcgt   74940
gagccaccgt gccccgcctg gtctcatctg attttttagca acggtggggt caacctgatc   75000
aattgccctg aattttccca cgttcttcct ctctccctct ctttcttcct aatgatgaca   75060
tttatgtact gcacatgaag ccctgtctga gtgccttatg ttgtaattgc taagcacctg   75120
cctattgttt gcaaggccct ggaatacaag gtgaagacac tggaaaaagt cctggcccct   75180
agccctagca aaacaatca tatgcatgag cattcgagtt ttttttggaa tattcagcaa   75240
ttacaatcaa aatgccatta acagttttta caaggccagg cacagtggct catgcccgta   75300
atcccagcac tttgggaggc tgaggtgggc agatcacctg aggtcaggag ttcaggacca   75360
gcccagccaa catggtgaaa cccagttct actaaaaata caaaaattag ccagatgtcg   75420
tggtgcacgc ctgtaatccc agctactcag gaggctgagg ctggataatt gcttgaacct   75480
gggaggtgga ggttgcagtg agccgaagtt gtgccattgc accaaagcct gggcaacaca   75540
gtgagactct gtctcaaaaa aaaaaaaaa atcaaaagga tactatttca cgacatatga   75600
aaatgatatg cacttcaaat gtcagcatcc ataaatagag ttttattgga ggaataccat   75660
gcctgtttgc ttagtatggt ctacagccac ttctgcactc caagggcaga gatgaatatt   75720
tgcaggagag gtggtgtggc ctccagtgta aaaagcatct actgtcttat cctttatgga   75780
aaagtaacta atgataatat tacaaatacc tacagggtac agttgtgtgc ctggcaccct   75840
tttaagtgct ttctacatat gggctcgttt aatgcctcag cccctctggg gcaggagtgc   75900
tactgttaat tatgatcctc acgttggaga caagaacagg aggcacagag agtagggt   75960 ccttgcacac agattcacaa ctgataagtg gtcagaagga ggatttgagc ctaggcagtt   76020
cccgatacag agtctaattt tatttttact tttatttatt tgttggagac agagtctcac   76080
tctgtcaccc aggctggagt gcagtggcat tatctcagct cactgcaact tccacctcca   76140
aggctcaagc gattctcctg cctcagcctc ctgagtggat ggggttatag cacccacca   76200 ctatgcccgg ctaattttg tatctttcag tagagacggg gttggccagg ctggtctgga   76260
actcctggcc tcaagtgatc cacctacctc acccccaaa ttgctgagat tataggcatg   76320
agccactgtg cctggcccag agtctgattt taattttaaa aagaaaatc ctataccaca   76380 acgttaaagg aatgaagttg gaaagtaaat gttttgtttg ttttgtttgg ttgtttcctg   76440
atggctactt tgtgtttttt gaacactaag tagcaatttt tccccctaaa atgttctcct   76500
cttgtgtttt gtggacagtg gctatggtgg tgcctcaggg ttactggtaa cttcaaaaca   76560
tggttaactt gcctactggg taccctaata gcacatgggg aagtatcaac gtcatcatca   76620
tcatctttct acagaggaaa ctgaggccca gagagggtga acttcctgcc caaggtcaag   76680
tgaaggtcat ccttattgag gacttttccc atcgtatcag acaatagtag gcaaattgag   76740
acaggattgg aggaggagga gaaggaggag atggggtgg aagggaggag gaaaaggag   76800 gagaggaaga agaaagggaa gagaaggaga gggaagagca gagggaagag agggaggacg   76860
gtagaggaga agaagggaga agggaagaag tgggagggaa gatgacaggg agcagaaagg   76920
aagaagaagg tggagcagga gagaggaaga ggaggaggag ggggaaggag gaaaaggaag   76980
gggtgcagga agaggagggg gtgcgtgggc agaaggtggg agagatgcag gaggagggag   77040
ggtgcaggga ggggtgcaag aggaggaggg caggaggagg aggctgggc agagggagag   77100 gggaggaagc cttatgagct tctacaccag gaatggaatc cagggtgatg aaggcagaac   77160
aagggtaaaa cctttcatgt gcctctctga caccaacctg gttctcccac agcctcagac   77220
```

```
ttgccctaac cctggggtca cagcggacct cttccagcct cttgaatgct aagtcaggag  77280
gaggaagggt gggagggggga aggacgaggg ggagaaggag ggggtggggg actccgttca  77340
aatcccgtct tcctcctctg gcatacctgc cagagataga cgaagcagac cacgatccag  77400
acgagaggca gccacagccc gttgaggtag aggacgctct cggtcagccg ctgcacgtcc  77460
acggacacca gattgaccac atcacccacc gcactggcct ttctggagcc gctggacaga  77520
gccaggacct ggcgggtggg cagaaggaga gaagtaaagt ggggaggccg gggcagaggg  77580
atgccccagg tggcttctcc acccactgag ccccacctca cacgtctgcg aggtgggtga  77640
gtaaagtctc ttaggccaac ctctcaggc tctttgagga tccacagaga tgacaaaaat  77700
gaaaatcctc caagatccct aaagcacggg aggcataata atgaataaca tgcacgaaaa  77760
caccagatta acacagataa cggtggtcat ctgcccagtg ctcaccatgt cgcaggcact  77820
gtgctaaatg aacagcctta tccttcccg gggtgctcac agccatgaat ggtaccaagc  77880
aggcactacc atattcattc cctctaatgc caggccaggt gcagtggcct ctgcctgtaa  77940
tcccgccact ctgggaggct gaggtgggag gattgcttga tcccaggagt tcgaaaccag  78000
cccgcgcgac atagtaagac ccaagctcta caaaatactt taaaaaatta gccagggggc  78060
cgggtgcggt gcctcacgtc tataatccca gcactttggg aggccgaggt ggacagatca  78120
cctgaggtca ggaggtggag accagcctgg ccaacatggt gaaacccgt ctctaccaaa  78180
aatacaaaaa ttagccgggc atggtggcag gcacctgtaa tcccagctac ttgggaggct  78240
gaggcaagag aatcgcttaa acccaggagg cagaggttgc agtgagccca gatcaagcca  78300
ttgcattcca gtctgggcaa caagagcaaa atccatttcg gggggaaaa aagaaaaaat  78360
tagccaggca tggttgtggt gcgcctgtgg tcctagctag ctactgggga ggctgaggtg  78420
ggaggattaa ttgagtacag gaggttgagg ctgcagtgag ccatgttggt gccactgcac  78480
tctagcctgg gcaacagagc aagaccctgt ctttaaaaaa aattctatgg ataaattgct  78540
ctctattatt ctctcaccaa ggaaaatacc acttccagtt aaattaagac atgtaagaga  78600
catctcgatt ttggaagtat tagagtgaaa aaaaaatgtg agacgagaat caatgaaatg  78660
aacatttact aaccccattc tatggctaaa gaaactgagg cagagagaag ttgagcaact  78720
tgcccaaagt cacaggcctt gtaagctcct acacaaggaa tggaatccag ggtgacgaag  78780
gcatgacaag ggtgagacct ttcatgtgct tctgtgacac caacctggtt ctctggcagc  78840
ctcacatctg ccttaaccct ggggtcacag tggacctctt ccagcctgtt gaatgctaaa  78900
ttccaaatgc agccctccct ttgtgactgc gtgagggtgt gaagaagtga tccaggaatg  78960
actggacata gaaattctcc acttagcaag tctttgaaga gtgctcactg tgtgactcac  79020
actgagctgg gaactgaaaa tacagctgtg aacaacagat gtgaggcttg ctctcccggg  79080
cctggagttt gaggtgggga acaaggctct ataataaaga tttatataac tggccgggca  79140
cagtggctca cacctgtaat cccagcactt tgggaggctg aggcgggtgg attgcttgag  79200
gccgggagtt cgagatcagc ctggccaata tggcaaaacc ccatctctag taaaaataca  79260
aaaattaact gggcatgctg gtgggcacct gtaatcccag ctatttggga gggtgaggca  79320
ggacaattgc ttgaacccag gaggcagagg ttgcagtgag ccaagattgc accgctgcac  79380
tacagcctgg gtgacagagt gagactctgt ctcaaaaaaa taagacaaaa caaaatatt  79440
tctaaaactc atgctttaat ggcagttatg atgagtaaca taaaaagta gcccaggctg  79500
agcgcgttgg ctcatgtctg taatcccagc actttgggag gctgaggtgg gtggatcacc  79560
tgaggtcagg agttcgatac cagcttggcc aacatggtaa aaccctgtct actaaaaata  79620
```

```
caaaattagc cgggcatggt ggcgcacacc tgtaatccca gctactcagg aagctgagac    79680
aggagaatca cttgaaccca gggggcggag gttgtagtga gccgggactg tgccactgca    79740
ctccagcctg ggcaacaaga gcgaaactct gtcagaaaaa aaaaaaaaaa aaaaagccca    79800
gaggttagag aggagggatc tgatctcatc aggagatcaa agaaggcctc ctggcgtgtg    79860 ggtgtgggaat aggaagatca atgcctgctc accaggcggc cttcctctta ggctcaagga   79920
aatgtggact ctcaagacag gatagggcac acctagctct ggcatgctca ggggaacagg    79980
agcctgggat gcagcactct ggcaggaaag catcaagagc tgccctctcg gccacctagg    80040
agctgtcccc tctgtcccct cctcccctag gtgacagctc aggtgtcagg gaatgacact    80100
tacatgggac gggacctgcc ctggctcaga tgctccatac cccacaggag ccaatagctc    80160
ttggggcagc agtccaggga cttagcttcc agagtcccag gaacggacaa gagccactgc    80220
acagagagaa gtctaaagct atggcctcca accaggtatt cacagtcaat ggacagaact    80280
tccagcccag atgcaatttg ggtttttttg ttttgttttt tttttgttct gagacgaggt    80340
ctcgctctct tacccaggct gcgctgtagt ggcgtgatct cagttcactg caacctccac    80400
ctcccgggtt caagcgattc tcctgtgtca gcttcccaag tagctggaat tacaggcaca    80460
tgccaccatg cctggctaat ttttgtattt ttagtagaga tggggtttcg ccatgttggc    80520
caggctggtc ttgaactcct gacctcaagt gatccgcctg tctcagcctc ccaaattgct    80580
ggaattacag gcgtgcacca ctgtgcccag cctaggggtc attttacc caagcagtat     80640 tgtctgggaa cacagctgac aggccacctt atcagaaggt taatccttta tcctcaaggg    80700
ggaatgagtg gaagttaaaa tcaggctcaa aaattaaaat tagattgggg gagtagaagt    80760
ggtgcctaga cagtgagaac agctgcaaag gccccaggg gggtgggggc ctggagtgtt     80820
tgaggaactg aaaggagacc tgtgtggctg gaggagagtg agcatgggag gaggtgacgg    80880
gatgaggtca gagacaccct aggacagat cacacaagc cttacaggaa taactaagga     80940
gctgagacag atcacttgag gctaggagtt cgagaccagc ctgaccaaca tggcaaaacc    81000
ttgtctctac caaaaatata aaaattagct gggcgtggtg acacgtgtct atagtcccag    81060
ttactcagga ggctgaggca ggagaatcac ttgaacccgg gaggcggagg ttgcagtgag    81120
ccgagattgc accactgcac tccagcctgg gtgacagagc aagactccat ctcaaaaaaa    81180
taaatacata taatacagag aaataactaa ggaagtgaga atgtatggtg agtgactcta    81240
ataagcaagg actgaatgcg ttctcagctg ctgataacat tactgcccgc tcagtgatac    81300
tgcttttcct ggctgggaag acctgcccct gtcccccagg gctcaccttt ctgtacacca    81360
ggccagtgat ggccgaccgc aacctcatct gcagcacctt gagcctgtac atgttctgct    81420
gctcaaacag cgtttgcagg caggctgaga ggaacatcag cacggcgagg aggtagccct    81480
tccaggctgg aggcttggga tcaccaataa actccaggaa aaggcttgca ggggaaggag    81540
ggagaaggta cagctggtga gaggaggtgc ctaagggtgt tgcctttgcc caaaccagtc    81600
cagatgtgga ggatcagtcg gcccaaacta gtccaggtgt ggaggatcag tcagtgtggt    81660 ttttttttgca ataatggtct ccgttatttc ccccactgtc catactcctt ttcaatctga   81720
ctgcagctcc tcaagatcaa gaggtggagt ttttgttccc acttgttata ggctaaattg    81780
tgtcctcaca aagtttatat gttgaagccc cgaccccag tacctctgaa tgtgactgta     81840
tttggaaata gggcctttaa agaggcaatg aagttaaaaa tgaggtcatt aggctgggcc    81900
ctaatccaat ctgactgggg tccttttaag aagaggaaat gtagacacac aaggagacac    81960
```

```
caggggcgc aaacagaaga aagaccatat ggggacacag ggaggaggtg gccaactgca    82020
agccaaggac agaggcctca gatggaacca ccttgcagat actaatctcg aacttccagc    82080
tttgagaatc atgataaaat acatttctgt tgttcaagcc actcagtctc agtctgtgat    82140
gctttgttat gtcagctgag cagacaccac ttgaatctgg gctggctaca aaaccggctt    82200
tggccaacag agtacagtgg aggtaaagcc atgctggctc tgagcctagg cctcaagaga    82260
aaatgtggtt tttggtctat ttcttagaac cctcccaagc acccacatga acaagtctga    82320
gctagccttt tggaggatgg ggacccacat ggagcagaga cagccatccc agtctcagat    82380
acacaactgc aggcacatga gaaacccag ccaagaaaag aaccaccacc cagctgagcc    82440
cagcccacat tactgaccca cattaccatg aactaaataa aagaatgttt gtcattttaa    82500
gccactcact tttgggcat tttacagcaa aaactaattg atgcagtcag gtaagagctt    82560
gcttatttgc ccttctgggg gtcagtcact ttctcattaa tccatttccc ttcctcagtg    82620
tccttctcac ccaccatcca gtgtcccgag caccagatgt ataggcagag gcaggagagc    82680
tgaagcccc tggccctgga aggatgccac taagagacca cccaccttag cagggcactt    82740
gaggtctggg actcacctga gcagcttggg gacagtgaac ctgaagacat cactgatgat    82800
gaggctgagg gtccccagga ggaaggtaga atggaacacc tgccagatgg ccttcagcag    82860
tgggcgccac tggctcccctt cttgccgtag aagggctcg gtctctggag ccttcatgcc    82920
actgccgcct ttccttttaa atgctattgc cttgttgtgc ctgagggaa gggagagatt    82980
agctctgggt cccatttat actctcagcc gccagcggca gggccaggca ttaaagggtt    83040
gttttcccaa cagtggagat gggtgggtgt ggatctagcc tggctccctc acctgttcct    83100
ccttatcacc ctgagtaccc acttaagagg caatcatggg agttgggggg cagggcagga    83160
gggcactctg aggcctctta gatggccatg ggaaagcaca cctgttgagc acctactatg    83220
tgccaggcac tccccagtca tcctaagacc ccctgagaag ccaggtgttg ttcccatttc    83280
acagatgaga aaactggggc tcagagaagc gaacttgccc aagggcacac agctgagaag    83340
taaaagaact ggaatttgat tccagctctc tgcctccaga gcccatgcac ttttcttttt    83400
tcttttcctt tttttttttt tgagacgaag tcttgctctg tcgcccaggc tggagtgcag    83460
tggtgtgatc tcagctcacg gcaacctcca cttcccagtt caagtgattg tcccacctca    83520
gcctctcgag tagctgggat tacaggcaag tgccaccata cccagctaat ttttgtattt    83580
tcagtagaga aggggttatg ccatgttggc caggttggtt ttgaactcct gacctgaggt    83640
gatctgctcg ccttggcctc ccaaagtgct gggattacag atgtgagcca ccacacctgg    83700
cctctcatgt acttttcaac ctatcgtgtt gtcaacctgg aggaagaaca gcaccccgtc    83760
cccaacacac acaatcatcc agcccttagg tggttttgaa ctggtggaga atcacggctg    83820
atgggcatgg ggcctggtgc tctagctctg ggtgaaagtg cagacagaag ctcaggctgc    83880
ctcaaactaa taagatcccc agcctttggc tataaccagg ggcacagag aagagctaag    83940
gtgagggagg gagaggagga gatgggggag gcccgagggc ccctgtgagg caggtcagaa    84000
gccctgggcc agaaaggaga ggctggggcg atgcagctgc tgacagtccg gttgctgtgt    84060
ggtcctgggc ggggacactg ctcctctctc tgtgtgtgag aggatgggtg tggtcccctg    84120
ctgagtcccc tgtggctctg acaacctata aggttatcag taatttcttt ttctttttct    84180
tttctttttt tttttttttt gagacagagt ttcgctcttg tcgcccaggc tggagtgcag    84240
tgtagcaatc tcggctcacc gcaacctctg cctcctgggt tcaagcaatt ctcctgcctc    84300
agcctcccaa gtagctggga ttacaggcac acaccaccat gcctggctaa tttttgtatt    84360
```

```
tttggtagag acagggtttc acaacgttag ccaggctggt cttaaactcc tgacctcagg    84420
tgatccacct gcctcggcct cccaaagtgc tgggattaca ggtgtgagcc accatgcccg    84480
gccacttatc agtaatttca atccccatta cagatctgtg acccgggcc acgtgctggg    84540
atcagctctt tacacgaagg agctcactga ctcccctgga tccccttgcc aggtgagcat    84600
tattaggttt tccattttac agaaggggaa gctgaggctc tgagagatgg cgacagccgc    84660
ccgaggtcac acagcaaggg cagagcaggg atttgagcct agatcttgat ttatggtttg    84720
taaagggttt cttgtgcact aaggaccccc aacctcacca taataaaata ataataaaaa    84780
aagaagcata agaaaaacct ctggtgagct caggtggcca gacccttcaa ggccaaggtc    84840
tctgtcccac attattggtc tgatctggtg tttggtttgg catctatgga gggttgtggt    84900
tcagctctgt tactgagtgg gtgtggcctg ctgctcacaa atattttggc atttggatct    84960
caaagccaag aagatgcccc ttccatacag agagcatccc tgcccaccct ttcctgtttg    85020
atcctgccat ttaattcatt gccttcacag ccatgtccat ggctccaacc ctctctttgt    85080
ctcgttagaa ccccaggtgg gtagactttg cctgtgtttt ccaccaagat gtccctagta    85140
tagagtccag ctcctgcaca cagtaggagc tcaataaaca cttgtcaaat gaatgggaaa    85200
aacagattga gtgatgtgtg caaagggcct aataagagtg cccctgcac atactgttat    85260
aaaaatttat agaaggaagg aaggagcttg gctgggtgga cagaacttgg cttggagcc    85320
aggagactgt ggttccaatg cctgctctgt ctcctctcct ctgagcctta gtgtttccat    85380
ctgcaaaatg gggtcgggga agagttcact ggaaagtttt cttctggct gaggttctgc    85440
tcagttctat ttgagctgtt taacccagag agtcagtgtg ttcagcctgc aggctccata    85500
gcaagtgttt tcctctcctg caggtctcac ctcccatcaa ggaagatgtc cagattgctg    85560
tctgacgtct ggtctctgga ctgaaggcca tttagtgcag atctcacaaa tgatggtggg    85620
gcaaggcagg gggtatgcat gagtggcatg ggcaaggtgt gagttgggg atacaaaagg    85680
gagtggtgga ggccgggcac ggtggctcac acctgtaatc ccagcacttt gggaggccaa    85740
tgcgggcgaa tcacctgagg tcaggagttc agggccagtc tgatagcctg agcaacatgg    85800
agaaaccccg cctctaataa aaatacaaa aattagtgaa gccgactgga ccagcaggtg    85860
gctgttgtgt ggcctctcag gaggacgccc tctcccttcc cccagtggtt gcaaaatact    85920
tcagaaagaa aaccaaagtt ctctgtgggt gcagtcggtt gtttcagaag ctgacggagc    85980
ctggtctttg tataacccca tctttcccct ttctttctgt caactgttta tgggaggatt    86040
ctcaaactgt tctggagaat gtttctaccc tttagttcta gtgttgggtg acctgtaatt    86100
ttcatgttgg ctggggatgc caggagttgg cagaggctcc ttccagagcc cctgtggact    86160
ggattctgcc acttccgtaa aatcattcaa agtagagggg tgagtcaggt gcagtagctc    86220
acatctgtaa tcccagcacc ttgagaggcc aaggcaggca gatcccctga ggtcaggagt    86280
tcaagatcac cctggccaac atggtgagac cctgtctcta ctaaaaaaa tttaaaaatc    86340
agctagatgt ggtggcacac gcctgtggtc ccagctactc agaaggctga ggcaggagaa    86400
ttgcttgaac ccaggaggtg gaggttgcag tgagctgaga tcataccaca acccagtgaa    86460
gggggtccag caagccatgc ctgggtgag agagaactga tgttttggtt ctctcacact    86520
acttattctg tttggaaaaa cacatgccct tcctttgtgg gaacagcccc tacccacttc    86580
tgtggctctg aagggaccac cagtcatggc accagccccc tgggcatggg attggcccct    86640
gacaggcaca tgacttgagc caggccaatt agaggccttc cttgggatt actatatgga    86700
```

-continued

```
cgttaggaga gagatgctct cttattctgc tggagtttgc tgaacttgca tgggaaggga    86760
taggccttat ggagagacca acacatagat aatagttggg atgggagatg aaaggagaga    86820
atcctgacat catttgagtc ccctgatcca gcaacacctg aggctagatc ctcttagctg    86880
tgtgagccta tagtatcagt ctctgtctcc tctgtctctc ttaatgtgtg ggattcagcc    86940
atctgcaaca actaccacaa aatcccggag tatgcaggga acttcccaca gagctaactt    87000 cctttttgt tctgtctcct aaaacaccaa gatccggtga ggttaagcaa cgtgtccaag     87060
gtcatcacta tttgaaggca gggcagcatt taacccaatt ttatctaatc ctatgcaggc    87120
tcatttatct agaccagagt ttctcaaatg aggcatccca ggctctaagg gctgcagaga    87180
agtttccaga gatgccactg agggcaggag tggacagagt ggataactcc aaagatctta    87240
acaccctctg gatgactaac agtgcttgag cacttcccat ttgcaagaca tttgcaagtt    87300
cttttccata aatcatcctt ttttttcatc cccataagct atgagctggg gctaatgaca    87360
tccccactga acagatgaga aaactgaggc ccaggaaagg aattgctcag gttatatagt    87420
aagtgagcag ctgcttgtgt gttgagtcac ctcccaaccc tccaccccgg ccttaaaata    87480
cctcttctgt ttgctgcctg tcattctgcc atttccccat ttgtaggaac ctgtttgttc    87540
cccgtttgta ggaacctgtg atgcgttctg ggaggaacca tatcttaagc ctgatactac    87600
ttagtgggat cagctggaag gcaaggtggg gaggcggcag tgccgccaga gtagcgttgg    87660
gggctggact gggggtcaaa tgatgaggtt ttttgtttt tgttttgtt tttgtcttgt      87720 ttgtttgttt ttttttttga tacggagtct ggccctgtca ctcaggctgg agtgcaatgg    87780
tgacatctcc actcactgca acctctgcct cctgggttca acgattctc ctgcctcaag     87840 cctcctgagt agctgggatt ataggtgcct accaccacgc ccagctaatt tttctatttt    87900
tagcagagat ggggtttcac tatgttggcc agattggtct tgaactcctg accttgtgat    87960
ccgcctgcct cggcctccca aaatgccggg attacagtcg tgagccaccg cacccggcca    88020
atgatgagct tttctgaagt agcatcaggt gagttcttga cctccaccca cttacctccg    88080
ggctgcactg cggttcctca tccactcctt ttcaagccgg gaaacaagtt cttctgagga    88140
gttttctctc ccaagcgacc agaggtcttt tggtctcagt ggcctcctgt atcccctcca    88200
gaccaggctg caaaagaggg gcaccaggga aagcttttcc tgccattcac ccctgcagga    88260
tcctggccag gcgagtagct gtgtgaccct gggtaagtca ctttacctct ctgtacctct    88320
actggcccct gggtaaaaag aaagcaattc actaaccca cctaatgtct gcagggcatt     88380
tctcgtttca caaagattgt ctcattaatt cttacatgaa cccataaggt aggttattat    88440
tgtttgtttg agatggagtc ttgttctgtc tcccaggctg gagtgcagtg gtgcaatctc    88500
ggctcactgc aacctccacc tcccaggttc aagcgattct cccacctcag cctcctgagt    88560
agctgggatt acaggcaccc accaccatac ccggctaatt tttgtatttt ttgtagagat    88620
ggagtttcac catgttggcc agactggtct cgaactcctg acctcaggtg atccacctgc    88680
ctcagcctcc caaagtgctg ggattacagg catgagccac cacacccagc ctgtaaattg    88740
atagtttata attgtataaa tgtatgagta tattattata gatctatttt acagatgggg    88800
aaggaaatag aagtgcagag agattcagtg gctaaaccaa gggatagccc ttggcaaggg    88860
aaacagacat ttccctggga atcagaagtc cgttgaccaa aactatcatt gtagaagaag    88920
cttgaactcc tccctcagct ttttttttt aattattatt atttttttg agatggagtc     88980 tcactctgtt gcctaggctg gagtgcactg atgtgatctg ggctcactgc aacctccgcc    89040
tccctggctc aagcgattct cacgcctcag ccttctgagt agttgaaatt acaagccacc    89100
```

-continued

```
atcacacctg gctaattttt gtgtttttgg atggtgtatc accatgctgg ccaggctggt    89160
ctcgacctac tggcctcaag caatcctccc acctcagcct cccaaagtgc taggactaca    89220
ggcgtaagcc accacacctg gctaattttt ttgtttatag tagagatggg atttcgccat    89280
gttggccagg ctggtctcga actcccggcc tcaagtgatc tgtcagggtt ggccttccaa    89340
agtgttggga ttatgggtgt gagccactgt gcctggcctc aggtctcttt aatctttctg    89400
atgacaccag ccagaaggtc ttgcctggtt ctggtctctg actcttctct aagccttacc    89460
aagttccctt tcttttttta ttttattct ttttattttt ttgagatgga atctcactct    89520
gttgctcagg ctggagtgca ctggtgtgat ctcggctcac cgcaacctcc acctcctggg    89580
ttcaagtgat tctcctgcct cagcctcctg agtgactggg attgcaggct cccaccacca    89640
cacctggcta attttatat ttttagtaga gatggggttt caccatgttg gtcaggctgg    89700
tctcgaaatc ctgaccctcag gtgatccacc tgcctcagcc tcccaaggtg ttgggattat    89760
aggcgtgagc cactgcgcca ggccaccaag ttccctttc taatgcagag ccaacttggg    89820
gaagcaaccg ttctgacata gaaattatta acgtggcttg attttccctg aaattatttt    89880
tggagttctc ctatatggca agtgatgcta tagatttttc ctatttagc agtgatagag    89940 agtttctttt taaaaacagt ttattcgagt aaaaaaagtg actcaattta gtttttgccc    90000
cagtaggaca aaaaagcatc aagagtggtc cataaatgct taagtttggg aagcaggggc    90060 tggaccccc agtagagctg tttcgaaaac ctctaagctc tttctaccag ttccacacat    90120
tcaaagcctg atatttttca tttatttaat agccatttag gccgggtgcg gtggcttatg    90180
cctgtaatcc cagcactttg ggaggtcgag tggggtagat cacttgaggt caggagtttg    90240
agaccagctt ggccaacgtg gtgaaacccg gtctctacaa aaaactacaa aaattagctg    90300
ggcatgatgg caggcgcctg taatcccagc tgctcgggag gctgaggcag gagaattgct    90360
tgaacctggg aggtggaggt tgcagtgagc tgagattgtg ccattgcact gcagcctggg    90420
caacaagagt gaaactctgt ctcaaaaaaa aaagagaaa atgaatagcc caggcacagt    90480
gggtcacacc tgtaatccca gcactttggg aagccgaggc gggcagatca cctgaggtcg    90540
ggagtttcag atcagcctga ccaacatgga gaaacactgt ctctactaaa aatacaaaat    90600
tagccgagca tagtggtgca tgcctgtaat ctcagctact cgggaggctg aggcaggaga    90660
atcgcttgaa cccaggaggc ggaggttgca gtgagccaag atagtgccat tgtactccag    90720
cctgggcaac aagaacggaa ctccatctca aagaaaaaa aataattac cacttaaact    90780 cattatttgc caggccctgt tctaagtgct ttacagatct catcttattt aagcttcaca    90840
accctatgag ctaagtgcta ctatcaatcc cattttgaag gagtggagac tgaggcacag    90900
agaggttaag taactgtcca aagcaacaca gctaggaagt ggtagggcca ggattcaaat    90960
ccatatgtca ggtgctactg aggtctgaat gccgtgtggt taggagagag cacatcctca    91020
agtgccttgt gagctggccc tggagaagca gctgttttct caatctgcct ggaaccctct    91080
agaaagtaga cacttgctcc tttatctcct caccctggg gcttagcaca tagtaggtgc    91140
ctattaaatg ttggtggaat gactgaaatc aagtattgga acaattcta attactatta    91200 agcacccgct gtgtgcaagc actaagcact ttccgtctca tgcaggttga gtcatcccca    91260
ttttacagag ggaaaactga gactccggag gttttgcgaca tggcctgcta acaggcagag    91320
ccgggattca aatcaagatc tcactccagt gagtgaatgg gaacaggatg cagatggtag    91380
acactgaaca cgaagaagaa agcactgagg ctgggatgga gaaagacttg ctggccttg    91440
```

-continued

```
taagcacagg ggaagggcca tggctgggaa tcagagcagc aaatgcaggc gggtgaggca    91500
ccaccccaac ccttccgtgc gactttactt acccagaaac ccaccagaac gtggctttgg    91560
aggggaaggc tgccccagtc tctggacagg ggttctgcaa cagacaaaaa tggagaaggg    91620
aagtatgtgg caagggtagg aagacaggac gaactgtgta tttttttttt tttcgagaca    91680
ggttttcgct ctgttgccca ggccagagta cagcggtgtg atcttggctc actactacct    91740
ctgcctcctg ggttcaagcg attctcctgc ctcagccttc caaagagctg ggatgacagg    91800
tgtgcgccac cacacacagc taattttttg tgttttagt agagacaggg tttcaccatg    91860
ttggccaggc tggtctcaaa ctcctaacct caagtgatct gcctatctcg gcctcccaaa    91920
gtgctgggat tacaggcatg agccactaca cccagccctg acggtgtatt tagtactgaa    91980
agtaaacatc gaggtgccct gtctccttgc caggggtgta gaccagtgag cttggtgctt    92040
cccagcaggc agcgtaaaaa gaggttgggc cacaggcctg acaatgtcca caaggtaaga    92100
aataacagtg gctcagaaga acaactatga ttatactgaa accaaaacct tgctttgctt    92160
ctcaaaagga aggacactgc ataacgaaga aattagatcc ttgacaatat ccctcggcaa    92220
atgttgtgaa gacagacctg tcgtgcgatt tttgtcaggt gctccaggaa gattacaaca    92280
gtctgtactc tttaccaata aggcgtgaag gtgcccattt caccacgttt tgccatcac    92340 agcttattaa ttttttaaatt ttgttgctac tctggtaggt acaaaaaaga ttcctatgat    92400
agttttaact attctcaagc cttcgagcaa tttttttttt tttttttttt tgaatacagg    92460
gtctcgctct gtcacccagg ctggagtgca atggtgcaat catagctcac tgcagccttt    92520
atctcttgga ttcaagcaat cctcctgctt tagtctccac agagctactc tgtagtggga    92580
ctacaggcat gcaccaccac actaggctat ttttaaaaac cttttttgtag agatggggtc    92640 tcactacatt gcctagtctg atctagaaca cctgggcaca aacaatcctc cttcctcggt    92700
ctcccaaagt gttgagatta caggcatgat ccactgcatc tggccccatt tgaacatctg    92760
tttatatgat gtcagatcag tctcttccac aaaagaattg tttcttgatt tcacagactg    92820
cttcactgtt accttattgta aatctctcaa tctctcatga gcttcttcta tggagcactt    92880
accccaaggg taatttttctt tttccttctt tttttttttt ttttttttgg tggagttccg    92940
ctcttgttgc ccaggctgga gtgcaaatgc acagtcttgg ctccctgcaa cctcccacatc    93000 ccggattcaa gcaattctcc tgcctcagcc tcccgagtag ctgggattac aggcgtgcac    93060
caccatgcct ggctaatttt tgtaatttta gaagagatga ggctttacca tgttggccag    93120
gctggctttg aactctcgac ctcaagtgat ccacctgcct tggcctccca aagtgttggg    93180
attacaggca tgagccactg tgaccatcca attttcaaca tatttgttta attttgtgac    93240
cagtgtctgg ttccctgct tgaccagtag ctacgtgaga acagaaactc tatctgcttg    93300
ttcaccatag atccttatgc ccttgctagg gcatagcggg gtttggcaaa ctatgaccaa    93360
atctggccca ctgcctgttt ctgcaaatag tgttattgca acacagccat gcaatttgtt    93420
gacatattct gcttttgcgt tcaatggcag agttgagtaa ttgccactga gatcactgta    93480
tggctcacag agtccaaaat attttctctt ggcccatata gaaaagtct gccaactgtg    93540 gcatcgagta gaaatgtggt acacttttttg ctgaatggct aaatgaataa aaaaattaaa    93600
gacttttggt caccctgggg agactgagac ctcaaagtgg aacaggaatg aggttggaac    93660
ttggtgactt acagactgct gggggtcttc agggaagaag gggggttgat ccgccaggca    93720
ggacagcaca aactgtgcca ccaccagaga caggcatagg taggtggaca ggtggcggac    93780
agggtcgctc tggaagccct gtgggaggga aagcagaaga taaggaatgg agacagagga    93840
```

```
gggtgctcag aggagagaaa aggtttctga tcttgggtca gtgcccactc tggggaccag   93900
ggcaagagta tttgaaagcc agagccctgg ctttcctagt ggttctaatt ttctttcttt   93960 ctttttttt taagacaaag tctcacttgg tcgcccaggc tgaagtgcag tggcatgatc   94020
tcggctccct gcaacctctg cctcctgggt tcaagtgatt ctcctgcttc tgcctcctta   94080
gtagttggga ttacaggtgc ccaccaccat gcctggctaa ctttttttaaa atattttag   94140 tagagatggg gttttgccat gttggctagg ctgacctcaa actgctgacc taaagtgatc   94200
tgcctgcctt ggcctcccaa agtgttggga ttacaggcat gagccaccat gcccagcagg   94260 tcctaattt caaataccca atttataata ttctgtctat acaaatggtg ggccagggct   94320
gcgtctgggt tttgtcctta gccacatgat gattggccac agctgctggg acaatgagat   94380
gaagaaacaa tttaccttct tctttgtgcc acaaagaaa tcctttctcc gttccaccct   94440
ctaccccaat cttcaaccct gctccccctt ggccagggtt ctctggtttg cagagatgag   94500
agctggtttt attgagcact gaccctgccc tgagcacatg cggcattctt gccatacaca   94560
gtctcatcag ctggagttta cttgcttcct ttgactcagg gggaaaccaa ggctcagaga   94620
agtgacagca ccttgttcaa ggacacgcag atgatctggt ccaaattgtg atgctcctgc   94680
tgccacacca caatgatttt tgcatctgct gccctgtcat ctggtcagaa acacctaat   94740 tttctttctt tttttaattt aaagcatttt ttattttta attttaggtg tgtgtgtgtg   94800 tgtgtgtg tgtgtgtg tgtatacttt tttttttttt gagacggagt cttgctttgt   94860
cacccaggct gatgtgcagt ggcatgatct tggctcactg caccctccgc ctcctgggtt   94920
caagcgattc tcctgcctta gcctcctgag tagctgggat tacaggcatg tgccacgacc   94980
cctggctaat ttttgtattt ttagtagaga tggagtttta ccatgtaggc caggctggtc   95040
ttgaactcct gacctcaggt gatccgcctg ccttggcctc ccaaagtgct gggattacag   95100
gcatgagcca ccgcgcccgg cctgatatat atatttctgg atgacgtgag atattttgat   95160
acaggcatgc aatgcataat aatcacatca aggtaaatga ggtctccatc cccgcaatca   95220
tttatccttt ctgttacaaa tgatccattc tactcttgta gttatttat tttttagttt   95280 attattgagt tggagtctca ctctgttgcc caggctggag tgcagtggct tgattttggc   95340
tcactgcaac ctccgtctcc tggattcaag tgattctcct gccttagcct cctgagtatc   95400
tgagattaca gatgtgtgcc agcacgcctg gctactttt ttgtattttt agtagagaca   95460
gggtttcacc atgttgccca tgctggtctt gaactcctga cctcagatga tcctcctgcc   95520
ttggcctccc aaagtgctgg aattacaggt gtgagccact gtgtccagcc tcttttagtt   95580
attttaaaat gtacaattaa attattattg actatagtca ccctgttgtg ctatcaaata   95640
gatattattc tttctgtttt tttgtaccca ttaaccatcc ccatttcccc cacccactgt   95700
ccttcctagc ctctagtaac cttccatcta ctctatatgt tcatgagtta cattgtttta   95760
atttttagct ttcacaaata agtgagaata tgtaaagttt gtctttctgt gcctggctta   95820
tttcacttaa catccatgtt gttgaaaatg acagtacctc attctttttt atggctgcat   95880
agtacttcat tgtgtatata taccacattt tctttatcag ttcgtctgtt gatggacact   95940
taggttgctt ccaaatcttg tttattgtga acagtgctgt aataatcatg ggagtgcaga   96000
gatctcttcc atgtactgat tttctttctt cctaagtttt ttgcttgtgt tcgggcgtgt   96060
gatttgtgca gaactgactc tactccgagg ctgggtgggt gaatgaggcc tggccaacga   96120
atacgttctg gtcttttggc taccatggca gggttaggaa tgcacatagc accccatgct   96180
```

-continued

```
gggtacttga gagctggaac catcgggaga ttctgctggc tttgctacat gctagaatgt   96240
aagtgtgaag gtattggtgg ctcttcttgc cactccattg gagaatcaag ctaacatggc   96300
agagccaaga ggcagaagtg gagatctggt gatggtacct ggtcccaggc ctggatcagt   96360
catgcctggg agatcccatg ggtatgagct aataaatgca tgagctaatg aaccccttg    96420 acttaccctt ttcattaagc tagtgtgaac tgaggtttta tggctttaaa ccagagccct   96480
agttttaaat catgattcct ctactggatt ttatactctt ctagttttgg gttttgttt    96540 gtttgtttgt tttttggcag atagcagaca attggatatt ccaatgacaa tatgcccat    96600 cttccctaaa ctcccactgt tttccccact gtttctctca gaaagtttgt tctgaatttg   96660
cctgagatga actcgggctc tgcactccca agctttgtgg ccctgaggcc gtcattccct   96720
tctcctagcc ttagtctccc tcatctttaa aatgggacgg ctagaattca tcattggctg   96780
gggcacattg gctcaagcct gtaatcccag cactttggga ggcttaggtg gaaagatcgc   96840
ttgagcccag gagtttgaga ccagccttgg gaacataatg agactttgtt tctatttcta   96900
tttaaaaaaa taaagaaccc atcactgtga actcttgtga gaatccagtg aggagacgtg   96960
tgtaagtgcc tgccacagtg cctggcacat ggttggaacc ccagaatgta tatggtccca   97020
gtattattgt ttctatgctg tgtcccaaaa agctgactta tgtcaactgt gggagcccac   97080
catttcagaa attactgaat aacctgtgga atttccccct tagttacaaag gttactcttt   97140 taaaaactct gtcctcggtc aggcgctgtg gctcacgcct gtaatcccag cactttggga   97200
ggccgaggcg ggtgagtcac ttgaggtcag gcatttgaga tgagcctggc caacatattg   97260
aaaccttgtc tctactaaaa atacaaaaat tagctgggca tggtggcaca tgcctgtaat   97320
cccagctact tgggaggctg aggtatggga atcgattgaa cccggaggtg gaggttgtag   97380
tgagccaaga tcgtgccact gcactccagc ctgggcaata gagcaagact ctgtctcaga   97440
atgaacaaac aaaaaataaa aactctgtcc ttaaggacag ggtgatgctt ctctaccttc   97500
tcctttaggg gcaggatgga gtaaccactg gactgaagaa atgatctgtg agtccagacg   97560
tggtggctca tgcctctaat cccagcattt taggaggctg aggtcagaga attgctcgag   97620
ccgaggagtt caagatcagc ctgggcaaca aagcatgatg ttgtctccac aaaaataaaa   97680
taatgaagta aaatatctga aacctgctgc agcctgttca ttggtgttaa gataactccc   97740
tctcccagaa gccttggcta agcacactgt tgaggccagt gcttctcaat aggtgggtga   97800
ctttgtcctc ctcaccccca gggacacttg gtaatatctg gagacatttt gggttactgc   97860
aattggatgg tatgctactg gcacctatgg gcagaagcca gggatgctgt ttcacaccct   97920
gcagcaaaca agacagccct gtccacccaa caaagaattg tctggccaca acattactaa   97980
agctgaggct gagggaagtt ggtctaggct acatgttttt ctctttacag agaaaatgac   98040
ccatcatgtc tcctaataga gaaacgctgc ttccggccga atgacaagag ctcacgcctg   98100
taatcccgac actttgggag gccaaggcag gtggatcact tgaggtcagg agctcgagac   98160
cagcctggcc aacatggtga aacctcgtct ctactaaaaa tacaaaaatt tttagtagaa   98220
atttagtaga aattttttagt agaaatttag tagaaattta gaataagcca ggtgtagtgg   98280
cacacacctg taatcccagc tacacaggaa gcagaggcag gagaagtgct tgaacccgag   98340
aggcagaaat tgcagtgagc tgagatcatg ccacttcatt ccagtctggg cgacagagca   98400
agcctctcaa aaaaaaaaaa aaaaaaaaa aaaaaaagc tgcttcccag attgggcaac   98460
agaaatacga gtggtgtgca gaatgagtgt gtaaatatag gtgcataggg acatggggag   98520
ggtgaatcca tgacatgagg ggaggtgtgc acggaggggt atgtgtgcac acaggtgtgt   98580
```

-continued

```
ctgtgcccag gttgtgtgtg tgtgcgtgca tgcatgtact tgtgcgatgt atgaatcagt   98640
gcctataagt gtgtgcatcg tgtgcaagtg gcacgtgtga tgtgggcctg taagacagga   98700
aattgtgttg ataagaaatg tatgggatga tgggtactga caggtgcggg agtggatttt   98760
gtgtctctag agtgtaagtg actggcttgt gtgtgtcact gtatagagaa taagttgtat   98820
gtggaaacag gaggagaaag gaagggaccc aaggcatgag ccaccatttt ggtttcccag   98880
ggtggcccac gccccgactt accgctccgg aggcctgctg ggcagcgttg gtagctggca   98940
agacaaagca gagaagccag taaccaaaca gcactccaga tgactggact ccctttttcc   99000
tctcggtgtg aatcaggaac actgcgaagc tctggacggg aaagtcaggg aggcccctta   99060 ggggaggggtg ggaggctgag gggagcctct tctcttcccc ttgttctcca ctgtggcagg   99120
caaagcagca gctgggagga agccgggctc cagactgaag gcatcattac catcgtggtg   99180
agccacacag taggatgaat gaggaattct ggggcctcag gcgttccctg ttggattttc   99240
caaagagcga cagccacgct ggaggtacac aggactatga gggcgaatcc aagcacctga   99300
ggatacaggc ttagataagc ttgggggca ataagagagg tcacagcaaa ctggtaggcg   99360
gccccatgtc caactgggag ctggttctgc aacatcctgg ctgatactga gtataccagg   99420
gtcaccagct agcaacgtgc caatgtgaac aatgtgtaaa gggcattgca gatcactcct   99480
gacctgtaac tgtcatataa ataatgcaca ggaagggctt gagccaaccg agtgttttcc   99540
aaaatgcagg aagtgctcca atcgtgcaca tatgagatga ctttgggtat ggagaaacag   99600
caggaaatga aatgtactca ccaggtaaaa aactatcctt tctccaagtc attttcaat   99660 ccctgctatg aaatcaagga gcaactctct gttgggccag taagtctcta gggtctctct   99720
aatatatttt ggtttctcta ttgaataaaa gaaaggaaga aatgagaga acgtgggcac   99780 accagaggga aggccagagc taggttacgt tggaggaact gctcaaagaa cctcagttta   99840
aagcagaagt tggcaaacta tcaatcatca aagaaaaaca aaaagcatat gtcatgacag   99900
gtgaaaatta catgaaatcc aaatttcagt gactacaaat aaagttttat tgaaacgcag   99960
tcggccgggg gtggtggctt acacctgtaa tcccagcact ttggcaggcc aaggcaggca  100020
gatcacctga ggtcaggagt tggagaccag cctggccaac atggcgaaac cctgtttcta  100080
ctaaaaatac aaaaaaatag cgaggtgtgg gggtgggcac ctgtaatccc agctactcgg  100140
gaagctgagg caggagaatc acttgaaccc aggaggcgga ggttgcagtg agccgagatc  100200
gcaccattgc actccagcct gggtaacaag agcaaaactg catctcaaaa aaaaaaaaca  100260
aacaaaaaag taacacagtc atgactattg tctatggtta tgactattgc gttcattctg  100320
gaatggcaga gttcagtgtt cggaaggaag attacctggc tcacaaagtc tcaaatactg  100380
tgtaccgctt ggctctttaa gtttgccaac ccctgggttg gtggcgggtg ataatgtaaa  100440
aattaataca atggcagaag aatgaatgaa ctctgaagaa cattctttgg aagcctacaa  100500
gaatggagta aagaggatg gatgagcaga aaggctcaca cttggaatgc cagtgtttat  100560
ttaacacact aaggtaaata catatcacat ataaaaattg tcctataata cagccagtgg  100620
gggaacataa aaataaatgc ataactttt aaaaggttca tcctaatgtg gctctaaaat  100680
taccttgtgt atccaagagt ctacatggta tgttttggaa aatgccaggt tatggtagct  100740
ataaactgtc caggaacatg ggagtgtatg cgtatgtttg cgcatgcgtg gattttcgga  100800
attacaaaat ctgtttggga gaaccgtgtt ccactgagtt gacctctgta gccttttctaa  100860 tattgctctg tttgattaac agattcccctt ctacaccccg ataggaggag tctactttaa  100920
```

```
gacttcacca ggttccagcc tgtcccctgc ctcccccgaa cattgcctgg ttccaggctc    100980
ccagggatgg cagctaccat cttggctttg aagagtgggg acatccacag gtagccccgg    101040
ccatggtggt ggatgaagag gaggtagatg ggaccaagga cccagaggta catgggggt     101100 acccagaccc ctgctgttct caggaagcac aggctcagca ggctggtggc ggcaggttca    101160
ggctctgtct ggttccagac ctgagggaac acaaagagga cccttaggat ggtacaaggc    101220
aggggtcccc agctcacctg cccaggggggc caggcaactt tttggatctt taacatttac   101280
acaaaaatgt accaagtact ctttggaata cctactaatt ctcaattcct ttcatcctga    101340
cattaaccct aggtagttgc aattatattg atttgcagat gaagaagctg aggaccagag    101400
aggttgagta actttgctga ctttacccag ctgaggagtg aagggctgg gatttgaacc     101460 cagggaactg ggccatgtgg tctaggagac ctgggctcca taatcattgc taggcatgga    101520
ctgtcagtta atccttataa caactccagg acgcagacag tactgtctcc atttcagaaa    101580
ccagcagact gaggcaccag tcggggaact gcctccccca gggacacaca aatgggaagt    101640
ggcaaagctg actctgaccc aggcttatct gaccccaaac ctcgttcgac tggtggtctt    101700
gatgtatgat ttgttttttat tttttattat taattaattt atgttttaga gacagggtct   101760
cactctgttg cccaggctga agtggcacaa tcaaagctca acaaagcttc gaatttcctg    101820
ggctcaagca atcctcccac ctcggcctcc cagagtgctg ggattacagg cataagcagc    101880
ctcaccaggc ctggctaatt tttttttttt atgttttgta gagatggggg tctctctatg    101940
ctggtctcga actcctggtc tcaagcaatc tccctgcctc agcctcctag gtactgggat    102000
tacaggcaag agccaccggc ccagcttgat ctgttatttt catctcagca ggtctgctgg    102060
tcctatctaa ccctagaaga aatttgaagt ttagtggacg tggcctcttc aattctctct    102120
ccgctgtctt tttactcctc ctggtttcac aactcaccgg ctgtgcaaac tttaacctct    102180
ctgtatctca gtttccttcc ctgtaaaagg gggaaaacga gactctacct ctatgagttg    102240
tattaaatgg attaatagca gcaaagttca tagcagcatg gcacaaggtt gggcacaagg    102300
ctaggcacag agaaagccct cagttcattg ccagtttatt gcttcaactc cctgccctc     102360 gaaatgctgg cagtttgcaa cccccacccc cactccatga actccactcc ctggagtcct    102420
ttgctaagag caatggaaaa agaaaccaga gaggtaaggg ctctccgggg gtaggagggc    102480
ttgggggacc cactagcttt atgcaaagaa gagtcaaagc ccctagtagc tgggaggtct    102540
ggtggcccct taaatagagc tgggctctcg gctgctggct tggtgaaaga aatccaaccc    102600
gctgcagtga gggggccgga gtaagtctcc tcgcttcccg ggtccaggaa tttggggtc    102660 tctcctctcc ccagtatcgc agcccgagag atctgcagcc aaaccaagcc tggaaaagga    102720
gagtggggcg cgatgggggg cactcacccc ctgccccgcg cagggctcag caggcgcggc    102780
catcggcgcc ttctgtcgtc gtgggtccca gcgtctgtct gtcgctaagt ctctgggcag    102840
actgctcggc cgcgatcctg ccggagaaga ggcggggctg ggctggtcgg gctgggctgg    102900
tccggctggg attcgagctc cgggatcggg aggccccggg caaggtccag ctgcgcggcg    102960
ggagtgaggc cacgggaggt gaaacaggc gaggtggggg atgggggaag agaggcgctc     103020
ggggagctgg gacgggcacc gggttggggg gtcccggaac ccctgaaagt tcagtgacac    103080
ctccatagtt ccctcttccc cctgcaacaa gaatcactcc agacttccta aacactttgg    103140
acccagcaat ttccaggagt tcatcctgat gagagaactg aaaggtgtgc acacgttagt    103200
aacaaggagg cctggtgacc gcctaagcgt ccaatcgcgg ggaccaccgg gtcgaggccg    103260
agaggatgga gaccgcgtca caggcacctc gctgctggaa tggagggtgg tggggagaac    103320
```

```
ttagaagatt atgcaatggg ctggcagggc tatacccagc cgccctggta agcagaaact    103380
caagaaacct ctagggtcct gttttctggt cgtatgatcc caggagtgca catgggcccc    103440
tcgggtgtct gaacagaagg gcataggagg gagggccgca gccctgcagt cttactctgc    103500
tggtgtagcg gtcacctgcc aactcccacc ccaccctgca ccgcgggctc ctgagtcggc    103560
agattaagca ttttataaat tctattttaa atacgtgttt taaacttgtc agatatttgt    103620
cttcatttca gtccctgcgc ctctacctct tgctgtggtc gcttatttaa cactgggggg    103680
ctacgttctg ctaagtccca gggagagact gttcctaata tccgagggag atattattcc    103740
taatatcacg ctgggtgaac accacgtgtg tacagcctct gatacgattg gtaatatcca    103800
agggagatat tatcctaaca tcccagtggg tgaacaccat gtgtgtaaac gctgtggtat    103860
tattagaaat atccaaggga gatattactc ctaatatcac agtgggtgta catcctgtga    103920
tattattcgt aatatctgaa ggagatttta ctcctaatat cacagtggga gtacacactg    103980
tgatattatt tgtaatatcc gagggagatt ttactcctaa tatcacagta ggtgtacaac    104040
ctgtgatatt attcataata tgctagagat atattactcc aaatctcatg gtgggtgtac    104100
actctgtcat agaattcgtg atatcctagg gagttattac cgctaatatc acagtgagag    104160
tacaccctgt gatattattc atactatcct agaaagatat tacttttaat atcacagagg    104220
gtgtacaccc tgtgatatta ttcataatat tctatgaaga tataactcct gatataaccg    104280
taggtgtata ccctgtgata ttatttgtta tatcctaggg agatactaca cctaatacca    104340
cagtgggtgt acaccctgtg atatgatttg taatatccta gggagatata actcctaata    104400
tcacagaggg agtacaccct gtaatattat tcataatatc ctagaaagat aatactttca    104460
atatcacagt gggtgtacac tctgtgataa tattcgtaat ttcctaggga gatactactc    104520
ctaatatcac cttgagtgta cactgcgtga tattattcgt aatatcgtag ggagctattg    104580
cttttaattt cacagtgggt gtataccccta tgatattatt cataatatct taagaaggta    104640
gtactcctaa aatcacagtg cctgtacaca ctgtgatatt attcataata ttctagggag    104700
atgttactcc taatctcata gtgggtgtac accttgtgat actatttgta atgttctaga    104760
aagatattcc ttttaatatc acagtgggtg tacaccctgt gatatgattc gaaatattct    104820
agggcgatat tactcctaat atcccagtga atttacacca tgcgtgtaca cgctgtgacc    104880
tcccagaaag atatgactcc taatatcaca gtggggtac accctgtgct attatttgta    104940
ataccctatg gatatcataa tatcacaatg aacgtacacc attgtgtaca tgctgtgata    105000
ttatttgtaa tattttgggg tgatattacc cctaatgtca cagtgcgtgt acatcttttg    105060
atattatttg taatattctg tggagatatt gcccctaata tcacagtggg tgtatactct    105120
ttgatactat tcgtaacatc ctggaagata ttatccatat tgtcacggtg ggtgtacacc    105180
ctgtgatatt attcgttata ttctgggggat atactattac ccctaatata ctgtgggtgt    105240
acccccctgtg atattattca ctatatcttg gagatataat attaccccta atcacagt    105300
gggtgtatac tttgtgatat tattcattat atcctgaaga gatattattt cctttaatat    105360
cacagtgcat gtacaccttg tgatattatt tgttatatcc tggggagata ctactatatt    105420
actcctagta tcacagtggc tgtacgcctt gtgatactat tcattatatc ctggggagat    105480
attattactc ctaatatcac agtaagtgta taccctgtga tattattcat aatatcctgg    105540
gagatattac ccatattgtc acagtgggtg tacatcctgt aatattattt gtaatatcct    105600
ggggagatat tattactcct aatagcacag tgggtgtaca ccctgtgata ttattggtta    105660
```

```
tatcctgggg aggtattatt attcctaata tcacagtggg tgaacattct gtaatattat    105720
tcattatatt ttggggagat attaattcct ctaatatcac agtgggtgta caccctgtga    105780
tattattcat tatatcctgg gaagatatta atccctctaa tatcacagtg ggtgtacacc    105840
ctgtaatatt attcattata tcctgggaag atattatttc ctctaatatc acagtgggtg    105900
tacaccctgt gatattattt gttgtatcct ggggagatat tattatgtct catatcacaa    105960
tgggtgaaca ccctgtgata gtattcgtta tatttgggga agatgttatt accccctaata   106020 tcacagtggt gtacactctg tgatattatt cattatgtag tggggagata gtattaccca    106080
taatatcaca gtggatgtac accctgtcat attatttgtt atatccttga gaaatattat    106140
tattcctctt atcacagtgg gtgtacaccc tgtgatatta ttcgttacat cctagggaga    106200
tattgttacc cataatatca cagtggatgt acaccctgtc atattattcg ttatatcctt    106260
gagagatgtt actacccta atatcacagt gggtgtatac cctgtgatat tattcatcaa    106320
attttctgga gatattatta cccataatat cacagtgtgt gtaccactg tgacagtatt    106380 gattatatct tggggcgata ttactcttaa tttcacagtg gctgtatccc tgtgtttaca    106440
ccctgtgatg ttattcataa tattttaggg agatattact cctaatatca gtcagtgt    106500 ataccatgtt tgtacaccct atgatattat ttgtaatatt taggggagat attactccta    106560
atatcgttgt gggtgtacag catgtttgta aacactgtga tattattcat aatatctgag    106620
agagatatta ctgccaatat cacagtgggt gtacaccctg tacaccgtgt gatacgattc    106680
ataatatccg agggagatat tactcccagt atcacagtgg gtttacaccc tgtggtatta    106740
ttcataatat tcgagggaga tattactctc aatatcacag tggatgtaca ccctgtgata    106800
ttatttgcaa tatccgaggg aaacattact gctaatatca gtgggagt acaccctgtg     106860 atattatttg ttttatcctg gagacatatt attcctatta tcacagtggt tgtacaccct    106920
gtgatattct tcgctatatt catggaagat gttattaccc ctaatatcac agttggtgta    106980
caccctgtga tattattcgt tatatcctgg ggagatattg ttaccctag tatcacagtg    107040 ggtgtacgcc ctgtcatatt atccattaca tcatgggaag atattattac atctaatatc    107100
actgtgggtg tacaccctgt gatattattt attatatcct ggtgagatgt tattactgct    107160
aatatcacag ggtgtgtcaa attttctgga gatattatta cccttaatat cacagtgggt    107220
gtgcaccctg tgtgtacact ctgtaatatt atttgtaata ttttagggag atattactac    107280
taatatcaca gtgggtgtac accctgagga gatattactt cctctgatat cacagtgggt    107340
gtacaccctc tcatattatt cgttatgtgc taagtagata ttattacccc taatatcaca    107400
gtgggtgtac accctgtgat gttattcctt atatcccaag aagatattat ataactaat    107460 atcacagtgg gtgtacaccc tatgatatta tctgttatat actgggggga tattatttgt    107520
aatattttag ggagatacta ctcctaatat catagtgggt gtactcatat tttacagata    107580
tattactttt aatatcacag tgggtgtaca ccctgtgtgt acaccctgta atattattag    107640 taatattta gggagatatt actcctaata tcatagtggg tgtacaccat gtttgtaaac    107700
cctaggatat tattcataat atccgaggga gatattactc ccaatatcac ggtgggttta    107760
caccctatga tatttattgt aatatctgag gcaggtatta ctctccatat cacagtgagt    107820
```

<210> SEQ ID NO 2  
<211> LENGTH: 4512  
<212> TYPE: DNA  
<213> ORGANISM: Homo sapiens  
<220> FEATURE:  
<221> NAME/KEY: CDS
<222> LOCATION: (1)..(4512)
<223> OTHER INFORMATION: cDNA for human MRP6 protein

<400> SEQUENCE: 2

| | | | | | | | | | | | | | | | | |
|---|---|---|---|---|---|---|---|---|---|---|---|---|---|---|---|---|
| atg | gcc | gcg | cct | gct | gag | ccc | tgc | gcg | ggg | cag | ggg | gtc | tgg | aac | cag | 48 |
| Met | Ala | Ala | Pro | Ala | Glu | Pro | Cys | Ala | Gly | Gln | Gly | Val | Trp | Asn | Gln | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| aca | gag | cct | gaa | cct | gcc | gcc | acc | agc | ctg | ctg | agc | ctg | tgc | ttc | ctg | 96 |
| Thr | Glu | Pro | Glu | Pro | Ala | Ala | Thr | Ser | Leu | Leu | Ser | Leu | Cys | Phe | Leu | |
| | | 20 | | | | | 25 | | | | | 30 | | | | |

| | | | | | | | | | | | | | | | | |
|---|---|---|---|---|---|---|---|---|---|---|---|---|---|---|---|---|
| aga | aca | gca | ggg | gtc | tgg | gta | ccc | ccc | atg | tac | ctc | tgg | gtc | ctt | ggt | 144 |
| Arg | Thr | Ala | Gly | Val | Trp | Val | Pro | Pro | Met | Tyr | Leu | Trp | Val | Leu | Gly | |
| | | 35 | | | | | 40 | | | | | 45 | | | | |

| | | | | | | | | | | | | | | | | |
|---|---|---|---|---|---|---|---|---|---|---|---|---|---|---|---|---|
| ccc | atc | tac | ctc | ctc | ttc | atc | cac | cac | cat | ggc | cgg | ggc | tac | ctg | tgg | 192 |
| Pro | Ile | Tyr | Leu | Leu | Phe | Ile | His | His | His | Gly | Arg | Gly | Tyr | Leu | Trp | |
| | 50 | | | | | 55 | | | | | 60 | | | | | |

| | | | | | | | | | | | | | | | | |
|---|---|---|---|---|---|---|---|---|---|---|---|---|---|---|---|---|
| atg | tcc | cca | ctc | ttc | aaa | gcc | aag | atg | gtg | ctt | gga | ttc | gcc | ctc | ata | 240 |
| Met | Ser | Pro | Leu | Phe | Lys | Ala | Lys | Met | Val | Leu | Gly | Phe | Ala | Leu | Ile | |
| 65 | | | | 70 | | | | | 75 | | | | | 80 | | |

| | | | | | | | | | | | | | | | | |
|---|---|---|---|---|---|---|---|---|---|---|---|---|---|---|---|---|
| gtc | ctg | tgt | acc | tcc | agc | gtg | gct | gtc | gct | ctt | tgg | aaa | atc | caa | cag | 288 |
| Val | Leu | Cys | Thr | Ser | Ser | Val | Ala | Val | Ala | Leu | Trp | Lys | Ile | Gln | Gln | |
| | | | | 85 | | | | | 90 | | | | | 95 | | |

| | | | | | | | | | | | | | | | | |
|---|---|---|---|---|---|---|---|---|---|---|---|---|---|---|---|---|
| gga | acg | cct | gag | gcc | cca | gaa | ttc | ctc | att | cat | cct | act | gtg | tgg | ctc | 336 |
| Gly | Thr | Pro | Glu | Ala | Pro | Glu | Phe | Leu | Ile | His | Pro | Thr | Val | Trp | Leu | |
| | | | | 100 | | | | | 105 | | | | | 110 | | |

| | | | | | | | | | | | | | | | | |
|---|---|---|---|---|---|---|---|---|---|---|---|---|---|---|---|---|
| acc | acg | atg | agc | ttc | gca | gtg | ttc | ctg | att | cac | acc | gag | agg | aaa | aag | 384 |
| Thr | Thr | Met | Ser | Phe | Ala | Val | Phe | Leu | Ile | His | Thr | Glu | Arg | Lys | Lys | |
| | | | 115 | | | | | 120 | | | | | 125 | | | |

| | | | | | | | | | | | | | | | | |
|---|---|---|---|---|---|---|---|---|---|---|---|---|---|---|---|---|
| gga | gtc | cag | tca | tct | gga | gtg | ctg | ttt | ggt | tac | tgg | ctt | ctc | tgc | ttt | 432 |
| Gly | Val | Gln | Ser | Ser | Gly | Val | Leu | Phe | Gly | Tyr | Trp | Leu | Leu | Cys | Phe | |
| | 130 | | | | | 135 | | | | | 140 | | | | | |

| | | | | | | | | | | | | | | | | |
|---|---|---|---|---|---|---|---|---|---|---|---|---|---|---|---|---|
| gtc | ttg | cca | gct | acc | aac | gct | gcc | cag | cag | gcc | tcc | gga | gcg | ggc | ttc | 480 |
| Val | Leu | Pro | Ala | Thr | Asn | Ala | Ala | Gln | Gln | Ala | Ser | Gly | Ala | Gly | Phe | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| cag | agc | gac | cct | gtc | cgc | cac | ctg | tcc | acc | tac | cta | tgc | ctg | tct | ctg | 528 |
| Gln | Ser | Asp | Pro | Val | Arg | His | Leu | Ser | Thr | Tyr | Leu | Cys | Leu | Ser | Leu | |
| | | | | 165 | | | | | 170 | | | | | 175 | | |

| | | | | | | | | | | | | | | | | |
|---|---|---|---|---|---|---|---|---|---|---|---|---|---|---|---|---|
| gtg | gtg | gca | cag | ttt | gtg | ctg | tcc | tgc | ctg | gcg | gat | caa | ccc | ccc | ttc | 576 |
| Val | Val | Ala | Gln | Phe | Val | Leu | Ser | Cys | Leu | Ala | Asp | Gln | Pro | Pro | Phe | |
| | | | 180 | | | | | 185 | | | | | 190 | | | |

| | | | | | | | | | | | | | | | | |
|---|---|---|---|---|---|---|---|---|---|---|---|---|---|---|---|---|
| ttc | cct | gaa | gac | ccc | cag | cag | tct | aac | ccc | tgt | cca | gag | act | ggg | gca | 624 |
| Phe | Pro | Glu | Asp | Pro | Gln | Gln | Ser | Asn | Pro | Cys | Pro | Glu | Thr | Gly | Ala | |
| | | | 195 | | | | | 200 | | | | | 205 | | | |

| | | | | | | | | | | | | | | | | |
|---|---|---|---|---|---|---|---|---|---|---|---|---|---|---|---|---|
| gcc | ttc | ccc | tcc | aaa | gcc | acg | ttc | tgg | tgg | gtt | tct | ggc | ctg | gtc | tgg | 672 |
| Ala | Phe | Pro | Ser | Lys | Ala | Thr | Phe | Trp | Trp | Val | Ser | Gly | Leu | Val | Trp | |
| | | 210 | | | | | 215 | | | | | 220 | | | | |

| | | | | | | | | | | | | | | | | |
|---|---|---|---|---|---|---|---|---|---|---|---|---|---|---|---|---|
| agg | gga | tac | agg | agg | cca | ctg | aga | cca | aaa | gac | ctc | tgg | tcg | ctt | ggg | 720 |
| Arg | Gly | Tyr | Arg | Arg | Pro | Leu | Arg | Pro | Lys | Asp | Leu | Trp | Ser | Leu | Gly | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| aga | gaa | aac | tcc | tca | gaa | gaa | ctt | gtt | tcc | cgg | ctt | gaa | aag | gag | tgg | 768 |
| Arg | Glu | Asn | Ser | Ser | Glu | Glu | Leu | Val | Ser | Arg | Leu | Glu | Lys | Glu | Trp | |
| | | | | 245 | | | | | 250 | | | | | 255 | | |

| | | | | | | | | | | | | | | | | |
|---|---|---|---|---|---|---|---|---|---|---|---|---|---|---|---|---|
| atg | agg | aac | cgc | agt | gca | gcc | cgg | agg | cac | aac | aag | gca | ata | gca | ttt | 816 |
| Met | Arg | Asn | Arg | Ser | Ala | Ala | Arg | Arg | His | Asn | Lys | Ala | Ile | Ala | Phe | |
| | | | 260 | | | | | 265 | | | | | 270 | | | |

| | | | | | | | | | | | | | | | | |
|---|---|---|---|---|---|---|---|---|---|---|---|---|---|---|---|---|
| aaa | agg | aaa | ggc | ggc | agt | ggc | atg | aag | gct | cca | gag | acc | gag | ccc | ttc | 864 |
| Lys | Arg | Lys | Gly | Gly | Ser | Gly | Met | Lys | Ala | Pro | Glu | Thr | Glu | Pro | Phe | |
| | | 275 | | | | | 280 | | | | | 285 | | | | |

| | | | | | | | | | | | | | | | | |
|---|---|---|---|---|---|---|---|---|---|---|---|---|---|---|---|---|
| cta | cgg | caa | gaa | ggg | agc | cag | tgg | cgc | cca | ctg | ctg | aag | gcc | atc | tgg | 912 |
| Leu | Arg | Gln | Glu | Gly | Ser | Gln | Trp | Arg | Pro | Leu | Leu | Lys | Ala | Ile | Trp | |

```
                      290                 295                 300
cag gtg ttc cat tct acc ttc ctc ctg ggg acc ctc agc ctc atc atc       960
Gln Val Phe His Ser Thr Phe Leu Leu Gly Thr Leu Ser Leu Ile Ile
305                 310                 315                 320 agt gat gtc ttc agg ttc act gtc ccc aag ctg ctc agc ctt ttc ctg      1008
Ser Asp Val Phe Arg Phe Thr Val Pro Lys Leu Leu Ser Leu Phe Leu
                325                 330                 335 gag ttt att ggt gat ccc aag cct cca gcc tgg aag ggc tac ctc ctc      1056
Glu Phe Ile Gly Asp Pro Lys Pro Pro Ala Trp Lys Gly Tyr Leu Leu
            340                 345                 350 gcc gtg ctg atg ttc ctc tca gcc tgc ctg caa acg ctg ttt gag cag      1104
Ala Val Leu Met Phe Leu Ser Ala Cys Leu Gln Thr Leu Phe Glu Gln
        355                 360                 365 cag aac atg tac agg ctc aag gtg ctg cag atg agg ttg cgg tcg gcc      1152
Gln Asn Met Tyr Arg Leu Lys Val Leu Gln Met Arg Leu Arg Ser Ala
370                 375                 380 atc act ggc ctg gtg tac aga aag gtc ctg gct ctg tcc agc ggc tcc      1200
Ile Thr Gly Leu Val Tyr Arg Lys Val Leu Ala Leu Ser Ser Gly Ser
385                 390                 395                 400 aga aag gcc agt gcg gtg ggt gat gtg gtc aat ctg gtg tcc gtg gac      1248
Arg Lys Ala Ser Ala Val Gly Asp Val Val Asn Leu Val Ser Val Asp
                405                 410                 415 gtg cag cgg ctg acc gag agc gtc ctc tac ctc aac ggg ctg tgg ctg      1296
Val Gln Arg Leu Thr Glu Ser Val Leu Tyr Leu Asn Gly Leu Trp Leu
            420                 425                 430 cct ctc gtc tgg atc gtg gtc tgc ttc gtc tat ctc tgg cag ctc ctg      1344
Pro Leu Val Trp Ile Val Val Cys Phe Val Tyr Leu Trp Gln Leu Leu
        435                 440                 445 ggg ccc tcc gcc ctc act gcc atc gct gtc ttc ctg agc ctc ctc cct      1392
Gly Pro Ser Ala Leu Thr Ala Ile Ala Val Phe Leu Ser Leu Leu Pro
450                 455                 460 ctg aat ttc ttc atc tcc aag aaa agg aac cac cat cag gag gag caa      1440
Leu Asn Phe Phe Ile Ser Lys Lys Arg Asn His His Gln Glu Glu Gln
465                 470                 475                 480 atg agg cag aag gac tca cgg gca cgg ctc acc agc tct atc ctc agg      1488
Met Arg Gln Lys Asp Ser Arg Ala Arg Leu Thr Ser Ser Ile Leu Arg
                485                 490                 495 aac tcg aag acc atc aag ttc cat ggc tgg gag gga gcc ttt ctg gac      1536
Asn Ser Lys Thr Ile Lys Phe His Gly Trp Glu Gly Ala Phe Leu Asp
            500                 505                 510 aga gtc ctg ggc atc cga ggc cag gag ctg ggc gcc ttg cgg acc tcc      1584
Arg Val Leu Gly Ile Arg Gly Gln Glu Leu Gly Ala Leu Arg Thr Ser
        515                 520                 525 ggc ctc ctc ttc tct gtg tcg ctg gtg tcc ttc caa gtg tct aca ttt      1632
Gly Leu Leu Phe Ser Val Ser Leu Val Ser Phe Gln Val Ser Thr Phe
530                 535                 540 ctg gtc gca ctg gtg gtg ttt gct gtc cac act ctg gtg gcc gag aat      1680
Leu Val Ala Leu Val Val Phe Ala Val His Thr Leu Val Ala Glu Asn
545                 550                 555                 560 gct atg aat gca gag aaa gcc ttt gtg act ctc aca gtt ctc aac atc      1728
Ala Met Asn Ala Glu Lys Ala Phe Val Thr Leu Thr Val Leu Asn Ile
                565                 570                 575 ctc aac aag gcc cag gct ttc ctg ccc ttc tcc atc cac tcc ctc gtc      1776
Leu Asn Lys Ala Gln Ala Phe Leu Pro Phe Ser Ile His Ser Leu Val
            580                 585                 590 cag gcc cgg gtg tcc ttt gac cgt ctg gtc acc ttc ctc tgc ctg gaa      1824
Gln Ala Arg Val Ser Phe Asp Arg Leu Val Thr Phe Leu Cys Leu Glu
        595                 600                 605 gaa gtt gac cct ggt gtc gta gac tca agt tcc tct gga agc gct gcc      1872
```

-continued

```
                    Glu Val Asp Pro Gly Val Val Asp Ser Ser Ser Gly Ser Ala Ala
                        610             615                 620 gggaagg atg tgc atc acc ata cac agt gcc acc ttc gcc tgg tcc cag        1920
Gly Lys Asp Cys Ile Thr Ile His Ser Ala Thr Phe Ala Trp Ser Gln
625                 630                 635                 640 gaa agc cct ccc tgc ctc cac aga ata aac ctc acg gtg ccc cag ggc        1968
Glu Ser Pro Pro Cys Leu His Arg Ile Asn Leu Thr Val Pro Gln Gly
                645                 650                 655 tgt ctg ctg gct gtt gtc ggt cca gtg ggg gca ggg aag tcc tcc ctg        2016
Cys Leu Leu Ala Val Val Gly Pro Val Gly Ala Gly Lys Ser Ser Leu
            660                 665                 670 ctg tcc gcc ctc ctt ggg gag ctg tca aag gtg gag ggg ttc gtg agc        2064
Leu Ser Ala Leu Leu Gly Glu Leu Ser Lys Val Glu Gly Phe Val Ser
        675                 680                 685 atc gag ggt gct gtg gcc tac gtg ccc cag gag gcc tgg gtg cag aac        2112
Ile Glu Gly Ala Val Ala Tyr Val Pro Gln Glu Ala Trp Val Gln Asn
    690                 695                 700 acc tct gtg gta gag aat gtg tgc ttc ggg cag gag ctg gac cca ccc        2160
Thr Ser Val Val Glu Asn Val Cys Phe Gly Gln Glu Leu Asp Pro Pro
705                 710                 715                 720 tgg ctg gag aga gta cta gaa gcc tgt gcc ctg cag cca gat gtg gac        2208
Trp Leu Glu Arg Val Leu Glu Ala Cys Ala Leu Gln Pro Asp Val Asp
                725                 730                 735 agc ttc cct gag gga atc cac act tca att ggg gag cag ggc atg aat        2256
Ser Phe Pro Glu Gly Ile His Thr Ser Ile Gly Glu Gln Gly Met Asn
                740                 745                 750 ctc tcc gga ggc cag aag cag cgg ctg agc ctg gcc cgg gct gta tac        2304
Leu Ser Gly Gly Gln Lys Gln Arg Leu Ser Leu Ala Arg Ala Val Tyr
            755                 760                 765 aga aag gca gct gtg tac ctg ctg gat gac ccc ctg gcg gcc ctg gat        2352
Arg Lys Ala Ala Val Tyr Leu Leu Asp Asp Pro Leu Ala Ala Leu Asp
        770                 775                 780 gcc cac gtt ggc cag cat gtc ttc aac cag gtc att ggg cct ggt ggg        2400
Ala His Val Gly Gln His Val Phe Asn Gln Val Ile Gly Pro Gly Gly
785                 790                 795                 800 cta ctc cag gga aca aca cgg att ctc gtg acg cac gca ctc cac atc        2448
Leu Leu Gln Gly Thr Thr Arg Ile Leu Val Thr His Ala Leu His Ile
                805                 810                 815 ctg ccc cag gct gat tgg atc ata gtg ctg gca aat ggg gcc atc gca        2496
Leu Pro Gln Ala Asp Trp Ile Ile Val Leu Ala Asn Gly Ala Ile Ala
                820                 825                 830 gag atg ggt tcc tac cag gag ctt ctg cag agg aag ggg gcc ctc gtg        2544
Glu Met Gly Ser Tyr Gln Glu Leu Leu Gln Arg Lys Gly Ala Leu Val
            835                 840                 845 tgt ctt ctg gat caa gcc aga cag cca gga gat aga gga gaa gga gaa        2592
Cys Leu Leu Asp Gln Ala Arg Gln Pro Gly Asp Arg Gly Glu Gly Glu
        850                 855                 860 aca gaa cct ggg acc agc acc aag gac ccc aga ggc acc tct gca ggc        2640
Thr Glu Pro Gly Thr Ser Thr Lys Asp Pro Arg Gly Thr Ser Ala Gly
865                 870                 875                 880 agg agg ccc gag ctt aga cgc gag agg tcc atc aag tca gtc cct gag        2688
Arg Arg Pro Glu Leu Arg Arg Glu Arg Ser Ile Lys Ser Val Pro Glu
                885                 890                 895 aag gac cgt acc act tca gaa gcc cag aca gag gtt cct ctg gat gac        2736
Lys Asp Arg Thr Thr Ser Glu Ala Gln Thr Glu Val Pro Leu Asp Asp
                900                 905                 910 cct gac agg gca gga tgg cca gca gga aag gac agc atc caa tac ggc        2784
Pro Asp Arg Ala Gly Trp Pro Ala Gly Lys Asp Ser Ile Gln Tyr Gly
            915                 920                 925
```

```
                                                      -continued agg gtg aag gcc aca gtg cac ctg gcc tac ctg cgt gcc gtg ggc acc      2832
Arg Val Lys Ala Thr Val His Leu Ala Tyr Leu Arg Ala Val Gly Thr
    930                 935                 940 ccc ctc tgc ctc tac gca ctc ttc ctc ttc ctc tgc cag caa gtg gcc      2880
Pro Leu Cys Leu Tyr Ala Leu Phe Leu Phe Leu Cys Gln Gln Val Ala
945                 950                 955                 960 tcc ttc tgc cgg ggc tac tgg ctg agc ctg tgg gcg gac gac cct gca      2928
Ser Phe Cys Arg Gly Tyr Trp Leu Ser Leu Trp Ala Asp Asp Pro Ala
                965                 970                 975 gta ggt ggg cag cag acg cag gca gcc ctg cgt ggc ggg atc ttc ggg      2976
Val Gly Gly Gln Gln Thr Gln Ala Ala Leu Arg Gly Gly Ile Phe Gly
            980                 985                 990 ctc ctc ggc tgt ctc caa gcc att ggg ctg ttt gcc tcc atg gct gcg      3024
Leu Leu Gly Cys Leu Gln Ala Ile Gly Leu Phe Ala Ser Met Ala Ala
        995                 1000                1005 gtg ctc cta ggt ggg gcc cgg gca tcc agg ttg ctc ttc cag agg          3069
Val Leu Leu Gly Gly Ala Arg Ala Ser Arg Leu Leu Phe Gln Arg
    1010                1015                1020 ctc ctg tgg gat gtg gtg cga tct ccc atc agc ttc ttt gag cgg          3114
Leu Leu Trp Asp Val Val Arg Ser Pro Ile Ser Phe Phe Glu Arg
    1025                1030                1035 aca ccc att ggt cac ctg cta aac cgc ttc tcc aag gag aca gac          3159
Thr Pro Ile Gly His Leu Leu Asn Arg Phe Ser Lys Glu Thr Asp
    1040                1045                1050 acg gtt gac gtg gac att cca gac aaa ctc cgg tcc ctg ctg atg          3204
Thr Val Asp Val Asp Ile Pro Asp Lys Leu Arg Ser Leu Leu Met
    1055                1060                1065 tac gcc ttt gga ctc ctg gag gtc agc ctg gtg gtg gca gtg gct          3249
Tyr Ala Phe Gly Leu Leu Glu Val Ser Leu Val Val Ala Val Ala
    1070                1075                1080 acc cca ctg gcc act gtg gcc atc ctg cca ctg ttt ctc ctc tac          3294
Thr Pro Leu Ala Thr Val Ala Ile Leu Pro Leu Phe Leu Leu Tyr
    1085                1090                1095 gct ggg ttt cag agc ctg tat gtg gtt agc tca tgc cag ctg aga          3339
Ala Gly Phe Gln Ser Leu Tyr Val Val Ser Ser Cys Gln Leu Arg
    1100                1105                1110 cgc ttg gag tca gcc agc tac tcg tct gtc tgc tcc cac atg gct          3384
Arg Leu Glu Ser Ala Ser Tyr Ser Ser Val Cys Ser His Met Ala
    1115                1120                1125 gag acg ttc cag ggc agc aca gtg gtc cgg gca ttc cga acc cag          3429
Glu Thr Phe Gln Gly Ser Thr Val Val Arg Ala Phe Arg Thr Gln
    1130                1135                1140 gcc ccc ttt gtg gct cag aac aat gct cgc gta gat gaa agc cag          3474
Ala Pro Phe Val Ala Gln Asn Asn Ala Arg Val Asp Glu Ser Gln
    1145                1150                1155 agg atc agt ttc ccg cga ctg gtg gct gac agg tgg ctt gcg gcc          3519
Arg Ile Ser Phe Pro Arg Leu Val Ala Asp Arg Trp Leu Ala Ala
    1160                1165                1170 aat gtg gag ctc ctg ggg aat ggc ctg gtg ttt gca gct gcc acg          3564
Asn Val Glu Leu Leu Gly Asn Gly Leu Val Phe Ala Ala Ala Thr
    1175                1180                1185 tgt gct gtg ctg agc aaa gcc cac ctc agt gct ggc ctc gtg ggc          3609
Cys Ala Val Leu Ser Lys Ala His Leu Ser Ala Gly Leu Val Gly
    1190                1195                1200 ttc tct gtc tct gct gcc ctc cag gtg acc cag aca ctg cag tgg          3654
Phe Ser Val Ser Ala Ala Leu Gln Val Thr Gln Thr Leu Gln Trp
    1205                1210                1215 gtt gtt cgc aac tgg aca gac cta gag aac agc atc gtg tca gtg          3699
Val Val Arg Asn Trp Thr Asp Leu Glu Asn Ser Ile Val Ser Val
    1220                1225                1230
```

| | | |
|---|---|---|
| gag cgg atg cag gac tat gcc tgg acg ccc aag gag gct ccc tgg<br>Glu Arg Met Gln Asp Tyr Ala Trp Thr Pro Lys Glu Ala Pro Trp<br>1235                           1240                       1245 | 3744 |
| agg ctg ccc aca tgt gca gct cag ccc ccc tgg cct cag ggc ggg<br>Arg Leu Pro Thr Cys Ala Ala Gln Pro Pro Trp Pro Gln Gly Gly<br>1250                         1255                        1260 | 3789 |
| cag atc gag ttc cgg gac ttt ggg cta aga tac cga cct gag ctc<br>Gln Ile Glu Phe Arg Asp Phe Gly Leu Arg Tyr Arg Pro Glu Leu<br>1265                         1270                       1275 | 3834 |
| ccg ctg gct gtg cag ggc gtg tcc ttc aag atc cac gca gga gag<br>Pro Leu Ala Val Gln Gly Val Ser Phe Lys Ile His Ala Gly Glu<br>1280                         1285                       1290 | 3879 |
| aag gtg ggc atc gtt ggc agg acc ggg gca ggg aag tcc tcc ctg<br>Lys Val Gly Ile Val Gly Arg Thr Gly Ala Gly Lys Ser Ser Leu<br>1295                         1300                       1305 | 3924 |
| gcc agt ggg ctg ctg cgg ctc cag gag gca gct gag ggt ggg atc<br>Ala Ser Gly Leu Leu Arg Leu Gln Glu Ala Ala Glu Gly Gly Ile<br>1310                         1315                       1320 | 3969 |
| tgg atc gac ggg gtc ccc att gcc cac gtg ggg ctg cac aca ctg<br>Trp Ile Asp Gly Val Pro Ile Ala His Val Gly Leu His Thr Leu<br>1325                         1330                       1335 | 4014 |
| cgc tcc agg atc agc atc atc ccc cag gac ccc atc ctg ttc cct<br>Arg Ser Arg Ile Ser Ile Ile Pro Gln Asp Pro Ile Leu Phe Pro<br>1340                         1345                       1350 | 4059 |
| ggc tct ctg cgg atg aac ctc gac ctg ctg cag gag cac tcg gac<br>Gly Ser Leu Arg Met Asn Leu Asp Leu Leu Gln Glu His Ser Asp<br>1355                         1360                       1365 | 4104 |
| gag gct atc tgg gca gcc ctg gag acg gtg cag ctc aaa gcc ttg<br>Glu Ala Ile Trp Ala Ala Leu Glu Thr Val Gln Leu Lys Ala Leu<br>1370                         1375                       1380 | 4149 |
| gtg gcc agc ctg ccc ggc cag ctg cag tac aag tgt gct gac cga<br>Val Ala Ser Leu Pro Gly Gln Leu Gln Tyr Lys Cys Ala Asp Arg<br>1385                         1390                       1395 | 4194 |
| ggc gag gac ctg agc gtg ggc cag aaa cag ctc ctg tgt ctg gca<br>Gly Glu Asp Leu Ser Val Gly Gln Lys Gln Leu Leu Cys Leu Ala<br>1400                         1405                       1410 | 4239 |
| cgt gcc ctt ctc cgg aag acc cag atc ctc atc ctg gac gag gct<br>Arg Ala Leu Leu Arg Lys Thr Gln Ile Leu Ile Leu Asp Glu Ala<br>1415                         1420                       1425 | 4284 |
| act gct gcc gtg gac cct ggc acg gag ctg cag atg cag gcc atg<br>Thr Ala Ala Val Asp Pro Gly Thr Glu Leu Gln Met Gln Ala Met<br>1430                         1435                       1440 | 4329 |
| ctc ggg agc tgg ttt gca cag tgc act gtg ctg ctc att gcc cac<br>Leu Gly Ser Trp Phe Ala Gln Cys Thr Val Leu Leu Ile Ala His<br>1445                         1450                       1455 | 4374 |
| cgc ctg cgc tcc gtg atg gac tgt gcc cgg gtt ctg gtc atg gac<br>Arg Leu Arg Ser Val Met Asp Cys Ala Arg Val Leu Val Met Asp<br>1460                         1465                       1470 | 4419 |
| aag ggg cag gtg gca gag agc ggc agc ccg gcc cag ctg ctg gcc<br>Lys Gly Gln Val Ala Glu Ser Gly Ser Pro Ala Gln Leu Leu Ala<br>1475                         1480                       1485 | 4464 |
| cag aag ggc ctg ttt tac aga ctg gcc cag gag tca ggc ctg gtc<br>Gln Lys Gly Leu Phe Tyr Arg Leu Ala Gln Glu Ser Gly Leu Val<br>1490                         1495                       1500 | 4509 |
| tga | 4512 |

<210> SEQ ID NO 3
<211> LENGTH: 1503
<212> TYPE: PRT

-continued

<213> ORGANISM: Homo sapiens

<400> SEQUENCE: 3

```
Met Ala Ala Pro Ala Glu Pro Cys Ala Gly Gln Gly Val Trp Asn Gln
1               5                   10                  15

Thr Glu Pro Glu Pro Ala Ala Thr Ser Leu Leu Ser Leu Cys Phe Leu
            20                  25                  30

Arg Thr Ala Gly Val Trp Val Pro Pro Met Tyr Leu Trp Val Leu Gly
        35                  40                  45

Pro Ile Tyr Leu Leu Phe Ile His His Gly Arg Gly Tyr Leu Trp
    50                  55                  60

Met Ser Pro Leu Phe Lys Ala Lys Met Val Leu Gly Phe Ala Leu Ile
65                  70                  75                  80

Val Leu Cys Thr Ser Ser Val Ala Val Ala Leu Trp Lys Ile Gln Gln
                85                  90                  95

Gly Thr Pro Glu Ala Pro Glu Phe Leu Ile His Pro Thr Val Trp Leu
            100                 105                 110

Thr Thr Met Ser Phe Ala Val Phe Leu Ile His Thr Glu Arg Lys Lys
        115                 120                 125

Gly Val Gln Ser Ser Gly Val Leu Phe Gly Tyr Trp Leu Leu Cys Phe
    130                 135                 140

Val Leu Pro Ala Thr Asn Ala Ala Gln Gln Ala Ser Gly Ala Gly Phe
145                 150                 155                 160

Gln Ser Asp Pro Val Arg His Leu Ser Thr Tyr Leu Cys Leu Ser Leu
                165                 170                 175

Val Val Ala Gln Phe Val Leu Ser Cys Leu Ala Asp Gln Pro Pro Phe
            180                 185                 190

Phe Pro Glu Asp Pro Gln Gln Ser Asn Pro Cys Pro Glu Thr Gly Ala
        195                 200                 205

Ala Phe Pro Ser Lys Ala Thr Phe Trp Trp Val Ser Gly Leu Val Trp
    210                 215                 220

Arg Gly Tyr Arg Arg Pro Leu Arg Pro Lys Asp Leu Trp Ser Leu Gly
225                 230                 235                 240

Arg Glu Asn Ser Ser Glu Glu Leu Val Ser Arg Leu Glu Lys Glu Trp
                245                 250                 255

Met Arg Asn Arg Ser Ala Ala Arg Arg His Asn Lys Ala Ile Ala Phe
            260                 265                 270

Lys Arg Lys Gly Gly Ser Gly Met Lys Ala Pro Glu Thr Glu Pro Phe
        275                 280                 285

Leu Arg Gln Glu Gly Ser Gln Trp Arg Pro Leu Leu Lys Ala Ile Trp
    290                 295                 300

Gln Val Phe His Ser Thr Phe Leu Leu Gly Thr Leu Ser Leu Ile Ile
305                 310                 315                 320

Ser Asp Val Phe Arg Phe Thr Val Pro Lys Leu Leu Ser Leu Phe Leu
                325                 330                 335

Glu Phe Ile Gly Asp Pro Lys Pro Pro Ala Trp Lys Gly Tyr Leu Leu
            340                 345                 350

Ala Val Leu Met Phe Leu Ser Ala Cys Leu Gln Thr Leu Phe Glu Gln
        355                 360                 365

Gln Asn Met Tyr Arg Leu Lys Val Leu Gln Met Arg Leu Arg Ser Ala
    370                 375                 380

Ile Thr Gly Leu Val Tyr Arg Lys Val Leu Ala Leu Ser Ser Gly Ser
385                 390                 395                 400
```

-continued

Arg Lys Ala Ser Ala Val Gly Asp Val Val Asn Leu Val Ser Val Asp
            405                 410                 415

Val Gln Arg Leu Thr Glu Ser Val Leu Tyr Leu Asn Gly Leu Trp Leu
            420                 425                 430

Pro Leu Val Trp Ile Val Val Cys Phe Val Tyr Leu Trp Gln Leu Leu
            435                 440                 445

Gly Pro Ser Ala Leu Thr Ala Ile Ala Val Phe Leu Ser Leu Leu Pro
450                 455                 460

Leu Asn Phe Phe Ile Ser Lys Lys Arg Asn His His Gln Glu Glu Gln
465                 470                 475                 480

Met Arg Gln Lys Asp Ser Arg Ala Arg Leu Thr Ser Ser Ile Leu Arg
            485                 490                 495

Asn Ser Lys Thr Ile Lys Phe His Gly Trp Glu Gly Ala Phe Leu Asp
            500                 505                 510

Arg Val Leu Gly Ile Arg Gly Gln Glu Leu Gly Ala Leu Arg Thr Ser
            515                 520                 525

Gly Leu Leu Phe Ser Val Ser Leu Val Ser Phe Gln Val Ser Thr Phe
530                 535                 540

Leu Val Ala Leu Val Val Phe Ala Val His Thr Leu Val Ala Glu Asn
545                 550                 555                 560

Ala Met Asn Ala Glu Lys Ala Phe Val Thr Leu Thr Val Leu Asn Ile
            565                 570                 575

Leu Asn Lys Ala Gln Ala Phe Leu Pro Phe Ser Ile His Ser Leu Val
            580                 585                 590

Gln Ala Arg Val Ser Phe Asp Arg Leu Val Thr Phe Leu Cys Leu Glu
            595                 600                 605

Glu Val Asp Pro Gly Val Val Asp Ser Ser Ser Gly Ser Ala Ala
            610                 615                 620

Gly Lys Asp Cys Ile Thr Ile His Ser Ala Thr Phe Ala Trp Ser Gln
625                 630                 635                 640

Glu Ser Pro Pro Cys Leu His Arg Ile Asn Leu Thr Val Pro Gln Gly
                    645                 650                 655

Cys Leu Leu Ala Val Val Gly Pro Val Gly Ala Gly Lys Ser Ser Leu
            660                 665                 670

Leu Ser Ala Leu Leu Gly Glu Leu Ser Lys Val Glu Gly Phe Val Ser
            675                 680                 685

Ile Glu Gly Ala Val Ala Tyr Val Pro Gln Glu Ala Trp Val Gln Asn
690                 695                 700

Thr Ser Val Val Glu Asn Val Cys Phe Gly Gln Glu Leu Asp Pro Pro
705                 710                 715                 720

Trp Leu Glu Arg Val Leu Glu Ala Cys Ala Leu Gln Pro Asp Val Asp
            725                 730                 735

Ser Phe Pro Glu Gly Ile His Thr Ser Ile Gly Glu Gln Gly Met Asn
            740                 745                 750

Leu Ser Gly Gly Gln Lys Gln Arg Leu Ser Leu Ala Arg Ala Val Tyr
            755                 760                 765

Arg Lys Ala Ala Val Tyr Leu Leu Asp Asp Pro Leu Ala Ala Leu Asp
            770                 775                 780

Ala His Val Gly Gln His Val Phe Asn Gln Val Ile Gly Pro Gly Gly
785                 790                 795                 800

Leu Leu Gln Gly Thr Thr Arg Ile Leu Val Thr His Ala Leu His Ile
            805                 810                 815

Leu Pro Gln Ala Asp Trp Ile Ile Val Leu Ala Asn Gly Ala Ile Ala

-continued

```
                820             825             830
Glu Met Gly Ser Tyr Gln Glu Leu Leu Gln Arg Lys Gly Ala Leu Val
            835             840             845
Cys Leu Leu Asp Gln Ala Arg Gln Pro Gly Asp Arg Gly Glu Gly Glu
            850             855             860
Thr Glu Pro Gly Thr Ser Thr Lys Asp Pro Arg Gly Thr Ser Ala Gly
865             870             875             880
Arg Arg Pro Glu Leu Arg Glu Arg Ser Ile Lys Ser Val Pro Glu
            885             890             895
Lys Asp Arg Thr Thr Ser Glu Ala Gln Thr Glu Val Pro Leu Asp Asp
            900             905             910
Pro Asp Arg Ala Gly Trp Pro Ala Gly Lys Asp Ser Ile Gln Tyr Gly
            915             920             925
Arg Val Lys Ala Thr Val His Leu Ala Tyr Leu Arg Ala Val Gly Thr
            930             935             940
Pro Leu Cys Leu Tyr Ala Leu Phe Leu Phe Leu Cys Gln Gln Val Ala
945             950             955             960
Ser Phe Cys Arg Gly Tyr Trp Leu Ser Leu Trp Ala Asp Asp Pro Ala
            965             970             975
Val Gly Gly Gln Gln Thr Gln Ala Ala Leu Arg Gly Gly Ile Phe Gly
            980             985             990
Leu Leu Gly Cys Leu Gln Ala Ile Gly Leu Phe Ala Ser Met Ala Ala
            995             1000            1005
Val Leu Leu Gly Gly Ala Arg Ala Ser Arg Leu Leu Phe Gln Arg
            1010            1015            1020
Leu Leu Trp Asp Val Val Arg Ser Pro Ile Ser Phe Phe Glu Arg
            1025            1030            1035
Thr Pro Ile Gly His Leu Leu Asn Arg Phe Ser Lys Glu Thr Asp
            1040            1045            1050
Thr Val Asp Val Asp Ile Pro Asp Lys Leu Arg Ser Leu Leu Met
            1055            1060            1065
Tyr Ala Phe Gly Leu Leu Glu Val Ser Leu Val Val Ala Val Ala
            1070            1075            1080
Thr Pro Leu Ala Thr Val Ala Ile Leu Pro Leu Phe Leu Leu Tyr
            1085            1090            1095
Ala Gly Phe Gln Ser Leu Tyr Val Val Ser Ser Cys Gln Leu Arg
            1100            1105            1110
Arg Leu Glu Ser Ala Ser Tyr Ser Ser Val Cys Ser His Met Ala
            1115            1120            1125
Glu Thr Phe Gln Gly Ser Thr Val Val Arg Ala Phe Arg Thr Gln
            1130            1135            1140
Ala Pro Phe Val Ala Gln Asn Asn Ala Arg Val Asp Glu Ser Gln
            1145            1150            1155
Arg Ile Ser Phe Pro Arg Leu Val Ala Asp Arg Trp Leu Ala Ala
            1160            1165            1170
Asn Val Glu Leu Leu Gly Asn Gly Leu Val Phe Ala Ala Ala Thr
            1175            1180            1185
Cys Ala Val Leu Ser Lys Ala His Leu Ser Ala Gly Leu Val Gly
            1190            1195            1200
Phe Ser Val Ser Ala Ala Leu Gln Val Thr Gln Thr Leu Gln Trp
            1205            1210            1215
Val Val Arg Asn Trp Thr Asp Leu Glu Asn Ser Ile Val Ser Val
            1220            1225            1230
```

```
Glu Arg Met Gln Asp Tyr Ala Trp Thr Pro Lys Glu Ala Pro Trp
    1235                1240                1245

Arg Leu Pro Thr Cys Ala Ala Gln Pro Pro Trp Pro Gln Gly Gly
    1250                1255                1260

Gln Ile Glu Phe Arg Asp Phe Gly Leu Arg Tyr Arg Pro Glu Leu
    1265                1270                1275

Pro Leu Ala Val Gln Gly Val Ser Phe Lys Ile His Ala Gly Glu
    1280                1285                1290

Lys Val Gly Ile Val Gly Arg Thr Gly Ala Gly Lys Ser Ser Leu
    1295                1300                1305

Ala Ser Gly Leu Leu Arg Leu Gln Glu Ala Ala Glu Gly Gly Ile
    1310                1315                1320

Trp Ile Asp Gly Val Pro Ile Ala His Val Gly Leu His Thr Leu
    1325                1330                1335

Arg Ser Arg Ile Ser Ile Ile Pro Gln Asp Pro Ile Leu Phe Pro
    1340                1345                1350

Gly Ser Leu Arg Met Asn Leu Asp Leu Leu Gln Glu His Ser Asp
    1355                1360                1365

Glu Ala Ile Trp Ala Ala Leu Glu Thr Val Gln Leu Lys Ala Leu
    1370                1375                1380

Val Ala Ser Leu Pro Gly Gln Leu Gln Tyr Lys Cys Ala Asp Arg
    1385                1390                1395

Gly Glu Asp Leu Ser Val Gly Gln Lys Gln Leu Leu Cys Leu Ala
    1400                1405                1410

Arg Ala Leu Leu Arg Lys Thr Gln Ile Leu Ile Leu Asp Glu Ala
    1415                1420                1425

Thr Ala Ala Val Asp Pro Gly Thr Glu Leu Gln Met Gln Ala Met
    1430                1435                1440

Leu Gly Ser Trp Phe Ala Gln Cys Thr Val Leu Leu Ile Ala His
    1445                1450                1455

Arg Leu Arg Ser Val Met Asp Cys Ala Arg Val Leu Val Met Asp
    1460                1465                1470

Lys Gly Gln Val Ala Glu Ser Gly Ser Pro Ala Gln Leu Leu Ala
    1475                1480                1485

Gln Lys Gly Leu Phe Tyr Arg Leu Ala Gln Glu Ser Gly Leu Val
    1490                1495                1500

<210> SEQ ID NO 4
<211> LENGTH: 20
<212> TYPE: DNA
<213> ORGANISM: Artificial
<220> FEATURE:
<223> OTHER INFORMATION: PCR primer for ABCC6

<400> SEQUENCE: 4
agccacgttc tggtgggttt                                          20

<210> SEQ ID NO 5
<211> LENGTH: 20
<212> TYPE: DNA
<213> ORGANISM: Artificial
<220> FEATURE:
<223> OTHER INFORMATION: PCR primer for ABCC6

<400> SEQUENCE: 5
ggaggcttgg gatcaccaat                                          20
```

```
<210> SEQ ID NO 6
<211> LENGTH: 20
<212> TYPE: DNA
<213> ORGANISM: Artificial
<220> FEATURE:
<223> OTHER INFORMATION: PCR primer for MRP-1

<400> SEQUENCE: 6
caactgcatc gttctgtttg                                               20

<210> SEQ ID NO 7
<211> LENGTH: 20
<212> TYPE: DNA
<213> ORGANISM: Artificial
<220> FEATURE:
<223> OTHER INFORMATION: PCR primer for MRP-1

<400> SEQUENCE: 7
atactccttg agcctctcca                                               20

<210> SEQ ID NO 8
<211> LENGTH: 4980
<212> TYPE: DNA
<213> ORGANISM: Mus musculus
<220> FEATURE:
<221> NAME/KEY: CDS
<222> LOCATION: (12)..(4508)
<223> OTHER INFORMATION: cDNA for mouse MRP6

<400> SEQUENCE: 8
ccgcgtcgac g atg aac agc ggg cgc tcc atg gcc acg cct gga gag cag     50
            Met Asn Ser Gly Arg Ser Met Ala Thr Pro Gly Glu Gln
              1               5                  10 tgc gcc ggc ctg agg gtc tgg aac cag aca gag cag gag cct gcg gcc     98
Cys Ala Gly Leu Arg Val Trp Asn Gln Thr Glu Gln Glu Pro Ala Ala
 15                  20                  25 tat cac ttg ctc agc ctg tgc ttc gtg aga gcc gcc agc agc tgg gtg    146
Tyr His Leu Leu Ser Leu Cys Phe Val Arg Ala Ala Ser Ser Trp Val
 30                  35                  40                  45 ccc ccc atg tac ctc tgg gtc ctc ggc ccc atc tac ctt ctc tac atc    194
Pro Pro Met Tyr Leu Trp Val Leu Gly Pro Ile Tyr Leu Leu Tyr Ile
                 50                  55                  60 cat cgc cat ggc cgg tgc tac ctc cgg atg tcc cac ctc ttc aaa acc    242
His Arg His Gly Arg Cys Tyr Leu Arg Met Ser His Leu Phe Lys Thr
             65                  70                  75 aaa atg gtg ctg ggc ttg gcc ctc atc ctt ctg tat acc ttc aac gtg    290
Lys Met Val Leu Gly Leu Ala Leu Ile Leu Leu Tyr Thr Phe Asn Val
 80                  85                  90 gcc gtg cct ctg tgg agg atc cac cag ggc gtg ccc cag gcc cca gag    338
Ala Val Pro Leu Trp Arg Ile His Gln Gly Val Pro Gln Ala Pro Glu
 95                 100                 105 ctt cta att cac cct act gtg tgg ctc acc acc atg agc ttt gcc acc    386
Leu Leu Ile His Pro Thr Val Trp Leu Thr Thr Met Ser Phe Ala Thr
110                 115                 120                 125 ttt ctg atc cac atg gag aga agg aag gga gtc cgg tca tcc ggg gtg    434
Phe Leu Ile His Met Glu Arg Arg Lys Gly Val Arg Ser Ser Gly Val
                130                 135                 140 ttg ttc ggg tac tgg ctg ctc tgc tgc atc ttg cca gga atc aac act    482
Leu Phe Gly Tyr Trp Leu Leu Cys Cys Ile Leu Pro Gly Ile Asn Thr
            145                 150                 155 gtg cag cag gcc tct gca ggg aac tta cgt cag gag ccc ctc cac cac    530
Val Gln Gln Ala Ser Ala Gly Asn Leu Arg Gln Glu Pro Leu His His
        160                 165                 170
```

-continued

| | |
|---|---|
| ctg gcc acc tac ctg tgc ttg tcc ctg gtg gtg gct gag ctg gtg ctg<br>Leu Ala Thr Tyr Leu Cys Leu Ser Leu Val Val Ala Glu Leu Val Leu<br>175                    180                    185 | 578 |
| tcc tgt ctg gtg gac cag cca ccc ttc ttc tcg gaa gac tcc cag cca<br>Ser Cys Leu Val Asp Gln Pro Pro Phe Phe Ser Glu Asp Ser Gln Pro<br>190                    195                    200                  205 | 626 |
| ttg aat ccg tgt cca gag gct gag gcc tcc ttt ccc tcc aag gcc atg<br>Leu Asn Pro Cys Pro Glu Ala Glu Ala Ser Phe Pro Ser Lys Ala Met<br>                    210                    215                  220 | 674 |
| ttc tgg tgg gcc tct gga ctg cta tgg agg ggc tac aaa aag ctg ctg<br>Phe Trp Trp Ala Ser Gly Leu Leu Trp Arg Gly Tyr Lys Lys Leu Leu<br>            225                    230                  235 | 722 |
| gga cca aaa gac ctc tgg tca ctt ggg aga gaa aac tct tca gaa gaa<br>Gly Pro Lys Asp Leu Trp Ser Leu Gly Arg Glu Asn Ser Ser Glu Glu<br>240                    245                    250 | 770 |
| ctc gtt tcc cag ctg gaa aga gaa tgg agg aga agc tgc aat ggg ctg<br>Leu Val Ser Gln Leu Glu Arg Glu Trp Arg Arg Ser Cys Asn Gly Leu<br>255                    260                    265 | 818 |
| cca ggg cac aaa ggg cac agt agt gtg ggg gcc cct gag aca gag gcc<br>Pro Gly His Lys Gly His Ser Ser Val Gly Ala Pro Glu Thr Glu Ala<br>270                    275                    280                  285 | 866 |
| ttc ctg cag cca gag agg agt cag agg ggc cca cta ctc agg gct atc<br>Phe Leu Gln Pro Glu Arg Ser Gln Arg Gly Pro Leu Leu Arg Ala Ile<br>                    290                    295                  300 | 914 |
| tgg cgc gtg ttc cgg tcc acc ttc ctg ctg ggg acc ctc agc ctg gtc<br>Trp Arg Val Phe Arg Ser Thr Phe Leu Leu Gly Thr Leu Ser Leu Val<br>            305                    310                  315 | 962 |
| att agc gat gcc ttc agg ttt gct gtt ccc aag ctc ctc agt ctg ttt<br>Ile Ser Asp Ala Phe Arg Phe Ala Val Pro Lys Leu Leu Ser Leu Phe<br>320                    325                    330 | 1010 |
| ctg gag ttc atg ggt gac cgc aac tcc tcg gcg tgg aca ggc tgg ctc<br>Leu Glu Phe Met Gly Asp Arg Asn Ser Ser Ala Trp Thr Gly Trp Leu<br>335                    340                    345 | 1058 |
| cta gct gtg ctg atg ttc gcg gca gcc tgc cta cag acg ttg ttt gaa<br>Leu Ala Val Leu Met Phe Ala Ala Ala Cys Leu Gln Thr Leu Phe Glu<br>350                    355                    360                  365 | 1106 |
| cag cag cac atg tac aga gcc aag gtc ctg cag atg agg ctg cga aca<br>Gln Gln His Met Tyr Arg Ala Lys Val Leu Gln Met Arg Leu Arg Thr<br>                    370                    375                  380 | 1154 |
| gcc atc act ggc ctg gtg tac aga aag gtc ctg gtc ctg tcc agt ggt<br>Ala Ile Thr Gly Leu Val Tyr Arg Lys Val Leu Val Leu Ser Ser Gly<br>            385                    390                  395 | 1202 |
| tcc aga aag tcc agc gca gca gga gac gtg gtc aac ctg gtg tcg gtg<br>Ser Arg Lys Ser Ser Ala Ala Gly Asp Val Val Asn Leu Val Ser Val<br>400                    405                    410 | 1250 |
| gac atc cag cgg ctg gcc gag agc atc atc tac ctc aac ggg ctg tgg<br>Asp Ile Gln Arg Leu Ala Glu Ser Ile Ile Tyr Leu Asn Gly Leu Trp<br>415                    420                    425 | 1298 |
| ctg ctc ttc ctg tgg atc ttt gtg tgc ttt gtc tac ctg tgg cag ctc<br>Leu Leu Phe Leu Trp Ile Phe Val Cys Phe Val Tyr Leu Trp Gln Leu<br>430                    435                    440                  445 | 1346 |
| ctt gga ccc tct gct ctc aca gcc gtt gct gtc ttc ctg agc ctc ctc<br>Leu Gly Pro Ser Ala Leu Thr Ala Val Ala Val Phe Leu Ser Leu Leu<br>                    450                    455                  460 | 1394 |
| cct ctg aac ttc ttc atc acc aag aag agg ggc ttc cat cag gaa gaa<br>Pro Leu Asn Phe Phe Ile Thr Lys Lys Arg Gly Phe His Gln Glu Glu<br>                    465                    470                  475 | 1442 |
| cag atg agg cag aag gcc tcc aga gca cgg ctc acc agc tcc atg ctc<br>Gln Met Arg Gln Lys Ala Ser Arg Ala Arg Leu Thr Ser Ser Met Leu | 1490 |

```
                480             485             490
aga act gtg aga acc atc aag tcc cac ggc tgg gag cat gcc ttc ctg      1538
Arg Thr Val Arg Thr Ile Lys Ser His Gly Trp Glu His Ala Phe Leu
    495                 500                 505 gag cga ctc ctt cac atc cgg ggc cag gag ctc agc gcc ctg aag acc      1586
Glu Arg Leu Leu His Ile Arg Gly Gln Glu Leu Ser Ala Leu Lys Thr
510                 515                 520                 525 tcc acc ctc ctc ttc tct gtg tct ctc gtg tcc ttc caa gtg tct aca      1634
Ser Thr Leu Leu Phe Ser Val Ser Leu Val Ser Phe Gln Val Ser Thr
            530                 535                 540 ttt ctg gtg gcg ctg gtc gtg ttt gct gtc cac acc ctg gtg gca gag      1682
Phe Leu Val Ala Leu Val Val Phe Ala Val His Thr Leu Val Ala Glu
                545                 550                 555 gac aat gcc atg gat gca gag aag gcc ttt gtg acg ctc aca gtg ctc      1730
Asp Asn Ala Met Asp Ala Glu Lys Ala Phe Val Thr Leu Thr Val Leu
            560                 565                 570 agc atc ctt aac aaa gcc cag gcc ttc ctc ccc ttc tct gtg cac tgc      1778
Ser Ile Leu Asn Lys Ala Gln Ala Phe Leu Pro Phe Ser Val His Cys
575                 580                 585 atc gtt cag gct cga gtg tcc ttt gac cgg ctg gct gcc ttc ctg tgc      1826
Ile Val Gln Ala Arg Val Ser Phe Asp Arg Leu Ala Ala Phe Leu Cys
590                 595                 600                 605 ctg gaa gaa gta gac ccc aat ggc atg atc gcg agt aac tcc agg cgc      1874
Leu Glu Glu Val Asp Pro Asn Gly Met Ile Ala Ser Asn Ser Arg Arg
                610                 615                 620 tcc tcg aag gat cga att tct gta cac aat ggc acc ttc gct tgg tcc      1922
Ser Ser Lys Asp Arg Ile Ser Val His Asn Gly Thr Phe Ala Trp Ser
            625                 630                 635 cag gag agc cca ccc tgc ctg cac ggg atc aac ctc acc gtg ccc cag      1970
Gln Glu Ser Pro Pro Cys Leu His Gly Ile Asn Leu Thr Val Pro Gln
                640                 645                 650 ggc tgt ctg ctg gct gtt gtg ggt cca gtg ggg gct ggg aag tcc tcc      2018
Gly Cys Leu Leu Ala Val Val Gly Pro Val Gly Ala Gly Lys Ser Ser
            655                 660                 665 ctg ctg tct gcc ctg ctt ggg gag ctg ttg aag gta gaa ggg tct gtg      2066
Leu Leu Ser Ala Leu Leu Gly Glu Leu Leu Lys Val Glu Gly Ser Val
670                 675                 680                 685 agc att gag ggt tcc gtg gct tac gtg cct cag gag gcc tgg gtc cag      2114
Ser Ile Glu Gly Ser Val Ala Tyr Val Pro Gln Glu Ala Trp Val Gln
                690                 695                 700 aat acc tct gtg gcg gag aat gtg tgc ttc agg caa gag ctg gac ctg      2162
Asn Thr Ser Val Ala Glu Asn Val Cys Phe Arg Gln Glu Leu Asp Leu
            705                 710                 715 ccc tgg ttg cag aaa gtt cta gac gcc tgt gcc ttg ggg tct gat gtg      2210
Pro Trp Leu Gln Lys Val Leu Asp Ala Cys Ala Leu Gly Ser Asp Val
        720                 725                 730 gcc agc ttc cct gca gga gtt cac acc cca ata ggg gag cag ggc atg      2258
Ala Ser Phe Pro Ala Gly Val His Thr Pro Ile Gly Glu Gln Gly Met
735                 740                 745 aat ctt tct ggg ggc cag aag cag cgg ctg agc ttg gct cgg gct gtg      2306
Asn Leu Ser Gly Gly Gln Lys Gln Arg Leu Ser Leu Ala Arg Ala Val
750                 755                 760                 765 tac aaa aag gct gcc atc tac ttg ctg gat gac ccc ctg gca gcg ctg      2354
Tyr Lys Lys Ala Ala Ile Tyr Leu Leu Asp Asp Pro Leu Ala Ala Leu
                770                 775                 780 gat gcc cac gtc agc cag cag gtc ttc aaa cag gtc atc ggg ccc agt      2402
Asp Ala His Val Ser Gln Gln Val Phe Lys Gln Val Ile Gly Pro Ser
            785                 790                 795 gga ttg ctc cag ggt acg act cgg atc ctt gta aca cac acg ctg cac      2450
```

```
                                                        -continued

Gly Leu Leu Gln Gly Thr Thr Arg Ile Leu Val Thr His Thr Leu His
        800                 805                 810 gtc ctg ccc cag gct gac cgg atc ctg gtg ctg gcc aat ggg acc atc      2498
Val Leu Pro Gln Ala Asp Arg Ile Leu Val Leu Ala Asn Gly Thr Ile
815                 820                 825 gca gag atg ggc tcc tac cag gac ctt ctg caa agg aac gga gcc ctg      2546
Ala Glu Met Gly Ser Tyr Gln Asp Leu Leu Gln Arg Asn Gly Ala Leu
830                 835                 840                 845 gtg ggt ctt ctg gat gga gcc aga cag cct gca gga aca cac gat gca      2594
Val Gly Leu Leu Asp Gly Ala Arg Gln Pro Ala Gly Thr His Asp Ala
                850                 855                 860 gct acc agt gac gac ctc gga ggc ttt cct gga ggt ggg agg ccc aca      2642
Ala Thr Ser Asp Asp Leu Gly Gly Phe Pro Gly Gly Gly Arg Pro Thr
            865                 870                 875 tgc aga cca gac agg ccc agg ccc acg gag gca gcc cct gtg aag ggc      2690
Cys Arg Pro Asp Arg Pro Arg Pro Thr Glu Ala Ala Pro Val Lys Gly
        880                 885                 890 agg agc aca tct gag gta cag atg gag gct tct ctg gat gac cct gag      2738
Arg Ser Thr Ser Glu Val Gln Met Glu Ala Ser Leu Asp Asp Pro Glu
895                 900                 905 gcc aca gga ttg aca gca gaa gag gat agt gtg cga tat ggc cgg gtg      2786
Ala Thr Gly Leu Thr Ala Glu Glu Asp Ser Val Arg Tyr Gly Arg Val
910                 915                 920                 925 aag atc acc ata tac ctg agc tac ctg cgg gcg gtg ggc aca ccc ctc      2834
Lys Ile Thr Ile Tyr Leu Ser Tyr Leu Arg Ala Val Gly Thr Pro Leu
                930                 935                 940 tgt acc tac acc ctg ttc ctc ttc ctc tgc cag caa gtg gca tcc ttc      2882
Cys Thr Tyr Thr Leu Phe Leu Phe Leu Cys Gln Gln Val Ala Ser Phe
            945                 950                 955 tcc caa ggc tac tgg ctg agc ctt tgg gcc gat gac ccg gtt gtg gat      2930
Ser Gln Gly Tyr Trp Leu Ser Leu Trp Ala Asp Asp Pro Val Val Asp
        960                 965                 970 ggg cgg cag atg cat gca gcc ctg cgt ggc tgg gtc ttt ggg ctc ctt      2978
Gly Arg Gln Met His Ala Ala Leu Arg Gly Trp Val Phe Gly Leu Leu
975                 980                 985 ggc tgt ctg caa gcc atc gga ctg ttt gcc tcc atg gct gcg gtg ttc      3026
Gly Cys Leu Gln Ala Ile Gly Leu Phe Ala Ser Met Ala Ala Val Phe
990                 995                 1000                1005 ctg ggt gga gcc cgg  gcc tca ggc ctc ctt  ttc cgg agt ctc ctg         3071
Leu Gly Gly Ala Arg  Ala Ser Gly Leu Leu  Phe Arg Ser Leu Leu
                1010                1015                1020 tgg gac gtg gct cgc  tct ccc atc ggc ttc  ttt gag cgc acg cca         3116
Trp Asp Val Ala Arg  Ser Pro Ile Gly Phe  Phe Glu Arg Thr Pro
                1025                1030                1035 gtc ggg aac ctg ctg  aac cgc ttt tcc aag  gag aca gac aca gtg         3161
Val Gly Asn Leu Leu  Asn Arg Phe Ser Lys  Glu Thr Asp Thr Val
                1040                1045                1050 gat gtg gac atc ccg  gac aag ctg agg tcc  ctt ctg acc tat gcc         3206
Asp Val Asp Ile Pro  Asp Lys Leu Arg Ser  Leu Leu Thr Tyr Ala
                1055                1060                1065 ttt ggg ctc ctg gag  gtc ggc ctg gca gtg  acg atg gcc acg cct         3251
Phe Gly Leu Leu Glu  Val Gly Leu Ala Val  Thr Met Ala Thr Pro
                1070                1075                1080 ctg gcc att gtg gcc  atc cta cct ctc atg  gtc ctc tat gct ggg         3296
Leu Ala Ile Val Ala  Ile Leu Pro Leu Met  Val Leu Tyr Ala Gly
                1085                1090                1095 ttt cag agc ctc tat  gtg gcc aca tct tgc  cag ctg aga cgt cta         3341
Phe Gln Ser Leu Tyr  Val Ala Thr Ser Cys  Gln Leu Arg Arg Leu
                1100                1105                1110
```

```
                                          -continued gag tca gcc cgc tac  tca tct gtg tgt tcc  cat atg gct gag acc       3386
Glu Ser Ala Arg Tyr  Ser Ser Val Cys Ser  His Met Ala Glu Thr
            1115                 1120                 1125 ttc cag gga agt ctg  gtg gtc agg gcc ttc  cgg gcc cag gcg tcc       3431
Phe Gln Gly Ser Leu  Val Val Arg Ala Phe  Arg Ala Gln Ala Ser
            1130                 1135                 1140 ttc acg gct cag cac  gat gct ctc atg gat  gag aac cag agg gtc       3476
Phe Thr Ala Gln His  Asp Ala Leu Met Asp  Glu Asn Gln Arg Val
            1145                 1150                 1155 agt ttc ccg aaa ctg  gtg gct gac agg tgg  ctg gct act aac ctg       3521
Ser Phe Pro Lys Leu  Val Ala Asp Arg Trp  Leu Ala Thr Asn Leu
            1160                 1165                 1170 gag ctt cta ggg aat  ggc ttg gta ttc gtg  gct gct aca tgt gct       3566
Glu Leu Leu Gly Asn  Gly Leu Val Phe Val  Ala Ala Thr Cys Ala
            1175                 1180                 1185 gtg ctg agc aag gct  cac cta agt gct ggc  ctc gtg ggc ttc tcg       3611
Val Leu Ser Lys Ala  His Leu Ser Ala Gly  Leu Val Gly Phe Ser
            1190                 1195                 1200 gtc tcc gct gcc ctc  cag gtg aca cag act  ctg cag tgg gtg gtc       3656
Val Ser Ala Ala Leu  Gln Val Thr Gln Thr  Leu Gln Trp Val Val
            1205                 1210                 1215 cgc agc tgg aca gat  ctg gag aac agc atg  gta gcc gtg gag cgc       3701
Arg Ser Trp Thr Asp  Leu Glu Asn Ser Met  Val Ala Val Glu Arg
            1220                 1225                 1230 gtg cag gac tac gct  cgc atc ccc aaa gag  gct ccc tgg agg ctg       3746
Val Gln Asp Tyr Ala  Arg Ile Pro Lys Glu  Ala Pro Trp Arg Leu
            1235                 1240                 1245 ccc acc tgc gca gcc  cag cct ctc tgg cct  tgt ggg gga cag att       3791
Pro Thr Cys Ala Ala  Gln Pro Leu Trp Pro  Cys Gly Gly Gln Ile
            1250                 1255                 1260 gag ttc cgg gac ttt  ggg ctc aga cac cga  cca gag ctg ccc ttg       3836
Glu Phe Arg Asp Phe  Gly Leu Arg His Arg  Pro Glu Leu Pro Leu
            1265                 1270                 1275 gct gtg cag gga gtg  tcc ctg aag atc cat  gca gga gag aag gtg       3881
Ala Val Gln Gly Val  Ser Leu Lys Ile His  Ala Gly Glu Lys Val
            1280                 1285                 1290 ggc atc gtg ggc aga  aca ggg gcc ggg aag  tcc tcc ctg gct tgg       3926
Gly Ile Val Gly Arg  Thr Gly Ala Gly Lys  Ser Ser Leu Ala Trp
            1295                 1300                 1305 ggc ctg ctg cgg ctt  cag gag gct gcc gag  ggt aat atc tgg atc       3971
Gly Leu Leu Arg Leu  Gln Glu Ala Ala Glu  Gly Asn Ile Trp Ile
            1310                 1315                 1320 gat ggg gtc cct atc  acc cat gtg ggg ctg  cac aca ctg agg tcc       4016
Asp Gly Val Pro Ile  Thr His Val Gly Leu  His Thr Leu Arg Ser
            1325                 1330                 1335 cga atc acc atc atc  cct cag gac cct gtc  ctg ttc cca ggc tct       4061
Arg Ile Thr Ile Ile  Pro Gln Asp Pro Val  Leu Phe Pro Gly Ser
            1340                 1345                 1350 ctg cgg atg aac ctg  gac ctg ctt cag gag  cac aca gat gaa ggc       4106
Leu Arg Met Asn Leu  Asp Leu Leu Gln Glu  His Thr Asp Glu Gly
            1355                 1360                 1365 atc tgg gca gcg ctg  gag aca gtg cag ctc  aag gcc ttc gtg acc       4151
Ile Trp Ala Ala Leu  Glu Thr Val Gln Leu  Lys Ala Phe Val Thr
            1370                 1375                 1380 agc ctg cct ggc cag  ctg caa tat gag tgt  gca ggc agg gga gat       4196
Ser Leu Pro Gly Gln  Leu Gln Tyr Glu Cys  Ala Gly Gln Gly Asp
            1385                 1390                 1395 gac ctg agc gtg ggt  cat aaa cag ctc ctg  tgc ctg gca cga gcc       4241
Asp Leu Ser Val Gly  His Lys Gln Leu Leu  Cys Leu Ala Arg Ala
            1400                 1405                 1410
```

```
ctt ctc cgg aaa acc cag atc ctc atc ctg gac gag gcg act gcc      4286
Leu Leu Arg Lys Thr Gln Ile Leu Ile Leu Asp Glu Ala Thr Ala
            1415                1420                1425 tct gtg gac cca ggg acg gag atg cag atg cag gcg gcc ctg gag      4331
Ser Val Asp Pro Gly Thr Glu Met Gln Met Gln Ala Ala Leu Glu
        1430                1435                1440 cgc tgg ttt aca cag tgt acc tta ctg ctt atc gct cac cgc ctg      4376
Arg Trp Phe Thr Gln Cys Thr Leu Leu Leu Ile Ala His Arg Leu
        1445                1450                1455 cgc tcc gtg atg gac tgt gcc aga gtc cta gtc atg gat gag ggg      4421
Arg Ser Val Met Asp Cys Ala Arg Val Leu Val Met Asp Glu Gly
        1460                1465                1470 cag gtg gca gaa agt ggc aat cct gct cag ctg ctg gcc cag aaa      4466
Gln Val Ala Glu Ser Gly Asn Pro Ala Gln Leu Leu Ala Gln Lys
        1475                1480                1485 ggc ctg ttt tac agg cta gcc cat gag tcg ggc ctc gct tga          4508
Gly Leu Phe Tyr Arg Leu Ala His Glu Ser Gly Leu Ala
        1490                1495 atgaggattc ttaccaaccc ccgtggagcc agccatagag cctgcagtgg ctggagatgc  4568
cagagactcc aatctaaact cctctttggg agggagatgg cagagaaagt gatggagtat  4628
tgggatacca gacccagaag aacccagcac gcccaggttg gcctgagcaa ggccatgccc  4688
accccaggcc aaagagaatg gtaactctca gcccaagctg tctacttcaa ggccacgccc  4748
actccaggcc aatcagattg gatgccctgg acccaggtga tggtgtgcac atattcccta  4808
actccttatt ttgaagtcat tgtagatttc agtcacagtt ttaagaaata acacggagag  4868
aaactgtgac ccctctgccc tgtttattcc aagggtgaca ccttgtccaa ctctagagca  4928
tcacaccgac tctgaccgac tcgtctttac aactccaaaa aaaaaaaaa aa           4980
```

<210> SEQ ID NO 9
<211> LENGTH: 1498
<212> TYPE: PRT
<213> ORGANISM: Mus musculus

<400> SEQUENCE: 9

```
Met Asn Ser Gly Arg Ser Met Ala Thr Pro Gly Glu Gln Cys Ala Gly
1               5                   10                  15

Leu Arg Val Trp Asn Gln Thr Glu Gln Glu Pro Ala Ala Tyr His Leu
            20                  25                  30

Leu Ser Leu Cys Phe Val Arg Ala Ala Ser Ser Trp Val Pro Pro Met
        35                  40                  45

Tyr Leu Trp Val Leu Gly Pro Ile Tyr Leu Leu Tyr Ile His Arg His
    50                  55                  60

Gly Arg Cys Tyr Leu Arg Met Ser His Leu Phe Lys Thr Lys Met Val
65                  70                  75                  80

Leu Gly Leu Ala Leu Ile Leu Leu Tyr Thr Phe Asn Val Ala Val Pro
                85                  90                  95

Leu Trp Arg Ile His Gln Gly Val Pro Gln Ala Pro Glu Leu Leu Ile
            100                 105                 110

His Pro Thr Val Trp Leu Thr Thr Met Ser Phe Ala Thr Phe Leu Ile
        115                 120                 125

His Met Glu Arg Arg Lys Gly Val Arg Ser Ser Gly Val Leu Phe Gly
    130                 135                 140

Tyr Trp Leu Leu Cys Cys Ile Leu Pro Gly Ile Asn Thr Val Gln Gln
145                 150                 155                 160
```

-continued

```
Ala Ser Ala Gly Asn Leu Arg Gln Glu Pro Leu His His Leu Ala Thr
            165                 170                 175
Tyr Leu Cys Leu Ser Leu Val Val Ala Glu Leu Val Leu Ser Cys Leu
            180                 185                 190
Val Asp Gln Pro Pro Phe Phe Ser Glu Asp Ser Gln Pro Leu Asn Pro
            195                 200                 205
Cys Pro Glu Ala Glu Ala Ser Phe Pro Ser Lys Ala Met Phe Trp Trp
    210                 215                 220
Ala Ser Gly Leu Leu Trp Arg Gly Tyr Lys Lys Leu Leu Gly Pro Lys
225                 230                 235                 240
Asp Leu Trp Ser Leu Gly Arg Glu Asn Ser Ser Glu Glu Leu Val Ser
            245                 250                 255
Gln Leu Glu Arg Glu Trp Arg Arg Ser Cys Asn Gly Leu Pro Gly His
            260                 265                 270
Lys Gly His Ser Ser Val Gly Ala Pro Glu Thr Glu Ala Phe Leu Gln
            275                 280                 285
Pro Glu Arg Ser Gln Arg Gly Pro Leu Leu Arg Ala Ile Trp Arg Val
            290                 295                 300
Phe Arg Ser Thr Phe Leu Leu Gly Thr Leu Ser Leu Val Ile Ser Asp
305                 310                 315                 320
Ala Phe Arg Phe Ala Val Pro Lys Leu Leu Ser Leu Phe Leu Glu Phe
            325                 330                 335
Met Gly Asp Arg Asn Ser Ser Ala Trp Thr Gly Trp Leu Leu Ala Val
            340                 345                 350
Leu Met Phe Ala Ala Ala Cys Leu Gln Thr Leu Phe Glu Gln Gln His
            355                 360                 365
Met Tyr Arg Ala Lys Val Leu Gln Met Arg Leu Arg Thr Ala Ile Thr
            370                 375                 380
Gly Leu Val Tyr Arg Lys Val Leu Val Leu Ser Ser Gly Ser Arg Lys
385                 390                 395                 400
Ser Ser Ala Ala Gly Asp Val Val Asn Leu Val Ser Val Asp Ile Gln
            405                 410                 415
Arg Leu Ala Glu Ser Ile Ile Tyr Leu Asn Gly Leu Trp Leu Leu Phe
            420                 425                 430
Leu Trp Ile Phe Val Cys Phe Val Tyr Leu Trp Gln Leu Leu Gly Pro
            435                 440                 445
Ser Ala Leu Thr Ala Val Ala Val Phe Leu Ser Leu Leu Pro Leu Asn
450                 455                 460
Phe Phe Ile Thr Lys Lys Arg Gly Phe His Gln Glu Gln Met Arg
465                 470                 475                 480
Gln Lys Ala Ser Arg Ala Arg Leu Thr Ser Ser Met Leu Arg Thr Val
            485                 490                 495
Arg Thr Ile Lys Ser His Gly Trp Glu His Ala Phe Leu Glu Arg Leu
            500                 505                 510
Leu His Ile Arg Gly Gln Glu Leu Ser Ala Leu Lys Thr Ser Thr Leu
            515                 520                 525
Leu Phe Ser Val Ser Leu Val Ser Phe Gln Val Ser Thr Phe Leu Val
            530                 535                 540
Ala Leu Val Val Phe Ala Val His Thr Leu Val Ala Glu Asp Asn Ala
545                 550                 555                 560
Met Asp Ala Glu Lys Ala Phe Val Thr Leu Thr Val Leu Ser Ile Leu
            565                 570                 575
Asn Lys Ala Gln Ala Phe Leu Pro Phe Ser Val His Cys Ile Val Gln
```

```
              580                 585                 590
Ala Arg Val Ser Phe Asp Arg Leu Ala Ala Phe Leu Cys Leu Glu Glu
            595                 600                 605
Val Asp Pro Asn Gly Met Ile Ala Ser Asn Ser Arg Arg Ser Ser Lys
        610                 615                 620
Asp Arg Ile Ser Val His Asn Gly Thr Phe Ala Trp Ser Gln Glu Ser
625                 630                 635                 640
Pro Pro Cys Leu His Gly Ile Asn Leu Thr Val Pro Gln Gly Cys Leu
                645                 650                 655
Leu Ala Val Val Gly Pro Val Gly Ala Gly Lys Ser Ser Leu Leu Ser
            660                 665                 670
Ala Leu Leu Gly Glu Leu Leu Lys Val Glu Gly Ser Val Ser Ile Glu
        675                 680                 685
Gly Ser Val Ala Tyr Val Pro Gln Glu Ala Trp Val Gln Asn Thr Ser
    690                 695                 700
Val Ala Glu Asn Val Cys Phe Arg Gln Glu Leu Asp Leu Pro Trp Leu
705                 710                 715                 720
Gln Lys Val Leu Asp Ala Cys Ala Leu Gly Ser Asp Val Ala Ser Phe
                725                 730                 735
Pro Ala Gly Val His Thr Pro Ile Gly Glu Gln Gly Met Asn Leu Ser
            740                 745                 750
Gly Gly Gln Lys Gln Arg Leu Ser Leu Ala Arg Ala Val Tyr Lys Lys
        755                 760                 765
Ala Ala Ile Tyr Leu Leu Asp Asp Pro Leu Ala Ala Leu Asp Ala His
    770                 775                 780
Val Ser Gln Gln Val Phe Lys Gln Val Ile Gly Pro Ser Gly Leu Leu
785                 790                 795                 800
Gln Gly Thr Thr Arg Ile Leu Val Thr His Thr Leu His Val Leu Pro
                805                 810                 815
Gln Ala Asp Arg Ile Leu Val Leu Ala Asn Gly Thr Ile Ala Glu Met
            820                 825                 830
Gly Ser Tyr Gln Asp Leu Leu Gln Arg Asn Gly Ala Leu Val Gly Leu
        835                 840                 845
Leu Asp Gly Ala Arg Gln Pro Ala Gly Thr His Asp Ala Ala Thr Ser
    850                 855                 860
Asp Asp Leu Gly Gly Phe Pro Gly Gly Gly Arg Pro Thr Cys Arg Pro
865                 870                 875                 880
Asp Arg Pro Arg Pro Thr Glu Ala Ala Pro Val Lys Gly Arg Ser Thr
                885                 890                 895
Ser Glu Val Gln Met Glu Ala Ser Leu Asp Asp Pro Glu Ala Thr Gly
            900                 905                 910
Leu Thr Ala Glu Glu Asp Ser Val Arg Tyr Gly Arg Val Lys Ile Thr
        915                 920                 925
Ile Tyr Leu Ser Tyr Leu Arg Ala Val Gly Thr Pro Leu Cys Thr Tyr
    930                 935                 940
Thr Leu Phe Leu Phe Leu Cys Gln Gln Val Ala Ser Phe Ser Gln Gly
945                 950                 955                 960
Tyr Trp Leu Ser Leu Trp Ala Asp Pro Val Val Asp Gly Arg Gln
                965                 970                 975
Met His Ala Ala Leu Arg Gly Trp Val Phe Gly Leu Gly Cys Leu
            980                 985                 990
Gln Ala Ile Gly Leu Phe Ala Ser  Met Ala Ala Val Phe  Leu Gly Gly
        995                 1000                1005
```

-continued

Ala Arg Ala Ser Gly Leu Leu Phe Arg Ser Leu Leu Trp Asp Val
    1010             1015                 1020

Ala Arg Ser Pro Ile Gly Phe Phe Glu Arg Thr Pro Val Gly Asn
    1025             1030                 1035

Leu Leu Asn Arg Phe Ser Lys Glu Thr Asp Thr Val Asp Val Asp
    1040             1045                 1050

Ile Pro Asp Lys Leu Arg Ser Leu Leu Thr Tyr Ala Phe Gly Leu
    1055             1060                 1065

Leu Glu Val Gly Leu Ala Val Thr Met Ala Thr Pro Leu Ala Ile
    1070             1075                 1080

Val Ala Ile Leu Pro Leu Met Val Leu Tyr Ala Gly Phe Gln Ser
    1085             1090                 1095

Leu Tyr Val Ala Thr Ser Cys Gln Leu Arg Arg Leu Glu Ser Ala
    1100             1105                 1110

Arg Tyr Ser Ser Val Cys Ser His Met Ala Glu Thr Phe Gln Gly
    1115             1120                 1125

Ser Leu Val Val Arg Ala Phe Arg Ala Gln Ala Ser Phe Thr Ala
    1130             1135                 1140

Gln His Asp Ala Leu Met Asp Glu Asn Gln Arg Val Ser Phe Pro
    1145             1150                 1155

Lys Leu Val Ala Asp Arg Trp Leu Ala Thr Asn Leu Glu Leu Leu
    1160             1165                 1170

Gly Asn Gly Leu Val Phe Val Ala Ala Thr Cys Ala Val Leu Ser
    1175             1180                 1185

Lys Ala His Leu Ser Ala Gly Leu Val Gly Phe Ser Val Ser Ala
    1190             1195                 1200

Ala Leu Gln Val Thr Gln Thr Leu Gln Trp Val Val Arg Ser Trp
    1205             1210                 1215

Thr Asp Leu Glu Asn Ser Met Val Ala Val Glu Arg Val Gln Asp
    1220             1225                 1230

Tyr Ala Arg Ile Pro Lys Glu Ala Pro Trp Arg Leu Pro Thr Cys
    1235             1240                 1245

Ala Ala Gln Pro Leu Trp Pro Cys Gly Gly Gln Ile Glu Phe Arg
    1250             1255                 1260

Asp Phe Gly Leu Arg His Arg Pro Glu Leu Pro Leu Ala Val Gln
    1265             1270                 1275

Gly Val Ser Leu Lys Ile His Ala Gly Glu Lys Val Gly Ile Val
    1280             1285                 1290

Gly Arg Thr Gly Ala Gly Lys Ser Ser Leu Ala Trp Gly Leu Leu
    1295             1300                 1305

Arg Leu Gln Glu Ala Ala Glu Gly Asn Ile Trp Ile Asp Gly Val
    1310             1315                 1320

Pro Ile Thr His Val Gly Leu His Thr Leu Arg Ser Arg Ile Thr
    1325             1330                 1335

Ile Ile Pro Gln Asp Pro Val Leu Phe Pro Gly Ser Leu Arg Met
    1340             1345                 1350

Asn Leu Asp Leu Leu Gln Glu His Thr Asp Glu Gly Ile Trp Ala
    1355             1360                 1365

Ala Leu Glu Thr Val Gln Leu Lys Ala Phe Val Thr Ser Leu Pro
    1370             1375                 1380

Gly Gln Leu Gln Tyr Glu Cys Ala Gly Gln Gly Asp Asp Leu Ser
    1385             1390                 1395

```
Val Gly His Lys Gln Leu Leu Cys Leu Ala Arg Ala Leu Leu Arg
    1400            1405                1410

Lys Thr Gln Ile Leu Ile Leu Asp Glu Ala Thr Ala Ser Val Asp
    1415            1420                1425

Pro Gly Thr Glu Met Gln Met Gln Ala Ala Leu Glu Arg Trp Phe
    1430            1435                1440

Thr Gln Cys Thr Leu Leu Leu Ile Ala His Arg Leu Arg Ser Val
    1445            1450                1455

Met Asp Cys Ala Arg Val Leu Val Met Asp Glu Gly Gln Val Ala
    1460            1465                1470

Glu Ser Gly Asn Pro Ala Gln Leu Leu Ala Gln Lys Gly Leu Phe
    1475            1480                1485

Tyr Arg Leu Ala His Glu Ser Gly Leu Ala
    1490            1495
```

<210> SEQ ID NO 10
<211> LENGTH: 20
<212> TYPE: DNA
<213> ORGANISM: Artificial
<220> FEATURE:
<223> OTHER INFORMATION: primer corresponding to a G to A mutation in
      exon 24 of the ABCC6 gene

<400> SEQUENCE: 10
cagtggtcca ggcattccga                                           20

<210> SEQ ID NO 11
<211> LENGTH: 20
<212> TYPE: DNA
<213> ORGANISM: Artificial
<220> FEATURE:
<223> OTHER INFORMATION: primer corresponding to a C to T mutation in
      exon 24 of the ABCC6 gene

<400> SEQUENCE: 11
cagtggtccg ggcattctga                                           20

<210> SEQ ID NO 12
<211> LENGTH: 26
<212> TYPE: DNA
<213> ORGANISM: Artificial
<220> FEATURE:
<223> OTHER INFORMATION: primer corresponding to a G to C mutation in
      exon 24 of the ABCC6 gene

<400> SEQUENCE: 12
gacccttgga gtcagccagc tactcg                                    26

<210> SEQ ID NO 13
<211> LENGTH: 26
<212> TYPE: DNA
<213> ORGANISM: Artificial
<220> FEATURE:
<223> OTHER INFORMATION: primer corresponding to a C to G mutation in
      exon 24 of the ABCC6 gene

<400> SEQUENCE: 13
gacgcttgga gtcagccagc tactgg                                    26

<210> SEQ ID NO 14
<211> LENGTH: 26
<212> TYPE: DNA
<213> ORGANISM: Artificial
<220> FEATURE:

```
<223> OTHER INFORMATION: primer corresponding to a C to T mutation in
      exon 26 of the ABCC gene

<400> SEQUENCE: 14
ggatgtagga ctatgcctgg acgccc                                          26

<210> SEQ ID NO 15
<211> LENGTH: 26
<212> TYPE: DNA
<213> ORGANISM: Artificial
<220> FEATURE:
<223> OTHER INFORMATION: primer corresponding to a G to C mutation in
      exon 26 of the ABCC6 gene

<400> SEQUENCE: 15
ggatgcagga ctatgcctgc acgccc                                          26

<210> SEQ ID NO 16
<211> LENGTH: 20
<212> TYPE: DNA
<213> ORGANISM: Artificial
<220> FEATURE:
<223> OTHER INFORMATION: primer corresponding to a C to A mutation in
      exon 27 of the ABCC6 gene

<400> SEQUENCE: 16
tgcagctaag ccccctggc                                                  20

<210> SEQ ID NO 17
<211> LENGTH: 19
<212> TYPE: DNA
<213> ORGANISM: Artificial
<220> FEATURE:
<223> OTHER INFORMATION: primer corresponding to a deletion of a T in
      exon 27 of the ABCC6 gene

<400> SEQUENCE: 17
tgcagctcag cccccggc                                                   19

<210> SEQ ID NO 18
<211> LENGTH: 20
<212> TYPE: DNA
<213> ORGANISM: Artificial
<220> FEATURE:
<223> OTHER INFORMATION: primer corresponding to a G to A mutation in
      exon 27 of the ABCC6 gene

<400> SEQUENCE: 18
gctccaagct ccctggaggc                                                 20

<210> SEQ ID NO 19
<211> LENGTH: 30
<212> TYPE: DNA
<213> ORGANISM: Artificial
<220> FEATURE:
<223> OTHER INFORMATION: primer corresponding to a C to T mutation in
      exon 28 of the ABCC6 gene

<400> SEQUENCE: 19
ctgtggctcc aggaggcagc tgagggtggg                                      30

<210> SEQ ID NO 20
<211> LENGTH: 30
<212> TYPE: DNA
<213> ORGANISM: Artificial
<220> FEATURE:
<223> OTHER INFORMATION: primer corresponding to a G to A mutation in
```

-continued exon 28 of the ABCC6 gene

<400> SEQUENCE: 20
ctgcagctcc aggaggcagc tgagggtggg                                        30

<210> SEQ ID NO 21
<211> LENGTH: 30
<212> TYPE: DNA
<213> ORGANISM: Artificial
<220> FEATURE:
<223> OTHER INFORMATION: primer corresponding to a G to A mutation in
      exon 28 of the ABCC6 gene

<400> SEQUENCE: 21
ctgcggctcc aggaggcagc tgagagtggg                                        30

<210> SEQ ID NO 22
<211> LENGTH: 25
<212> TYPE: DNA
<213> ORGANISM: Artificial
<220> FEATURE:
<223> OTHER INFORMATION: primer corresponding to a G to T mutation in
      exon 28 of the ABCC6 gene

<400> SEQUENCE: 22
gtgggcatct ttggcaggac cgggg                                             25

<210> SEQ ID NO 23
<211> LENGTH: 25
<212> TYPE: DNA
<213> ORGANISM: Artificial
<220> FEATURE:
<223> OTHER INFORMATION: primer corresponding to a C to T mutation in
      exon 28 of the ABCC6 gene

<400> SEQUENCE: 23
gtgggcatcg ttggcaggac tgggg                                             25

<210> SEQ ID NO 24
<211> LENGTH: 25
<212> TYPE: DNA
<213> ORGANISM: Artificial
<220> FEATURE:
<223> OTHER INFORMATION: primer corresponding to a G to A mutation in
      exon 28 of the ABCC6 gene

<400> SEQUENCE: 24
gtgggcatcg ttggcaggac caggg                                             25

<210> SEQ ID NO 25
<211> LENGTH: 25
<212> TYPE: DNA
<213> ORGANISM: Artificial
<220> FEATURE:
<223> OTHER INFORMATION: primer corresponding to a G to C mutation in
      exon 28 of the ABCC6 gene

<400> SEQUENCE: 25
gtgggcatcg ttggcaggac cgggc                                             25

<210> SEQ ID NO 26
<211> LENGTH: 21
<212> TYPE: DNA
<213> ORGANISM: Homo sapiens
<220> FEATURE:
<221> NAME/KEY: CDS
<222> LOCATION: (1)..(12)

```
-continued

<223> OTHER INFORMATION: Mutation in Exon 24 of human MRP6 gene

<400> SEQUENCE: 26 cgg gca ttc tga acccaggcc                                          21
Arg Ala Phe
1

<210> SEQ ID NO 27
<211> LENGTH: 18
<212> TYPE: DNA
<213> ORGANISM: Homo sapiens
<220> FEATURE:
<221> NAME/KEY: misc_feature
<223> OTHER INFORMATION: mutation in Intron 21 of human MRP6 gene

<400> SEQUENCE: 27
tacggcaggt taaccacc                                                18
```

METHODS FOR DIAGNOSING PSEUDOXANTHOMA ELASTICUM

RELATED APPLICATIONS

This application claims priority to, and the benefit of U.S. Ser. No. 60/184,269, filed Feb. 23, 2000, the disclosure of which is incorporated by reference herein.

GOVERNMENT SUPPORT

Work described heroin was supported, in part, by Federal Grant No. EY 13019 and National Institutes of Health Grant No. HL 50665. The U.S. Government has certain rights in the invention.

FIELD OF THE INVENTION

The present invention relates generally to the field of physiological dysfunctions associated with *Pseudoxanthoma elasticum*. More particularly, the invention is concerned with the identification of a gene associated with *Pseudoxanthoma elasticum*, as well as mutations in the gene that cause the disease. The present invention also relates to methods for detecting and diagnosing *Pseudoxanthoma elasticum*, to methods for identifying carriers of mutant and normal alleles of the gene associated with *Pseudoxanthoma elasticum*, to methods for screening compounds to identify potential therapeutics for *Pseudoxanthoma elasticum*, to treatment methods for *Pseudoxanthoma elasticum*, and to useful cell lines and animal models of the disease.

BACKGROUND OF THE INVENTION

*Pseudoxanthoma elasticum* (PXE) is a heritable disorder characterized by mineralization of elastic fibers in skin, arteries and the retina, that result in dermal lesions with associated laxity and loss of elasticity, arterial insufficiency, cardiovascular disease and retinal hemorrhages leading to macular degeneration.

The skin manifestations are among the most common characteristics of PXE, but the ocular and cardiovascular symptoms are responsible for the morbidity of the disease. Characteristic skin lesions are generally an early sign of PXE and were first described by a French dermatologist in 1896. Skin lesions are usually detected during childhood or adolescence and progress slowly and often unpredictably. Therefore, the initial diagnosis of PXE is sometimes made by a dermatologist. The skin lesions consist of yellowish papules and plaques and laxity with loss of elasticity, and result from an accumulation of abnormal mineralized elastic fibers in the mid-dermis. Lesions are typically seen on the face, neck, axilla, antecubital fossa, popliteal fossa, groin and periumbilical areas. A PXE diagnosis can be confirmed by a skin biopsy that shows calcification of fragmented elastic fibers in the mid- and lower dermis.

Another characteristic of PXE is the presence of ocular lesions due to the accumulation of abnormal elastic fibers in the Bruch's membrane, resulting in angioid streaks. Doyne was the first to describe these ocular streaks in 1889, and Knapp introduced the term "angioid streaks" for their resemblance to blood vessels. The combination of PXE and ocular manifestations was initially referred to as the Gronblad-Strandberg syndrome, after the names of two ophthalmologists who independently related the occurrence of angioid streaks to PXE in 1929. The majority of PXE patients (approximately 85%) develop ocular manifestations during their second decade of life. Bilateral angioid streaks are normally seen as linear gray or dark red lines with irregular serrated edges lying beneath normal retinal blood vessels and represent breaks in the Bruch's membrane. The Bruch's membrane is not in a true sense a "membrane" but rather a heterogeneous elastin-rich layer separating the chorioid from the retina. The elastic laminae of the Bruch's membrane is located between two layers of collagen (type I, III and IV) which lie in direct contact with the basement membranes of the retinal pigmented epithelium (RPE) and the capillaries in the choriocapillary layer of the chorioid. As a consequence of angioid streaks, a PXE patient progressively develops a chorioidal neovascularization with a subsequent hemorrhagic detachment of the fovea and later scarring. Optic nerve drusen may also be associated with angioid streaks and results in visual field deficits and even advanced visual impairment.

Common cardiovascular complications of PXE are due to the presence of abnormal calcified elastic fibers in the internal elastic lamina of medium-sized arteries. The broad spectrum of phenotypes includes premature atherosclerotic changes, intimal fibroplasia causing angina or intermittent claudication or both, early myocardial infarction and hypertension. Fibrous thickening of the endocardium and atrioventricular valves can also result in restrictive cardiomyopathy. Approximately 10% of PXE patients also develop gastrointestinal bleeding and central nervous system complications (such as stroke and dementia) as a consequence of systemic arterial wall mineralization. In addition, renovascular hypertension and atrial septal aneurysm can be seen in PXE patients.

Strikingly, lung abnormalities are not a significant phenotypic feature of PXE, even though pulmonary tissues are rich in elastic fibers. Mineralization of pulmonary elastic fibers has only been noted in a few patients.

PXE is usually found as a sporadic disorder but examples of both autosomal recessive and autosomal dominant forms of PXE have been reported. Partial manifestations of the PXE phenotype have also been described in presumed carriers in PXE families. Recent reports have linked both the dominant and recessive forms of PXE to a 5 cM domain on chromosome 16P 13.1 However, the mechanisms underlying the physiological defects characteristic of PXE are not understood.

Therefore, there is a need in the art for methods and compositions for diagnosing and treating PXE and PXE associated phenotypes.

SUMMARY OF THE INVENTION

The invention provides methods and compositions for diagnosing and treating PXE and PXE associated physiological dysfunctions. According to the invention, mutations associated with PXE are located in the (MRP6) ABCC6 gene. Therefore, methods for detecting the presence of a mutation associated with PXE involve interrogating the (MRP6) ABCC6 gene, or a portion thereof, for the presence of one or more mutations that are associated with PXE. Accordingly, one aspect of the invention provides methods for identifying individuals that have one or two mutant alleles at the PXE locus. PXE is most often an autosomal recessive disease. Therefore, an individual with two mutant (MRP6) ABCC6 alleles associated with PXE will develop symptoms characteristic of the disease. In contrast, an individual with one mutant (MRP6) ABCC6 allele associated with PXE is a carrier of the disease and does not develop full-blown PXE. However, according to one embodiment of the invention, a PXE carrier may develop mild forms of the characteristic manifestations. Accordingly, a PXE carrier status can be indicative of a predisposition to PXE related symptoms such as eye, skin, or cardiovascular problems. In a preferred embodiment of the invention, genetic counseling is provided to an individual identified as having a mutation associated with PXE in one or both alleles of the PXE ((MRP6) ABCC6) locus.

In another aspect, the invention provides compositions for detecting the presence of a mutation associated with PXE at the (MRP6) ABCC6 locus. In a preferred embodiment, an oligonucleotide that hybridizes to the (MRP6) ABCC6 locus is used in a diagnostic assay. In a more preferred embodiment, the oligonucleotide includes a sequence complementary to a mutation that is associated with PXE. Alternatively, an antibody-based diagnostic assay is used to detect the presence of a mutation associated with PXE at the (MRP6) ABCC6 locus.

Other aspects of the invention include therapeutic uses of the (MRP6) ABCC6 gene or protein, drug screening, the identification of (MRP6) ABCC6 homologues in other organisms (including mammalian organisms), cellular and animal models of PXE, the identification of (MRP6) ABCC6 functional domains related to the PXE phenotype, the identification of regulators of (MRP6) ABCC6 expression (mutations in these regulators can also result in PXE related symptoms), the identification of genes/proteins that interact with (MRP6) ABCC6 (alterations in these interacting molecules can also cause PXE related symptoms).

Thus, in one series of embodiments the invention provides methods for screening for the presence of a PXE mutation by interrogating an MRP6 nucleic acid obtained from a patient for the presence of a PXE mutation. The screen is positive is the presence of a PXE associated mutation is detected. A PXE associated mutation is a mutation that causes the PXE phenotype in an individual that is homozygous for the mutation. PXE associated mutations also causes the PXE phenotype in an individual that is a compound heterozygote with two different mutant alleles at the MRP6 locus, wherein each allele is a PXE associated allele. Nucleic acid is isolated from a patient biological sample, and the biological sample is preferably blood, saliva, amniotic fluid, or tissue such as a biopsy tissue. According to the invention, an MRP6 nucleic acid is a nucleic acid obtained from the MRP6 locus. An MRP6 nucleic acid can be mRNA, genomic DNA or cDNA from the MRP6 locus, or a PCR product of any of the above. According to the invention, the MRP6 locus includes the MRP6 exons, introns, and associated promoter and regulatory sequences in the genome surrounding the MRP6 exons.

In one series of embodiments, a PXE associated mutation is detected in MRP6 using a nucleic acid based detection assay. Preferred nucleic acid based detection assays include hybridization assays, primer extension assays, SSCP, DGGE, RFLP, LCR, DHPLC, and enzymatic cleavage assays. In another series of embodiments, a PXE associated mutation is detected in a protein based detection assay. Preferred protein based detection assays include ELISA and a Western blot assays. In one embodiment of the invention, mutation detection assays are provided to screen the MRP6 locus or a portion thereof to determine whether a mutation is present. The lack of MRP6 expression or the expression of a physically aberrant form of MRP6 may be sufficient to determine that an individual has a PXE associated mutation at the MRP6 locus. Alternatively, the determination that a mutation is present in the MRP6 locus may not be sufficient to determine the PXE status of an individual in the absence of information concerning the specific identity of the mutation. If such a mutation is present, it may be identified according to methods of the invention, for example by sequencing the region of the MRP6 locus that contains the mutation. Once a mutation is identified in a patient sample, the PXE status of the patient can be determined according to methods of the invention. In an alternative embodiment of the invention, specific mutation detection assays are provided to detect a known PXE associated MRP6 mutation in a patient sample.

In another series of embodiments, the invention provides oligonucleotide probes or primers and antibodies for use in mutation detection assays or screens according to the invention.

In another series of embodiments, the invention provides methods for screening candidate drug compounds to identify therapeutic compounds for treating PXE patients (individuals that have PXE due to the presence of two recessive PXE associated MRP6 alleles, or one apparently dominant PXE allele) or PXE carriers (individuals with one normal MRP6 allele and one allele with a PXE associated mutation).

In another series of embodiments, the invention provides methods for treating PXE patients or carriers using a normal MRP6 nucleic acid or protein to restore normal MRP6 function to the individual or to specific cells or tissues or the individual.

In another series of embodiments, the invention provides methods for creating transgenic or knockout cell lines and animals in order to provide a model system for PXE.

In another series of embodiments, the invention provides methods for identifying compounds such as other intracellular proteins that interact with MRP6 thereby to identify additional therapeutic targets for PXE treatment.

Accordingly, the invention provides methods and compositions for unambiguously determining the PXE status of an individual. The invention provides methods for detecting deletions, substitutions, insertions, and rearrangements in the MRP6 locus that are associated with PXE. In preferred embodiments, the invention provides methods for identifying mutations known to be associated with PXE. Preferred mutations include mutations that affect one or more of the bases in codons 1114, 1138, 1141, 1298, 1302, 1303, 1314, 1321 and other codons identified herein as being important for normal MRP6 function. Alternatively, the invention provides methods to identify mutations that result in non-conservative substitutions in the MRP6 locus. In a further embodiment, the invention provides assays to detect PXE associated mutations at intron/exon splice sites of the MRP6 gene. The invention also provides methods to detect mutations that affect one or more regulatory elements of the MRP6 gene, including the promoter, the polyA site and other transcriptional or translational control sequences.

Methods of the invention are also useful to screen a population in order to identify individuals with one or more PXE associated MRP6 alleles. According to the invention, these individuals are provided with appropriate genetic counseling in view of their PXE status.

BRIEF DESCRIPTION OF THE DRAWINGS

FIG. 1 shows the structure of the MRP6 gene and the surrounding genomic regions. Two (MRP6) ABCC6 mutations that cause PXE are indicated. FIG. 1c shows the intron/ exon structure of the (MRP6) ABCC6 gene with intron sizes drawn approximately to scale and exons numbered from the 5' end of the (MRP6) ABCC6 gene; FIG. 1d shows chromatograms of partial DNA sequence from two unrelated PXE patients containing a nonsense and a splice site mutation in exon 24 and intron 21 respectively; FIG. 1e shows the sequence of the normal and mutant nucleotide and amino acid sequences for the nonsense mutation in exon 24 and the splice site variant within intron 21.

FIG. 3 shows conserved amino acids in the human MRP6 protein.

DETAILED DESCRIPTION OF THE INVENTION

The invention provides methods and compositions for diagnosing and treating PXE and PXE related symptoms. Methods and compositions of the invention rely in part on the discovery that mutations associated with PXE map to the (MRP6) ABCC6 gene locus on chromosome 16. Accordingly, the invention provides useful PXE related diagnostic and therapeutic methods and compositions by exploiting wild-type and mutant (MRP6) ABCC6 genes and proteins.

Figure 1A:
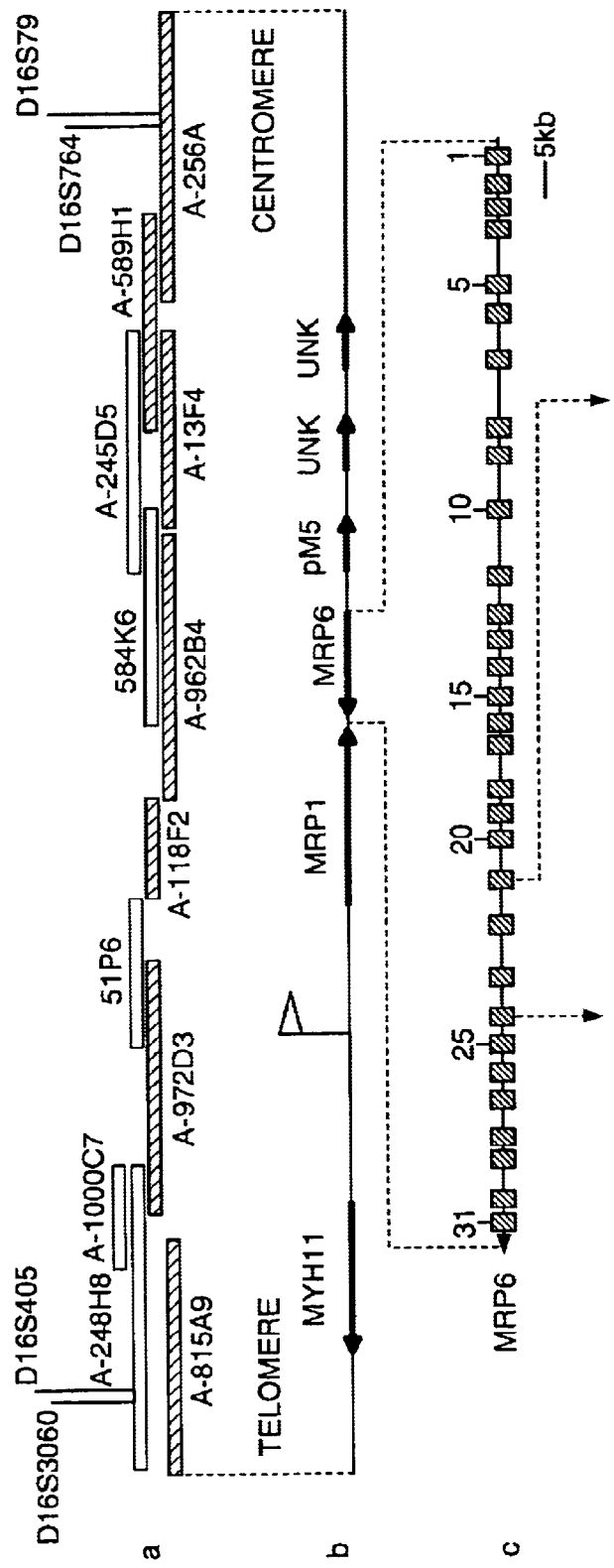
FIG. 1a shows the 820 kb genomic region between markers D16S3060 and D16S79 at 16p13.1.

I. PXE Associated Mutations in the (MRP6) ABCC6 Gene
a) Mapping of PXE Associated Mutations to the (MRP6) ABCC6 Genetic Locus Although the first case of PXE was reported by Darier in 1896, most PXE cases have been reported since the 1970s. In most reports, PXE is inherited as an autosomal recessive (AR) phenotype or appears as a sporadic phenotype. However, kindreds showing apparent autosomal dominant (AD) inheritance have also been reported. Using DNA from patients and unaffected family members from 21 unrelated PXE families, the PXE phenotype was linked to the short arm of chromosome 16. A very significant linkage with an 8 cM region was demonstrated with a maximum lod score of 8.07. A subsequent haplotype analysis and recombination mapping reduced the locus from 8 cM to 820 kb where six candidate genes were identified. The locus was later reduced to less than 600 kb and one candidate gene was excluded. All 109 exons of the five remaining candidate genes were screened by a combination of single-strand conformation polymorphism (SSCP), heteroduplex analysis (HA) or direct sequencing using genomic DNA from a cohort of 17 unrelated PXE patients and three unrelated normal individuals. The first six mutations, clearly associated with the PXE phenotype, were found in the (MRP6) ABCC6 gene (also known as the ABCC-6 gene). This analysis is described in further detail in Example 2. According to the invention, the MRP6 gene has 31 exons as shown in FIG. 1. A 107.7 kb genomic sequence that includes the MRP6 locus is shown in SEQ ID NO: 1. The sequence of SEQ ID NO: 1 shows the complementary strand of the MRP6 gene. The intron/exon boundaries are as follows (on the complementary strand of SEQ ID NO: 1): Ex1: 102783–102748; Ex2: 101180–100998; Ex3: 99296–99171; Ex4: 99031–98903; Ex5: 93798–93676; Ex6: 91594–91533; Ex7: 88207–88076; Ex8: 82954–82757; Ex9: 81524–81347; Ex10: 77528–77367; Ex11: 72268–72176; Ex12: 69718–69515; Ex13: 68325–68182; Ex14: 66562–66475; Ex15: 64385–64310; Ex16: 62282–62156; Ex17: 61940–61764; Ex18: 58324–58157; Ex19: 56985–56811; Ex20: 55345–55270; Ex21: 52757–52637; Ex22: 49588–49381; Ex23: 45578–45268; Ex24: 42837–42638; Ex25: 41209–41083; Ex26: 39226–39125; Ex27: 37453–37307; Ex28: 34674–34516; Ex29: 34437–34271; Ex30: 30412–30218; Ex31: 29881–29773. The mRNA coding sequence for human MRP6 is shown in SEQ ID NO: 2, and the encoded protein sequence is shown in SEQ ID NO: 3.

b) Identifying PXE Associated Mutations in the (MRP6) ABCC6 Locus

According to methods of the invention, additional PXE associated mutations were identified in the (MRP6) ABCC6 locus using a combination of single strand conformation polymorphism (SSCP), heteroduplex analysis (HA) and direct sequencing. Single nucleotide mutations in the (MRP6) ABCC6 gene were identified in several cohorts of individuals originating from the United States, South Africa and several European countries (Belgium, Germany, Holland, Italy and United Kingdom). To confirm the causative or polymorphic nature of new variants, a control panel of 300 alleles (150 normal individuals) was screened and the co-segregation of the identified variant and the PXE phenotype was verified. It is noteworthy that two single-allele mutations (R1141X, R1339C) were found in control panels of normal individuals indicating that heterozygote mutant (MRP6) ABCC6 alleles can be found in the normal population. However, the missense mutation (R1339C) was identified in the genetically distinct Afrikaners of South Africa. The frequency of heterozygote carriers deduced only from the appearance of these heterozygote mutations is 1.3 percent and is consistent with the commonly accepted figures of 0.6 to 2.5%. Indeed, while most mutations appeared to be private, a few have been clearly identified as recurrent (R1141X, R518Q, 3775delT, 16.5 kb deletion between exon 22 and 29. Most of the mutations (63%) were missense substitutions, 17% were nonsense mutations (5), 13% were frameshift mutations (4 deletions or an insertions of a single nucleotide) and 7% were likely to affect splicing (2).

Twenty-seven of the mutations (90%) affected the C-terminal half of the (MRP6) ABCC6 protein and particularly the various domains of the C-terminal ATP-binding site, which are encoded by exons 28 to 30, where 12 (40%) mutations were clustered. Remarkably, 10 mutations (33%) affected arginyl residues. Eight of these were missense substitutions, suggesting an essential structural or functional role for these arginyl residues in (MRP6) ABCC6.

Large deletions, which are not detected by SSCP or HA, can be identified by the loss of heterozygosity of informative polymorphic markers. Seven highly informative microsatellites present in a 300 kb region encompassing both ABCC1 and ABCC6, have been successfully used to detect large deletions involving parts or the entire ABCC6 gene. The loss of heterozygosity can also be efficiently implemented by using several highly polymorphic variants present in the ABCC6 gene. The latter approach was used to detect a partial deletion of the (MRP6) ABCC6 gene, in a compound heterozygous state, in a family with an apparent dominant form of PXE, as discussed in Example 3. A non-limiting list of known PXE associated mutations at the MRP6 locus are shown in Table 1.

TABLE 1

Known PXE associated mutations at the human MRP6 locus.

| | Mutations | Status | | |
|---|---|---|---|---|
| Effect | Nt change | Status | Origin | Exons |
| — | 938-939insT | ch, ht | A | 8 |
| R568Q | 1553G>A | ch, ht | a,u | 12 |
| F568S | 1703T>C | ht | U | 13 |
| L673P | 2018T>C | ch | A | 16 |
| — | 1995delG | ch | G | 16 |
| — | 2322delC | ht | U | 18 |
| Y768X | 2204C>A | ch, ht | A | 18 |
| — | IVS21+1G>T | ch | U | Intron 21 |
| R1030X | 3088C>T | ht | A | 23 |
| R1114P | 3341G>C | hm | Uk | 24 |
| S1121W | 3362C>G | ch | G | 24 |
| R1138P | 3413G>C | ch | G | 24 |
| R1138Q | 3413G>A | ch | Uk | 24 |
| R1141X | 3421C>T | all | All | 24 |
| G1203D | 3608G>A | | | 25 |
| — | IVS26-1G>A | ch | B | Intron 26 |
| W1241C | 3723G>C | | | 26 |
| Q1237X | 3709C>T | ch | B | 26 |
| — | 3775delT | ht, hm | a, u, h | 27 |
| V1298F | 3892G>T | ht | U | 28 |
| T1301I | 3902C>T | ch | B | 28 |
| G1302R | 3904G>A | ht | U | 28 |
| A1303P | 3907G>C | ch | B | 28 |
| R1314W | 3940C>T | hm | U | 28 |
| R1314Q | 3941G>A | ht | G | 28 |
| G1321S | 3961G>A | ht | U | 28 |
| R1339C | 4015C>T | all | a, u | 28 |
| Q1347H | 4041G>C | ht | U | 28 |
| D1361N | 4081G>A | ch | G | 29 |
| R1398X | 4192C>T | ch | B | 29 |
| I1424T | 4271T>C | ht | U | 30 | ch = compound heterozygote;
ht = heterozygote;
hm = homozygote;
ivs = intervening sequence According to methods of the invention, additional PXE associated mutations can be identified in the (MRP6) ABCC6 locus according to methods of the invention. For example, single strand conformation polymorphism (SSCP), heteroduplex analysis (HA), or direct sequence analysis can be used to identify additional mutations at the MRP6 locus. In one embodiment, the analysis is performed on genomic DNA. Alternatively, the analysis is performed on cDNA or on exon containing DNA amplification products such as exon containing PCR products. Deletion mutations are preferably detected using diagnostic PCR assays of genomic DNA and by Southern hybridization according to methods known in the art. In addition, fluorescent in situ hybridization (FISH) analysis of human chromosome preparations can be used to identify a deletion at the MRP6 locus or a deletion that encompasses all or part of the MRP6 locus. Specific mutations are preferably identified using DNA arrays including mutation specific oligonucleotide probes. Alternatively, mutation-specific antibodies can be used to detect mutations that alter an existing epitope or create a new specific epitope on the MRP6 protein. Preferably, specific antibodies are used on proteomic chips to detect protein altering mutations in the MRP6 gene. Mutations can also be detected using mass spectrometry, and mutation-specific mass spectrometer profiles can be generated for MRP6 nucleic acid or protein analysis according to methods known in the art.

c) PXE Associated Mutations at the (MRP6) ABCC6 Locus
i) The (MRP6) ABCC6 Gene and Protein The (MRP6) ABCC6 gene, also known as the ABBC6 gene, encodes an ATP-binding cassette transporter (an ABC transporter) belonging to sub-family "C" which includes genes involved in drug-resistance such as MRP1 to 6 (ABCC1–6). (MRP6) ABCC6/ABCC6 encodes a 165 kDa protein that is located in the plasma membrane and has 17 membrane-spanning helices grouped into three transmembrane domains. MRP6 is highly homologous to MRP 1 and may act as an efflux pump of amphipathic anion conjugates. Accordingly, in one aspect of the invention, MRP6 transports glutathione anion conjugates and also anionic drugs. Therefore, an individual that is a PXE carrier or a PXE homozygote or compound heterozygote may have reduced transport of anionic drugs and may be more receptive to chemotherapy using such drugs. The ABCC family of genes also includes the cystic fibrosis transmembrane conductance regulator gene (ABCC7 or CFTR) and the sulfonylurea receptor genes (ABCC8 and 9 or SUR).

Therefore, in contrast to genetic changes involved in other elastic fiber diseases such as Supravalvular Aortic Stenosis (SVAS), Marfan syndrome, and Cutis laxa, PXE associated mutations in the (MRP6) ABCC6 gene are not directly related to elastic fibers. The (MRP6) ABCC6/ABCC6 gene is expressed at relatively high levels in a limited range of tissues, notably in kidney and liver. However, low levels of expression are also observed in smooth muscle cells and macrophages. According to the invention, this tissue distribution suggests that (MRP6) ABCC6 has a function related to cellular detoxification which may affect the calcification of elastic fibers in skin, arteries and the retina. Alternatively, calcification of elastic fibers in skin, arteries, and the retina may result from MRP6 functional deficiencies in those tissues.

Figure 2:
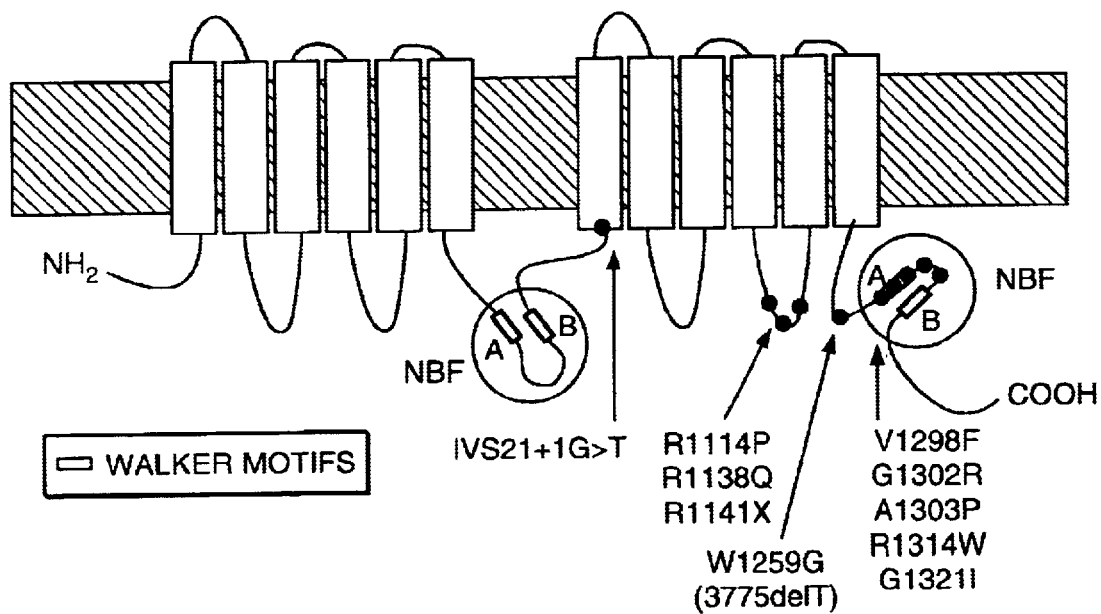
FIG. 2 shows the predicted topology of the MRP6 protein and the location of ten mutations causing PXE.

The predicted structure of the MRP6 protein is shown in FIG. 2. Transmembrane domains (unshaded rectangles), nucleotide-binding fold regions (NBF) and Walker motifs are indicated and were identified by amino acid sequence homology with similar transporters. Arrows indicate the positions of several PXE associated mutations. The large shaded rectangle represents the cell membrane.

According to the invention, the transmembrane domains of the MRP6 protein shown in FIG. 2 are hydrophobic stretches of amino acids identified via transmembrane domain predictions (SOSUI and DAS transmembrane prediction programs, http://www.biokemi.su.se/-server/DAS/; http://azusa.proteome.bio.tuat.ac.jp/sosui/). Regions of MRP6/ABCC6 with a high degree of conservation when compared with similar proteins (ABC transporters) include the regions involved in the binding and hydrolysis of ATP also known as nucleotide binding folds (NBF). According to the invention, the MRP6 protein has two nucleotide-binding fold regions (NBF1 and NBF2) as shown in FIG. 2. These regions correspond to the following amino acid segments of the human MRP6 protein: NBF1 residues 656–679, 747–768, and 775–784 of SEQ ID NO: 3; and NBF2 residues 1292–1307, 1321–1327, and 1403–1433 of SEQ ID NO: 3.

According to one embodiment of the invention, conserved amino acids in the MRP6 protein are amino acids identified by comparing 12 ABC transporter proteins from Human, Rat, Mouse, C. elegans, Yeast (S. cerevisiae) and A. thaliana. Preferred conserved amino acids are shown in FIG. 3 (conserved amino acids are underlined). According to the invention, conserved domains are concentrated in the C-terminal portion of the protein, where over 90% of the PXE causing mutations have been identified.

ii) Mutations in the (MRP6) ABCC6 Gene

According to one aspect of the invention, PXE is caused by a mutation at the (MRP6) ABCC6 locus that results in reduced MRP6 protein function. PXE associated mutations include mutations that affect the level of MRP6 protein expression in addition to mutations that alter the functional properties of an expressed MRP6 protein. PXE associated mutations at the (MRP6) ABCC6 locus include chain-terminating mutations. Such mutations are typically recessive and account for the autosomal recessive nature of the associated PXE phenotype. However, PXE associated mutations identified at the (MRP6) ABCC6 locus include chain terminating mutations at different positions in the (MRP6) ABCC6 gene, and several substitution, deletion and insertion mutations. According to the invention, the C-terminal half of the MRP6 protein is functionally important. Indeed, many of the PXE associated mutations were identified in exons 23–29. However, even a I to T substitution at position 1424 (out of 1503 amino acid residues) results in a PXE associated phenotype. Accordingly, a chain terminating or frameshift mutation in any one of exons 1–29, even up to position 1424 in exon 30, and maybe even beyond is expected to be associated with PXE. According to the invention, the PXE phenotype associated with different mutations in the (MRP6) ABCC6 gene varies in relation to the functional properties of the mutant (MRP6) ABCC6 protein product. Therefore, individuals with different PXE associated mutations can have PXE symptoms of differing severity. In addition, different individuals having the same PXE mutations, but in different genetic backgrounds, can also develop PXE symptoms of differing severity. Accordingly, different mutations at the PXE locus are expected to result in PXE phenotypes of differing severity. For example, in one embodiment of the invention, a mutation that results in the absence of MRP6 protein expression (for example a deletion of part or all of the gene, a chain terminating mutation, a mutation that prevents mRNA production, or a mutation that prevents translation of the mRNA) is expected to have a more severe PXE phenotype than a mutation that interferes with normal MRP6 protein function without destroying the function (for example an amino acid substitution that alters the structure and function of the protein without inactivating it. In particular, an individual that is a homozygote for a mutation that prevents MRP6 protein expression, or that is a compound heterozygote with two different mutations each of which prevents MRP6 protein expression, is expected to have a more severe phenotype than an individual that has a mutation with less severe effects on MRP6 protein function at one or both alleles of the MRP6 locus.

In a further embodiment of the invention, a heterozygote carrier of a PXE mutation can exhibit characteristic manifestations of PXE. In particular, a carrier of a recessive mutation can show partial skin, eye or cardiovascular symptoms. According to the invention, heterozygote carriers of different (MRP6) ABCC6 mutations can develop different subsets of PXE related symptoms and can have symptoms of varying severity. Indeed, there are numerous examples of dermal "elastic fibers changes" or cardiovascular abnormalities ranging from hypertension to myocardial infarction, in family members of severely affected individuals. According to the invention, cases of partial expression of PXE symptoms in heterozygote carriers are cases that had been assumed to be examples of dominant inheritance with for example 10 to 20% penetrance.

The various subtypes of a disorder or a dual mode of inheritance of a disease are frequently due either to mutations in different genes or different mutations in the same gene. Epidermolysis buflosa (EB) is an excellent example of a disorder characterized by several clinical types caused by distinct mutations in the same gene or mutations in different genes. EB is viewed as a group of heritable mechano-bullous skin diseases classified into three major categories of simplex, junctional and dystrophic forms. EB simplex is due to mutations in the genes encoding keratins 5 and 14, the junctional form is associated with mutations in the kalinin17aminin 5 genes; and the dystrophic disorder result from mutations in the type VII collagen gene (COL7Al). The dystrophic EB presents clinical sub-types: the Hallopeau-Siemens type is autosomal recessive and caused by nonsense mutations and glycine substitutions result in the autosomal dominant form.

In contrast to EB, no locus heterogeneity has been shown for PXE. According to the invention, most cases of PXE, if not all, are due to (MRP6) ABCC6 mutations. While the clinical heterogeneity in PXE patients may be caused by different types of (MRP6) ABCC6 mutations, the different PXE lesions (vascular, ocular, and dermal) observed for different autosomal recessive and seemingly dominant PXE mutations are clinically indistinguishable. Furthermore, identical PXE mutations can be either recessive or apparently dominant in unrelated pedigrees. Accordingly, different PXE mutations in different genetic backgrounds are associated with different severities of PXE symptoms. Furthermore, a PXE mutation can result in a partial PXE phenotype in a carrier individual (thereby accounting for observations of apparent dominant forms of PXE).

iii) Population Distributions of (MRP6) ABCC6 Mutations

According to the invention, different PXE associated (MRP6) ABCC6 mutations exist in the population, and new (MRP6) ABCC6 mutations arise sporadically. Based on current estimations of the prevalence of PXE in the United States (between 1:100,000 and 1:25,000), the frequency of appearance of heterozygote individuals with PXE mutations should be between 0.6 and 2.5 percent of the general population (1.5 to 6.0 million individuals). Given the risk of heterozygote individuals having children with PXE, an important aspect of the invention is to provide a genetic screen to identify heterozygote carriers of PXE mutations. According to the invention, a PXE carrier is an individual with one mutant allele of the (MRP6) ABCC6 gene, wherein the mutant allele is an allele that results in a PXE phenotype in an individual that is homozygous for that allele (or in an individual that is heterozygous with two different (MRP6) ABCC6 mutant alleles, each of which is associated with PXE).

According to a further embodiment of the invention, a significant factor in the complex phenotype of the PXE multi-organ disorder is partial expression of the fill range of the PXE symptoms in heterozygote carriers in recessive pedigrees. For example, a single mutant-ABCC6 allele, for example R1141X, within heterozygote carriers can manifest a partial, mostly vascular-related phenotype. Indeed, cardiovascular abnormalities are frequently seen in obligate carriers but ocular and dermal lesions have also been diagnosed. The PXE phenotype, as observed in several heterozygous carriers, range from sub-clinical manifestations to visible lesions. The spectrum of these partial phenotypes overlaps with that of the less severely affected PXE patients. There is, therefore, a continuum in the PXE phenotype between heterozygous carriers and PXE patients, which make the clinical diagnosis of the less severe forms of PXE equivocal. According to the invention, cardiovascular symptoms associated with PXE mutations at the MRP6 gene include atherosclerosis, hypertension, stroke, gastrointestinal bleeding, intermittent claudication. Ocular symptoms include macular or retinal degeneration and skin related symptoms include premature aging and solar elastosis.

According to the invention, the identification of the PXE gene provides methods for an unambiguous molecular diagnosis of patients and the identification of heterozygous carriers in families with autosomal recessive PXE or apparent autosomal dominant PXE, and the identification of homozygous PXE individuals or PXE carriers in the general population.

According to the invention, different populations can contain different characteristic PXE associated MRP6 mutations or different frequencies of PXE associated MRP6 mutations due to factors such as founder effects. For example, a founder effect in the South African Afrikaner population is thought to have caused the observed higher frequency of PXE in Afrikaners. According to the invention, a higher frequency of PXE in a population correlates with a higher frequency of PXE associated MRP6 mutations.

Intra-familial variation of the phenotype is a well known characteristic of PXE. These variations may be due to genetic and/or environmental causes. A few environmental factors are thought to influence the PXE phenotype. Among these, calcium and Vitamin D have been reported to contribute to the severity of the phenotype in some cases. Life style, smoking, diet, sun-exposure and obesity are also likely to modulate the penetrance of the phenotype. Indeed, remarkably dissimilar PXE phenotypes have been observed recently in identical twins. According to the invention, non-genetic factors contributing to the development of PXE symptoms in heterozygote carriers can be identified. Studies involving large cohorts of twins for example, such as those used by the Queensland Institute of Medical Research of Australia (http://gene12i.qimr.ed are also useful to identify both genetic and environmental factors related to the development of the PXE phenotype.

II. Diagnostic Applications (MRP6) ABCC6 genes and gene products, including mutant genes and gene products, as well as probes, primers, and antibodies, are useful for identifying carriers of PXE associated mutations. According to the invention, PXE associated mutations can be identified in families with a PXE pedigree or in individuals not previously known to be at risk of carrying a PXE related mutation. PXE associated mutations can be routinely screened using probes to detect the presence of a mutant (MRP6) ABCC6 gene or protein by a variety of methods. In preferred embodiments of the invention, individuals are screened for the presence of a recurrent mutation that is known to be present at a relatively high frequency in the population. For example, a preferred method of the invention screens an individual from a population for the presence of an MRP6 mutation that accounts for about 30%, and preferably 50%, and more preferably over 50%, of known incidences of PXE in the population. An alternative method of the invention screens an individual for the presence of two or more, preferably about five, more preferably about ten, and even more preferably over ten PXE associated MRP6 mutations. In methods that include assays for a plurality of PXE associated MRP6 mutations, the plurality of mutations preferably account for about 30%, and more preferably 50%, and even more preferably over 50%, of known incidences of PXE in the population.

In one aspect of the invention, the identification of a specific mutation is not necessary. A diagnostic assay may be based on the detection of an MRP6 protein expression defect resulting from, for example, reduced levels of mRNA expression. Indeed, the analysis of steady state levels of (MRP6) ABCC6 mRNA in skin fibroblasts from a PXE patient carrying a homozygous R1141X mutation showed that MRP6 mRNA levels were lower than in skin fibroblasts from a normal individual. Accordingly, low levels MRP6 mNRA can result from a mutation within the coding sequence, such as a nonsense mutation that results in nonsense mediated decay. In addition, low mRNA levels can be caused by mutations either an intron or an exon that destabilizes the RNA, or by a mutation in a regulatory region (including a promoter region) that reduces transcription of the MRP6 gene. Furthermore, the presence of a truncated MRP6 mRNA can be used as a diagnostic indicator for the presence of a PXE associated mutation.

Alternatively, the presence of a mutation that affects the amount, size, or other physical properties of the MRP6 protein can be detected without knowing the identity of the mutation. For example a decreased level of MRP6 protein or a the presence of a truncation in the MRP6 protein can be used as a diagnostic indicator for the presence of a PXE associated mutation. In addition, the presence of a larger than expected MRP6 protein (that may result for example, from a gene fusion or from one or more frameshift mutations that produce a larger and possibly non-functional protein) can be used as a diagnostic inidicator for the presence of a PXE associated mutation.

Accordingly the invention provides a method for screening for the presence of a PXE associated mutation at the MRP6 locus without specifically identifying the mutation. Such methods are useful to identify homozyogtes, compound heterozygotes, or carriers.

According to the invention, the identification of the presence of any PXE associated mutation at the MRP6 locus can be used as a positive diagnosis of PXE in an individual with PXE symptoms or to diagnose a PXE patient who has not yet developed PXE symptoms but who is identified as a homozygote or a compound heterozygote for PXE associated MRP6 mutations. Alternatively, the detection of the presence of a PXE associated MRP6 mutation according to the invention provides a method for screening a population to identify individuals who are carriers of a PXE associated mutation.

In general, a PXE carrier is distinguished from a PXE homozygote by the presence of both a normal allele and a PXE mutant allele in the carrier and the presence of two PXE mutant alleles in the homozygote. According to the invention, a normal allele can contain a neutral polymorphism as disclosed herein.

a) Nucleic Acid Based Diagnostics

When a diagnostic assay is to be based upon nucleic acids from a sample, the assay may be based upon mRNA, cDNA or genomic DNA. If mRNA is used from a sample, there may be little or no expression of transcripts unless appropriate tissue sources are chosen or available. Preferred tissue sources are biopsies of full thickness skin or skin fibroblasts cultured from dermal biopsies. Whether mRNA, cDNA or genomic DNA is assayed, standard methods well known in the art may be used to detect the presence of a particular sequence either in situ or in vitro (see, e.g., Sambrook et al., (1989) *Molecular Cloning: A Laboratory Manual*, 2nd ed., Cold Spring Harbor Press, Cold Spring Harbor, N.Y.). As a general matter, however, any tissue with nucleated cells may be examined.

Genomic DNA used for the diagnosis may be obtained from body cells, such as those present in the blood, tissue biopsy, surgical specimen, or autopsy material. The DNA may be isolated and used directly for detection of a specific sequence or may be amplified by the polymerase chain reaction (PCR) prior to analysis. Similarly, RNA or cDNA may also be used, with or without PCR amplification. To detect a specific nucleic acid sequence, direct nucleotide sequencing, hybridization using specific oligonucleotides, restriction enzyme digest and mapping, PCR mapping, RNase protection, chemical mismatch cleavage, ligase-mediated detection, and various other methods may be employed. Oligonucleotides specific to particular sequences can be chemically synthesized and labeled radioactively or non-radioactively (e.g., biotin tags, ethidium bromide), and hybridized to individual samples immobilized on membranes or other solid-supports (e.g., by dot-blot or transfer from gels after electrophoresis), or in solution. The presence or absence of the target sequences may then be visualized using methods such as autoradiography, fluorometry, or colorimetry. These procedures can be automated using redundant, short oligonucleotides of known sequence fixed in high density to silicon chips, or in other oligonucleotide array formats.

Whether for hybridization, RNase protection, ligase-mediated detection, PCR amplification or any other standards methods described herein and well known in the art, a variety of subsequences of the MRP6 sequences disclosed or otherwise enabled herein will be useful as probes and/or primers. These sequences or subsequences will include both normal MRP6 sequences and PXE associated MRP6 mutant sequences. In general, useful oligonucleotide probes or primer sequences will include at least 8–9, more preferably 10–50, and most preferably 18–24 consecutive nucleotides from the MRP6 introns, exons or intron/exon boundaries. Depending upon the target sequence, the specificity required, and future technological developments, shorter sequences may also have utility. Therefore, any MRP6 derived sequence which is employed in a diagnostic assay may be regarded as an appropriate probe or primer. Particularly useful sequences include nucleotide positions from the MRP6 gene for which PXE associated mutations are known, or sequences which flank these positions.

As discussed above, a variety of PXE causing mutations have now been identified at the human MRP6 gene locus. Detection of these and other PXE associated mutations is now enabled using isolated nucleic acid probes or primers derived from normal or mutant MRP6 genes. According to the invention, useful oligonucleotide probes or primers are derived from sequences encoding the C-terminal half of the MRP6 protein, the conserved NBF sequences, and conserved amino acid sequence shown in FIG. 3. Particularly usefull oligonucleotides are derived from sequences known to have PXE associated mutations, such as the sequences including the mutations shown in Table 1. As disclosed above, a number of PXE associated MRP6 mutations have already identified, and it is expected that more will be identified according to the compositions and methods disclosed herein. Therefore, the present invention provides isolated nucleic acid probes and primers corresponding to normal and mutant sequences from any portion of the MRP6 gene, including exons, introns, and 5' and 3' UTRs, which may be shown to be associated with the development of PXE.

Merely as an example, and without limiting the invention, useful diagnostic probes and primers derived from the MRP6 DNA are disclosed in Example 5.

For in situ hybridization-based detection of a normal or mutant MRP6, a sample of tissue may be prepared by standard techniques and then contacted with one or more of the nucleic acids described herein, preferably one which is labeled to facilitate detection, and an assay for nucleic acid hybridization is conducted under stringent conditions which permit hybridization only between the probe and highly or perfectly complementary sequences. For the single nucleotide substitutions associated with PXE, high stringency hybridization conditions will be required to distinguish most mutant sequences from normal sequences. When the MRP6 genotypes of an individual's parents are known, probes may be chosen accordingly. Alternatively, probes to a variety of mutants may be employed sequentially or in combination. Because PXE carriers will be heterozygous, probes to normal sequences also may be employed and homozygous normal individuals may be distinguished from mutant heterozygotes by the amount of binding (e.g., by intensity of radioactive signal). In another variation, competitive binding assays may be employed in which both normal and mutant probes are used but only one is labeled.

In addition to oligonucleotide-based hybridization assays, methods of the invention include direct sequencing, loss of heterozygosity, SSCP, HA, and Conformation-Sensitive Gel Electrophoresis (CSGE) to detect a PXE associated MRP6 mutation. As discussed above, preferred mutations to be screened for are those shown in Table 1. However, additional mutations identified according to the invention are also useful as markers of PXE, including deletions in the (MRP6) ABCC6 locus.

According to one embodiment of the invention, a diagnostic test can be a nucleic scanning test where the assay detects the presence of a mutation in the nucleic acid being interrogated. In an alternative embodiment, a diagnostic test can interrogate a nucleic acid for the presence of a specific mutation.

According to this invention, base pair deletions or alterations leading to the omission of amino acid residues in the gene product are determined. Nucleic acid primers and probes are used in a variety of PCR-based amplification and hybridization assays to screen for and detect the presence of defective ABCC6 gene or mRNA in a patient. The genetic information derived from the intron/exon boundaries is also very useful in various screening and diagnosis procedures.

Various nucleic acid scanning methods are used for scanning the MRP6 genomic, mRNA or cDNA sequence obtained from a patient for detecting, for example, large deletions and substitutions in the sequence that would be indicative of the disease. These nucleic acid scanning techniques include PCR-based techniques and using oligonucleotide probes that hybridize to specific regions of the gene.

In one embodiment of the invention, preferred mutations for nucleic acid scanning techniques include large deletions in the genomic sequence for the ABCC6 gene for example a 16.5 kb deletion spanning from exon 22 to exon 29. Primers are designed to various regions of the ABCC6 gene which are used for PCR-based detection of large deletions in the gene.

In another embodiment of the invention, primers are designed to the ABCC6 gene that are able to differentiate between the size of the amplified wild-type sequence and sequence containing a specific mutation, for example a deletion.

In a preferred embodiment of the invention, nucleic acid probes are provided which comprise either ribonucleic or deoxyribonucleic acids. Typically, the size of the probes varies from approximately 18 to 22 nucleotides. Functionally, the probe is long enough to bind specifically to the homologous region of the ABCC6 gene, but short enough such that a difference of one nucleotide between the probe and the DNA being tested disrupts hybridization. Thus the nucleic acid probes of the present invention are capable of detecting single nucleotide changes in the ABCC6 gene.

In a preferred embodiment of the invention, nucleic acid probes are 100% homologous to a mutant allele of the ABCC6 gene, but not to the wild-type gene.

In another embodiment of the invention, the nucleic acid probes are 100% homologous to the wild-type allele. Accordingly, the invention provides methods for determining whether an individual is homozygous or heterozygous for a particular allele using both a wild-type and an allele-specific probe.

According to one method of the invention, mutations are detected by sequencing specific regions of the ABCC6 gene. In a preferred embodiment, the specific regions encompass one or more mutations presented in Table 1. In an alternative embodiment, a specific region being interrogated includes one of exons 1–31. Preferred exons include exons 25–29, and more preferably exon 28 in which many PXE associated mutations have been identified.

According to still other methods of the present invention rapid screening techniques are used to determine whether exons of the ABCC6 gene carry any mutations. Such techniques can be followed by one of the techniques already described above which are specific for a particular allele or mutation. One such rapid screening technique involves the determination of the conformation of single strands of DNA which have been amplified from exon sequences that are known to carry mutations, including the mutations presented in Table 1. The single strands are run in non-denaturing electrophoretic gels, such as are typically used for sequencing DNA. The mobility of single stranded DNA on such gels is sensitive to the conformation of the DNA fragments. The conformation of the single stranded DNA is dependent on its base sequence, alterations in even one base affecting the conformation. Thus the presence of a wild-type or mutant allele described herein can be detected by amplifying an exon sequence, denaturing the duplex molecules, and separating them on the basis of their conformation on non-denaturing polyacrylamide gels. If mutant alleles are present, they will have a different mobility than wild-type sequences amplified with the same primers. Most conveniently, the amplified sequences will be radiolabeled to facilitate visualization on gels. This can be readily accomplished using labeled primers or a labeled nucleotide. For a general reference on this technique see Orira, et al., Genomics vol. 5, pp. 874–879 (1989). A preferred nucleic acid amplification product for SSCP analysis is between about 100 and 500 bp, and more preferably between about 140 and 300 bp.

According to another rapid screening technique of the present invention, an amplified fragment containing a mutation is detected using denaturing gradient gel electrophoresis (DGGE). For a general reference on this technique see Sheffield, et al., Proc. Natl. Acad. Sci. vol. 86, pp. 232–236 (1989). Briefly, double stranded fragments which are generated by amplification (PCR) can be subjected to DGGE. "DGGE is a gel system that separates DNA fragments according to their melting properties. When a DNA fragment is electrophoresed through a linearly increasing gradient of denaturants, the fragment remains double stranded until it reaches the concentration of denaturants equivalent to a melting temperature (Tm) that causes the lower-temperature melting domains of the fragment to melt. At this point, the branching of the molecule caused by partial melting sharply decreases the mobility of the fragment in the gel. The lower-temperature melting domains of DNA fragments differing by as little as a single-base substitution will melt at slightly different denaturant concentrations because of differences in stacking interactions between adjacent bases in each DNA strand. These differences in melting cause two DNA fragments to begin slowing down at different levels in the gel, resulting in their separation from each other." Sheffield, et al., ibid. Use of a GC clamp as taught in Myers et al., Nucleic Acids Res. vol. 13, pp. 3111–3146 (1985) increases the sensitivity of detection of this method from about 40% to about 100%. If mismatches are present, which would be the case if the DNA sample amplified was heterozygous for an ABCC6 allele, they will be visible on these DGGE gels. Double stranded fragments containing one wild-type strand and one mutant strand will have a different mobility on these gels than will double stranded fragments which contain two wild-type or two mutant strands, due to the different melting temperatures of these species. Thus, the melting temperature of fragments amplified from different regions of the ABCC6 gene can be determined by DGGE and can be used to indicate whether a mutant allele is present.

In one embodiment, a region of the (MRP6) ABCC6 gene that encodes an important functional domain of the (MRP6) ABCC6 protein is screened for the presence of any mutation. For example, a preferred diagnostic assay interrogates the region of the (MRP6) ABCC6 gene that encodes an ATP binding site of the (MRP6) ABCC6 protein, a region that encodes a hydrophobic transmembrane domain, or a region that encodes a conserved amino acid, preferably in the C-terminal half of the MRP6 protein.

One major application of the nucleic acid based diagnostics is in the area of genetic testing, carrier detection and prenatal diagnosis. Individuals carrying mutations in the ABCC6 gene (disease carrier or patients) may be detected at the DNA level with the use of a variety of techniques. The genomic DNA used for the diagnosis may be used directly for detecting specific sequences or may be amplified enzymatically in vitro, for example by PCR. The detection of specific DNA sequence may be achieved by methods such as hybridization using specific oligonucleotides (Wallace et al. Cold Spring Harbour Symp. Quant. Biol. 51: 257–261 (1986)), direct DNA sequencing (Church and Gilbert, Proc. Nat. Acad. Sci. U. S. A. 81: 1991–1995 (1988)), the use of restriction enzymes (Flavell et al. Cell 15: 25 (1978), Geever et al Proc. Nat. Acad. Sci. U. S. A. 78: 5081 (1981)), discrimination on the basis of electrophoretic mobility in gels with denaturing reagent (Myers and Maniatis, Cold Spring Harbour Sym. Quant. Biol. 51: 275–284 (1986)), RNase protection (Myers, R. M., Larin, J., and T. Maniatis Science 230: 1242 (1985)), chemical cleavage (Cotton et al Proc. Nat. Acad. Sci. U. S. A. 85: 4397–4401, (1985)) and the ligase-mediated detection procedure (Landegren et al Science 241:1077 (1988)).

Oligonucleotides specific to normal or mutant sequences are chemically synthesized using commercially available machines, labelled radioactively with isotopes or non-radioactively (with tags such as biotin (Ward and Langer et al. Proc. Nat. Acad. Sci. U. S. A. 78: 6633–6657 (1981)), and hybridized to individual DNA samples immobilized on membranes or other solid supports by dot-blot or transfer from gels after electrophoresis. The presence or absence of these specific sequences are visualized by methods such as autoradiography or fluorometric (Landegren et al, 1989) or colorimetric reactions (Gebeyshu et al. Nucleic Acids Research 15: 4513–4534 (1987)).

Sequence differences between normal and mutants may be revealed by the direct DNA sequencing method of Church and Gilbert. Cloned DNA segments may be used as probes to detect specific DNA segments. The sensitivity of this method is greatly enhanced when combined with PCR (Wrichnik et al, Nucleic Acids Res. 15:529–542 (1987); Wong et al, Nature 330:384–386 (1987); Stoflet et al, Science 239:491–494 (1988)). In the latter procedure, a sequencing primer which lies within the amplified sequence is used with double-stranded PCR product or single-stranded template generated by a modified PCR. The sequence determination is performed by conventional procedures with radiolabeled nucleotides or by automatic sequencing procedures with fluorescent-tags.

Genetic testing based on DNA sequence differences may be achieved by detection of alteration in electrophoretic mobility of DNA fragments in gels with or without denaturing reagent. Small sequence deletions and insertions can be visualized by high resolution gel electrophoresis. For example, a PCR product with a small deletion is clearly distinguishable from the normal sequence on an 8% non-denaturing polyacrylamide gel. DNA fragments of different sequence compositions may be distinguished on denaturing formamide gradient gel in which the mobilities of different DNA fragments are retarded in the gel at different positions according to their specific "partial-melting" temperature (Myers, supra). In addition, sequence alterations, in particular small deletions, may be detected as changes in the migration pattern of DNA heteroduplexes in non-denaturing gel electrophoresis, as have been detected for the 3 dp (1507) mutation and in other experimental systems (Nagamine et al, Am. J. Hum. Genet, 45:337–339 (1989)). Alternatively, a method of detecting a mutation comprising a single base substitution or other small change could be based on differential primer length in a PCR. For example, one invariant primer could be used in addition to a primer specific for a mutation. The PCR products of the normal and mutant genes can then be differentially detected in acrylamide gels.

Sequence alterations may occasionally generate fortuitous restriction enzyme recognition sites which are revealed by the use of appropriate enzyme digestion followed by conventional gel-blot hybridization (Southern, J. Mol. Biol 98: 503 (1975)). DNA fragments carrying the site (either normal or mutant) are detected by their reduction in size or increase of corresponding restriction fragment numbers. Genomic DNA samples may also be amplified by PCR prior to treatment with the appropriate restriction enzyme; fragments of different sizes are then visualized under UV light in the presence of ethidium bromide after gel electrophoresis.

In another embodiment of the invention, sequence changes at specific locations may also be revealed by nuclease protection assays, such as RNase (Myers, supra) and S1 protection (Berk, A. J., and P. A. Sharpe Proc. Nat. Acad. Sci. U. S. A. 75: 1274 (1978)), the chemical cleavage method (Cotton, supra) or the ligase-mediated detection procedure (Landegren supra).

In addition to conventional gel-electrophoresis and blot-hybridization methods, DNA fragments may also be visualized by methods where the individual DNA samples are not immobilized on membranes. The probe and target sequences may be both in solution or the probe sequence may be immobilized (Saiki et al, Proc. Natl. Acad. Sci USA, 86:6230–6234 (1989)). A variety of detection methods, such as autoradiography involving radioisotopes, direct detection of radioactive decay (in the presence or absence of scintillant), spectrophotometry involving colorigenic reactions and fluorometry involving fluorogenic reactions, may be used to identify specific individual genotypes.

In a preferred embodiment of the invention, for example, a PCR with multiple, specific oligonucleotide primers and hybridization probes, may be used to identify a plurality of possible mutations at the same time (Chamberlain et al. Nucleic Acids Research 16: 1141–1155 (1988)). The procedure may involve immobilized sequence-specific oligonucleotides probes (Saiki et al, supra).

According to the invention, assays are performed to detect a deletion within or including the MRP6 gene using Southern hybridization, FISH analysis, or diagnostic PCR. It is expected that most deletions will occur between repetitive Alu sequences that are common within the introns of the MRP6 gene. Preferred PCR primers for detecting these deletions are primers that flank intron Alu sequences.

According to one aspect of the invention, many of the PXE associated MRP6 mutations are found in exons 22–30. Accordingly, preferred assays of the invention interrogate any one of exons 22–30, taken alone or in combination, for the presence of a PXE associated MRP6 mutation.

In a preferred embodiment of the invention, a diagnostic assay interrogates the entire (MRP6) ABCC6 locus for the presence of a mutation, using for example SSCP, HA, or CSGE, and direct sequencing. In a more preferred embodiment, an assay interrogates a portion of the ABCC6 locus for the presence of a mutation. If a mutation is detected, it is first compared to known mutations associated with PXE (Table 1) and known neutral polymorphisms (Table 2) that are not associated with PXE. If the mutation has not yet been observed as either a PXE associated mutation or as a neutral polymorphism, the nature of the mutation is considered. If the mutation is a deletion, nonsense, frameshift or other mutation that affects expression of a normal MRP6 protein, the mutation is considered to be a PXE mutation. Similarly, if the mutation results in a nonconservative amino acid change or an amino acid change in a conserved sequence such as an NBF, a transmembrane sequence, or a change in a conserved amino acid shown in FIG. 3, the mutation is considered to be a PXE mutation. In addition, if the mutation results in low levels of MRP6 expression, the mutation is considered to be a PXE mutation. However, if the mutation results in a conservative amino acid change in a non-conserved part of the MRP6 protein the mutation is considered to be a neutral polymorphism. Nonetheless, a patient identified with a previously unknown neutral polymorphism according to this analysis should be subjected to additional diagnostic tests to look for known PXE associated symptoms or subclinical symptoms.

According to one aspect of the invention, the detection of PXE carriers and PXE patients is determined through the identification of mutant MRP6 alleles in DNA from patients, family members and apparently unrelated and normal individuals. A single allele, with no evidence of a second mutant allele and the presence of a normal allele will be considered a carrier. Patients may be identified as either compound heterozygotes (having two different mutant alleles) or homozygotes (two identical mutant alleles).

b) Protein Based Diagnostics

Different approaches to a MRP6 protein-based diagnostic assay can be used to detect the presence of a PXE related mutation in a patient. Preferred assays include detecting a mutant electrophoretic mobility, the presence of a mutant epitope, the absence of a normal epitope, or by identifying altered biological activity, for example altered ATP binding or altered transport of a synthetic, preferably radiolabeled molecule.

In one embodiment, diagnosis can be achieved by monitoring differences in the electrophoretic mobility of normal and mutant proteins. Such an approach will be particularly useful in identifying mutants in which charge substitutions are present, or in which insertions, deletions or substitutions have resulted in a significant change in the electrophoretic migration of the resultant protein. Alternatively, diagnosis may be based upon differences in the proteolytic cleavage patterns of normal and mutant proteins, differences in molar ratios of the various amino acid residues, or by functional assays demonstrating altered function of the gene products.

In preferred embodiments, protein-based diagnostics will employ differences in the ability of antibodies to bind to normal and mutant MRP6 proteins. Such diagnostic tests may employ antibodies which bind to the normal proteins but not to mutant proteins, or vice versa. In particular, an assay in which a plurality of monoclonal antibodies, each capable of binding to a mutant epitope, may be employed. The levels of anti-mutant antibody binding in a sample obtained from a test subject (visualized by, for example, radiolabelling, ELISA or chemiluminescence) may be compared to the levels of binding to a control sample. Alternatively, antibodies which bind to normal but not to mutant MRP6 protein may be employed, and decreases in the level of antibody binding may be used to distinguish homozygous normal individuals from mutant heterozygotes or homozygotes. Such antibody diagnostics may be used for in situ immunohistochemistry using biopsy samples of tissues obtained from patients.

c) Genetic Counseling

According to one embodiment of the invention, genetic counseling is provided to an individual identified as a PXE carrier, a PXE homozygote, or a PXE compound heterozygote (an individual with two different PXE mutant alleles). According to the invention, individuals carrying two PXE mutant alleles are provided information about ameliorating treatments for some of the symptoms of PXE. For example, a person who inherits PXE recessively is cautioned with regard to diet and activity. A low fat, high fibre, heart healthy diet is critical for maintaining cardiovascular health. Regular exercise appears to alleviate some of the symptoms of peripheral vascular disease. Medications to allow the passage of blood through narrowed arteries may be recommended. Individuals exhibiting eye manifestations should not engage in activities that put them at risk for injury to the eye that could subsequently lead to hemorrhage and vision loss. Smoking should be avoided at all costs since it appears to increase the rate and severity of eye disease. In one embodiment of the invention, a patient identified as being a carrier of a PXE associated mutation or as being a homozygote or a compound heterozygote for PXE associated mutations should be advised to reduce calcium intake or to use drugs that reduce calcium intake in order to reduce the severity of the phenotype.

III. Therapeutic Applications

The present invention provides a basis for therapeutic treatments of PXE related symptoms caused by mutations at the (MRP6) ABCC6 locus. According to the invention, normal (MRP6) ABCC6 nucleic acid or protein is provided to cells and/or a patient having a PXE associated mutation at the (MRP6) ABCC6 locus.

Preferred target tissues include the kidney and liver, but also other tissues where low levels of MRP6 expression have been observed, such as smooth muscle cells and macrophages. Preferred target tissues also include tissues or cells that exhibit PXE related symptoms, such as a blood vessel, the gastrointestinal tract, occular tissue, the urinary tract, and skin.

a) Nucleic Acid-based Therapeutics

According to the invention, PXE or PXE associated symptoms can be prevented or treated by providing a normal PXE gene or cDNA to a patient that is diagnosed as having on or more PXE associated mutations at the (MRP6) ABCC6 locus. The fact that PXE is a recessive disease makes it particularly amenable to gene therapy, because it is expected that most, if not all, PXE associated MRP6 mutations reduce the amount of functional MRP6 protein in a cell and can be compensated for by providing normal MRP6 to the cell.

In one series of embodiments, normal copies of the MRP6 gene are introduced into patients to code successfully for normal protein in one or more different affected cell types. The gene must be delivered to those cells in a form in which it can be taken up and code for sufficient protein to provide effective function. Thus, it is preferred that the recombinant gene be operably joined to a strong promoter so as to provide a high level of expression which will compensate for the absence of sufficient amounts of normal MRP6. As noted above, the recombinant construct may contain endogenous or exogenous regulatory elements, inducible or repressible regulatory elements, or tissue-specific regulatory elements.

Preferred vectors for introducing an MRP6 gene to a cell or a patient include retroviral vectors, because of their high efficiency of infection and stable integration and expression. Other viral vectors which can be used include adeno-associated virus, vaccinia virus, bovine papilloma virus, or a herpes virus such as Epstein-Barr virus. Alternative vectors include plasmids that are replicated in human cells.

In another series of embodiments, a mutant MRP6 gene may be replaced by homologous recombination with a recombinant construct. The recombinant construct preferably contains a normal copy of the MRP6 gene. Alternatively, a regulatory region of a normal MRP6 gene in a PXE carrier may be altered to increase expression of normal MRP6.

i) Wild Type Genes

In one series of embodiments, a normal human (MRP6) ABCC6 gene is introduced to cells or a patient. A normal (MRP6) ABCC6 gene includes a gene with one or more polymorphic variations that are not associated with PXE. In one embodiment, an MRP6 genomic sequence is used. In an alternative embodiment an MRP6 cDNA sequence is used.

ii) Related Genes

In an alternative series of embodiments, an (MRP6) ABCC6 related gene is provided to a cell or tissue having a PXE associated mutation. According to the invention, an (MRP6) ABCC6 related gene encodes a protein that has similar functional properties as a normal human MRP6 protein and can compensate for the absence of sufficient amounts of normal human MRP6 protein in a patient cell or tissue. Preferably, an (MRP6) ABCC6 homologue from another mammalian species is used. For example the mouse or rat MRP6 genes or cDNAs could be used. In one embodiment of the invention, a homologue from a non-mammalian species is used. Alternatively, a nucleic acid encoding a different ABC protein is used, for example an MRP1 encoding nucleic acid.

The present invention also provides for cells or cell lines, both prokaryotic and eukaryotic, which have been transformed or transfected with the nucleic acids of the present invention so as to cause clonal propagation of those nucleic acids and/or expression of the proteins or peptides encoded thereby. Such cells or cell lines will have utility both in the propagation and production of the nucleic acids and proteins of the present invention but also, as further described herein, as model systems for diagnostic and therapeutic assays. As used herein, the term "transformed cell" is intended to embrace any cell, or the descendant of any cell, into which has been introduced any of the nucleic acids of the invention, whether by transformation, transfection, infection, or other means. Methods of producing appropriate vectors, transforming cells with those vectors, and identifying transformants are well known in the art.

b) Protein Based Therapeutics

Treatment of PXE symptoms may be performed by directly providing normal protein to a patient cell or tissue. Sufficient amounts of substantially pure MRP6 protein can be obtained from cultured cell systems which express the protein. Delivery of the protein to the affected tissue can then be accomplished using appropriate packaging or administrating systems including, for example, liposome mediated protein delivery to the target cells.

c) Drug Therapies

In one embodiment of the invention, a drug identified according to methods of the invention is administered to a patient diagnosed with PXE or a PXE carrier with PXE related symptoms. Alternatively, a drug is administered to prevent or minimize the development of PXE or PXE associated symptoms in individuals identified as having one or more PXE mutations at the ABCC6 locus.

IV. Drug Discovery Applications

The present invention provides a basis for screening drug candidates to identify useful therapeutic compositions to treat or alleviate the symptoms of PXE. In a series of embodiments, the invention provides screens based on MRP6 activity. As used with respect to this series of embodiments, the term "activity" broadly includes gene and protein expression, protein post-translation processing, trafficking and localization, and any functional activity (e.g., enzymatic, receptor-effector, binding, channel), as well as downstream effects of any of these. MRP6 appears to be an integral membrane protein and may have transport related functions, and it also has ATP binding cassettes. Accordingly, these functional properties can be used as a basis for a screen to identify compounds that increase MRP6 function.

In one embodiment, a drug candidate is screened for its ability to increase expression of the MRP6 gene. A preferred screen monitors the level of normal MRP6 mRNA in cells grown in culture in the presence and absence of the candidate compound. Alternatively, normal MRP6 protein levels are monitored. Useful cells for these assays are preferably normal cells or PXE carrier cells. However, a PXE cell can also be used and the levels of mutant MRP6 expression can also be monitored. A compound that increases the level of MRP6 expression is particularly useful to treat a PXE carrier in order to increase the level of MRP6 expressed from the normal allele. However, a compound that increases the level of MRP6 expression can also be useful to treat a PXE homozygote or compound heterozygote if the PXE associated MRP6 allele(s) encodes an MRP6 protein that retains some normal MRP6 function or if the allele is a mutation that reduces the level of normal MRP6 function.

Other assays are useful for screening candidate compounds to identify a compound that increases normal MRP6 function. In one embodiment, an assay screens a compound for the ability to restore normal phenotype to dermal fibroblasts isolated from a PXE patient. Dermal fibroblasts isolated from patients with PXE exhibit abnormal phenotype when grown in vitro (Quaglino et al., Biochimica et Biophysica Acta 1501 (2000) 51–62). These phenotypes include an increased proliferation index compared to normal fibroblasts when grown in monolayer. PXE fibroblasts also have lower adhesion properties to collagen type I and to plasma fibronectin when compared to normal fibroblasts. Accordingly, these phenotypes provide a basis for an assay to identify a compound that restores normal MRP6 function to dermal fibroblasts isolated from a patient that was identified as having a PXE associated MRP6 mutation.

In another embodiment of the invention, an assay is used to screen candidate compounds for their ability to increase the ATPase activity of an MRP6 proteins. In a preferred embodiment, the assay monitors the ATPase activity of an MRP6 protein encoded by an MRP6 gene with a PXE associated mutation in the presence and absence of the candidate compound. ATPase activity of purified MRP6 can be assayed according to methods known in the art (see, for example, Mao et al., Biochimica et Biophysica Acta 1461, 69–82 (1999). According to the invention, a compound that increases the ATPase activity of a PXE associated MRP6 protein variant is useful to treat a patient that is heterozygous or homozygous for the PXE allele that encodes the protein variant used in the assay.

In a similar embodiment of the invention, an assay is used to screen candidate compounds for their ability to increase the transport activities of an MRP6 protein, in particular a PXE associated MRP6 protein variant. A useful transport assay is provided in Oude et al., Biochim Biophys Acta, 1241(2), 215–68, 1995. A compound identified according to this screen is useful to treat PXE patients and PXE carriers as described above.

V. Disease Models

The invention provides a basis for designing cellular and animal models of PXE. Such models are useful to study the development of the PXE disease in PXE homozygotes and compound heterozygotes and to identify potential PXE associated physiological dysfunctions in PXE carriers. Such models are also useful in screens to identify therapeutic compounds to prevent or treat PXE symptoms.

a) Cellular Models

According to the invention, cellular models can be made by deleting one or both MRP6 alleles, or by introducing one or more PXE associated MRP6 alleles into a cell line grown in vitro, using methods known in the art. Preferred cell lines include renal and hepatic cell lines. Other useful cell lines include those derived from skin (keratinocytes and fibroblasts) and ocular tissue (ganglioma cells).

b) Animal Models

The present invention also provides for the production of transgenic non-human animal models for the study of PXE, for the screening of candidate pharmaceutical compounds, and for the evaluation of potential therapeutic interventions.

Animal species which suitable for use in the animal models of the present invention include, but are not limited to, rats, mice, hamsters, guinea pigs, rabbits, dogs, cats, goats, sheep, pigs, and non-human primates (e.g., Rhesus monkeys, chimpanzees). For initial studies, transgenic rodents (e.g., mice) are preferred due to their relative ease of maintenance and shorter life spans. Transgenic yeast or invertebrates (e.g., nematodes, insects) may be preferred for some studies because they will allow for even more rapid and inexpensive screening. Transgenic non-human primates, however, may be preferred for longer term studies due to their greater similarity to humans.

Based on the identification of MRP6 as the gene associated with PXE, there are now several available approaches for the creation of a transgenic animal models for PXE, including animal models with one or both MRP6 alleles deleted and animal models with one or two MRP6 alleles with mutations similar to known PXE associated human MRP6 mutations.

To create an animal model (e.g., a transgenic mouse), a mutant MRP6 gene can be inserted into a germ line or stem cell using standard techniques of oocyte microinjection, or transfection or microinjection into embryonic stem cells. Animals produced by these or similar processes are referred to as transgenic. If the mutation knocks out the MRP6 gene or a portion thereof, the animals are referred to as knockouts.

For oocyte injection, one or more copies of the recombinant DNA constructs of the present invention may be inserted into the pronucleus of a just-fertilized oocyte. This oocyte is then reimplanted into a pseudo-pregnant foster mother. The liveborn animals are screened for integrants using analysis of DNA (e.g., from the tail veins of offspring mice) for the presence of the inserted recombinant transgene sequences. The transgene may be either a complete genomic sequence injected as a YAC, BAC, PAC or other chromosome DNA fragment, a cDNA with either the natural promoter or a heterologous promoter, or a minigene containing all of the coding region and other elements found to be necessary for optimum expression.

Retroviral infection of early embryos can also be done to insert the recombinant DNA constructs of the invention. In this method, the transgene is inserted into a retroviral vector which is used to infect embryos (e.g., mouse or non-human primate embryos) directly during the early stages of development to generate chimeras, some of which will lead to germline transmission.

Homologous recombination using stem cells allows for the screening of gene transfer cells to identify the rare homologous recombination events. Once identified, these can be used to generate chimeras by injection of blastocysts, and a proportion of the resulting animals will show germline transmission from the recombinant line. In a preferred embodiment, inactivation of the MRP6 gene in mice may be accomplished by designing a DNA fragment which contains sequences from an MRP6 exon flanking a selectable marker. Homologous recombination leads to the insertion of the marker sequences in the middle of an exon, causing inactivation of the MRP6 gene and/or deletion of internal sequences. DNA analysis of individual clones can then be used to recognize the homologous recombination events.

The techniques of generating transgenic animals, as well as the techniques for homologous recombination or gene targeting, are now widely accepted and practiced. A laboratory manual on the manipulation of the mouse embryo, for example, is available detailing standard laboratory techniques for the production of transgenic mice (Hogan et al., 1986). A large number vectors are available to accomplish this and appropriate sources of genomic DNA for mouse and other animal genomes to be targeted are commercially available from companies such as GenomeSystems Inc. (St. Louis, Mo., USA). The typical feature of these targeting vector constructs is that 2 to 4 kb of genomic DNA is ligated 5' to a selectable marker (e.g., a bacterial neomycin resistance gene under its own promoter element termed a "neomycin cassette"). A second DNA fragment from the gene of interest is then ligated downstream of the neomycin cassette but upstream of a second selectable marker (e.g., thymidine kinase). The DNA fragments are chosen such that mutant sequences can be introduced into the germ line of the targeted animal by homologous replacement of the endogenous sequences by either one of the sequences included in the vector. Alternatively, the sequences can be chosen to cause deletion of sequences that would normally reside between the left and right arms of the vector surrounding the neomycin cassette. The former is known as a knock-in, the latter is known as a knock-out. Example 5 describes a knockout of most of exons 28 and 29 in mouse MRP6.

VI. (MRP6) ABCC6 Interacting Molecules

According to the invention, molecules that interact with a normal MRP6 gene product gene product provide candidates 1) for identifying additional types of mutations that result in a PXE phenotype and 2) for additional levels of therapeutic intervention to overcome or minimize the effect of a mutant PXE gene product. For example, the identification of a protein that interacts with a normal MRP6 protein but not with a PXE mutant protein provides a potential target for therapeutic intervention if the function of the interacting protein can be modified to compensate for the absence of normal MRP6 protein.

According to the invention, (MRP6) ABCC6 interacting molecules can be identified according to a number of biochemical and genetic methods known in the art, including affinity chromatography, mutational analysis, and yeast two hybrid analysis. As will be obvious to one of ordinary skill in the art, there are numerous other methods of screening individual proteins or other compounds, as well as large libraries of proteins or other compounds (e.g., phage display libraries and cloning systems from Stratagene, La Jolla, Calif.) to identify molecules which bind to normal or mutant MRP6 proteins. All of these methods comprise the step of mixing a normal or mutant MRP6 protein or protein fragment with test compounds, allowing for binding (if any), and assaying for bound complexes.

The invention is further illustrated by the following non-limiting examples. de

EXAMPLES

Example 1

Materials and Methods a) Sources of Patient Samples

PXE International, Inc.

To date, PXE International has assembled a database of over 2100 PXE patients from 1400 families from 31 countries including North America, several European and South American countries and South Africa. From this cohort of patients and family members, genomic DNA has been prepared from whole blood samples obtained from over 1200 PXE patients and family members.

Honolulu Heart Program

In the early 1950's, studies around the world were reporting geographic differences in coronary heart disease (CHD) mortality, pathology, prevalence, and incidence. Among these reports were those of significant differences in the CHD and cerebrovascular disease rates in Japan and in the United States. The overall mortality for men in Japan and in the United States was similar, but the rates for CHD were strikingly different. Reported CHD mortality among Japanese was approximately twenty percent of that among U.S. Caucasians. At about the same time, Japanese living in Hawaii and California were reported to have a lower overall mortality than either U.S. Caucasians or Japanese living in Japan. The reasons for these differences were not apparent. However, it was felt that the study of these populations might offer important clues to the etiology of heart and vascular disease. The compared populations, living in Japan, Hawaii and California were of Japanese ancestry to limit genetic variation between study groups. The Honolulu cohort of the Ni-Hon-San (Nippon-Honolulu, San Francisco) study formed the basis for the Honolulu Heart Program (HHP). That study has now been underway for 35 years, providing extensive information about the role of lifestyle, diet, and other risk factors to development of chronic diseases of major public health importance in 8,000 Japanese-American men.

Although several studies have suggested that PXE is more frequent in females there is no evidence that the observed gender difference is caused by genetic factors. Indeed, men would often report skin lesions, usually the first signs of PXE, later in life, than women. Therefore, a study of an exclusively male cohort from the HHP should not compromise the general applicability of the conclusions. PXE has also no particular predilection for any ethnic or racial group. PXE has indeed largely been described in Caucasians but also in African and Asian populations. PXE cases reported in Japan have shown no phenotypic or prevalence differences when compared to those observed in Caucasian populations.

Unaffected Control Subjects

DNA has been prepared from 150 unrelated individuals with no evidence of PXE. These samples have been aliquoted and are currently stored at −80° C. They are routinely used as control DNA samples and will be used to confirm that any new and potential mutation detected in a PXE patient or relative is indeed a mutation and not a neutral polymorphism. The donors of these DNA samples were adults of either sex from various ethnic backgrounds.

b) Mutation Detection Methods

Detection of Single Nucleotide Mutations

Single strand conformation polymorphism (SSCP) analysis is based on the observation that single stranded DNA will adopt, in non-denaturing conditions, a secondary structure that is strictly sequence-dependant. Slight variations in sequence, such as a single nucleotide change can alter the conformation of a DNA fragment, which can be resolved on a non-denaturing polyacrylamide gel. Heteroduplex analysis (HA) is based on the observation that heteroduplexes formed between two DNA strands with one or more mismatches have electrophoretical mobility distinctly different from homoduplexes. While both methods (SSCP and HA) can detect point mutations, some sequence variants are more readily detected by one procedure than the other. Accordingly, a preferred screening method, uses a combination of SSCP and modified HA called Conformation-Sensitive Gel Electrophoresis or CSGE.

In a preferred assay, each characterized PCR primer pair is radioactively labeled using T4 polynucleotide kinase and $\gamma$-[$P^{32}$]-ATP. For SSCP analysis, radiolabeled PCR products are mixed with denaturing loading buffer and loaded onto a 0.5×MDE (MDE is a mutation detection enhancement polyacrylamide-derived matrix provided by FMC products), 0.6×TBE native polyacrylamide gel and electrophoresed overnight at 8 watts in a sequencing gel apparatus. Separated, radiolabeled conformers are visualized by autoradiography. For CSGE, EDTA is added to the incubated PCR reaction mix to a final concentration of 1 mM and the reaction will be heat-denatured and incubated for 60 minutes at 68° C. to allow heteroduplex formation. Heteroduplex products are analyzed on a 6% polyacrylamide gel (29:1 ratio of acrylamide/bisacrylamide), 10% (v/v) ethylene glycol and 15% (w/v) formamide in 0.5×TTE buffer (1×TTE is 89 mM Tris, 15 mM taurine, 0.5 mM EDTA, pH 9.0). A solution of 20% (v/v) ethylene glycol, 30% (w/v) formamide and 0.05% xylene cyanol and bromophenol blue is mixed equally with the samples. The gel is run at 35 to 45 watts for 2 to 4 hours at room temperature. As for SSCP, CSGE conformers are revealed by autoradiography.

When an abnormal conformer or heteroduplex is detected, the segregation of the variant is analyzed for DNA samples from the entire family. Subsequently, the DNA sequence of the variant is determined by eluting normal and altered DNA conformers directly from the electrophoresis gel. These PCR fragments are eluted in water, re-amplified and directly used as a template for sequencing using an ABI 310 automated sequencer (Perking Elmer). A panel of 150 DNA samples of normal unrelated individuals is used to identify abnormal variants that are common polymorphisms in the ABCC6 locus.

Mutation Detection by Enzymatic Cleavage

Single nucleotide substitutions often modify the recognition site of a restriction enzyme. Polymorphisms and mutations can, therefore, be detected in a rapid and convenient manner by the enzymatic cleavage of a PCR fragment containing the nucleotide change. This method is frequently employed to verify the presence of previously characterized mutations or polymorphisms in DNA samples for control, study or diagnostic purposes. It can also be used for screening a large number of samples. Out of the ABCC6 mutations listed in Table 1, 10 mutations were identified with a unique restriction pattern. For example, three possible HhaI restriction profiles for one of these mutations, R1339C (4015C to T) can be visualized by electrophoresis. According to the invention, single nucleotide mutations in ABCC6 are detectable by enzymatic cleavage. Accordingly, this method is useful as an initial step to appropriately complement the screening of large cohorts with more traditional mutations detection techniques.

PCR Mapping

A single base substitution mutation may be detected based on differential PCR product length or production in PCR. Thus, primers which span mutant sites or which, preferably, have 3' termini at mutation sites, may be employed to amplify a sample of genomic DNA, mRNA or cDNA from a subject. A mismatch at a mutational site may be expected to alter the ability of the normal or mutant primers to promote the polymerase reaction and, thereby, result in product profiles which differ between normal subjects and heterozygous and/or homozygous MRP6 mutants. The PCR products of the normal and mutant gene may be differentially separated and detected by standard techniques, such as polyacrylamide or agarose gel electrophoresis and visualization with labeled probes, ethidium bromide or the like. Because of possible non-specific priming or readthrough of mutation sites, as well as the fact that most carriers of mutant alleles will be heterozygous, the power of this technique may be low.

Electrophoretic Mobility

Genetic testing based on DNA sequence differences also may be achieved by detection of alterations in electrophoretic mobility of DNA, mRNA or cDNA fragments in gels. Small sequence deletions and insertions, for example, can be visualized by high resolution gel electrophoresis of single or double stranded DNA, or as changes in the migration pattern of DNA heteroduplexes in non-denaturing gel electrophoresis. MRP6 mutations or polymorphisms may also be detected by methods which exploit mobility shifts due to single-stranded conformational polymorphisms (SSCP) associated with mRNA or single-stranded DNA secondary structures.

Chemical Cleavage of Mismatches

Mutations in MRP6 may also be detected by employing the chemical cleavage of mismatch (CCM) method. In this technique, probes (up to ~1 kb) may be mixed with a sample of genomic DNA, cDNA or mRNA obtained from a subject. The sample and probes are mixed and subjected to conditions which allow for heteroduplex formation (if any). Preferably, both the probe and sample nucleic acids are double-stranded, or the probe and sample may be PCR amplified together, to ensure creation of all possible mismatch heteroduplexes. Mismatched T residues are reactive to osmium tetroxide and mismatched C residues are reactive to hydroxylamine. Because each mismatched A will be accompanied by a mismatched T, and each mismatched G will be accompanied by a mismatched C, any nucleotide differences between the probe and sample (including small insertions or deletions) will lead to the formation of at least one reactive heteroduplex. After treatment with osmium tetroxide and/or hydroxylamine to modify any mismatch sites, the mixture is subjected to chemical cleavage at any modified mismatch sites by, for example, reaction with piperidine. The mixture may then be analyzed by standard techniques such as gel electrophoresis to detect cleavage products which would indicate mismatches between the probe and sample.

Other Methods

Various other methods of detecting MRP6 mutations, based upon the MRP6 sequences disclosed and otherwise enabled herein, will be apparent to those of ordinary skill in the art. Any of these may be employed in accordance with the present invention. These include, but are not limited to, nuclease protection assays (S1 or ligase-mediated), ligated PCR, denaturing gradient gel electrophoresis (DGGE), restriction endonuclease fingerprinting combined with SSCP (REF-SSCP), and the like.

Methods for Analyzing MRP6 mRNA Levels

The steady state levels of (MRP6) ABCC6 mRNA was analyzed in skin fibroblasts from a PXE patient carrying a homozygous R1141X mutation. Total skin fibroblast RNA from an unaffected control individual and a PXE patient was used to synthesize single stranded cDNA using oligo(dT). PCR primers derived from (MRP6) ABCC6 mRNA sequence were then used in two consecutive rounds of 25 cycles of PCR. Poly(A)+ RNA from normal human kidney (obtained from Clontech) was used as a positive control for detection of (MRP6) ABCC6 mRNA. MRP-1 mRNA was detected in the same cDNA samples used for ABCC6 mRNA with 30 cycles of PCR. The 390 bp and 180 bp DNA fragments detected correspond to the expected size of (MRP6) ABCC6 and MRP-1 mRNA domains encoded within exons 6–9 and 2–3 of the (MRP6) ABCC6 and MRP-1 genes respectively. No reverse transcriptase (No RT) controls were included to confirm that no PCR products were obtained in the absence of cDNA synthesis.

Stringent Hybridization Conditions

High stringency conditions are at least equivalent to a temperature in the range of about 40–70 degrees C., and between about 0.05 and 0.5 M sodium ion. High stringency hybridization conditions are well known in the art and can be optimized for a specific oligonucleotide based on the length and GC content of the oligonucleotide as described in, for example, Sambrook et al., *Molecular Cloning, A Laboratory Manual* (Cold Spring Harbor, N.Y., 1982).

An oligonucleotide selected for hybridizing to the target nucleic acid, whether synthesized chemically or by recombinant DNA methodologies, is isolated and purified using standard techniques and then preferably labeled (e.g., with $^{35}S$ or $^{32}P$) using standard labeling protocols. A sample containing the target nucleic acid then is run on an electrophoresis gel, the dispersed nucleic acids transferred to a nitrocellulose filter and the labeled oligonucleotide exposed to the filter under stringent hybridizing conditions, e.g. 50% formamide, 5×SSPE, 2×Denhardt's solution, 0.1% SDS at 420° C., as described in Sambrook et al. (1989) supra. The filter may then be washed using 2×SSPE, 0.1% SDS at 68° C., and more preferably using 0.1×SSPE, 0.1% SDS at 68° C. Other useful procedures known in the art include solution hybridization, and dot and slot RNA hybridization. Optionally, the amount of the target nucleic acid present in a sample is then quantitated by measuring the radioactivity of hybridized fragments, using standard procedures known in the art.

Example 2

The Positional Cloning of the PXE Gene

Blood samples and skin biopsies from PXE patients and unaffected relatives in the United States were collected by PXE International Inc., by Dr. Ivonne Pasquali-Ronchetti in Italy, by Dr. F. Michael Pope in the United Kingdom and by Dr. Anne de Paepe in Belgium. Blood samples were obtained from 100 Caucasian control individuals with no family history of PXE. Genomic DNA was isolated from aliquots of blood. Low passage and confluent skin fibroblasts were obtained from 3 mm full thickness skin biopsies using known procedures.

Figure 1B:
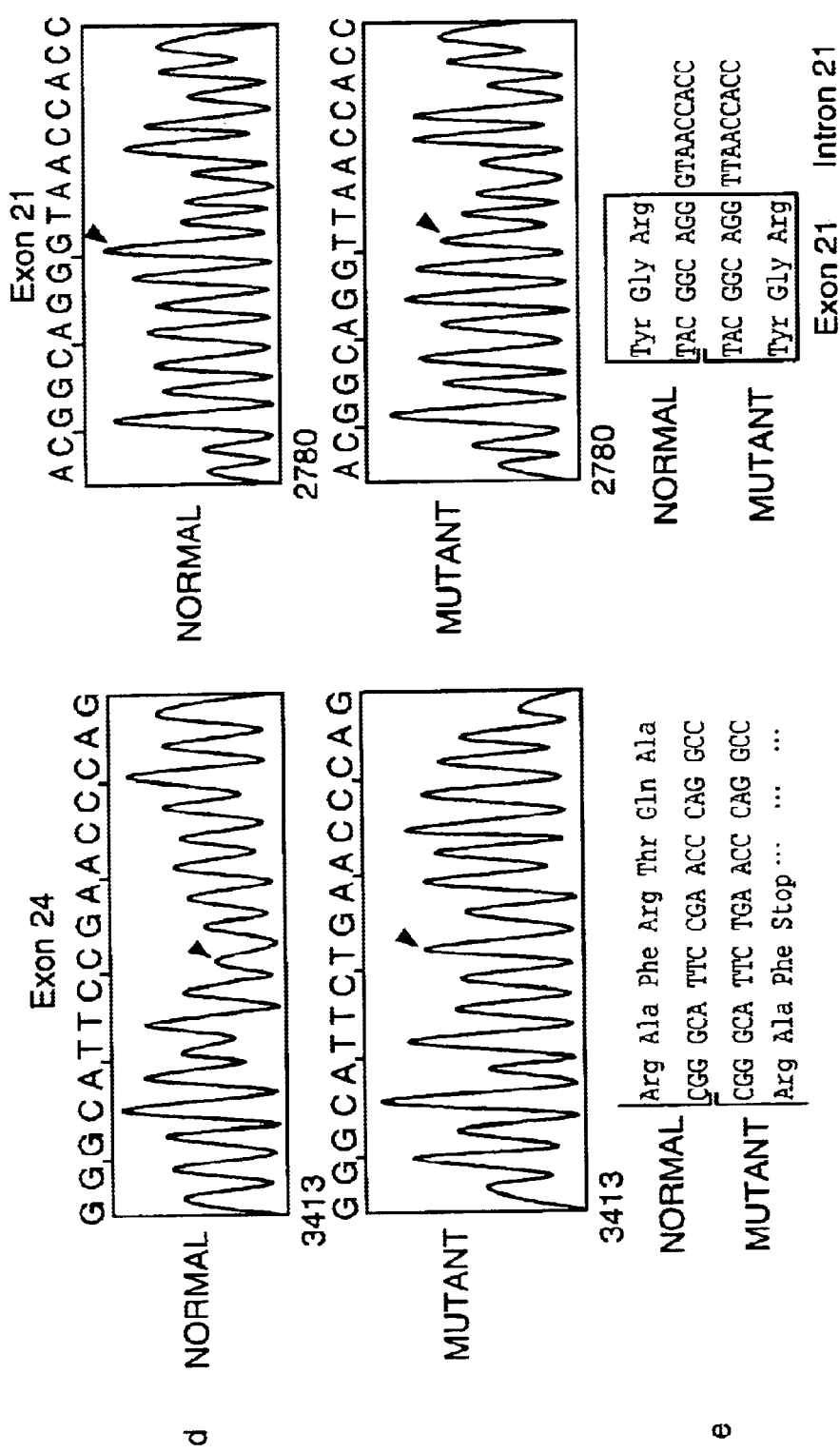
FIG. 1b shows the gene content of the genomic region with the transcriptional orientation of the genes indicated by arrows and a flag representing the position of polymorphic marker (GAAA$_{17}$)

To identify the gene that contains mutations responsible for PXE, the disease locus was confined to a region of about 8 cM between markers D16S500 and- D16S3041. Recombination mapping reduced this large critical region to an 820 kb domain containing six candidate genes. These genes encode an isoform of Myosin Heavy Chain (MYH11), two Multidrug Resistance-associated Proteins (MRP-1 and (MRP6) ABCC6), an unknown protein called pM5 and two identical unknown proteins referred to as UNK. Using a polymorphic microsatellite repeat $(GAAA_{17})$ located at the 5' end of the MRP-1 gene (FIG. 1) an informative meiotic recombination in one PXE patient was identified and this permitted the exclusion of the MYH11 as a candidate gene and reduced the size of the PXE region to 570 kb and 5 candidate genes. FIG. 1 shows the previously defined PXE locus covering 820 kb between markers D16S3060 and D16S79 at 16p13.1. The BAC contig that covers this region is shown along with the identity of the BACs. FIG. 1b shows the gene content of the PXE locus represented from the telomere (left) to the centromere (right). The transcriptional orientation of the genes is indicated by arrows. A flag represents the position of a polymorphic marker $(GAAA_{17})$ used to identify an additional meiotic recombination in one PXE patient that excluded the MYH11 gene as the PXE gene.

The 109 exons within the five candidate genes were then screened for mutations by Single-Strand Conformation Polymorphism (SSCP) and Heteroduplex Analysis (HA) using genomic DNA from a cohort of 20 unrelated PXE patients.

Mutation detection, sequence analysis and RT-PCR, SSCP, and Heteroduplex Analysis (HA) were carried out as previously described. Intron-derived primers for PCR amplification of exons present in the genes encoding MRP-1, (MRP6) ABCC6, pM5 and both UNK gene were synthesized using intron sequences available in the TIGR database (http://www.tigr.org). PCR products were typically 150–350 bp in length and included complete intron/exon boundaries. Typical PCR reactions, were performed in the presence of $^{32}P$-labelled primers in a 9700 thermocycler (Perkin Elmer). Radioactive PCR products were analyzed either by SSCP or HA using MDE polyacrylamide gel (FMC) according to the manufacturer's instructions. DNA conformers were eluted in water from gel slices, re-amplified and sequenced utilizing the same primers used to generate these PCR products. DNA sequence analysis was performed using ABI BigDye terminator cycle sequencing with an ABI310 automated DNA sequencer. The sequence information generated by the sequencer was analyzed using the ABI software. The Sequencher™ 3.1 program was used to identify variation between the sequence of putative mutations and control sequences. RT-PCR was performed on total RNA from cultured human skin fibroblasts and human kidney poly(A)+ RNA. The sequences of the PCR primers used are: (MRP6) ABCC6: 5'-AGCCACGTTCTGGTGGGTTT-3' (SEQ ID NO: 4); 5'-GGAGGCTTGGGATCACCAAT-3' (SEQ ID NO: 5); MRP-1: 5-CAACTGCATCGTTCTGTTTG-3' (SEQ ID NO: 6); and 5'-ATACTCCTTGAGCCTCTCCA-3' (SEQ ID NO: 7). Following synthesis, PCR products were separated by electrophoresis through 1.2% agarose and visualized by staining with ethidium bromide.

DNA sequence analysis of two conformers detected in PCR products containing exons 19 and 28 of the pM5 gene revealed two private single nucleotide polymorphisms (SNPs) within the intronic sequence flanking these exons (Table 2). These were the only sequence variants detected in the 31 exons of the pM5 gene using a cohort of 20 PXE patients. Screening all eight exons of each of the two UNK genes revealed only one SNP in the first exon of either one or both UNK genes in 5 PXE patients. This was a silent nucleotide change (C33T) within the $11^{th}$ codon (S11) of the open reading frame of either one or both unknown genes and therefore unrelated to PXE. Screening all 31 exons of the MRP-1 gene in a panel of PXE patients identified several sequence variants (Table 2) that are not functionally related to PXE as they either occurred in intronic sequences or did not encode changes in amino acids. In addition, two missense variants (R633Q and G671V) were seen in exons-14 and 16 in two unrelated PXE patients but these substitutions were unlikely to be responsible for PXE as they were also found in a panel of 200 alleles from unaffected, ethnically matched control individuals.

Finally, in screening the 31 exons of the (MRP6) ABCC6 gene, the first mutations that are clearly responsible for PXE were identified. A C->T substitution within exon 24 (C3421T) of the (MRP6) ABCC6 gene generated a stop codon at position 1141 (R1141X; FIG. 1 and Table 2). FIG. 1c shows the intron/exon structure of the (MRP6) ABCC6 gene. Intron sizes are drawn approximately to scale and the exons are numbered from the 5' end of the (MRP6) ABCC6 gene. FIG. 1d shows chromatograms of partial DNA sequence from two unrelated PXE patients containing a nonsense and a splice site mutation in exon 24 and intron 21 respectively. In exon 24, the sequence shows a 3421C>T substitution (arrowhead), which would generate a stop codon at position 1141 (R1141X). PXE patients in a consanguineous Italian pedigree were found to be homozygous for this stop codon mutation. In intron 21, a G to T substitution (IVS21+1G>T) was observed within the invariant GT sequence of the donor splice site. This mutation would influence constitutive splicing of (MRP6) ABCC6 pre-mRNA and was found in two unrelated PXE patients as a compound heterozygote in association with either R1141X or R1138Q. FIG. 1c shows the sequence of the normal and mutant nucleotide and amino acid sequences for the nonsense mutation in exon 24 and the splice site variant within intron 21.

Figure 4:
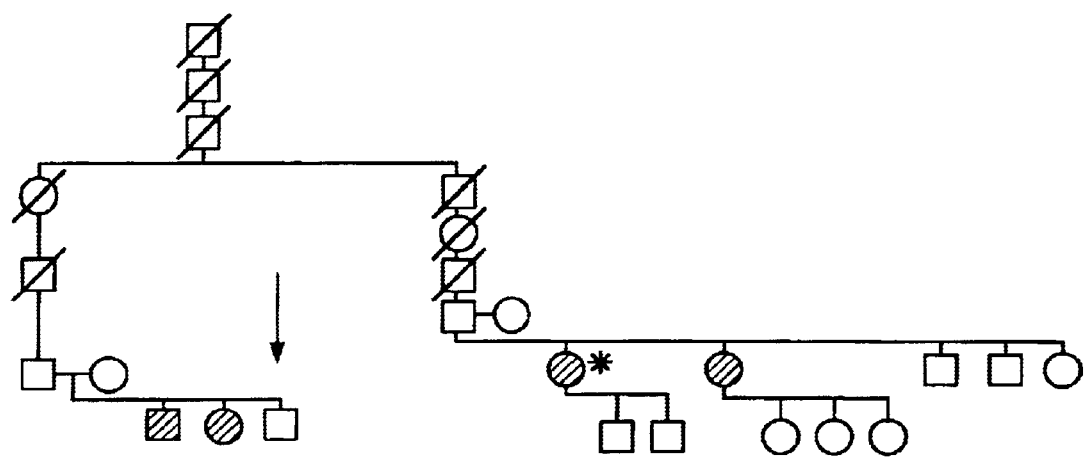
FIG. 4 shows co-segregation of the PXE phenotype with the R1141X mutation in exon 24 of the (MRP6) ABCC6 gene.
Figure 5:
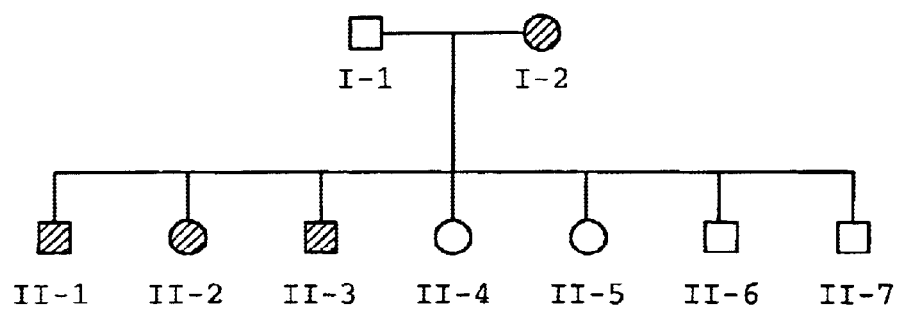
FIG. 5 shows segregation of the PXE phenotype for an apparent autosomal dominant mutation.

The C3421T variant in exon 24, which was not found in the control panel of 200 normal alleles, co-segregated in a homozygous form with a recessive PXE phenotype in an Italian family in which all unaffected individuals but one were heterozygote carriers (FIG. 4). FIG. 4 shows a large consanguineous Italian pedigree, SSCP conformers for a homozygous variant (R1141X) in exon 24 were noted in all four PXE patients (shaded symbols). All other unaffected family members were heterozygote for this nonsense mutation except one unaffected family member, indicated by an arrow. SSCP conformers from normal unrelated control DNA have been included. Total RNA from the PXE patient indicated by was used for an RT PCR analysis of (MRP6) ABCC6 mRNA and shown to have low levels of MRP6 mRNA.

This R1141X mutation results either in an (MRP6) ABCC6 protein lacking 362 amino acids at the C-terminal domain (FIG. 3) or a null allele, produced through nonsense mediated decay of a truncated (MRP6) ABCC6 mRNA. Indeed, an analysis of steady state (MRP6) ABCC6 mRNA levels in skin fibroblasts from PXE patients of this Italian pedigree indicated the absence of detectable (MRP6) ABCC6 mRNA, suggesting that the homozygous R1141X mutation results in the total loss of MRP6 gene product rather than the production of a truncated protein. R1141X was also found in a homozygous state in unrelated patients with autosomal recessive PXE from the United Kingdom and Belgium. Haplotype analysis of the PXE locus in families with the R1141X mutation revealed that this mutation is travelling within different haplotypes, suggesting that R1141X may be a recurrent mutation.

In two families with a recessive form of PXE from the United Kingdom and the United States, PXE patients were found to be compound heterozygotes. Affected individuals carried a substitution (TVS21+1G>T) affecting the donor-splice site of exon 21 of (MRP6) ABCC6, in association with either the nonsense R1141X substitution in exon 24 or a missense mutation, R1138Q also in exon 24. The splice site mutation occurred at the donor invariant dinucleotide and lowered the splice potential score from 72.1 to 53.8. Several other missense variants (Table 2) were also found within exon 24 and 28 of the (MRP6) ABCC6 gene. These single nucleotide substitutions, none of which were detected in the control panel of 200 alleles, occurred within highly conserved coding domains, particularly the domain in exon 28 encoding the Walker A region of the second ATP binding fold (FIG. 2).

All the detected homozygous or compound heterozygous mutations were found to be associated with autosomal recessive PXE. One missense mutation (3961G>A) was observed in a family with an apparently dominant form of PXE. All the other heterozygous alterations were detected in individuals with sporadic PXE. The mode of inheritance of these sporadic PXE cases is presently unknown.

Elastic fibers within elastic tissues such as skin and the arterial wall are fragmented and calcified in PXE patients. Dermal and vascular elastic fiber calcification is patchy and does not involve all elastic fibers in these tissues. Therefore, without wishing to be bound by any particular theory, calcification of elastic fibers in PXE is probably therefore, a secondary consequence of a primary defect of either elastic fiber assembly or the interaction of elastic fibers with other extracellular matrix components. Accordingly, MRP6 function is more likely to be related to fiber assembly or matrix interactions than calcium transport. Another possibility is that the maintenance of the integrity of normal elastic fibers, extracellular matrix polymers subject to constant mechanical stress, is modulated by (MRP6) ABCC6 in a way that has yet to be explained.

Polymorphic markers in genes encoding known elastic fiber proteins (tropoelastin, lysyl oxidase, fibrillin 1 and 2) were used in a linkage and sib pair analysis, performed with families with both autosomal recessive (AR) and dominant (AD) forms of PXE. No obvious linkage between these markers and the PXE phenotype was found.

TABLE 2

A summary of all variants identified in the PXE locus in a cohort of 20 unrelated PXE patients. Nucleotide (nt) numbering was derived either from full length published cDNA sequences or from putative cDNA deduced from genomic DNA sequence. Hetero indicates that a variant was identified in a heterozygous state. Homo indicates that a variant was found in a homozygous state. Both, indicates that a variant was seen in both heterozygous and homozygous states. Compound, indicates that a variant was characterized as a compound heterozygote.

| nt change | Codon # | Effect | Location | Status |
|---|---|---|---|---|
| UNK gene polymorphisms | | | | |
| 33C>T | 11 | Ser to Ser | Exon 1 | Hetero |
| pM5 gene polymorphisms | | | | |
| 2187C>T | 729 | Gly to Gly | Exon 19 | Hetero |
| 3241G>A | 1081 | Glu to Lys | Exon 28 | Hetero |
| MRP-1 gene polymorphisms | | | | |
| 1062T>C | 354 | Asn to Asn | Exon 9 | Hetero |
| 1898G>A | 633 | Arg to Gln | Exon 14 | Hetero |
| 2001C>T | 667 | Ser to Ser | Exon 16 | Hetero |
| 2012G>T | 671 | Gly to Val | Exon 16 | Both |
| 4002G>A | 1334 | Ser to Ser | Exon 28 | Hetero |
| IVS29-18delT | — | — | Intron 29 | Hetero |
| (MRP6) ABCC6 gene polymorphisms | | | | |
| 549G>A | 183 | Leu to Leu | Exon 5 | Hetero |
| IVS11-41A>G | — | — | Intron 11 | Both |
| 1841T>C | 614 | Val to Ala | Exon 14 | Both |
| 2490C>T | 830 | Ala to Ala | Exon 19 | Both |
| IVS25+90G>A | — | — | Intron 25 | Both |
| IVS27-46A>G | — | — | Intron 27 | Hetero |
| IVS28+49C>T | — | — | Intron 28 | Hetero |
| 3'UTR+17G>A | — | — | 3'UTR | Hetero |
| (MRP6) ABCC6 gene mutations | | | | |
| IVS21+1G>T | — | mRNA splicing | Intron 21 | Compound |
| 3341G>C | 1114 | Arg to Pro | Exon 24 | Homo |
| 3413G>A | 1138 | Arg to Gln | Exon 24 | Compound |
| 3421C>T | 1141 | Arg to X | Exon 24 | Compound + Both |
| 3775delT | 1259 | Fram Shift | Exon 27 | Hetero |
| 3892G>T | 1298 | Val to Phe | Exon 28 | Hetero |
| 3904G>A | 1302 | Gly to Arg | Exon 28 | Homo |
| 3907G>C | 1303 | Ala to Pro | Exon 28 | Hetero |
| 3940C>T | 1314 | Arg to Trp | Exon 28 | Homo |
| 3961G>A | 1321 | Gly to Ile | Exon 28 | Hetero |

Example 3
Mutation Detection in Dominant Pedigrees

The segregation of ABCC6 mutations with the PXE phenotype was studied in three pedigrees with an apparent dominant inheritance. Two of the dominant families (families 1 and 3) presented three generations of individuals, while the remaining pedigree contained only two generations. In all 3 families, a heterozygous mutation, R1141X in exon 24, was found to segregate with the PXE phenotype. In the two-generation family (family 2), an apparent loss of heterozygosity of the R1141X allele was detected in the second generation of affected individuals (II-1 to -3). Several polymorphic variants in the surrounding exons and introns were subsequently analyzed by SSCP. Only one variant, V614A in exon 14, was found to be informative.

These results suggested a heterozygous sub-microscopic deletion, which was paternally inherited. This deletion, with a breakpoint between exon 14 and 24, extended beyond exon 24, probably corresponds to a recurrent deletion recently characterized in 4 unrelated families. The latter deletion, confined to a region of the gene between intron 22 and 29 eliminated 16.5 kb of genomic DNA. Therefore, individuals II-1, II-2 and II-3 of family 2 have inherited compound heterozygote mutations, clearly indicating the recessive nature of PXE in this pedigree. Moreover, the phenotype displayed by the mother (Individual I-2) carrying a heterozygous allele R1141X, suggested the partial expression of the phenotype in an obligate carrier. Indeed, individual I-2 showed discreet skin lesions on the neck associated with a positive von Kossa staining of a skin biopsy—(from lesional skin) indicating the presence of calcium salt precipitates typical of PXE. No angioid streaks were reported for this obligate carrier and no cardiovascular examination has been performed yet. In the remaining families (family 1 and 3) no other mutations were found. However, the PXE phenotype of the family members dramatically varied with the generations, clearly suggesting either pseudo-dominance or partial penetrance in obligate carriers. In family 1, the paternal grandmother and the father presented discreet skin lesions on the neck region associated with a positive von Kossa staining of a skin biopsy (no other manifestation were diagnosed), while both children, although very young, had already visible signs of plaques of coalesced papules on the neck and angioids streaks following ocular examination. In family 3, the paternal grandfather was severely affected with lax and redundant skin, disciform scaring of the retina (the vision is severely impaired at this stage) in addition to active gastrointestinal bleeding and intermittent claudication. The father was only diagnosed with a positive von Kossa staining of a skin biopsy while 3 of his children presented with the characteristic PXE skin lesions and angioid streaks.

Accordingly, heterozygote carriers of PXE mutations can develop PXE related phenotypes including sub-clinical manifestations of PXE. According to the invention, the penetrance of PXE lesions associated with a single mutant (MRP6) ABCC6 allele is between about 10 to 20% of all carriers, based on the frequency of described AD PXE cases. Therefore, a pedigree with AR PXE presents sub-clinical manifestations of PXE in 10 to 20% of the obligate carriers. These carriers will be parents of an affected individual and 25% of the unaffected siblings.

Example 4
PXE Heterozygote Frequencies

Upon screening a small sample of the general population (150 normal individuals) as part of a control panel to verify whether nucleotide substitutions found in the (MRP6) ABCC6 gene from PXE patients were indeed mutations, two heterozygote mutations were found in unrelated subjects. The first of these variants was a founder mutation (R1339C) only present in South African Afrikaners while the second substitution is a recurrent nonsense mutation (R1141X). R1141X is one of the four recurrent mutations that have been identified. These mutations are far more likely to be found in the general population than private mutations, which, in principle, can only be found in related individuals. The frequency of heterozygote carriers deduced from the presence of one recurrent mutation in the relatively small sample of the general population is 0.7%. However, four recurrent mutations have thus far been identified. Although each of the recurrent mutations is likely to have a different frequency, the frequency of carriers can be as high as 2.8%, which is consistent with the commonly accepted prevalence of heterozygote carriers in the general population (0.6 to 2.5%).

Based upon these frequency of heterozygotes and the predicted penetrance of the PXE phenotype in heterozygote carriers (10–20%), heterozygote carriers with PXE symptoms are expected at a frequency of about 0.25% of the general population. In a cohort of about 3000 individuals between 8 and 15 persons presenting cardiovascular, ocular or dermal symptoms would be expected. These numbers provide a basis for a statistical analysis of the correlation between single (MRP6) ABCC6 mutations and partial manifestations of PXE. Additional cohorts with clinically defined cardiovascular abnormalities such as the 1200 sib-pairs group from the Family Blood Pressure Program with hypertension, or the NHLBI Framingham study (http://www.nhlbi.nih.gov/about/framingham/) from which an appropriate cohort of 2400 to 4500 individuals is available, can be used to provide additional statistical significance.

Example 5

Creating a Mouse Knockout

Figure 6:
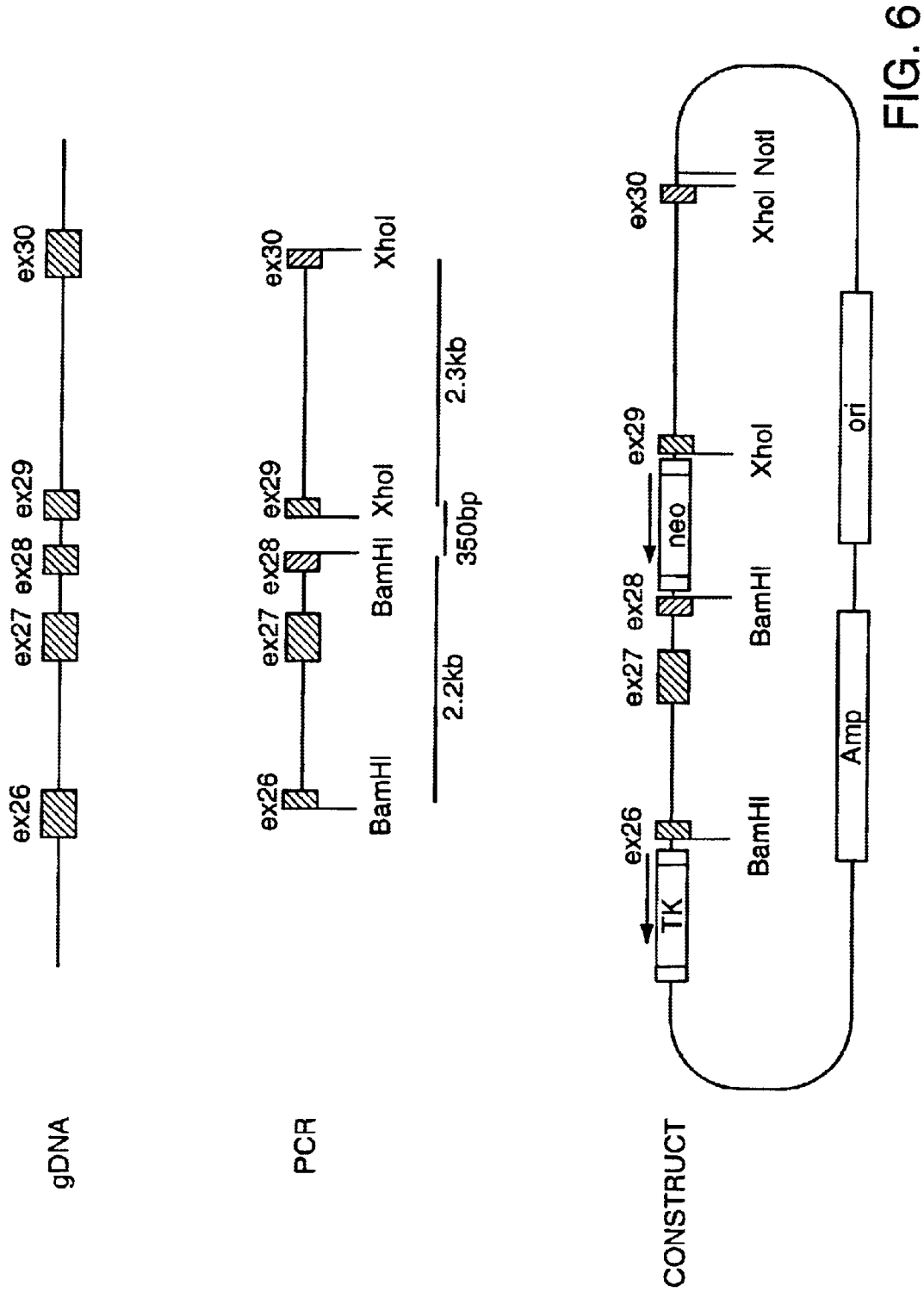
FIG. 6 shows a construct for deleting exon 28 in a mouse.

To create a knock-out mouse for ABCC6 a neomycin resistance cassette is introduced between exons 28 and 29 as shown in FIG. 6. This results in the destruction of the second ATP binding domain whose Walker A domain is encoded by exon 28 and which is essential for the function of any ABC transporter.

Based on the cDNA sequence for the mouse ABCC6 gene (SEQ ID NO: 8), primers with restriction sites were designed to amplify genomic DNA and allow cloning into vector pPNT described in Tybulewicz et al., Cell vol. 65, 1153–1163, 1991. Specifically, a 2.2 kb DNA fragment from exon 26 to exon 28 is cloned into the unique BamHI of pPNT, and a 2.3 kb DNA fragment containing exon 29 to 30 was cloned in the XhoI site of pPNT. In the resulting construct, the neomycin cassette from the vector interrupts the reading frame of ABCC6 in exon 28 after the conserved Lysine in the walker A domain.

This construct will be linearized by NotI digestion and transfected into mouse 129 stem cells. The two resistance cassettes provided by the vector (TK and Neo) will allow screening for homologous recombination and knock out of an ABCC6 locus according to methods known in the art (see, for example, Tybulewicz et al., Cell vol. 65, 1153–1163, 1991).

The deletion construct shown in FIG. 6 will be transfected into E. coli and amounts of DNA sufficient for the targeted mutagenesis process will be produced. This construct will be inserted into embryonic cell lines and cells that incorporate the construct will be implanted into surrogate mothers and MRP6 null mice will be obtained according to methods known in the art.

According to the invention, the production of MRP6 null mice with symptoms resembling those of human PXE would provide further proof that mutations at the MRP6 locus are responsible for PXE. However, a more important use for MRP6 null mice, or mice that are carriers of an MRP6 deletion (heterozygotes having an allele with the MRP6 deletion and a wild-type MRP6 allele) is to provide an animal model to study the development and progression of PXE, and to provide an animal model useful in the development of therapeutic approaches (including identifying therapeutic drugs) to treat existing PXE or to prevent or reduce the symptoms of PXE before they develop.

Example 6

Examples of Oligonucleotide Probes and Probes Useful to Detect PXE Associated MRP Mutations.

Various probes corresponding to regions of specific mutations in ABCC6 are used in standard oligonucleotide hybridization, in oligonucleotide array or nucleic acid chip assays (see www.brownlab.stanford.edu), and in PCR-based techniques for the detection of PXE. Each of the mutations shown below are indicative of a mutation in the ABCC6 gene that leads to PXE.

In a preferred embodiment, the probe shown in SEQ ID NO: 10 is used for the detection of a G to A mutation in Exon 24 of the ABCC6 gene. CAGTGGTCCAGGGCATTCCGA (SEQ ID NO: 10)

In another embodiment, the probe shown in SEQ ID NO: 11 is used for the detection of a C to T mutation in Exon 24 of the ABCC6 gene. CAGTGGTCCGGGCATTCTGA (SEQ ID NO: 11)

In yet another embodiment of the invention, the probe in SEQ ID NO: 12 is used for the detection of a G to C mutation in Exon 24 of the ABCC6 gene. GACCGTTGGAGTCAGCCAGCTACTCG (SEQ ID NO: 12).

In another embodiment of the invention, the probe in SEQ ID NO: 13 is used for the detection of a C to G mutation in Exon 24 of the ABCC6 gene. GACCCTTGGAGTCAGCCAGCTACTGG (SEQ ID NO: 13)

In another embodiment, the following probes are used for the detection of specific mutations in Exon 26 of the ABCC6 gene.

In a preferred embodiment of the invention, the probe in SEQ ID NO: 14 is used for the detection of a C to T mutation in Exon 26 of the ABCC6 gene. GGATGTAGGACTATGCCTGGACGCCC (SEQ ID NO: 14)

In a preferred embodiment of the invention, the probe in SEQ ID NO: 15 is used for the detection of a G to C mutation in Exon 26 of the ABCC6 gene. GGATGCAGGACTATGCCTGCACGCCC (SEQ ID NO: 15)

In yet another preferred embodiment of the invention, specific mutations in Exon 27 of the ABCC6 gene are detected using the probes shown below.

In a preferred embodiment of the invention, the probe in SEQ ID NO: 16 is used for the detection of a C to A substitution in Exon 27 of the ABCC6 gene TGCAGCTAAGCCCCCCTGGC (SEQ ID NO: 16)

The probe sequence in SEQ ID NO: 17 is used for the detection of a deletion in Exon 27 of the ABCC6 gene. TGCAGCTCAGCCCCCCGGC (SEQ ID NO: 17)

In yet another embodiment of the invention, the probe in SEQ ID NO: 18 is used for the detection of a G to A mutation in Exon 27 of the ABCC6 gene. GCTCCAAGCTCCCTGGAGGC (SEQ ID NO: 18)

Mutations in Exon 28 of the ABCC6 gene in patients are detected using the probes shown in SEQ ID NOs. 19, 20, 21, 22, 23, 24 and 25.

In a preferred embodiment of the invention, the probe in SEQ ID. 19 is used for the detection of a C to T mutation in Exon 28 of the ABCC6 gene. CTGTGGCTCCAGGAGGCAGCTGAGGGTGGG (SEQ ID NO: 19)

In yet another preferred embodiment of the invention, the probe in SEQ ID NO: 20 is used for the detection of a G to A mutation in Exon 28 of the ABCC6 gene. CTGCAGCTCCAGGAGGCAGCTGAGGGTGGG (SEQ ID NO: 20)

Similarly, in a preferred embodiment of the invention, the probe in SEQ ID NO: 21 is used for the detection of a G to A mutation in a different region of Exon 28 of the ABCC6 gene. CTGCGGCTCCAGGAGGCAGCTGAGAGTGGG (SEQ ID NO: 21)

Probes in SEQ ID NOs. 22, 23, 24 and 25 are used for the detection of additional specific mutations in Exon 28 of the ABCC6 gene.

| | |
|---|---|
| GTGGGCATCTTTGGCAGGACCGGGG | (SEQ ID NO: 22) |
| GTGGGCATCGTTGGCAGGACTGGGG | (SEQ ID NO: 23) |
| GTGGGCATCTTTGGCAGGACCAGGG | (SEQ ID NO: 24) |
| GTGGGCATCTTTGGCAGGACCGGGC | (SEQ ID NO: 25) |

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are intended to be embraced therein.

INCORPORATION BY REFERENCE

Each of the patent documents and scientific publications disclosed herein is incorporated by reference into this application in its entirety.

What is claimed is:

1. A method for screening a patient for the presence of a PXE mutation, the method comprising the steps of:
   a) interrogating an MRP6 nucleic acid in a patient sample for the presence of a mutation shown to be associated with PXE, wherein said mutation is selected from the group consisting of:
      i) at codon 1114, nucleotide 3341G>C;
      ii) at codon 1138, nucleotide 3413G>A;
      iii) at codon 1141, nucleotide 3421C>T;
      iv) at codon 1259, nucleotide 3775delT;
      v) at codon 1298, nucleotide 3892G>T;
      vi) at codon 1302, nucleotide 3904G>A;
      vii) at codon 1303, nucleotide 3907G>C;
      viii) at codon 1314, nucleotide 3940C>T; and
      ix) at codon 1321, nucleotide 3961G>A; and
   b) identifying said patient as having a PXE mutation if the mutation from step a) is detected in said MRP6 nucleic acid.

2. The method according to claim 1, wherein the patient sample is selected from the group consisting of blood, saliva, amniotic fluid, and tissue.

3. The method according to claim 2, wherein the patient sample is blood.

4. The method according to claim 1, wherein said interrogating step is a nucleic acid sequence scanning assay.

5. The method according to claim 4, wherein said scanning assay is selected from the group consisting of SSCP, DGGE, RFLP, LCR, DHPLC, and enzymatic cleavage.

6. The method according to claim 1, wherein said interrogating step is a specific mutation detection assay.

7. The method according to claim 6, wherein said detection assay is selected from the group consisting of oligonucleotide hybridization and primer extension essays.

8. The method according to claim 1, wherein said interrogating step is a nucleic acid sequencing assay.

9. The method according to claim 1, wherein said nucleic acid is selected from the group consisting of mRNA, genomic DNA, and cDNA.

10. The method according to claim 1, wherein said interrogating step is a hybridization assay.

* * * * *

UNITED STATES PATENT AND TRADEMARK OFFICE
CERTIFICATE OF CORRECTION

PATENT NO. : 6,780,587 B2
DATED : August 24, 2004
INVENTOR(S) : Boyd et al.

Page 1 of 1

It is certified that error appears in the above-identified patent and that said Letters Patent is hereby corrected as shown below:

Column 170,
Line 34, replace "essays" with -- assays --.

Signed and Sealed this

Seventh Day of December, 2004

JON W. DUDAS
*Director of the United States Patent and Trademark Office*